US010279027B2

(12) United States Patent
Parks et al.

(10) Patent No.: US 10,279,027 B2
(45) Date of Patent: May 7, 2019

(54) TRANSGENIC VERO-CD4/CCR5 CELL LINE

(71) Applicant: International AIDS Vaccine Initiative, New York, NY (US)

(72) Inventors: Christopher L. Parks, New York, NY (US); Wayne C. Koff, New York, NY (US)

(73) Assignee: INTERNATIONAL AIDS VACCINE INITIATIVE, New York, NY (US)

( * ) Notice: Subject to any disclaimer, the term of this patent is extended or adjusted under 35 U.S.C. 154(b) by 0 days.

(21) Appl. No.: 15/481,108

(22) Filed: Apr. 6, 2017

(65) Prior Publication Data

US 2017/0266272 A1 Sep. 21, 2017

Related U.S. Application Data

(63) Continuation-in-part of application No. 15/280,710, filed on Sep. 29, 2016, now Pat. No. 9,925,258.

(60) Provisional application No. 62/236,448, filed on Oct. 2, 2015.

(51) Int. Cl.
| | |
|---|---|
| *A61K 39/00* | (2006.01) |
| *A61K 39/12* | (2006.01) |
| *A61K 39/395* | (2006.01) |
| *A61K 45/06* | (2006.01) |
| *C07K 16/28* | (2006.01) |
| *C07K 14/73* | (2006.01) |
| *C07K 14/715* | (2006.01) |
| *C07K 14/005* | (2006.01) |
| *C12N 7/00* | (2006.01) |
| *A61P 31/18* | (2006.01) |

(52) U.S. Cl.
CPC .............. *A61K 39/12* (2013.01); *A61P 31/18* (2018.01); *C07K 14/005* (2013.01); *C07K 14/70514* (2013.01); *C07K 14/7158* (2013.01); *C12N 7/00* (2013.01); *A61K 2039/5254* (2013.01); *A61K 2039/5256* (2013.01); *A61K 2039/542* (2013.01); *A61K 2039/543* (2013.01); *A61K 2039/575* (2013.01); *A61K 2039/58* (2013.01); *C07K 2319/03* (2013.01); *C12N 2740/15022* (2013.01); *C12N 2740/15034* (2013.01); *C12N 2740/15071* (2013.01); *C12N 2740/16122* (2013.01); *C12N 2740/16134* (2013.01); *C12N 2740/16171* (2013.01); *C12N 2760/20222* (2013.01); *C12N 2760/20243* (2013.01); *C12N 2810/6054* (2013.01); *C12N 2810/6081* (2013.01)

(58) Field of Classification Search
CPC .. A61K 2039/505; A61K 45/06; A61K 39/12; A61K 39/3955; C07K 2317/21
See application file for complete search history.

(56) References Cited

U.S. PATENT DOCUMENTS

| | | | | |
|---|---|---|---|---|
| 8,486,420 B2 * | 7/2013 | Johnston | A61K 39/21 | 424/208.1 |
| 2013/0095556 A1 | 4/2013 | Parks et al. | | |
| 2013/0266611 A1 * | 10/2013 | Rabinovich | A61K 39/21 | 424/208.1 |

FOREIGN PATENT DOCUMENTS

| | | |
|---|---|---|
| EP | 2568289 A2 | 3/2013 |
| EP | 2 586 461 | 5/2013 |
| EP | 2 644 701 | 10/2013 |
| EP | 2 676 676 | 12/2013 |
| WO | 2005/098009 | 10/2005 |
| WO | 2010/096678 | 8/2010 |

OTHER PUBLICATIONS

European Search Report dated Feb. 28, 2017, which issued during prosecution of European Application No. 16002117.6.
Clarke, et al. "Neurovirulence and Immunogenicity of Attenuated Recombinant Vesicular Stomatitis Viruses in Nonhuman Primates" Journal of Virology, Jun. 2014, 88(12):6690-6701.
Lorenz, et al. "The Stem of Vesicular Stomatitis Virus G Can Be Replaced With the HIV-1 Env Membrane-Proximal External Region Without Loss of G Function or Membrane-Proximal External Region Antigenic Properties" AIDS Research and Human Retroviruses, Nov. 2014, 30(11):1130-1144.
Parks. "Development of Live VSV Vectors for Delivery of AIDS Vaccines" Conference Abstracts, 14th International NegativeStrand Virus Meeting, Jan. 2010, Bruges, Belgium.
Parks, et al. "Development of replication-competent viral vectors for HIV vaccine delivery" Current Opinion in HIV and AIDS, Sep. 2013, 8(5):402-411.
Parks, et al. "Development of VSV Vectors for Delivery of ENV Immunogens" Conference Abstracts, AIDS Vaccine, Oct. 2010, Atlanta, Georgia.
Parks, et al. "Viral vector delivery of Env trimer immunogens" Retrovirology, Sep. 2012, 9(Suppl 2):341.
Wright, et al. "Optimizing expression of functional HIV envelopes in rVSV-ΔG vaccine vectors", Retrovirology, Sep. 2012, 9(Suppl 2):342.
Stefan H. Stricker, et al. P-GAP-43 Is Enriched in Horizontal Cell Divisions Throughout Rat Cortical Development, Cerebral Cortex (2006) vol. 16, p. 1121-1131.

Simon Hoffengerg, et al., Identification of an HIV-1 Clade A Envelope that Exhibits Broad Antigenicity and Neutralization Sensitivity and Elicits Antibodies Targeting Three Distinct Epitopes, Journal of Virology (May 2013) vol. 87, No. 10, p. 5372-5383.

(Continued)

*Primary Examiner* — Barry A Chestnut

(74) *Attorney, Agent, or Firm* — Duane Morris LLP; Thomas J. Kowalski; Deborah L. Lu

(57) ABSTRACT

The present relation relates to a transgenic Vero cell line expressing CD4 and CCR5. The present invention encompasses the preparation and purification of immunogenic compositions which are formulated into the vaccines of the present invention.

11 Claims, 42 Drawing Sheets

Specification includes a Sequence Listing.

(56) References Cited

OTHER PUBLICATIONS

Ulla Wewer, et al., Human Laminin Isoalted in a Nearly Intact, Biologically Active Form from Placenta by Limited Proteolysis, The Journal of Biological Chemistry (1983) vol. 258, No. 20, p. 12654-12660.

Communication pursuant to Article 94(3) EPC dated Jul. 4, 2018, in EP Application No. 16002117.6.

* cited by examiner

▲ Vaccination
△ SHIV Challenge

FIG. 9

Recombinant VSVΔG-Env.BG505 pre-Master Virus Seed (preMVS)

Plasmids required for recombinant VSVΔG-Env.BG505 rescue prepared using animal-product free conditions

↓

Recombinant VSVΔG-Env.BG505 rescue by electroporation of VeroCD4/CCR5 cells ⎤
⎥
↓ ⎥
⎥
Expansion of rescued virus in VeroCD4/CCR5 cell monolayers ⎥
⎥ VeroCD4/CCR5 cells
↓ ⎥
⎥
Verify Env expression and Env gene sequence ⎥
⎥
↓ ⎥
⎥
Three rounds of clonal isolation by limiting dilution or plaque isolation ⎥
⎥
↓ ⎥
⎥
Expand clonal isolates and verify Env expression, Env insert integrity, and genomic sequence ⎥
⎥
↓ ⎥
⎥
Select clonal isolate and amplify preMVS ⎥
⎥
↓ ⎥
⎥
Confirm Env expression, Env insert integrity, and genomic sequence of preMVS ⎥
⎥
↓ ⎥
⎥
Mock manufacturing amplification of preMVS and confirm Env expression, gene insert integrity, gene insert sequence ⎦

↓

Confirm preMVS sterility and lack of mycoplasma contamination

FIG. 12

Preparation of VSVΔG-Env.BG505 with G pseudotype

Electroporate VeroCD4/CCR5 cells with solution containing pDNA-G and VSVΔG-Env.BG505 particles G supplied in trans Culture 48-72 hours Harvest medium supernatant VSVΔG-Env.BG505 seed virus — Env VSVΔG-Env.BG505 with G pseudotype — Env + G

1. VERT3 P1
2. VERT3 P2
3. VERT3 P3
4. (+) control
5. Vero cells (-) control

| Sample | Copies | | Number of |
|---|---|---|---|
| | CD4 | B-Glo | CD4 Copies per Cell |
| VERT3 P1 | 1.71E+04 | 1.65E+04 | 2.08 |
| VERT3 P2 | 1.78E+04 | 1.70E+04 | 2.10 |
| VERT3 P3 | 2.22E+04 | 2.34E+04 | 1.90 |

Sera wk 48
VSVΔGps-Env.BG505

11 12 13 14 15 16 17 18 19 20

160 -
120 -

Clade A
BG505

Clade B
SF162p3

Clade C
CH505.w100

SEQUENCE LISTING

```
<160> NUMBER OF SEQ ID NOS: 8

<210> SEQ ID NO 1
<211> LENGTH: 14258
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (3198)..(5354)

<400> SEQUENCE: 1
aaattaatac gactcactat agggagacca caacggtttc cctctagcgt tgtcttcgtc      60
tgatgagtcc gtgaggacga aactatagga aaggaattcc tatagtcacg aagacaaaca    120
aaccattatt atcattaaaa ggctcaggag aaactttaac agtaatcaaa atgtctgtta    180
cagtcaagag aatcattgac aacacagtca tagttccaaa acttcctgca aatgaggatc    240
cagtggaata cccggcagat tacttcagaa aatcaaagga gattcctctt tacatcaata    300
ctacaaaaag tttgtcagat ctaagaggat atgtctacca aggcctcaaa tccggaaatg    360
tatcaatcat acatgtcaac agctacttgt atggagcatt gaaggacatc cggggtaagt    420
tggataaaga ttggtcaagt ttcggaataa acatcggaa ggcaggggat acaatcggaa    480
tatttgacct tgtatccttg aaagccctgg acggtgtact tccagatgga gtatcggatg    540
cttccagaac cagcgcagat gacaaatggt tgcctttgta tctacttggc ttatacagag    600
tgggcagaac acaaatgcct gaatacagaa aaaggctcat ggatgggctg acaaatcaat    660
gcaaaatgat caatgaacag tttgaacctc ttgtgccaga aggtcgtgac atttttgatg    720
tgtggggaaa tgacagtaat tacacaaaaa ttgtcgctgc agtggacatg ttcttccaca    780
tgttcaaaaa acatgaatgt gcctcgttca gatacgaac tattgtttcc agattcaaag    840
attgtgctgc attggcaaca tttggacacc tctgcaaaat aaccggaatg tctacagaag    900
atgtgacgac ctggatcttg aaccgagaag ttgcagatga gatggtccaa atgatgcttc    960
caggccaaga aattgacaag gctgattcat acatgcctta tttgatcgac tttggattgt   1020
cttctaagtc tccatattct tccgtcaaaa accctgcctt ccacttctgg gggcaattga   1080
cagctcttct gctcagatcc accagagcaa ggaatgcccg acagcctgat gacattgagt   1140
atacatctct tactacagca ggtttgttgt acgcttatgc agtaggatcc tctgctgact   1200
tggcacaaca gttttgtgtt ggagatagca aatacactcc agatgatagt accggaggat   1260
tgacgactaa tgcaccgcca caaggcagag atgtggtcga atggctcgga tggtttgaag   1320
atcaaaacag aaaaccgact cctgatatga tgcagtatgc gaaacgagca gtcatgtcac   1380
tgcaaggcct aagagagaag acaattggca gtatgctaa gtcagagttt gacaaatgac   1440
cctataattc tcagatcacc tattatatat atgctagct atgaaaaaaa ctaacagata   1500
tcatggataa tctcacaaaa gttcgtgagt atctcaagtc ctattctcgt ctagatcagg   1560
```

```
cggtaggaga gatagatgag atcgaagcac aacgagctga aaagtccaat tatgagttgt    1620
tccaagagga cggagtggaa gagcatacta ggccctctta ttttcaggca gcagatgatt    1680
ctgacacaga atctgaacca gaaattgaag acaatcaagg cttgtatgta ccagatccgg    1740
aagctgagca agttgaaggc tttatacagg ggcctttaga tgactatgca gatgaggacg    1800
tggatgttgt attcacttcg gactggaaac agcctgagct tgaatccgac gagcatggaa    1860
agaccttacg gttgacattg ccagagggtt taagtggaga gcagaaatcc cagtggcttt    1920
tgacgattaa agcagtcgtt caaagtgcca acactggaa tctggcagag tgcacatttg     1980
aagcatcggg agaaggggtc atcataaaaa agcgccagat aactccggat gtatataagg    2040
tcactccagt gatgaacaca catccgtccc aatcagaagc cgtatcagat gtttggtctc    2100
tctcaaagac atccatgact ttccaaccca agaaagcaag tcttcagcct ctcaccatat    2160
ccttggatga attgttctca tctagaggag aattcatctc tgtcggaggt aacggacgaa    2220
tgtctcataa agaggccatc ctgctcggtc tgaggtacaa aaagttgtac aatcaggcga    2280
gagtcaaata ttctctgtag actagtatga aaaaaagtaa cagatatcac aatctaagtg    2340
ttatcccaat ccattcatca tgagttcctt aaagaagatt ctcggtctga aggggaaagg    2400
taagaaatct aagaaattag ggatcgcacc accccttat gaagaggaca ctaacatgga     2460
gtatgctccg agcgctccaa ttgacaaatc ctattttgga gttgacgaga tggacactca    2520
tgatccgaat caattaagat atgagaaatt cttctttaca gtgaaaatga cggttagatc    2580
taatcgtccg ttcagaacat actcagatgt ggcagccgct gtatcccatt gggatcacat    2640
gtacatcgga atggcaggga acgtcccctt ctacaagatc ttggcttttt tgggttcttc    2700
taatctaaag gccactccag cggtattggc agatcaaggt caaccagagt atcatgctca    2760
ctgtgaaggc agggcttatt tgccacacag aatggggaag acccctccca tgctcaatgt    2820
accagagcac ttcagaagac cattcaatat aggtctttac aagggaacga ttgagctcac    2880
aatgaccatc tacgatgatg agtcactgga agcagctcct atgatctggg atcatttcaa    2940
ttcttccaaa ttttctgatt tcagagagaa ggccttaatg tttggcctga ttgtcgagaa    3000
aaaggcatct ggagcttggg tcctggattc tgtcagccac ttcaaatgag ctagtctagc    3060
ttccagcttc tgaacaatcc ccggtttact cagtctctcc taattccagc cttcgaaca    3120 actaatatcc tgtcttctct atccctatga aaaaaactaa cagagatcga tctgtttcct    3180
tgacaccagg agccacc atg aag tgc ctt ttg tac tta gct ttt tta ttc     3230
                    Met Lys Cys Leu Leu Tyr Leu Ala Phe Leu Phe
                     1               5                   10 atc ggg gtg aat tgc aag gct agc gca gag aat ttg tgg gta aca gtc     3278
Ile Gly Val Asn Cys Lys Ala Ser Ala Glu Asn Leu Trp Val Thr Val
                15                  20                  25 tac tat gga gtc cct gta tgg aag gat gca gag aca aca ttg ttc tgt     3326
Tyr Tyr Gly Val Pro Val Trp Lys Asp Ala Glu Thr Thr Leu Phe Cys
            30                  35                  40 gct agt gac gca aag gct tac gag acg gag aag cac aat gtg tgg gca     3374
Ala Ser Asp Ala Lys Ala Tyr Glu Thr Glu Lys His Asn Val Trp Ala
        45                  50                  55 act cac gca tgt gtc cca acc gat cca aat cct caa gag att cat cta     3422
Thr His Ala Cys Val Pro Thr Asp Pro Asn Pro Gln Glu Ile His Leu
 60                  65                  70                  75 gag aat gtg act gaa gaa ttc aat atg tgg aag aat aat atg gta gag    3470
Glu Asn Val Thr Glu Glu Phe Asn Met Trp Lys Asn Asn Met Val Glu
                80                  85                  90 caa atg cat aca gat atc att agt tta tgg gac cag tca ctt aaa ccc    3518
```

-continued

```
            Gln Met His Thr Asp Ile Ile Ser Leu Trp Asp Gln Ser Leu Lys Pro
                         95                  100                 105 tgc gtt aaa ttg acg cct cta tgt gtg aca ctt caa tgt act aat gtt       3566
Cys Val Lys Leu Thr Pro Leu Cys Val Thr Leu Gln Cys Thr Asn Val
            110                 115                 120 aca aac aac ata aca gat gat atg aga gga gaa ctg aag aac tgt agt       3614
Thr Asn Asn Ile Thr Asp Asp Met Arg Gly Glu Leu Lys Asn Cys Ser
125                 130                 135 ttc aac atg acg aca gag ttg cgt gac aag aaa cag aaa gtg tat tca       3662
Phe Asn Met Thr Thr Glu Leu Arg Asp Lys Lys Gln Lys Val Tyr Ser
140                 145                 150                 155 cta ttc tat cgg ttg gat gta gta cag ata aat gag aat caa gga aac       3710
Leu Phe Tyr Arg Leu Asp Val Val Gln Ile Asn Glu Asn Gln Gly Asn
                160                 165                 170 agg tcc aac aac tct aac aaa gag tac aga ctt att aat tgc aat acc       3758
Arg Ser Asn Asn Ser Asn Lys Glu Tyr Arg Leu Ile Asn Cys Asn Thr
            175                 180                 185 agt gct atc acg caa gcc tgc cca aag gtt tca ttt gaa cca ata cct       3806
Ser Ala Ile Thr Gln Ala Cys Pro Lys Val Ser Phe Glu Pro Ile Pro
        190                 195                 200 att cat tat tgt gca cct gct gga ttc gcc atc ctc aaa tgt aaa gac       3854
Ile His Tyr Cys Ala Pro Ala Gly Phe Ala Ile Leu Lys Cys Lys Asp
205                 210                 215 aag aag ttc aat gga aca gga ccc tgc cca tca gtt tca acc gtt cag       3902
Lys Lys Phe Asn Gly Thr Gly Pro Cys Pro Ser Val Ser Thr Val Gln
220                 225                 230                 235 tgc acc cac gga atc aag cct gta gtt agt act caa tta ttg tta aat       3950
Cys Thr His Gly Ile Lys Pro Val Val Ser Thr Gln Leu Leu Leu Asn
                240                 245                 250 ggg agc tta gct gaa gaa gaa gtt atg att aga tca gag aat att acc       3998
Gly Ser Leu Ala Glu Glu Glu Val Met Ile Arg Ser Glu Asn Ile Thr
            255                 260                 265 aat aat gcg aag aac atc ttg gtt caa ttc aat act cca gtc cag atc       4046
Asn Asn Ala Lys Asn Ile Leu Val Gln Phe Asn Thr Pro Val Gln Ile
        270                 275                 280 aat tgc aca agg cct aat aat aat acc aga aag agt ata aga att ggg       4094
Asn Cys Thr Arg Pro Asn Asn Asn Thr Arg Lys Ser Ile Arg Ile Gly
285                 290                 295 cca gga cag gca ttc tat gca aca gga gat ata atc gga gac att cga       4142
Pro Gly Gln Ala Phe Tyr Ala Thr Gly Asp Ile Ile Gly Asp Ile Arg
300                 305                 310                 315 caa gcg cac tgc act gtt tct aag gcc act tgg aat gaa aca ttg ggt       4190
Gln Ala His Cys Thr Val Ser Lys Ala Thr Trp Asn Glu Thr Leu Gly
                320                 325                 330 aaa gtt gta aag caa ctt cgg aag cat ttc gga aat aac aca att att       4238
Lys Val Val Lys Gln Leu Arg Lys His Phe Gly Asn Asn Thr Ile Ile
            335                 340                 345 aga ttt gcg aac tca tct gga ggg gat ctg gaa gtg aca aca cac tct       4286
Arg Phe Ala Asn Ser Ser Gly Gly Asp Leu Glu Val Thr Thr His Ser
        350                 355                 360 ttc aat tgc ggt ggc gag ttc ttc tat tgt aat aca agt gga tta ttt       4334
Phe Asn Cys Gly Gly Glu Phe Phe Tyr Cys Asn Thr Ser Gly Leu Phe
365                 370                 375 aac tct act tgg att tca aat acc tca gtc caa gga tct aat tca aca       4382
Asn Ser Thr Trp Ile Ser Asn Thr Ser Val Gln Gly Ser Asn Ser Thr
380                 385                 390                 395 ggg tct aac gat tct ata aca tta cct tgc cgt ata aag caa att att       4430
Gly Ser Asn Asp Ser Ile Thr Leu Pro Cys Arg Ile Lys Gln Ile Ile
                400                 405                 410
```

```
aat atg tgg caa aga atc ggg caa gcg atg tat gct cca cct att caa    4478
Asn Met Trp Gln Arg Ile Gly Gln Ala Met Tyr Ala Pro Pro Ile Gln
        415                 420                 425 ggc gtg att cgt tgc gtt tca aac ata aca ggg ttg atc ctg acc agg    4526
Gly Val Ile Arg Cys Val Ser Asn Ile Thr Gly Leu Ile Leu Thr Arg
            430                 435                 440 gat gga ggc tct acc aat tcc acc acc gag acc ttc cgt ccc ggt ggc    4574
Asp Gly Gly Ser Thr Asn Ser Thr Thr Glu Thr Phe Arg Pro Gly Gly
                445                 450                 455 gga gat atg cgg gat aac tgg aga tca gag ctc tat aag tat aag gtt    4622
Gly Asp Met Arg Asp Asn Trp Arg Ser Glu Leu Tyr Lys Tyr Lys Val
460                 465                 470                 475 gtg aag att gaa cct ctt gga gtt gcc cct aca aga gca aag aga agg    4670
Val Lys Ile Glu Pro Leu Gly Val Ala Pro Thr Arg Ala Lys Arg Arg
                480                 485                 490 gtg gtt ggc cga gag aag aga gca gtt ggc atc ggt gct gtc ttt ctc    4718
Val Val Gly Arg Glu Lys Arg Ala Val Gly Ile Gly Ala Val Phe Leu
                    495                 500                 505 gga ttt ctt gga gca gct gga tcc act atg gga gca gca tca atg aca    4766
Gly Phe Leu Gly Ala Ala Gly Ser Thr Met Gly Ala Ala Ser Met Thr
            510                 515                 520 cta aca gtg cag gct aga aat ttg ctt agc gga atc gtt cag cag cag    4814
Leu Thr Val Gln Ala Arg Asn Leu Leu Ser Gly Ile Val Gln Gln Gln
525                 530                 535 agc aat tta cta aga gca att gaa gca cag caa cat ctc tta aag ttg    4862
Ser Asn Leu Leu Arg Ala Ile Glu Ala Gln Gln His Leu Leu Lys Leu
540                 545                 550                 555 acg gtg tgg ggc att aaa caa cta caa gcg aga gtg ctt gcc gtc gaa    4910
Thr Val Trp Gly Ile Lys Gln Leu Gln Ala Arg Val Leu Ala Val Glu
                560                 565                 570 aga tat ttg cga gac caa cag cta ttg ggt att tgg ggt tgt tct ggg    4958
Arg Tyr Leu Arg Asp Gln Gln Leu Leu Gly Ile Trp Gly Cys Ser Gly
            575                 580                 585 aaa tta att tgc aca aca aat gtt cca tgg aac tcc tcc tgg agt aat    5006
Lys Leu Ile Cys Thr Thr Asn Val Pro Trp Asn Ser Ser Trp Ser Asn
        590                 595                 600 agg aat tta agt gag ata tgg gac aac atg aca tgg ttg cag tgg gac    5054
Arg Asn Leu Ser Glu Ile Trp Asp Asn Met Thr Trp Leu Gln Trp Asp
605                 610                 615 aag gaa atc tca aat tat aca cag ata atc tat gga tta tta gaa gag    5102
Lys Glu Ile Ser Asn Tyr Thr Gln Ile Ile Tyr Gly Leu Leu Glu Glu
620                 625                 630                 635 tct cag aat cag caa gag aag aat gaa cag gat ttg ctt gca ttg gat    5150
Ser Gln Asn Gln Gln Glu Lys Asn Glu Gln Asp Leu Leu Ala Leu Asp
                640                 645                 650 aag tgg gct tct cta tgg aac tgg ttc gat att agt aat tgg ctc tgg    5198
Lys Trp Ala Ser Leu Trp Asn Trp Phe Asp Ile Ser Asn Trp Leu Trp
            655                 660                 665 tat att aag agc tct att gcc tct ttt ttc ttt atc ata ggg tta atc    5246
Tyr Ile Lys Ser Ser Ile Ala Ser Phe Phe Phe Ile Ile Gly Leu Ile
        670                 675                 680 att gga cta ttc ttg gtt ctc cga gtt ggt att tat ctt tgc att aaa    5294
Ile Gly Leu Phe Leu Val Leu Arg Val Gly Ile Tyr Leu Cys Ile Lys
685                 690                 695 tta aag cac acc aag aaa aga cag att tat aca gac ata gag atg aac    5342
Leu Lys His Thr Lys Lys Arg Gln Ile Tyr Thr Asp Ile Glu Met Asn
700                 705                 710                 715 cga ctt gga aag taaagctcaa atcctgcaca acagattctt catgtttgaa       5394
Arg Leu Gly Lys
```

```
ccaaatcaac ttgtgatatc atgctcaaag aggccttaat taaattttaa ttttttaattt      5454
ttatgaaaaa aactaacagc aatcatggaa gtccacgatt ttgagaccga cgagttcaat      5514
gatttcaatg aagatgacta tgccacaaga gaattcctga atcccgatga gcgcatgacg      5574
tacttgaatc atgctgatta caatttgaat tctcctctaa ttagtgatga tattgacaat      5634
ttgatcagga aattcaattc tcttccgatt ccctcgatgt gggatagtaa gaactgggat      5694
ggagttcttg agatgttaac atcatgtcaa gccaatccca tctcaacatc tcagatgcat      5754
aaatggatgg gaagttggtt aatgtctgat aatcatgatg ccagtcaagg gtatagttttt     5814
ttacatgaag tggacaaaga ggcagaaata acatttgacg tggtggagac cttcatccgc      5874
ggctggggca acaaaccaat tgaatacatc aaaaaggaaa gatggactga ctcattcaaa      5934
attctcgctt atttgtgtca aaagttttg gacttacaca agttgacatt aatcttaaat       5994
gctgtctctg aggtggaatt gctcaacttg gcgaggactt tcaaaggcaa agtcagaaga      6054
agttctcatg gaacgaacat atgcaggctt agggttccca gcttgggtcc tacttttatt      6114
tcagaaggat gggcttactt caagaaactt gatattctaa tggaccgaaa cttctctgtta    6174
atggtcaaag atgtgattat agggaggatg caaacggtgc tatccatggt atgtagaata     6234
gacaacctgt tctcagagca agacatcttc tcccttctaa atatctacag aattggagat    6294
aaaattgtgg agaggcaggg aaatttttct tatgacttga ttaaaatggt ggaaccgata     6354
tgcaacttga agctgatgaa attagcaaga gaatcaaggc ctttagtccc acaattccct    6414
cattttgaaa atcatatcaa gacttctgtt gatgaagggg caaaaattga ccgaggtata    6474
agattcctcc atgatcagat aatgagtgtg aaaacagtgg atctcacact ggtgatttat    6534
ggatcgttca gacattgggg tcatcctttt atagattatt acgctggact agaaaaatta    6594
cattcccaag taaccatgaa gaaagatatt gatgtgtcat atgcaaaagc acttgcaagt    6654
gatttagctc ggattgttct atttcaacag ttcaatgatc ataaaagtg gttcgtgaat      6714
ggagacttgc tccctcatga tcatccctt aaaagtcatg ttaaagaaaa tacatggcct      6774
acagctgctc aagttcaaga ttttggagat aaatggcatg aacttccgct gattaaatgt    6834
tttgaaatac ccgacttact agacccatcg ataatatact ctgacaaaag tcattcaatg    6894
aataggtcag aggtgttgaa acatgtccga atgaatccga acactcctat ccctagtaaa    6954
aaggtgttgc agactatgtt ggacacaaag gctaccaatt ggaaagaatt tcttaaagag    7014
attgatgaga agggcttaga tgatgatgat ctaattattg gtcttaaagg aaaggagagg    7074
gaactgaagt tggcaggtag attttttctcc ctaatgtctt ggaaattgcg agaatacttt    7134
gtaattaccg aatatttgat aaagactcat ttcgtcccta tgtttaaagg cctgacaatg   7194
gcggacgatc taactgcagt cattaaaaag atgttagatt cctcatccgg ccaaggattg    7254
aagtcatatg aggcaatttg catagccaat cacattgatt acgaaaaatg gaataaccac    7314
caaaggaagt tatcaaacgg cccagtgttc cgagttatgg gccagttctt aggttatcca    7374
tccttaatcg agagaactca tgaattttt gagaaaagtc ttatatacta caatggaaga     7434
ccagacttga tgcgtgttca caacaacaca ctgatcaatt caacctccca acgagtttgt    7494
tggcaaggac aagagggtgg actggaaggt ctacggcaaa aaggatggag tatcctcaat    7554
ctactggtta ttcaaagaga ggctaaaatc agaaacactg ctgtcaaagt cttggcacaa    7614
ggtgataatc aagttatttg cacacagtat aaaacgaaga atcgagaaa cgttgtagaa     7674
ttacagggtg ctctcaatca aatggtttct aataatgaga aaattatgac tgcaatcaaa    7734
ataggggacag ggaagttagg acttttgata aatgacgatg agactatgca atctgcagat    7794
```

```
tacttgaatt atggaaaaat accgattttc cgtggagtga ttagagggtt agagaccaag    7854
agatggtcac gagtgacttg tgtcaccaat gaccaaatac ccacttgtgc taatataatg    7914
agctcagttt ccacaaatgc tctcaccgta gctcattttg ctgagaaccc aatcaatgcc    7974
atgatacagt acaattattt tgggacattt gctagactct tgttgatgat gcatgatcct    8034
gctcttcgtc aatcattgta tgaagttcaa gataagatac cgggcttgca cagttctact    8094
ttcaaatacg ccatgttgta tttgacccct tccattggag gagtgtcggg catgtctttg    8154
tccaggtttt tgattagagc cttcccagat cccgtaacag aaagtctctc attctggaga    8214
ttcatccatg tacatgctcg aagtgagcat ctgaaggaga tgagtgcagt atttggaaac    8274
cccgagatag ccaagttccg aataactcac atagacaagc tagtagaaga tccaacctct    8334
ctgaacatcg ctatgggaat gagtccagcg aacttgttaa agactgaggt taaaaaatgc    8394
ttaatcgaat caagacaaac catcaggaac caggtgatta aggatgcaac catatatttg    8454
tatcatgaag aggatcggct cagaagtttc ttatggtcaa taaatcctct gttccctaga    8514
tttttaagtg aattcaaatc aggcactttt tgggagtcg cagacgggct catcagtcta    8574
tttcaaaatt ctcgtactat tcggaactcc tttaagaaaa agtatcatag ggaattggat    8634
gatttgattg tgaggagtga ggtatcctct ttgacacatt tagggaaact tcatttgaga    8694
aggggatcat gtaaaatgtg gacatgttca gctactcatg ctgacacatt aagatacaaa    8754
tcctggggcc gtacagttat tgggacaact gtacccatc cattagaaat gttgggtcca    8814
caacatcgaa aagagactcc ttgtgcacca tgtaacacat cagggttcaa ttatgtttct    8874
gtgcattgtc cagacgggat ccatgacgtc tttagttcac ggggaccatt gcctgcttat    8934
ctagggtcta aaacatctga atctacatct attttgcagc cttgggaaag ggaaagcaaa    8994
gtcccactga ttaaaagagc tacacgtctt agagatgcta tctcttggtt tgttgaaccc    9054
gactctaaac tagcaatgac tatactttct aacatccact cttaacagg cgaagaatgg    9114 accaaaaggc agcatgggtt caaaagaaca gggtctgccc ttcataggtt ttcgacatct    9174
cggatgagcc atggtgggtt cgcatctcag agcactgcag cattgaccag gttgatggca    9234
actacagaca ccatgaggga tctgggagat cagaatttcg actttttatt ccaagcaacg    9294
ttgctctatg ctcaaattac caccactgtt gcaagagacg gatggatcac cagttgtaca    9354
gatcattatc atattgcctg taagtcctgt ttgagaccca tagaagagat caccctggac    9414
tcaagtatgg actacacgcc cccagatgta tcccatgtgc tgaagacatg gaggaatggg    9474
gaaggttcgt ggggacaaga gataaaacag atctatcctt tagaagggaa ttggaagaat    9534
ttagcacctg ctgagcaatc ctatcaagtc ggcagatgta taggttttct atatggagac    9594
ttggcgtata gaaaatctac tcatgccgag gacagttctc tatttcctct atctatacaa    9654
ggtcgtatta gaggtcgagg tttcttaaaa gggttgctag acggattaat gagagcaagt    9714
tgctgccaag taatacaccg gagaagtctg gctcatttga gaggccggc caacgcagtg    9774 tacggaggtt tgatttactt gattgataaa ttgagtgtat cacctccatt cctttctctt    9834
actagatcag gacctattag agacgaatta gaaacgattc cccacaagat cccaaccctcc    9894 tatccgacaa gcaaccgtga tatggggtg attgtcagaa attacttcaa ataccaatgc    9954
cgtctaattg aaaagggaaa atacagatca cattattcac aattatggtt attctcagat   10014
gtcttatcca tagacttcat tggaccattc tctatttcca ccaccctctt gcaaatccta   10074
tacaagccat tttatctggg gaaagataag aatgagttga gagagctggc aaatctttct   10134
```

```
tcattgctaa gatcaggaga ggggtgggaa gacatacatg tgaaattctt caccaaggac   10194
atattattgt gtccagagga aatcagacat gcttgcaagt tcgggattgc taaggataat   10254
aataaagaca tgagctatcc cccttgggga agggaatcca gagggacaat tacaacaatc   10314
cctgtttatt atacgaccac cccttaccca aagatgctag agatgcctcc aagaatccaa   10374
aatcccctgc tgtccggaat caggttgggc caattaccaa ctggcgctca ttataaaatt   10434
cggagtatat tacatggaat gggaatccat tacagggact tcttgagttg tggagacggc   10494
tccggaggga tgactgctgc attactacga gaaaatgtgc atagcagagg aatattcaat   10554
agtctgttag aattatcagg gtcagtcatg cgaggcgcct ctcctgagcc ccccagtgcc   10614
ctagaaactt taggaggaga taaatcgaga tgtgtaaatg gtgaaacatg ttgggaatat   10674
ccatctgact tatgtgaccc aaggacttgg gactatttcc tccgactcaa agcaggcttg   10734
gggcttcaaa ttgatttaat tgtaatggat atggaagttc gggattcttc tactagcctg   10794
aaaattgaga cgaatgttag aaattatgtg caccggattt tggatgagca aggagtttta   10854
atctacaaga cttatggaac atatatttgt gagagcgaaa agaatgcagt aacaatcctt   10914
ggtcccatgt tcaagacggt cgacttagtt caaacagaat ttagtagttc tcaaacgtct   10974
gaagtatata tggtatgtaa aggtttgaag aaattaatcg atgaacccaa tcccgattgg   11034
tcttccatca atgaatcctg gaaaaacctg tacgcattcc agtcatcaga acaggaattt   11094
gccagagcaa agaaggttag tacatacttt accttgacag gtattccctc ccaattcatt   11154
cctgatcctt ttgtaaacat tgagactatg ctacaaatat tcggagtacc cacgggtgtg   11214
tctcatgcgg ctgccttaaa atcatctgat agacctgcag atttattgac cattagcctt   11274
ttttatatgg cgattatatc gtattataac atcaatcata tcagagtagg accgatacct   11334
ccgaaccccc catcagatgg aattgcacaa aatgtgggga tcgctataac tggtataagc   11394
ttttggctga gtttgatgga gaaagacatt ccactatatc aacagtgttt agcagttatc   11454
cagcaatcat tcccgattag gtgggaggct gtttcagtaa aaggaggata caagcagaag   11514
tggagtacta gaggtgatgg gctcccaaaa gatacccgaa tttcagactc cttggcccca   11574
atcgggaact ggatcagatc tctggaattg gtccgaaacc aagttcgtct aaatccattc   11634
aatgagatct tgttcaatca gctatgtcgt acagtggata atcatttgaa atggtcaaat   11694
ttgcgaaaaa acacaggaat gattgaatgg atcaatagac gaatttcaaa agaagaccgg   11754
tctatactga tgttgaagag tgacctacac gaggaaaaact cttggagaga ttaaaaaatc   11814
atgaggagac tccaaacttt aagtatgaaa aaaactttga tccttaagac cctcttgtgg   11874
ttttattttt ttatctggtt ttgtggtctt cgtggccggc atggtcccag cctcctcgct   11934
ggcgccggct gggcaacatt ccgagggggac cgtcccctcg gtaatggcga atgggacctg   11994
ctaacaaagc ccgaaaggaa gctgagttgg ctgctgccac cgctgagcaa taactagcat   12054
aaccccttgg ggcctctaaa cgggtcttga ggggtttttt gctgaaagga ggaactatat   12114
ccggatgcgc ccgatccggc tgctaacaaa gcccgaaagg aagctgagtt ggctgctgcc   12174
accgctgagc aataactagc ataaccccct ggggcctcta acgggtcttg aggggttttt   12234
tgctgaaaag gaggaactat atccgggtta acctgcatta atgaatcggc caacgcgcgg   12294
ggagaggcgg tttgcgtatt gggcgctctt ccgcttcctc gctcactgac tcgctgcgct   12354
cggtcgttcg gctgcggcga gcggtatcag ctcactcaaa ggcggtaata cggttatcca   12414
cagaatcagg ggataacgca ggaaagaaca tgtgagcaaa aggccagcaa aaggccagga   12474
accgtaaaaa ggccgcgttg ctggcgtttt tccataggct ccgcccccct gacgagcatc   12534
```

```
acaaaaatcg acgctcaagt cagaggtggc gaaacccgac aggactataa agataccagg    12594
cgtttccccc tggaagctcc ctcgtgcgct ctcctgttcc gaccctgccg cttaccggat    12654
acctgtccgc ctttctccct tcgggaagcg tggcgctttc tcaatgctca cgctgtaggt    12714
atctcagttc ggtgtaggtc gttcgctcca agctgggctg tgtgcacgaa ccccccgttc    12774
agcccgaccg ctgcgcctta tccggtaact atcgtcttga gtccaacccg gtaagacacg    12834
acttatcgcc actggcagca gccactggta acaggattag cagagcgagg tatgtaggcg    12894
gtgctacaga gttcttgaag tggtggccta actacggcta cactagaagg acagtatttg    12954
gtatctgcgc tctgctgaag ccagttacct tcggaaaaag agttggtagc tcttgatccg    13014
gcaaacaaac caccgctggt agcggtggtt ttttgtttg caagcagcag attacgcgca    13074 gaaaaaagg atcctttga tcttttctac ggggtctgac gctcagtgga    13134
acgaaaactc acgttaaggg attttggtca tgagattatc aaaaaggatc ttcacctaga    13194 tcctttaaa ttaaaaatga agttttaaat caatctaaag tatatatgag taaacttggt    13254
ctgacagtta ccaatgctta atcagtgagg cacctatctc agcgatctgt ctatttcgtt    13314
catccatagt tgcctgactc cccgtcgtgt agataactac gatacgggag ggcttaccat    13374
ctggccccag tgctgcaatg ataccgcgag acccacgctc accggctcca gatttatcag    13434
caataaacca gccagccgga agggccgagc gcagaagtgg tcctgcaact ttatccgcct    13494
ccatccagtc tattaattgt tgccgggaag ctagagtaag tagttcgcca gttaatagtt    13554
tgcgcaacgt tgttgccatt gctacaggca tcgtggtgtc acgctcgtcg tttggtatgg    13614
cttcattcag ctccggttcc caacgatcaa ggcgagttac atgatccccc atgttgtgca    13674
aaaaagcggt tagctccttc ggtcctccga tcgttgtcag aagtaagttg gccgcagtgt    13734
tatcactcat ggttatggca gcactgcata attctcttac tgtcatgcca tccgtaagat    13794
gcttttctgt gactggtgag tactcaacca agtcattctg agaatagtgt atgcggcgac    13854
cgagttgctc ttgcccggcg tcaatacggg ataataccgc gccacatagc agaactttaa    13914
aagtgctcat cattggaaaa cgttcttcgg ggcgaaaact ctcaaggatc ttaccgctgt    13974
tgagatccag ttcgatgtaa cccactcgtg cacccaactg atcttcagca tcttttactt    14034
tcaccagcgt ttctgggtga gcaaaaacag gaaggcaaaa tgccgcaaaa agggaataa    14094 gggcgacacg gaaatgttga atactcatac tcttcctttt tcaatattat tgaagcattt    14154
atcagggtta ttgtctcatg agcggataca tatttgaatg tatttagaaa aataaacaaa    14214
taggggttcc gcgcacattt ccccgaaaag tgccacctga cgtc                    14258
```

<210> SEQ ID NO 2
<211> LENGTH: 719
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Lys Cys Leu Leu Tyr Leu Ala Phe Leu Phe Ile Gly Val Asn Cys
1               5                   10                  15

Lys Ala Ser Ala Glu Asn Leu Trp Val Thr Val Tyr Tyr Gly Val Pro
                20                  25                  30

Val Trp Lys Asp Ala Glu Thr Thr Leu Phe Cys Ala Ser Asp Ala Lys
        35                  40                  45

```
Ala Tyr Glu Thr Glu Lys His Asn Val Trp Ala Thr His Ala Cys Val
 50                  55                  60

Pro Thr Asp Pro Asn Pro Gln Glu Ile His Leu Glu Asn Val Thr Glu
 65                  70                  75                  80

Glu Phe Asn Met Trp Lys Asn Asn Met Val Glu Gln Met His Thr Asp
                 85                  90                  95

Ile Ile Ser Leu Trp Asp Gln Ser Leu Lys Pro Cys Val Lys Leu Thr
                100                 105                 110

Pro Leu Cys Val Thr Leu Gln Cys Thr Asn Val Thr Asn Asn Ile Thr
            115                 120                 125

Asp Asp Met Arg Gly Glu Leu Lys Asn Cys Ser Phe Asn Met Thr Thr
130                 135                 140

Glu Leu Arg Asp Lys Lys Gln Lys Val Tyr Ser Leu Phe Tyr Arg Leu
145                 150                 155                 160

Asp Val Val Gln Ile Asn Glu Asn Gln Gly Asn Arg Ser Asn Asn Ser
                165                 170                 175

Asn Lys Glu Tyr Arg Leu Ile Asn Cys Asn Thr Ser Ala Ile Thr Gln
                180                 185                 190

Ala Cys Pro Lys Val Ser Phe Glu Pro Ile Pro Ile His Tyr Cys Ala
            195                 200                 205

Pro Ala Gly Phe Ala Ile Leu Lys Cys Lys Asp Lys Lys Phe Asn Gly
210                 215                 220

Thr Gly Pro Cys Pro Ser Val Ser Thr Val Gln Cys Thr His Gly Ile
225                 230                 235                 240

Lys Pro Val Val Ser Thr Gln Leu Leu Leu Asn Gly Ser Leu Ala Glu
                245                 250                 255

Glu Glu Val Met Ile Arg Ser Glu Asn Ile Thr Asn Asn Ala Lys Asn
            260                 265                 270

Ile Leu Val Gln Phe Asn Thr Pro Val Gln Ile Asn Cys Thr Arg Pro
                275                 280                 285

Asn Asn Asn Thr Arg Lys Ser Ile Arg Ile Gly Pro Gly Gln Ala Phe
290                 295                 300

Tyr Ala Thr Gly Asp Ile Ile Gly Asp Ile Arg Gln Ala His Cys Thr
305                 310                 315                 320

Val Ser Lys Ala Thr Trp Asn Glu Thr Leu Gly Lys Val Val Lys Gln
                325                 330                 335

Leu Arg Lys His Phe Gly Asn Asn Thr Ile Ile Arg Phe Ala Asn Ser
                340                 345                 350

Ser Gly Gly Asp Leu Glu Val Thr Thr His Ser Phe Asn Cys Gly Gly
            355                 360                 365

Glu Phe Phe Tyr Cys Asn Thr Ser Gly Leu Phe Asn Ser Thr Trp Ile
370                 375                 380

Ser Asn Thr Ser Val Gln Gly Ser Asn Ser Thr Gly Ser Asn Asp Ser
385                 390                 395                 400

Ile Thr Leu Pro Cys Arg Ile Lys Gln Ile Ile Asn Met Trp Gln Arg
                405                 410                 415

Ile Gly Gln Ala Met Tyr Ala Pro Pro Ile Gln Gly Val Ile Arg Cys
            420                 425                 430

Val Ser Asn Ile Thr Gly Leu Ile Leu Thr Arg Asp Gly Gly Ser Thr
                435                 440                 445

Asn Ser Thr Thr Glu Thr Phe Arg Pro Gly Gly Gly Asp Met Arg Asp
450                 455                 460

Asn Trp Arg Ser Glu Leu Tyr Lys Tyr Lys Val Val Lys Ile Glu Pro
```

```
            465                 470                 475                 480
    Leu Gly Val Ala Pro Thr Arg Ala Lys Arg Val Val Gly Arg Glu
                    485                 490                 495
    Lys Arg Ala Val Gly Ile Gly Ala Val Phe Leu Gly Phe Leu Gly Ala
                    500                 505                 510
    Ala Gly Ser Thr Met Gly Ala Ala Ser Met Thr Leu Thr Val Gln Ala
                    515                 520                 525
    Arg Asn Leu Leu Ser Gly Ile Val Gln Gln Ser Asn Leu Leu Arg
                530                 535                 540
    Ala Ile Glu Ala Gln Gln His Leu Leu Lys Leu Thr Val Trp Gly Ile
    545                 550                 555                 560
    Lys Gln Leu Gln Ala Arg Val Leu Ala Val Glu Arg Tyr Leu Arg Asp
                    565                 570                 575
    Gln Gln Leu Leu Gly Ile Trp Gly Cys Ser Gly Lys Leu Ile Cys Thr
                    580                 585                 590
    Thr Asn Val Pro Trp Asn Ser Ser Trp Ser Asn Arg Asn Leu Ser Glu
                    595                 600                 605
    Ile Trp Asp Asn Met Thr Trp Leu Gln Trp Asp Lys Glu Ile Ser Asn
                    610                 615                 620
    Tyr Thr Gln Ile Ile Tyr Gly Leu Leu Glu Glu Ser Gln Asn Gln Gln
    625                 630                 635                 640
    Glu Lys Asn Glu Gln Asp Leu Leu Ala Leu Asp Lys Trp Ala Ser Leu
                    645                 650                 655
    Trp Asn Trp Phe Asp Ile Ser Asn Trp Leu Trp Tyr Ile Lys Ser Ser
                    660                 665                 670
    Ile Ala Ser Phe Phe Phe Ile Ile Gly Leu Ile Ile Gly Leu Phe Leu
                    675                 680                 685
    Val Leu Arg Val Gly Ile Tyr Leu Cys Ile Lys Leu Lys His Thr Lys
                    690                 695                 700
    Lys Arg Gln Ile Tyr Thr Asp Ile Glu Met Asn Arg Leu Gly Lys
    705                 710                 715

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Gly Gly Gly Ser
1               5

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cactagrtgt ctctgcacta tytgttt                                        27

<210> SEQ ID NO 5
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 5
gtctgcgtca tytggtgcat                                                 20

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
cttcytcagt rtgtttca                                                   18

<210> SEQ ID NO 7
<211> LENGTH: 6415
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1888)..(4158)

<400> SEQUENCE: 7
cggatccttg gccggccaaa ctagaaaacc ctaaaatcat cttaaaataa ctaaagatta     60
accactcatt tacatatttt tatttggaag tgtttatatc agtacaagga aacaattttg    120
gagacactgg atgtcattag ttatcattag tttattataa aagagaaata tggaaattat    180
ttacatgacg aaagatttca gaacttcagt ggaatgggca gcatcatgtg cggccgctcg    240
acaggcgcgc ccccagggat gtaattacgt ccctaacccg ctaggggca gcaggcgcgc    300 ctctcgacag gcgcgccccc agggatgtaa ttacgtccct aacccgctag ggggcagcag    360
gcgcgcctct ctcaatattg gccattagcc atattattca ttggttatat agcataaatc    420
aatattggct attggccatt gcatacgttg tatctatatc ataatatgta catttatatt    480
ggctcatgtc caatatgacc gccatgttgg cattgattat tgactagtta ttaatagtaa    540
tcaattacgg ggtcattagt tcatagccca tatatggagt tccgcgttac ataacttacg    600
gtaaatggcc cgcctggctg accgcccaac gacccccgcc cattgacgtc aataatgacg    660
tatgttccca tagtaacgcc aatagggact ttccattgac gtcaatgggt ggagtattta    720
cggtaaactg cccacttggc agtacatcaa gtgtatcata tgccaagtcc gccccctatt    780
gacgtcaatg acggtaaatg gcccgcctgg cattatgccc agtacatgac cttacgggac    840
tttcctactt ggcagtacat ctacgtatta gtcatcgcta ttaccatggt gatgcggttt    900
tggcagtaca ccaatgggcg tggatagcgg tttgactcac ggggatttcc aagtctccac    960
cccattgacg tcaatgggag tttgttttgg caccaaaatc aacgggactt tccaaaatgt   1020
cgtaacaact gcgatcgccc gccccgttga cgcaaatggg cggtaggcgt ggcggccgcg   1080
gtgaaagaac taccccttcg tcccctcccg gaaatgacgc gatttgaccc ttgagccgta   1140
gggagcgcgg cattgcgatc gctccagatc tttctggaac gttctgtaac cttctcgaac   1200
gttccgtgct gttctcgaac gttctgtgtg gttctcgaac gttccggcta attctcgaac   1260
gttccgggtg attctcgaac gttcaagcga tcgcccgagc gaggcccggg aactagacta   1320
```

-continued

```
agccggccgg agagggctga gcgcgctagc acaccctgcg cgggtaggga ggggcggggc      1380
tcgcgcgcag ggtgtgcaga ttgcagggcc cgggctgacg ggaagtgggt gggagctgcc      1440
tgcacacgcg gggccgcggg gcgggagtag aggcggaggg aggggacacg ggctcattgc      1500
ggtgtgcgcc ctgcactctg tccctcactc gccgccgacg acctgtctcg ccgagcgcac      1560
gccttgccgc cgccccgcag gtaagtggaa agttaccttt taaatgagtt tgtggcctga      1620
ttttagtttt tcttagaata ataatgttgc agtcccctaa atggaatagc acattcattt      1680
cctgaataac agaagtagaa tagtgctaat gtcagagcta acatgcatc acatctttt       1740 cagaggaaat gatttgatct gtagtaggat tgggatttcc ctacatcaat atcctcacaa     1800
cttataaatg tgttacaata tttacaaatg aaagtattaa aattttgctg aaatttctct     1860
```

| | | | | | | | | | | | | | | | | |
|---|---|---|---|---|---|---|---|---|---|---|---|---|---|---|---|---|
| gtaggtctcg actcgagacc agccacc | atg | gac | tac | cag | gtc | tcc | agc | ccc | atc | | | | | | | 1914 |
| | Met | Asp | Tyr | Gln | Val | Ser | Ser | Pro | Ile | | | | | | | |
| | 1 | | | | 5 | | | | | | | | | | | |

| tac | gac | atc | aac | tac | tac | acc | agc | gag | ccc | tgc | cag | aag | atc | aac | gtg | 1962 |
|---|---|---|---|---|---|---|---|---|---|---|---|---|---|---|---|---|
| Tyr | Asp | Ile | Asn | Tyr | Tyr | Thr | Ser | Glu | Pro | Cys | Gln | Lys | Ile | Asn | Val | |
| 10 | | | | 15 | | | | | 20 | | | | | 25 | | |

| aag | cag | atc | gcc | gcc | cgc | ctg | ctg | cct | ccc | ctg | tac | tcc | ctg | gtg | ttc | 2010 |
|---|---|---|---|---|---|---|---|---|---|---|---|---|---|---|---|---|
| Lys | Gln | Ile | Ala | Ala | Arg | Leu | Leu | Pro | Pro | Leu | Tyr | Ser | Leu | Val | Phe | |
| | | 30 | | | | | | 35 | | | | | 40 | | | |

| atc | ttc | ggc | ttc | gtg | ggc | aac | atg | ctg | gtg | atc | ctg | atc | ctg | atc | aac | 2058 |
|---|---|---|---|---|---|---|---|---|---|---|---|---|---|---|---|---|
| Ile | Phe | Gly | Phe | Val | Gly | Asn | Met | Leu | Val | Ile | Leu | Ile | Leu | Ile | Asn | |
| | | 45 | | | | | 50 | | | | | 55 | | | | |

| tgc | aag | cgc | ctg | aag | agc | atg | acc | gac | atc | tac | ctg | ctg | aac | ctg | gcc | 2106 |
|---|---|---|---|---|---|---|---|---|---|---|---|---|---|---|---|---|
| Cys | Lys | Arg | Leu | Lys | Ser | Met | Thr | Asp | Ile | Tyr | Leu | Leu | Asn | Leu | Ala | |
| | 60 | | | | | 65 | | | | | 70 | | | | | |

| atc | agc | gac | ctg | ttc | ttc | ctg | ctg | acc | gtg | ccc | ttc | tgg | gcc | cac | tac | 2154 |
|---|---|---|---|---|---|---|---|---|---|---|---|---|---|---|---|---|
| Ile | Ser | Asp | Leu | Phe | Phe | Leu | Leu | Thr | Val | Pro | Phe | Trp | Ala | His | Tyr | |
| 75 | | | | | 80 | | | | | 85 | | | | | | |

| gcc | gcc | gcc | cag | tgg | gac | ttc | ggc | aac | acc | atg | tgc | cag | ctg | ctg | acc | 2202 |
|---|---|---|---|---|---|---|---|---|---|---|---|---|---|---|---|---|
| Ala | Ala | Ala | Gln | Trp | Asp | Phe | Gly | Asn | Thr | Met | Cys | Gln | Leu | Leu | Thr | |
| 90 | | | | 95 | | | | | 100 | | | | | 105 | | |

| ggc | ctg | tac | ttc | atc | ggc | ttc | ttc | agc | ggc | atc | ttc | ttc | atc | atc | ctg | 2250 |
|---|---|---|---|---|---|---|---|---|---|---|---|---|---|---|---|---|
| Gly | Leu | Tyr | Phe | Ile | Gly | Phe | Phe | Ser | Gly | Ile | Phe | Phe | Ile | Ile | Leu | |
| | | | 110 | | | | | 115 | | | | | 120 | | | |

| ctg | acc | atc | gac | cgc | tac | ctg | gcc | gtg | gtg | cac | gcc | gtg | ttc | gcc | ctg | 2298 |
|---|---|---|---|---|---|---|---|---|---|---|---|---|---|---|---|---|
| Leu | Thr | Ile | Asp | Arg | Tyr | Leu | Ala | Val | Val | His | Ala | Val | Phe | Ala | Leu | |
| | | 125 | | | | | 130 | | | | | 135 | | | | |

| aag | gcc | cgc | acc | gtg | acc | ttc | ggc | gtg | gtg | acc | agc | gtg | atc | acc | tgg | 2346 |
|---|---|---|---|---|---|---|---|---|---|---|---|---|---|---|---|---|
| Lys | Ala | Arg | Thr | Val | Thr | Phe | Gly | Val | Val | Thr | Ser | Val | Ile | Thr | Trp | |
| | 140 | | | | | 145 | | | | | 150 | | | | | |

| gtg | gtg | gcc | gtg | ttc | gcc | agc | ctg | ccc | ggc | atc | atc | ttc | acc | cgc | tcc | 2394 |
|---|---|---|---|---|---|---|---|---|---|---|---|---|---|---|---|---|
| Val | Val | Ala | Val | Phe | Ala | Ser | Leu | Pro | Gly | Ile | Ile | Phe | Thr | Arg | Ser | |
| 155 | | | | | 160 | | | | | 165 | | | | | | |

| caa | aag | gag | ggc | ctg | cac | tac | acc | tgc | agc | agc | cac | ttc | ccc | tac | tcc | 2442 |
|---|---|---|---|---|---|---|---|---|---|---|---|---|---|---|---|---|
| Gln | Lys | Glu | Gly | Leu | His | Tyr | Thr | Cys | Ser | Ser | His | Phe | Pro | Tyr | Ser | |
| 170 | | | | 175 | | | | | 180 | | | | | 185 | | |

| cag | tac | cag | ttc | tgg | aag | aac | ttc | cag | acc | ctg | aag | atc | gtg | atc | ctg | 2490 |
|---|---|---|---|---|---|---|---|---|---|---|---|---|---|---|---|---|
| Gln | Tyr | Gln | Phe | Trp | Lys | Asn | Phe | Gln | Thr | Leu | Lys | Ile | Val | Ile | Leu | |
| | | | 190 | | | | | 195 | | | | | 200 | | | |

| ggc | ctg | gtg | ctg | ccc | ctg | ctg | gtg | atg | gtg | atc | tgc | tac | agc | ggc | atc | 2538 |
|---|---|---|---|---|---|---|---|---|---|---|---|---|---|---|---|---|
| Gly | Leu | Val | Leu | Pro | Leu | Leu | Val | Met | Val | Ile | Cys | Tyr | Ser | Gly | Ile | |
| | | | 205 | | | | | 210 | | | | | 215 | | | |

| ctg | aag | acc | ctg | ctg | cgc | tgc | cgc | aac | gag | aag | aag | cgc | cac | cgc | gcc | 2586 |
|---|---|---|---|---|---|---|---|---|---|---|---|---|---|---|---|---|
| Leu | Lys | Thr | Leu | Leu | Arg | Cys | Arg | Asn | Glu | Lys | Lys | Arg | His | Arg | Ala | |
| | | 220 | | | | | 225 | | | | | 230 | | | | |

| gtg | cgc | ctg | atc | ttc | acc | atc | atg | atc | gtg | tac | ttc | ctg | ttc | tgg | gct | 2634 |
|---|---|---|---|---|---|---|---|---|---|---|---|---|---|---|---|---|

-continued

| | | |
|---|---|---|
| Val Arg Leu Ile Phe Thr Ile Met Ile Val Tyr Phe Leu Phe Trp Ala<br>235                      240                          245 | | |
| ccc tac aac atc gtg ctg ctg aac acc ttc cag gag ttc ttc ggc<br>Pro Tyr Asn Ile Val Leu Leu Leu Asn Thr Phe Gln Glu Phe Phe Gly<br>250                      255                      260                      265 | 2682 |
| ctg aac aac tgc agc agc agc aac cgc ctg gac cag gcc atg cag gtg<br>Leu Asn Asn Cys Ser Ser Ser Asn Arg Leu Asp Gln Ala Met Gln Val<br>                      270                      275                      280 | 2730 |
| acc gag acc ctg ggc atg acc cac tgc tgc atc aac ccc atc atc tac<br>Thr Glu Thr Leu Gly Met Thr His Cys Cys Ile Asn Pro Ile Ile Tyr<br>                  285                      290                      295 | 2778 |
| gcc ttc gtg ggc gag aag ttc cgc aac tac ctg cgc aag cgg cgc gag<br>Ala Phe Val Gly Glu Lys Phe Arg Asn Tyr Leu Arg Lys Arg Arg Glu<br>        300                      305                      310 | 2826 |
| ggc cgg ggc agc ctg ctg acc tgc ggc gac gtg gag gag aac ccc ggc<br>Gly Arg Gly Ser Leu Leu Thr Cys Gly Asp Val Glu Glu Asn Pro Gly<br>315                      320                      325 | 2874 |
| ccc atg aac cgc ggc gtg ccc ttc cgc cac ctg ctg ctg gtg ctg cag<br>Pro Met Asn Arg Gly Val Pro Phe Arg His Leu Leu Leu Val Leu Gln<br>330                      335                      340                      345 | 2922 |
| ctg gcc ctg ctg ccc gcc gcc acc cag ggc aag aag gtg gtg ctg ggc<br>Leu Ala Leu Leu Pro Ala Ala Thr Gln Gly Lys Lys Val Val Leu Gly<br>                  350                      355                      360 | 2970 |
| aag aag ggc gac acc gtg gag ctg acc tgc acc gcc agc cag aag aag<br>Lys Lys Gly Asp Thr Val Glu Leu Thr Cys Thr Ala Ser Gln Lys Lys<br>                365                      370                      375 | 3018 |
| agc atc cag ttc cac tgg aag aac agc aac cag atc aag atc ctg ggc<br>Ser Ile Gln Phe His Trp Lys Asn Ser Asn Gln Ile Lys Ile Leu Gly<br>        380                      385                      390 | 3066 |
| aac cag ggc agc ttc ctg acc aag gga ccc agc aag ctg aac gac cgc<br>Asn Gln Gly Ser Phe Leu Thr Lys Gly Pro Ser Lys Leu Asn Asp Arg<br>395                      400                      405 | 3114 |
| gcc gac agc cgc cgc agc ctg tgg gac cag ggc aac ttc cct ctg atc<br>Ala Asp Ser Arg Arg Ser Leu Trp Asp Gln Gly Asn Phe Pro Leu Ile<br>410                      415                      420                      425 | 3162 |
| atc aag aac ctg aag atc gag gac agc gac acc tac atc tgc gag gtg<br>Ile Lys Asn Leu Lys Ile Glu Asp Ser Asp Thr Tyr Ile Cys Glu Val<br>                      430                      435                      440 | 3210 |
| gag gac cag aag gag gag gtg cag ctg ctg gtg ttc ggc ctg acc gcc<br>Glu Asp Gln Lys Glu Glu Val Gln Leu Leu Val Phe Gly Leu Thr Ala<br>                445                      450                      455 | 3258 |
| aac agc gac acc cac ctg ctg cag ggc cag agc ctg acc ctg acc ctg<br>Asn Ser Asp Thr His Leu Leu Gln Gly Gln Ser Leu Thr Leu Thr Leu<br>        460                      465                      470 | 3306 |
| gag agc cct ccc ggc agc agc ccc agc gtg cag tgc cgc agc cca cgc<br>Glu Ser Pro Pro Gly Ser Ser Pro Ser Val Gln Cys Arg Ser Pro Arg<br>475                      480                      485 | 3354 |
| ggc aag aac atc cag ggc ggc aag acc ctg agc gtg agc cag ctg gag<br>Gly Lys Asn Ile Gln Gly Gly Lys Thr Leu Ser Val Ser Gln Leu Glu<br>490                      495                      500                      505 | 3402 |
| ctg cag gac agc ggc acc tgg acc tgc acc gtg ctg cag aac cag aag<br>Leu Gln Asp Ser Gly Thr Trp Thr Cys Thr Val Leu Gln Asn Gln Lys<br>                      510                      515                      520 | 3450 |
| aag gtg gag ttc aag atc gac atc gtg gtg ctg gcc ttc cag aag gcc<br>Lys Val Glu Phe Lys Ile Asp Ile Val Val Leu Ala Phe Gln Lys Ala<br>                525                      530                      535 | 3498 |
| agc agc atc gtg tac aag aag gag ggc gag cag gtg gag ttc agc ttc<br>Ser Ser Ile Val Tyr Lys Lys Glu Gly Glu Gln Val Glu Phe Ser Phe<br>540                      545                      550 | 3546 |

| | | |
|---|---|---|
| cct ctg gcc ttc acc gtg gag aag ctg acc ggc agc ggc gag ctg tgg<br>Pro Leu Ala Phe Thr Val Glu Lys Leu Thr Gly Ser Gly Glu Leu Trp<br>555                    560                    565 | | 3594 |
| tgg cag gcc gag cgc gcc agc agc agc aag agc tgg atc acc ttc gac<br>Trp Gln Ala Glu Arg Ala Ser Ser Ser Lys Ser Trp Ile Thr Phe Asp<br>570                    575                    580                    585 | | 3642 |
| ctg aag aac aag gag gtc tcc gtg aag cgc gtg acc cag gac ccc aag<br>Leu Lys Asn Lys Glu Val Ser Val Lys Arg Val Thr Gln Asp Pro Lys<br>                   590                    595                    600 | | 3690 |
| ctg cag atg ggc aag aag ctg ccc ctg cac ctg acc ctg cca caa gcc<br>Leu Gln Met Gly Lys Lys Leu Pro Leu His Leu Thr Leu Pro Gln Ala<br>                   605                    610                    615 | | 3738 |
| ctg ccc caa tac gcc ggc agc ggc aac ctg acc ctg gcc ctg gag gcc<br>Leu Pro Gln Tyr Ala Gly Ser Gly Asn Leu Thr Leu Ala Leu Glu Ala<br>                   620                    625                    630 | | 3786 |
| aag acc ggc aag ctg cac cag gag gtg aac ctg gtg gtg atg cgc gcc<br>Lys Thr Gly Lys Leu His Gln Glu Val Asn Leu Val Val Met Arg Ala<br>635                    640                    645 | | 3834 |
| acc cag ctg cag aag aac ctg acc tgc gag gtc tgg gga ccc acc agc<br>Thr Gln Leu Gln Lys Asn Leu Thr Cys Glu Val Trp Gly Pro Thr Ser<br>650                    655                    660                    665 | | 3882 |
| ccc aag ctg atg ctg agc ctg aag ctg gag aac aag gag gcc aag gtc<br>Pro Lys Leu Met Leu Ser Leu Lys Leu Glu Asn Lys Glu Ala Lys Val<br>                   670                    675                    680 | | 3930 |
| tcc aag cgc gag aag gcc gtg tgg gtg ctg aac ccc gag gcc ggc atg<br>Ser Lys Arg Glu Lys Ala Val Trp Val Leu Asn Pro Glu Ala Gly Met<br>                   685                    690                    695 | | 3978 |
| tgg cag tgc ctg ctg agc gac agc ggc cag gtg ctg ctg gag agc aac<br>Trp Gln Cys Leu Leu Ser Asp Ser Gly Gln Val Leu Leu Glu Ser Asn<br>700                    705                    710 | | 4026 |
| atc aaa gtc ctg ccc acc tgg agc aca ccc gtg cag ccc atg gcc ctg<br>Ile Lys Val Leu Pro Thr Trp Ser Thr Pro Val Gln Pro Met Ala Leu<br>     715                    720                    725 | | 4074 |
| atc gtg ctg ggc ggc gtg gcc ggc ctg ctg ctg ttc atc ggc ctg ggc<br>Ile Val Leu Gly Gly Val Ala Gly Leu Leu Leu Phe Ile Gly Leu Gly<br>730                    735                    740                    745 | | 4122 |
| atc ttc ttc tgc gtg cgc tgc cgc cac cgc cgg agg taggccgagc<br>Ile Phe Phe Cys Val Arg Cys Arg His Arg Arg Arg<br>                   750                    755 | | 4168 |
| gcatgaggcc gctaactcct agactagtgc tttacccttta ttaatgaact gtgacaggaa | | 4228 |
| gcccaaggca gtgttcctca ccaataactt cagagaagtc agttggagaa atgaagaaa | | 4288 |
| aaggctggct gaaaatcact ataaccatca gttactggtt tcagttgaca aaatatataa | | 4348 |
| tggtttactg ctgtcattgt ccatgcctac agataattta ttttgtattt ttgaataaaa | | 4408 |
| aacatttgta cattcctgat actgggtaca agagccatgt accagtgtac tgctttcaac | | 4468 |
| ttaaatcact gaggcatttt tactactatt ctgttaaaat caggatttta gtgcttgcca | | 4528 |
| ccaccagatg agaagttaag cagcctttct gtggagagtg agaataattg tgtacaaagt | | 4588 |
| agagaagtat ccaattatgt gacaaccttt gtgtaataaa aatttgttta aagttaataa | | 4648 |
| ttgtgttagc atttccatga ttagaagata ctgaaaattg aaagccagtt gaagggcagg | | 4708 |
| ctgcttaatt aagttggcgc gccttgcacg tagtgggcca tcgccctgat agacggtttt | | 4768 |
| tcgccctttg acgttggagt ccacgttctt taatagtgga ctcttgttcc aaactggaac | | 4828 |
| aacactcaac cctatctcgg tctattcttt tgatttataa gggattttgc cgatttcggc | | 4888 |
| ctattggtta aaaaatgagc tgatttaaca aaaatttaac gcgaatttta acaaaatatt | | 4948 |
| aacgcttaca atttcctgat gcggtatttt ctccttacgc atctgtgcgg tatttcacac | | 5008 |

-continued

```
cgcatacgcg gatctgcgca gcaccatggc ctgaaataac ctctgaaaga ggaacttggt    5068
taggtacctt ctgaggcgga agaaccagc tgtggaatgt gtgtcagtta gggtgtggaa     5128
agtccccagg ctccccagca ggcagaagta tgcaaagcat gcatctcaat tagtcagcaa    5188
ccaggtgtgg aaagtcccca ggctccccag caggcagaag tatgcaaagc atgcatctca    5248
attagtcagc aaccatagtc ccgcccctaa ctccgcccat cccgcccta actccgccca     5308 gttccgccca ttctccgccc catggctgac taatttttttt tatttatgca gaggccgagg   5368
ccgcctcggc ctctgagcta ttccagaagt agtgaggagg cttttttgga ggcctaggct    5428
tttgcaaaaa gcttgattct tctgacacaa cagtctcgaa cttaaggcta gagccaccat    5488
gattgaacaa gatggattgc acgcaggttc tccggccgct tgggtggaga ggctattcgg    5548
ctatgactgg gcacaacaga caatcggctg ctctgatgcc gccgtgttcc ggctgtcagc    5608 gcagggcgc ccggttcttt tgtcaagac cgacctgtcc ggtgccctga atgaactgca      5668
ggacgaggca gcgcggctat cgtggctggc cacgacgggc gttccttgcg cagctgtgct    5728
cgacgttgtc actgaagcgg gaagggactg gctgctattg ggcgaagtgc cggggcagga    5788
tctcctgtca tctcaccttg ctcctgccga gaaagtatcc atcatggctg atgcaatgcg    5848
gcggctgcat acgcttgatc cggctacctg cccattcgac caccaagcga acatcgcat    5908 cgagcgagca cgtactcgga tggaagccgg tcttgtcgat caggatgatc tggacgaaga    5968
gcatcagggg ctcgcgccag ccgaactgtt cgccaggctc aaggcgcgca tgcccgacgg    6028
cgaggatctc gtcgtgaccc atggcgatgc ctgcttgccg aatatcatgg tggaaaatgg    6088
ccgcttttct ggattcatcg actgtggccg gctgggtgtg gcggaccgct atcaggacat    6148
agcgttggct acccgtgata ttgctgaaga gcttggcggc gaatgggctg accgcttcct    6208
cgtgctttac ggtatcgccg ctcccgattc gcagcgcatc gccttctatc gccttcttga    6268
cgagttcttc tgagcgggac tctggggttc gaaatgaccg accaagcgac gcccaacctg    6328
ccatcacgat ggccgcaata aaatatcttt attttcatta catctgtgtg ttggtttttt    6388
gtgtgaatcg atagcgataa ggatccg                                        6415
```

<210> SEQ ID NO 8
<211> LENGTH: 757
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 8

```
Met Asp Tyr Gln Val Ser Ser Pro Ile Tyr Asp Ile Asn Tyr Tyr Thr
1               5                   10                  15

Ser Glu Pro Cys Gln Lys Ile Asn Val Lys Gln Ile Ala Ala Arg Leu
                20                  25                  30

Leu Pro Pro Leu Tyr Ser Leu Val Phe Ile Phe Gly Phe Val Gly Asn
            35                  40                  45

Met Leu Val Ile Leu Ile Leu Ile Asn Cys Lys Arg Leu Lys Ser Met
        50                  55                  60

Thr Asp Ile Tyr Leu Leu Asn Leu Ala Ile Ser Asp Leu Phe Phe Leu
65                  70                  75                  80

Leu Thr Val Pro Phe Trp Ala His Tyr Ala Ala Ala Gln Trp Asp Phe
                85                  90                  95

Gly Asn Thr Met Cys Gln Leu Leu Thr Gly Leu Tyr Phe Ile Gly Phe
```

-continued

```
                100                 105                 110
Phe Ser Gly Ile Phe Phe Ile Ile Leu Leu Thr Ile Asp Arg Tyr Leu
            115                 120                 125
Ala Val Val His Ala Val Phe Ala Leu Lys Ala Arg Thr Val Thr Phe
        130                 135                 140
Gly Val Val Thr Ser Val Ile Thr Trp Val Ala Val Phe Ala Ser
145                 150                 155                 160
Leu Pro Gly Ile Ile Phe Thr Arg Ser Gln Lys Glu Gly Leu His Tyr
                165                 170                 175
Thr Cys Ser Ser His Phe Pro Tyr Ser Gln Tyr Gln Phe Trp Lys Asn
            180                 185                 190
Phe Gln Thr Leu Lys Ile Val Ile Leu Gly Leu Val Leu Pro Leu Leu
        195                 200                 205
Val Met Val Ile Cys Tyr Ser Gly Ile Leu Lys Thr Leu Leu Arg Cys
    210                 215                 220
Arg Asn Glu Lys Lys Arg His Arg Ala Val Arg Leu Ile Phe Thr Ile
225                 230                 235                 240
Met Ile Val Tyr Phe Leu Phe Trp Ala Pro Tyr Asn Ile Val Leu Leu
                245                 250                 255
Leu Asn Thr Phe Gln Glu Phe Phe Gly Leu Asn Asn Cys Ser Ser Ser
            260                 265                 270
Asn Arg Leu Asp Gln Ala Met Gln Val Thr Glu Thr Leu Gly Met Thr
        275                 280                 285
His Cys Cys Ile Asn Pro Ile Ile Tyr Ala Phe Val Gly Glu Lys Phe
    290                 295                 300
Arg Asn Tyr Leu Arg Lys Arg Glu Gly Arg Gly Ser Leu Leu Thr
305                 310                 315                 320
Cys Gly Asp Val Glu Glu Asn Pro Gly Pro Met Asn Arg Gly Val Pro
                325                 330                 335
Phe Arg His Leu Leu Leu Val Leu Gln Leu Ala Leu Leu Pro Ala Ala
            340                 345                 350
Thr Gln Gly Lys Lys Val Val Leu Gly Lys Lys Gly Asp Thr Val Glu
        355                 360                 365
Leu Thr Cys Thr Ala Ser Gln Lys Lys Ser Ile Gln Phe His Trp Lys
    370                 375                 380
Asn Ser Asn Gln Ile Lys Ile Leu Gly Asn Gln Gly Ser Phe Leu Thr
385                 390                 395                 400
Lys Gly Pro Ser Lys Leu Asn Asp Arg Ala Asp Ser Arg Arg Ser Leu
                405                 410                 415
Trp Asp Gln Gly Asn Phe Pro Leu Ile Ile Lys Asn Leu Lys Ile Glu
            420                 425                 430
Asp Ser Asp Thr Tyr Ile Cys Glu Val Glu Asp Gln Lys Glu Glu Val
        435                 440                 445
Gln Leu Leu Val Phe Gly Leu Thr Ala Asn Ser Asp Thr His Leu Leu
    450                 455                 460
Gln Gly Gln Ser Leu Thr Leu Thr Leu Glu Ser Pro Pro Gly Ser Ser
465                 470                 475                 480
Pro Ser Val Gln Cys Arg Ser Pro Arg Gly Lys Asn Ile Gln Gly Gly
                485                 490                 495
Lys Thr Leu Ser Val Ser Gln Leu Glu Leu Gln Asp Ser Gly Thr Trp
            500                 505                 510
Thr Cys Thr Val Leu Gln Asn Gln Lys Lys Val Glu Phe Lys Ile Asp
        515                 520                 525
```

```
Ile Val Val Leu Ala Phe Gln Lys Ala Ser Ser Ile Val Tyr Lys Lys
        530             535             540

Glu Gly Glu Gln Val Glu Phe Ser Phe Pro Leu Ala Phe Thr Val Glu
545             550             555             560

Lys Leu Thr Gly Ser Gly Glu Leu Trp Trp Gln Ala Glu Arg Ala Ser
            565             570             575

Ser Ser Lys Ser Trp Ile Thr Phe Asp Leu Lys Asn Lys Glu Val Ser
            580             585             590

Val Lys Arg Val Thr Gln Asp Pro Lys Leu Gln Met Gly Lys Lys Leu
        595             600             605

Pro Leu His Leu Thr Leu Pro Gln Ala Leu Pro Gln Tyr Ala Gly Ser
        610             615             620

Gly Asn Leu Thr Leu Ala Leu Glu Ala Lys Thr Gly Lys Leu His Gln
625             630             635             640

Glu Val Asn Leu Val Val Met Arg Ala Thr Gln Leu Gln Lys Asn Leu
            645             650             655

Thr Cys Glu Val Trp Gly Pro Thr Ser Pro Lys Leu Met Leu Ser Leu
            660             665             670

Lys Leu Glu Asn Lys Glu Ala Lys Val Ser Lys Arg Glu Lys Ala Val
            675             680             685

Trp Val Leu Asn Pro Glu Ala Gly Met Trp Gln Cys Leu Leu Ser Asp
            690             695             700

Ser Gly Gln Val Leu Leu Glu Ser Asn Ile Lys Val Leu Pro Thr Trp
705             710             715             720

Ser Thr Pro Val Gln Pro Met Ala Leu Ile Val Leu Gly Gly Val Ala
            725             730             735

Gly Leu Leu Leu Phe Ile Gly Leu Gly Ile Phe Phe Cys Val Arg Cys
            740             745             750

Arg His Arg Arg Arg
            755
```

TRANSGENIC VERO-CD4/CCR5 CELL LINE

INCORPORATION BY REFERENCE

This application is a continuation-in-part application of U.S. patent application Ser. No. 15/280,710 filed Sep. 29, 2016, which claims benefit of and priority to U.S. provisional patent application Ser. No. 62/236,448 filed Oct. 2, 2015.

The foregoing applications, and all documents cited therein or during their prosecution ("appln cited documents") and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

SEQUENCE LISTING

The instant application contains a Sequence Listing which has been submitted electronically in ASCII format and is hereby incorporated by reference in its entirety. Said ASCII copy, created on May 10, 2017, is named 43094_02_2039_SL.txt and is 57,121 bytes in size.

FIELD OF THE INVENTION

The present invention relates to a transgenic Vero cell line expressing CD4 and CCR5 for use to manufacture prophylactic and therapeutic vaccines.

BACKGROUND OF THE INVENTION

AIDS, or Acquired Immunodeficiency Syndrome, is caused by human immunodeficiency virus (HIV) and is characterized by several clinical features including wasting syndromes, central nervous system degeneration and profound immunosuppression that results in opportunistic infections and malignancies. HIV is a member of the lentivirus family of animal retroviruses, which include the visna virus of sheep and the bovine, feline, and simian immunodeficiency viruses (SIV). Two closely related types of HIV, designated HIV-1 and HIV-2, have been identified thus far, of which HIV-1 is by far the most common cause of AIDS. However, HIV-2, which differs in genomic structure and antigenicity, causes a similar clinical syndrome.

An infectious HIV particle consists of two identical strands of RNA, each approximately 9.2 kb long, packaged within a core of viral proteins. This core structure is surrounded by a phospholipid bilayer envelope derived from the host cell membrane that also includes virally-encoded membrane proteins (Abbas et al., Cellular and Molecular Immunology, 4th edition, W.B. Saunders Company, 2000, p. 454). The HIV genome has the characteristic 5'-LTR-Gag-Pol-Env-LTR-3' organization of the retrovirus family. Long terminal repeats (LTRs) at each end of the viral genome serve as binding sites for transcriptional regulatory proteins from the host and regulate viral integration into the host genome, viral gene expression, and viral replication.

The HIV genome encodes several structural proteins. The gag gene encodes structural proteins of the nucleocapsid core and matrix. The pol gene encodes reverse transcriptase (RT), integrase (IN), and viral protease (PR) enzymes required for viral replication. The tat gene encodes a protein that is required for elongation of viral transcripts. The rev gene encodes a protein that promotes the nuclear export of incompletely spliced or unspliced viral RNAs. The vif gene product enhances the infectivity of viral particles. The vpr gene product promotes the nuclear import of viral DNA and regulates G2 cell cycle arrest. The vpu and nef genes encode proteins that down regulate host cell CD4 expression and enhance release of virus from infected cells. The env gene encodes the viral envelope glycoprotein that is translated as a 160-kilodalton (kDa) precursor (gp160) and cleaved by a cellular protease to yield the external 120-kDa envelope glycoprotein (gp120) and the transmembrane 41-kDa envelope glycoprotein (gp41), which are required for the infection of cells (Abbas, pp. 454-456). gp140 is a modified form of the Env glycoprotein, which contains the external 120-kDa envelope glycoprotein portion and the extracellular part of the gp41 portion of Env and has characteristics of both gp120 and gp41. The nef gene is conserved among primate lentiviruses and is one of the first viral genes that is transcribed following infection. In vitro, several functions have been described, including down-regulation of CD4 and MHC class I surface expression, altered T-cell signaling and activation, and enhanced viral infectivity.

HIV infection initiates with gp120 on the viral particle binding to the CD4 and chemokine receptor molecules (e.g., CXCR4, CCR5) on the cell membrane of target cells such as CD4+ T-cells, macrophages and dendritic cells. The bound virus fuses with the target cell and reverse transcribes the RNA genome. The resulting viral DNA integrates into the cellular genome, where it directs the production of new viral RNA, and thereby viral proteins and new virions. These virions bud from the infected cell membrane and establish productive infections in other cells. This process also kills the originally infected cell. HIV can also kill cells indirectly because the CD4 receptor on uninfected T-cells has a strong affinity for gp120 expressed on the surface of infected cells. In this case, the uninfected cells bind, via the CD4 receptor-gp120 interaction, to infected cells and fuse to form a syncytium, which cannot survive. Destruction of CD4+ T-lymphocytes, which are critical to immune defense, is a major cause of the progressive immune dysfunction that is the hallmark of AIDS disease progression. The loss of CD4+ T cells seriously impairs the body's ability to fight most invaders, but it has a particularly severe impact on the defenses against viruses, fungi, parasites and certain bacteria, including mycobacteria.

Research on the Env glycoprotein has shown that the virus has many effective protective mechanisms with few vulnerabilities (Wyatt & Sodroski, Science. 1998 Jun. 19; 280(5371):1884-8). For fusion with its target cells, HIV-1 uses a trimeric Env complex containing gp120 and gp41 subunits (Burton et al., Nat Immunol. 2004 March; 5(3): 233-6). The fusion potential of the Env complex is triggered by engagement of the CD4 receptor and a coreceptor, usually CCR5 or CXCR4. Neutralizing antibodies seem to work either by binding to the mature trimer on the virion surface and preventing initial receptor engagement events, or by binding after virion attachment and inhibiting the fusion process (Parren & Burton, Adv Immunol. 2001; 77:195-262). In the latter case, neutralizing antibodies may bind to epitopes whose exposure is enhanced or triggered by receptor binding. However, given the potential antiviral effects of neutralizing antibodies, it is not unexpected that HIV-1 has evolved multiple mechanisms to protect it from antibody binding (Johnson & Desrosiers, Annu Rev Med. 2002; 53:499-518).

There remains a need to express immunogens that elicit broadly neutralizing antibodies. Strategies include producing molecules that mimic the mature trimer on the virion surface, producing Env molecules engineered to better present neutralizing antibody epitopes than wild-type molecules, generating stable intermediates of the entry process to expose conserved epitopes to which antibodies could gain access during entry and producing epitope mimics of the broadly neutralizing monoclonal antibodies determined from structural studies of the antibody-antigen complexes (Burton et al., Nat Immunol. 2004 March; 5(3):233-6). However, none of these approaches have yet efficiently elicited neutralizing antibodies with broad specificity.

Citation or identification of any document in this application is not an admission that such document is available as prior art to the present application.

SUMMARY OF THE INVENTION

The present invention relates to a transgenic Vero cell line that express CD4/CCR5. In an advantageous embodiment, the CD4/CCR5 is derived from either human or rhesus macaque. In an advantageous embodiment, the transgenic Vero-CD4/CCR5 cell lines support Env-dependent infection and replication by VSV- and CDV-Env chimeras, wherein the Env expressed by infected cells comprises a native conformation and antigenicity. The invention encompasses manufacturing of replicating viral vectored HIV vaccines that express functional Env immunogens. Because Vero is a FDA-approved cell substrate for human vaccine production, the transgenic Vero-CD4/CCR5 cell line is suitable for manufacturing human vaccines.

Transgenic Vero-CD4/CCR5 cells are useful for HIV vaccine production since many safety risks associated with cell substrates have been addressed for the Vero cell background. The unique CD4/CCR5 transgene design directs expression of a CCR5 and CD4 polyprotein linked by a 2A sequence (de Felipe P, Luke G A, Hughes L E, Gani D, Halpin C, Ryan M D. E unum pluribus: multiple proteins from a self-processing polyprotein. Trends Biotechnol. 2006; 24(2):68-75) that is subsequently self-cleaved resulting in 1 to 1 ratio of CD4 and CCR5 molecules.

The transgenic Vero-CD4/CCR5 cell lines are useful for producing replicating viral vectors expressing HIV or SIV Env. Their use can also be expanded for use in assays requiring cells expressing CD4 and CCR5.

As the expression cassette proved effective with CD4 and CCR5, it is useful for making cell lines expressing other polypeptides.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following detailed description, given by way of example, but not intended to limit the invention solely to the specific embodiments described, may best be understood in conjunction with the accompanying drawings, in which:

FIGS. 2A-2D. Summary of VSVΔG-Env.BG505 rescue and vaccine preparation.

Steps in the process are summarized along with virus particle illustrations that show glycoprotein composition at different stages. Chimeric virus rescue is initiated by electroporating DNA (A) into Vero or VeroCD4/CCR5 cells. Virus that buds from electroporated cells then is expanded using VeroCD4/CCR5 cells before conducting 3 rounds of clonal isolation (B). Clonal isolates are characterized, and candidates are selected for seed virus amplification and storage. Conducting these steps using CD4+/CCR5+ ensures that the vector is genetically stable and will propagate efficiently using Env. When a pseudotyped vaccine preparation is produced (C), virus infection is performed using VeroCD4/CCR5 cells electroporated with DNA encoding G. Replication in vivo (D) produces virus particles that lack the G glycoprotein.

Figures 3A, 3B, 4A:
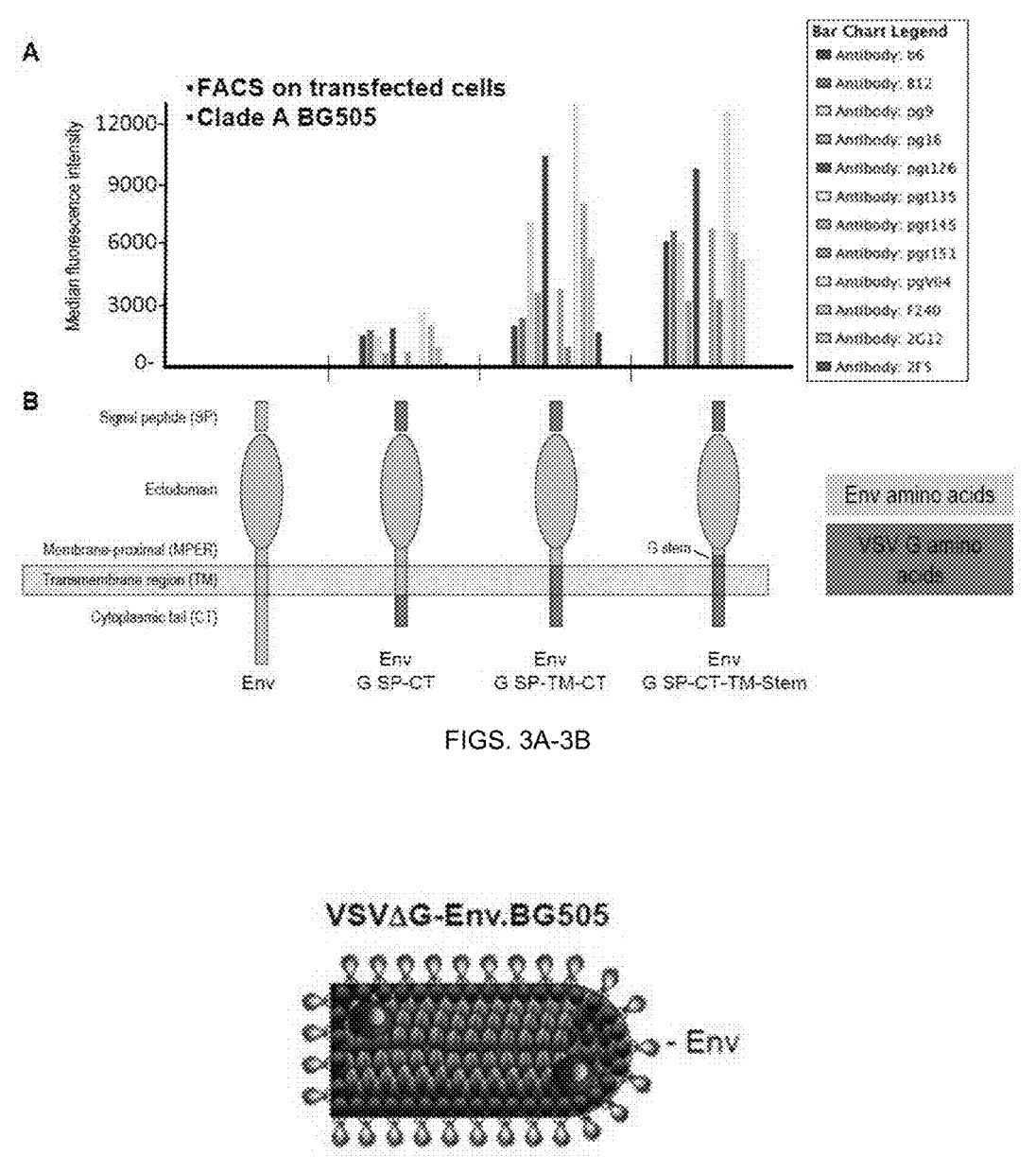

FIGS. 3A-3B. Improvement of Env spike surface expression. A) Flow cytometry conducted with transfected 293T cells expressing modified Envs. Monoclonal bnAbs used for detection are indicated at the right. Notably, antibodies PG16, PGT151, and PGT145 preferentially react with epitopes that are formed by well-ordered trimers. A linear illustration of an Env monomer and corresponding Env-G hybrids (B) is shown below the flow cytometry data in Part A. SP, signal peptide, which is cleaved during translational processing; TM, transmembrane; CT, cytoplasmic tail; MPER, the Env membrane proximal external region; G stem; membrane proximal external region of G.

Figure 4B:
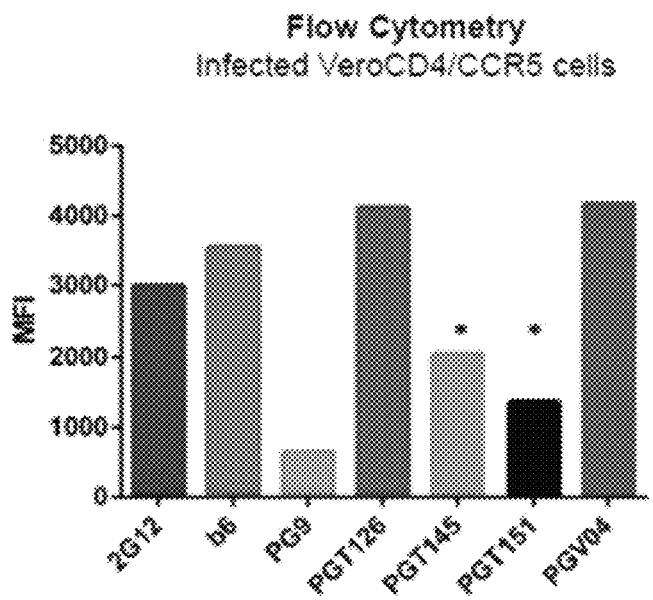
Figure 4C:
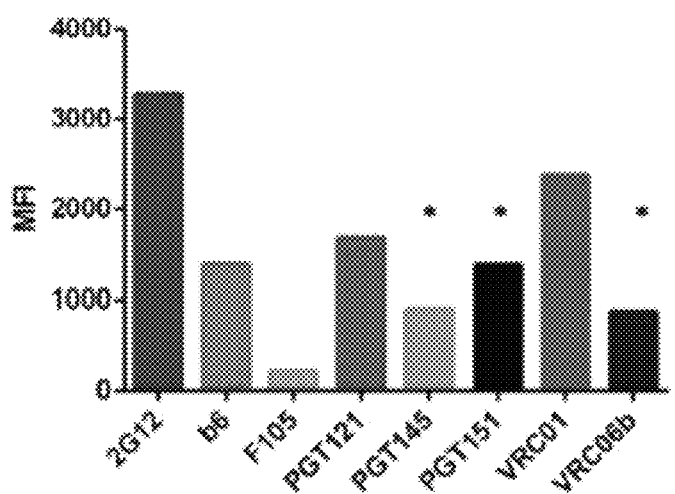

FIGS. 4A-4C. Antigenicity of Env.BG505 trimers delivered with VSVΔG-Env.BG505. Chimeric virus particles containing Env.BG505 only (A) were used for analyses in panels C-D. In B, infected VeroCD4/CCR5 were analyzed by flow cytometry using antibodies listed on the X-axis. In C, purified virus was adsorbed to alum after which the alum-virus complexes were reacted with mAbs and analyzed by flow cytometry. The asterisks in B and C highlight antibodies that preferentially recognized well order trimers.

Figures 5A, 5B, 5C:
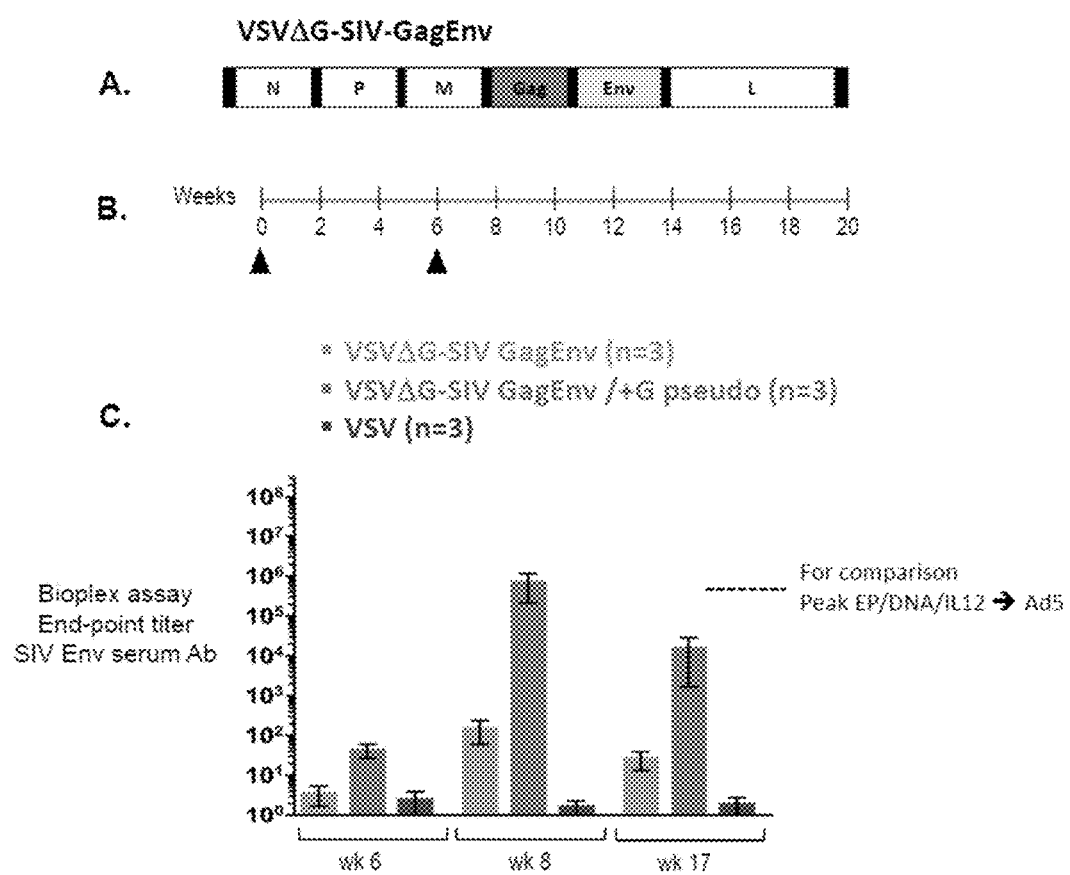

FIGS. 5A-5C. Immunogenicity of a prototype VSVΔG-SIV-GagEnv chimera in rhesus macaques. A) Genome map of the VSVΔG-SIV-GagEnv chimera, which contains the SIV Gag and Env genes. The C-terminus of Env was truncated leaving a six-amino acid cytoplasmic domain. This was required to improve express of SIV Env by the VSV vector. B) Three groups of animals (3 per group) were vaccinated with VSVΔG-SIV-GagEnv, VSVΔG-SIV-GagEnv prepared with a G pseudotype, or a negative control, which was live recombinant VSV. Animals were vaccinated twice (0 and 6 weeks) with $2 \times 10^8$ pfus. Live virus in buffered solution was administered in drops applied to the nasal and oral cavities ($1 \times 10^8$ pfu per site). C) Anti-SIV Env serum antibody titers were quantified by bioplex assay. To the right side of the chart, the peak antibody titer elicited in an earlier study with a DNA-SIV Env prime (electroporation) and Ad5-SIV Env boost is indicated with a dotted line for comparison. Assay background is subtracted from the data presented in the graph.

Figures 1A, 1B, 1C:
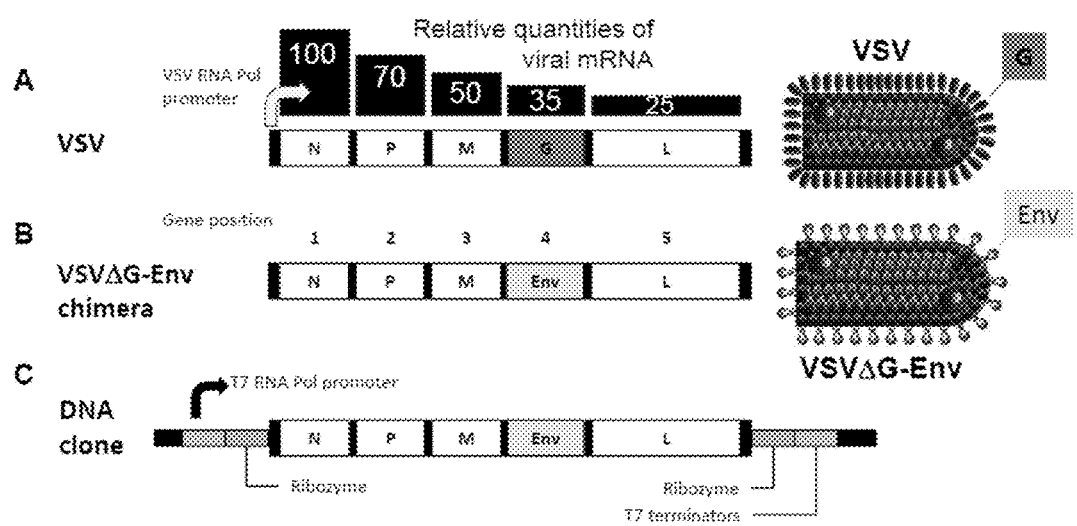
FIGS. 1A-1C. Recombinant VSVΔG-Env. A) A linear map of the VSV genome, which contains 5 gene regions encoding the Nucleocapsid protein (N), the Phosphoprotein (P) RNA-dependent RNA polymerase subunit, Matrix protein (M), Glycoprotein (G), and the catalytic subunit of the polymerase (Large protein or L). The 11-kb RNA genome is single-stranded, nonsegmented, and negative-sense. A single promoter at the 3' end controls mRNA synthesis. Transcription initiated at the 3' end terminates and reinitiates at each gene boundary. Because reinitiation is not 100% efficient, gene regions distal to the promoter are transcribed less efficiently generating a protein expression gradient. Changing the gene order, particularly when N is placed downstream, attenuates virus replication. A schematic of the VSV particle is show next to the genome map. B) Genome of the VSVΔG-Env.BG505 chimera in which the G gene is replaced with sequence encoding HIV Env.BG505. C) Map of the VSVΔG-Env genomic clone. The VSV (Indiana serotype) genomic sequence was derived from a lab-adapted virus. The Env.BG505 gene sequence is optimized to reflect VSV codon usage and relatively A+T-rich nucleotide content. To support rescue of recombinant virus, the T7 bacteriophage promoter is positioned to transcribe a positive-sense genome copy precursor and subsequent cleavage by cis-acting ribozymes generate precise termini.
Figures 6A, 6B, 6C:
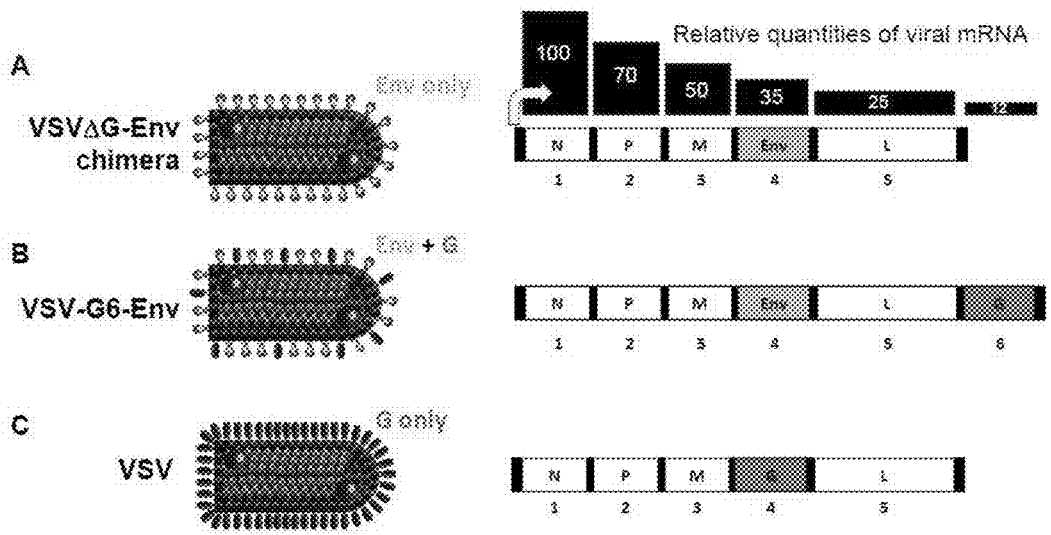

FIGS. 6A-6C. Genome maps comparing VSVΔG-Env.BG505 and an alternative vector design, VSV-G6-Env.BG505. A) The VSVΔG-Env.BG505 chimera genome contains 5 genes with Env.BG505 coding sequence inserted in place of G (position 4, also see FIG. 1). Gene expression declines with increasing distance from the transcriptional promoter located at the left end (yellow arrow, and see FIG. 1). The VSVΔG-Env.BG505 particle is illustrated with only Env incorporated on the surface, which is representative of the progeny virus particles that will be produced as the vector replicates in the vaccinee. B) In the VSV-G6-Env-vBG505 vector, the G gene was reintroduced, but placed in position 6, which down-regulates G expression and enables stable coexpression of both glycoproteins. C) VSV schematic for comparison to the two vectors illustrated above.

Figure 7:
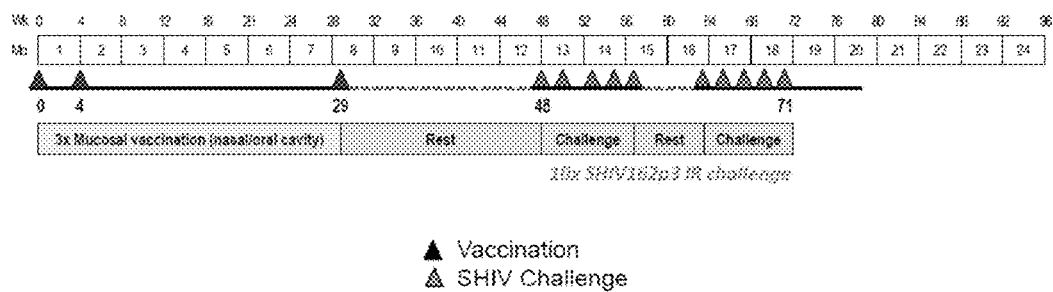

FIG. 7. Preclinical efficacy study design. Three groups of 10 Indian rhesus macaques were vaccinated according to the timeline at the top, which shows months and weeks. The three vaccine groups included: VSVΔG-Env.BG505 chimeria, VSV-G6-Env.BG505, and saline control. Vaccination and repeated rectal challenge time points are illustrated by filled triangles. Challenge was conducted with a heterologous clade B SHIV (SHIV SF162p3).

Figure 8:
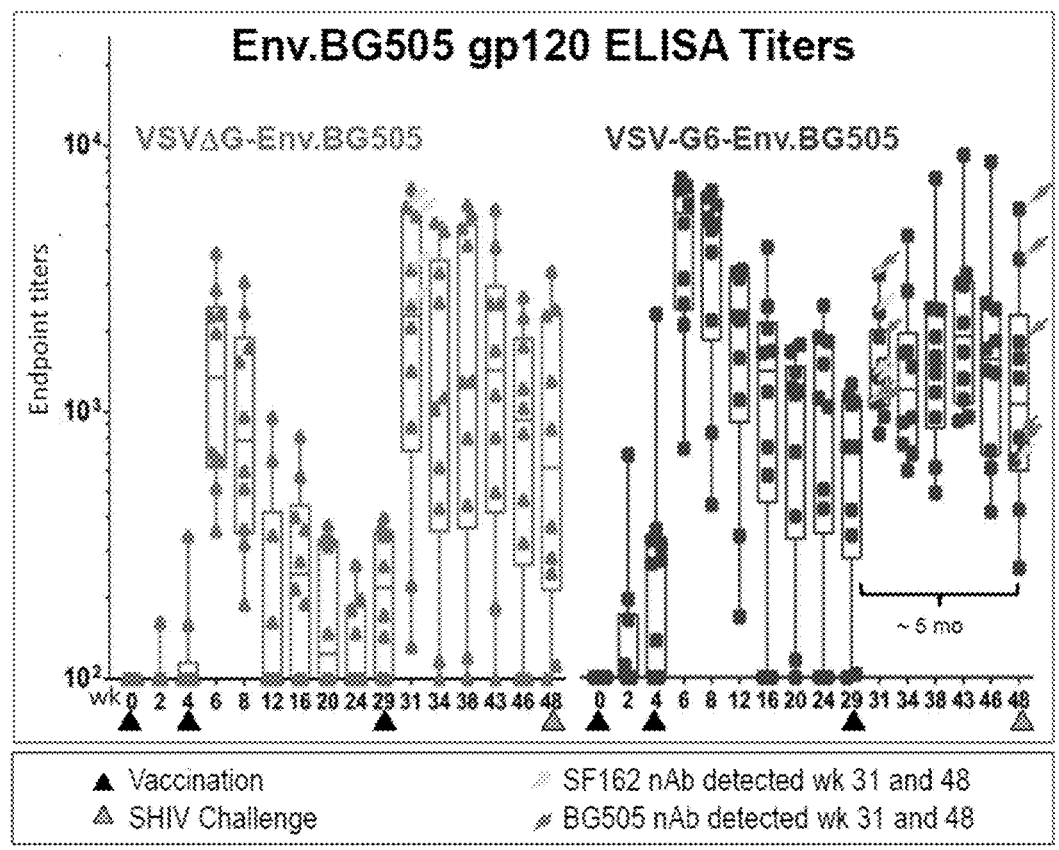

FIG. 8. Serum antibodies elicited by vaccination. Antibody binding to Env.BG505 gp120 was quantified by ELISA over the course of the vaccination phase.

Figure 9:
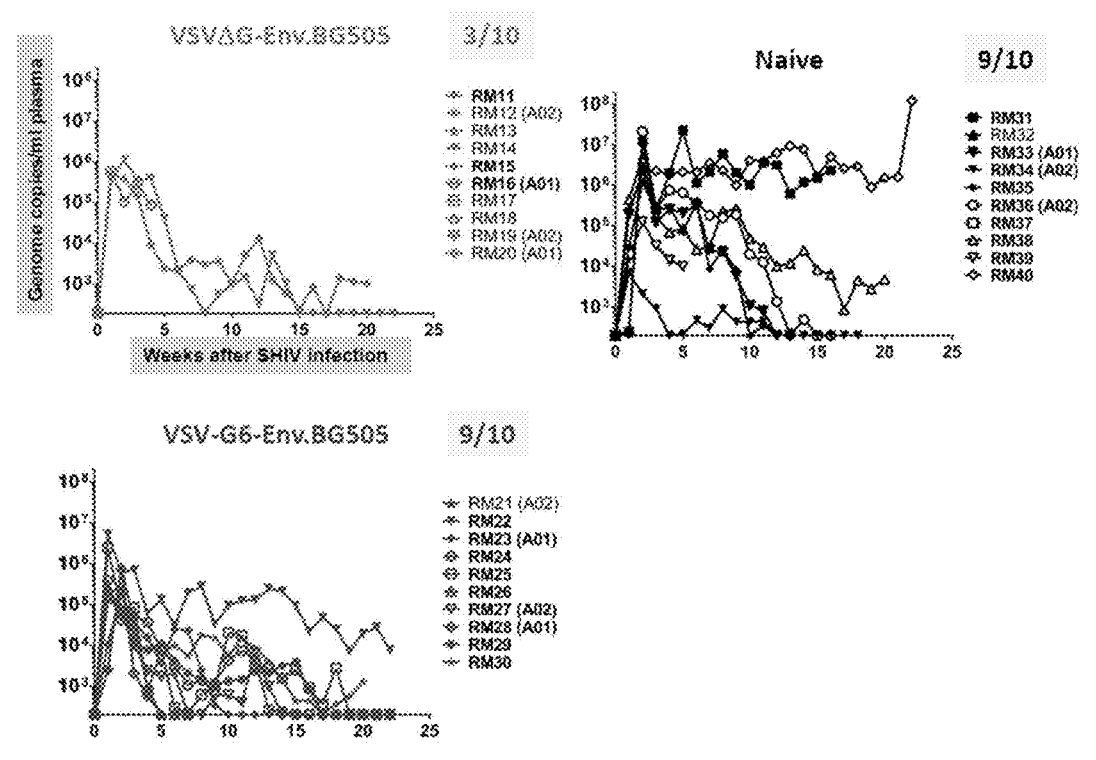

FIG. 9. Monitoring SHIV genome copies in the blood of infected animals. SHIV genome copies in blood samples were quantified by real-time quantitative PCR (RT-qPCR). Genome copies per ml of plasma are plotted from the time infection was first detected by a qPCR signal of ≥200 genome copies per ml. Animal identifiers are located to the right of the graphs. Bold indicates infected animals through the 10th challenge.

Figure 10:
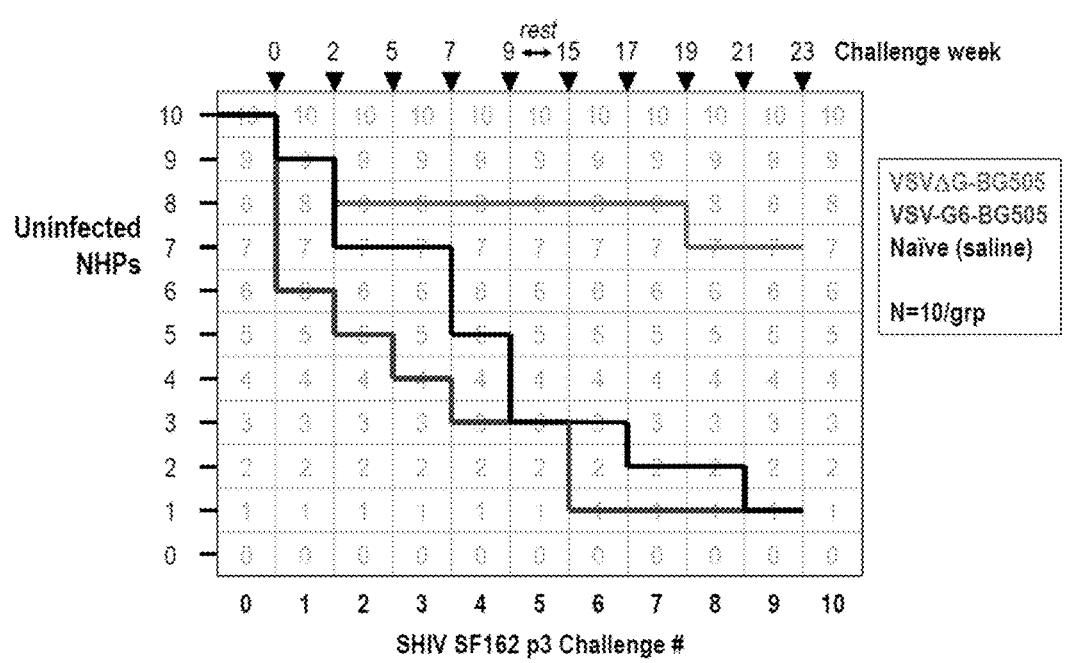

FIG. 10. SHIV infection rate during repetitive rectal challenge. As described in FIG. 7, three groups of 10 animals were vaccinated with VSVΔG-Env.BG505 (red line), VSV-G6-Env.BG505 (blue line), or saline (black line). About 5 months after the third vaccination at week 48, challenge commenced using $2.2 \times 10^4$ TCID50 per rectal inoculation (TCID50: tissue culture infectious dose required to produce cytopathic effect in 50% of inoculated cell cultures). The graph shows the number of uninfected animals (Y axis) per group prior to commencing the SHIV challenge protocol. SHIV challenge 10 has been completed.

Figure 11:
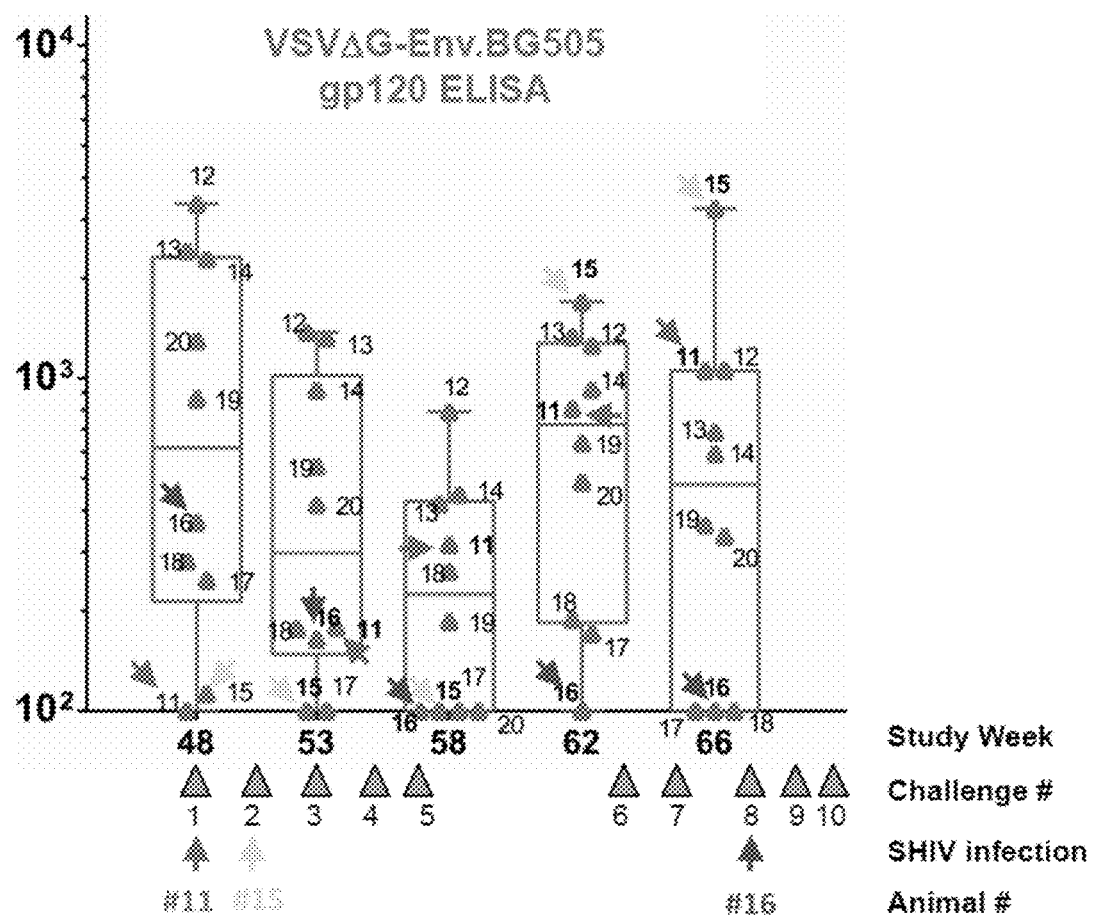

FIG. 11. Env.BG505 binding antibody titers at time of SHIV infection in animals vaccinated with VSVΔG-Env.BG505. ELISA was conducted with Env.BG505 gp120 bound to the plate using serum samples collected from macaques at the time challenge commenced (week 48) and periodically during the challenge protocol (FIG. 7). Animals 11 and 15 were infected at SHIV challenge 1 and 2, respectively. Animal 16 was infected at challenge 8, which was 19 weeks after the challenge protocol commenced. Colored arrows point to ELISA titers for animals 11, 15, and 16.

FIG. 12. Generation of VSVΔG-Env.BG505 from DNA and summary of steps to produce a seed virus for use in vaccine manufacturing.

FIG. 13. Preparation of VSVΔG-Env.BG505 with G pseudotype. The schematic summarizes a procedure for preparing pseudotyped VSVΔG-Env.BG505.

Figures 14, 15:
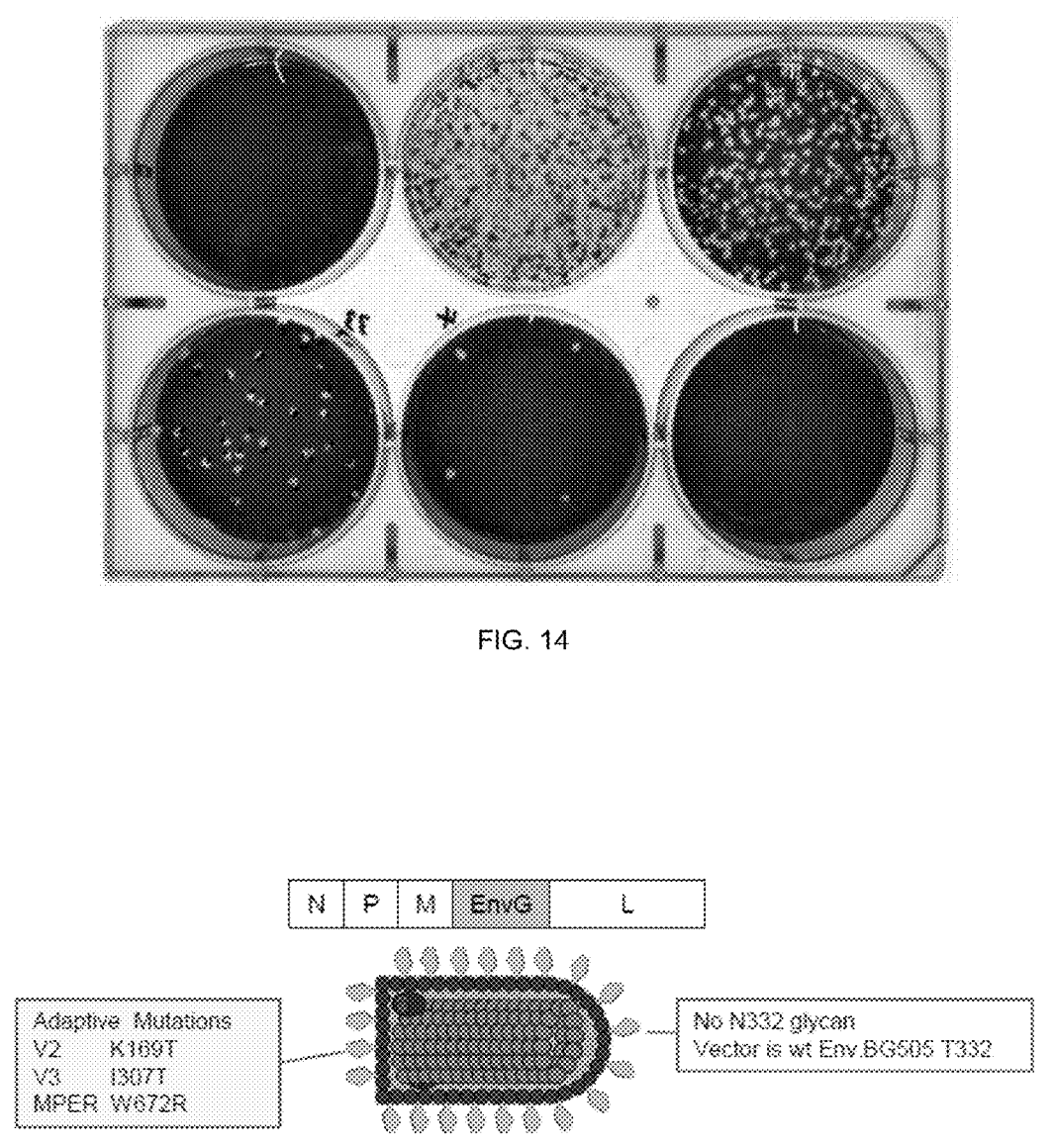

FIG. 14 shows that VSVΔG-Env.BG505 is cytolytic and that it forms plaques after an overnight incubation on GHOST cells.

FIG. 15 shows that three Env mutations were present in the protective VSVΔG-Env.BG505 vaccine. Adaptive mutations emerged in Env during vector rescue and propagation that increased Env-dependent replication in VeroCD4/CCR5 cells (human CD4/CCR5). The substitutions are stable and were included in vaccine vector tested in macaques. The 'adapted Env' gene was incorporated into a new VSVDG-Env.BG505 genomic DNA clone that allowed rescue of a recombinant virus containing these mutations.

Figures 16A, 16B:
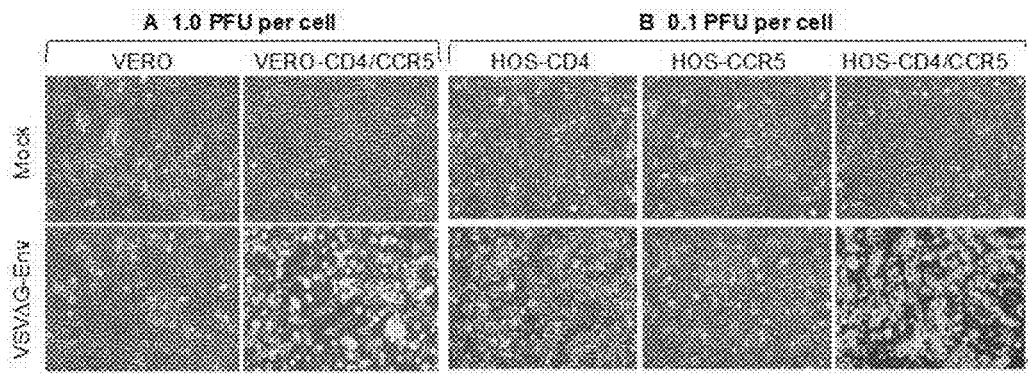

FIGS. 16A-16B show dependence of VSVΔG-EnvG.BG505 infection on CD4 and CCR5. The virus used in this experiment contained three adaptive amino substitutions in Env.BG505: K169T, I307T, and W672R. (A) VERO or VERO-CD4/CCR5 cell lines were infected with 1 plaque-forming unit per cell (PFU/cell) of VSVΔG-Env.BG505 or a mock control. Cytopathic effect caused by VSVΔG-Env.BG505 infection is evident only VERO-CD4/CCR5 cells. (B) HOS cells expressing CD4, CCR5 or both were infected with 0.1 PFU/cell of VSVΔG-Env.BG505 or a mock control. Cytopathic effect produced by infection is only evident on cells expressing both CD4 and CCR5.

Figures 17A, 17B:
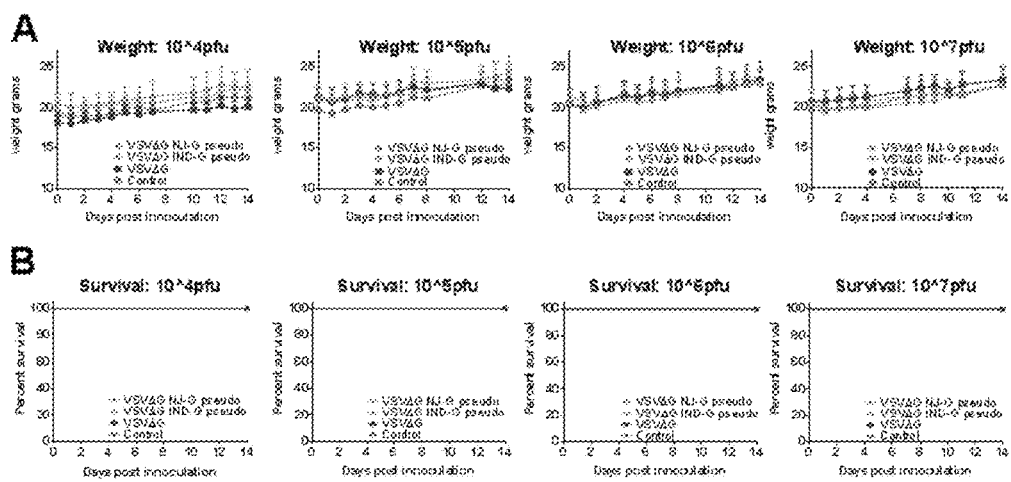

FIG. 17A-17B shows results from a maximal tolerated dose study conducted by intracranial injection in mice. Three VSVΔG-Env.BG505 vaccine preparations were analyzed: VSVΔG-Env.BG505 with a New Jersey G-pseudotype, VSVΔG-Env.BG505 with an Indiana G-pseudotype and VSVΔG-Env.BG505. No adverse events were observed following intracranial inoculation with VSVΔG vectors. (A) No substantial weight loss in animals over the 14 days apart from a small decrease at day 1. There was 100% survival in 10^4, 10^5 and 10^6 pfu groups. (B) No mortality and no paralysis, limb weakness or loss of coordination was observed in any of the groups.

Figure 18:
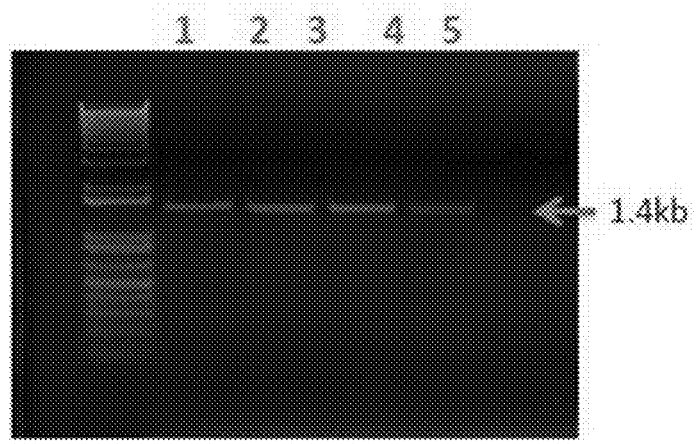

FIG. 18 depicts an evaluation of CD4 gene copy number in a VERO-CD4/CCR5 preclinical cell line. VERO-CD4/CCR5 cells were thawed, 3 passages were produced (P1, P2 and P3), cellular genomic DNA (gDNA) was purified and RNase treated, DNA concentrations were determined by UV spectrophotometry and diluted to a stock concentration of 100 ng/ml, genetic integrity was determined by PCR/gel electrophoresis and stability was monitored by qPCR. Stability of CD4 and CCR5 genes in the VERO-CD4/CCR5 cell line is determined. Passage to passage consistency of the VERO-CD4/CCR5 cells was monitored. Three SYBR green qPCR assays (CD4, CCR5 and a reference gene β-glucuronidase) are designed. Absolute quantification is by a standard curve method. The stability of CD4 and CD4 copy number/cell is determined by the copy ratio of CD4 to β-glucuronidase and likewise CCR5 stability.

FIGS. 19A-19E. VSV-HIV vectors evaluated in Indian rhesus macaques. (A) The VSV genome map is colored to correspond with proteins in the virus particle illustration. The 11-kb single-stranded, negative-sense, nonsegmented RNA genome encodes 5 proteins: (N) Nucleocapsid; Phosphoprotein (P); Large (L) RNA-dependent RNA polymerase subunit; (M) Matrix protein; (G) Glycoprotein. A single 3' promoter controls mRNA synthesis, with promoter-proximal genes being transcribed more frequently. The G gene was replaced with Env.BG505 sequence in VSVΔG-Env.BG505 (B) and VSV-G6-Env.BG505 (C), with G being reintroduced at the 5' terminus (position 6) of the VSV-G6-Env.BG505 genome. Env.BG505 encoded by both vectors was modified (FIG. 23A) to increase incorporation into the virus particle. (D) The surface of infected VERO or VERO-CD4/CCR5 cells was analyzed by flow cytometry using monoclonal antibodies specific for: high-manose glycans (2G12); a V3 epitope composed of polypeptide and glycan (PGT121); the CD4 binding site in native spikes (VRC01 and VRC06b) or in less compact Env species (F105 and IgGb6); and, native structures formed at the interface of spike subunits (PGT145 and PGT151). (E) Purified virus particles also were analyzed with the same antibodies using alum as a carrier for flow cytometry.

Figures 20A, 20B:
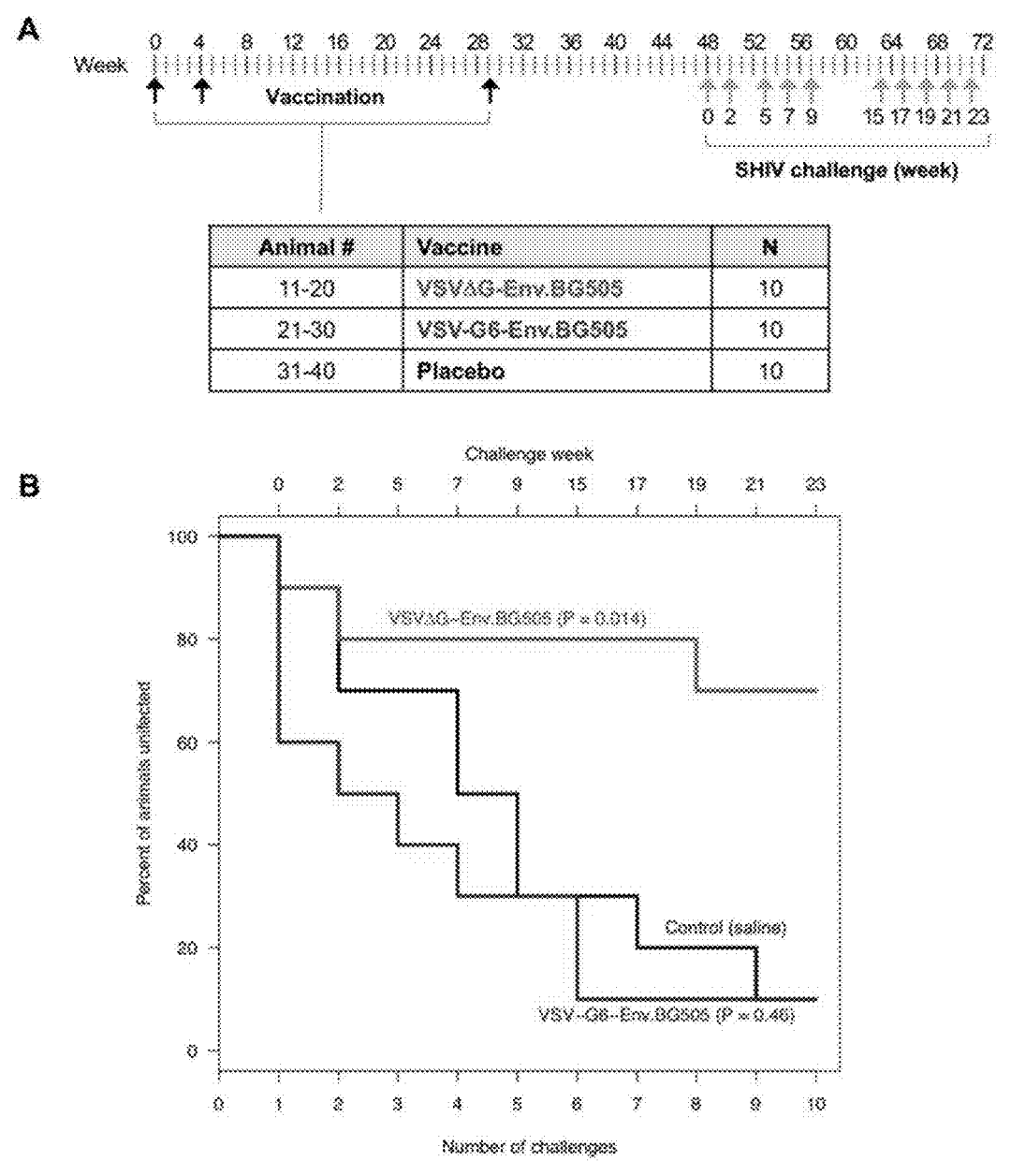

FIGS. 20A-20B. Preclinical efficacy study. (A) Macaques were vaccinated three times by applying VSVΔG-EnvG505, VSV-G6-Env.BG505, or buffered solution to both intranasal (1×10$^8$ pfus) and intraoral mucosal surfaces (1×10$^8$ pfus). Intrarectal challenge with SHIV began 5 months after the final vaccination (study week 48). The SHIV SF162p3 challenge stock was prepared in macaque PBMCs and has been used in prior studies. Consensus nucleotide sequencing conducted with the challenge virus verified that the Env gene matched Genbank Accession KF042063. Macaques with SHIV genome copies ≥200 per ml on two successive blood draws were considered positive (FIG. 26) and further challenge was ended. (B) Kaplan-Meier survival curves by treatment assignment. P-values are from an exact log-rank test comparing each active treatment group to the control group.

Figures 30A, 30B, 30C:
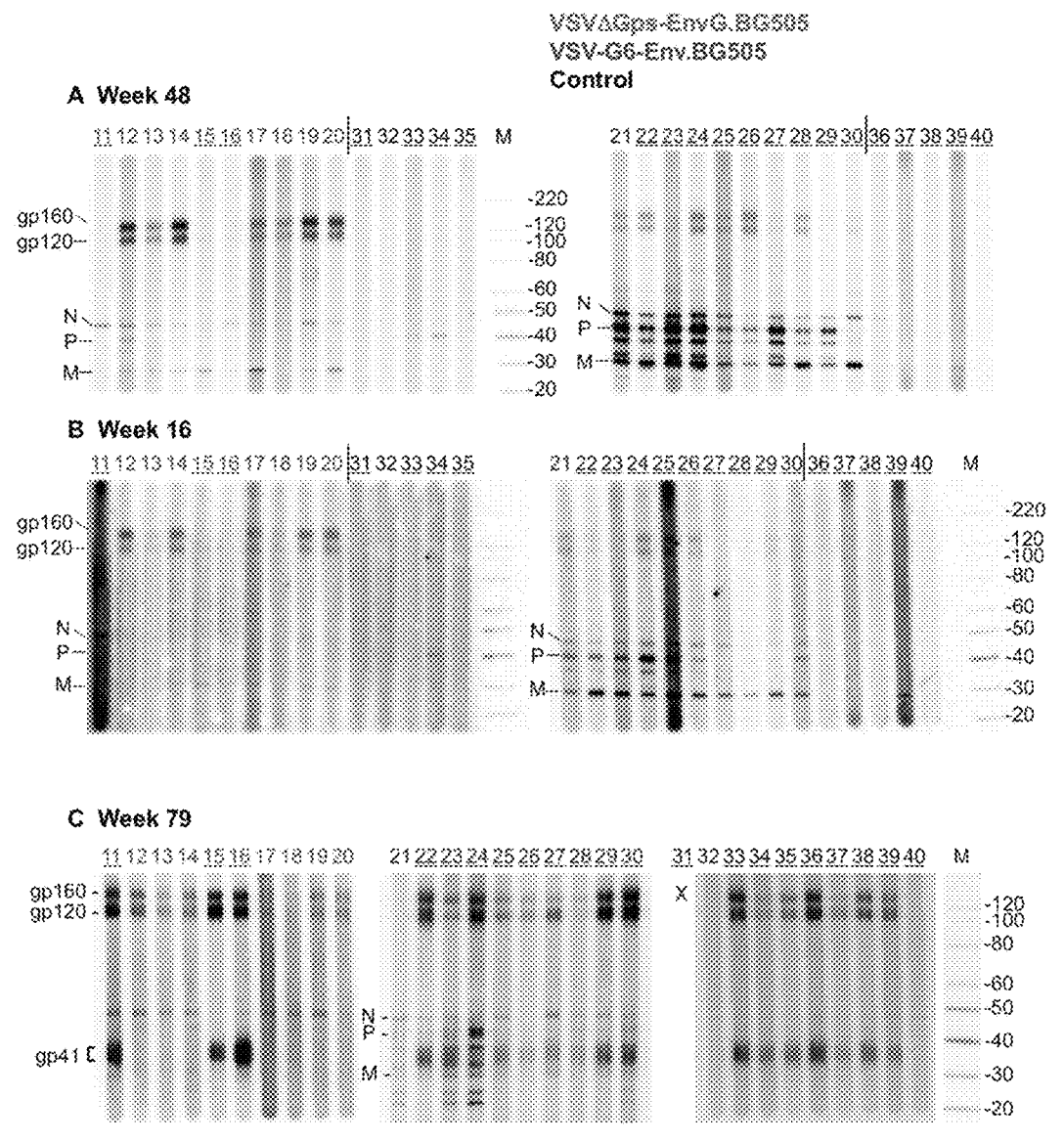

FIGS. 21A-21D. Serum antibody analysis by Western blot. Western blot membranes were prepared using purified VSVΔG-Env.BG505 as a source of Env.BG505 and VSV polypeptides. The membranes were placed in multichannel devices to allow analysis of sera from individual animals. (A) Analysis of week-43 sera from all vaccinated animals and two controls. Labeled above the blot are the vaccine groups, animal numbers (NHP, nonhuman primate), and the SHIV challenge when infection occurred. Underlined NHP numbers indicate an animal that became infected during SHIV challenge. Polypeptide identities are labeled at the left side. Bands corresponding to Env gp41 were not clearly evident until after SHIV infection (FIG. 30). (B) Sera were analyzed from week 48. An independent full-length blot is included in FIG. 30A with all control animal sera. (C) Sera was analyzed from week 62 when 5 of 10 challenges were complete. Asterisks indicate animals infected after 5 challenges. Infected Control animal 31 did not produce an Env signal probably because it had a more severe progressive infection (FIG. 26) that interfered with humoral responses against Env and Gag (FIG. 27). (D) Analysis of sera from week 79, which was ~1 year after the final vaccination.

Figures 22A, 22B:
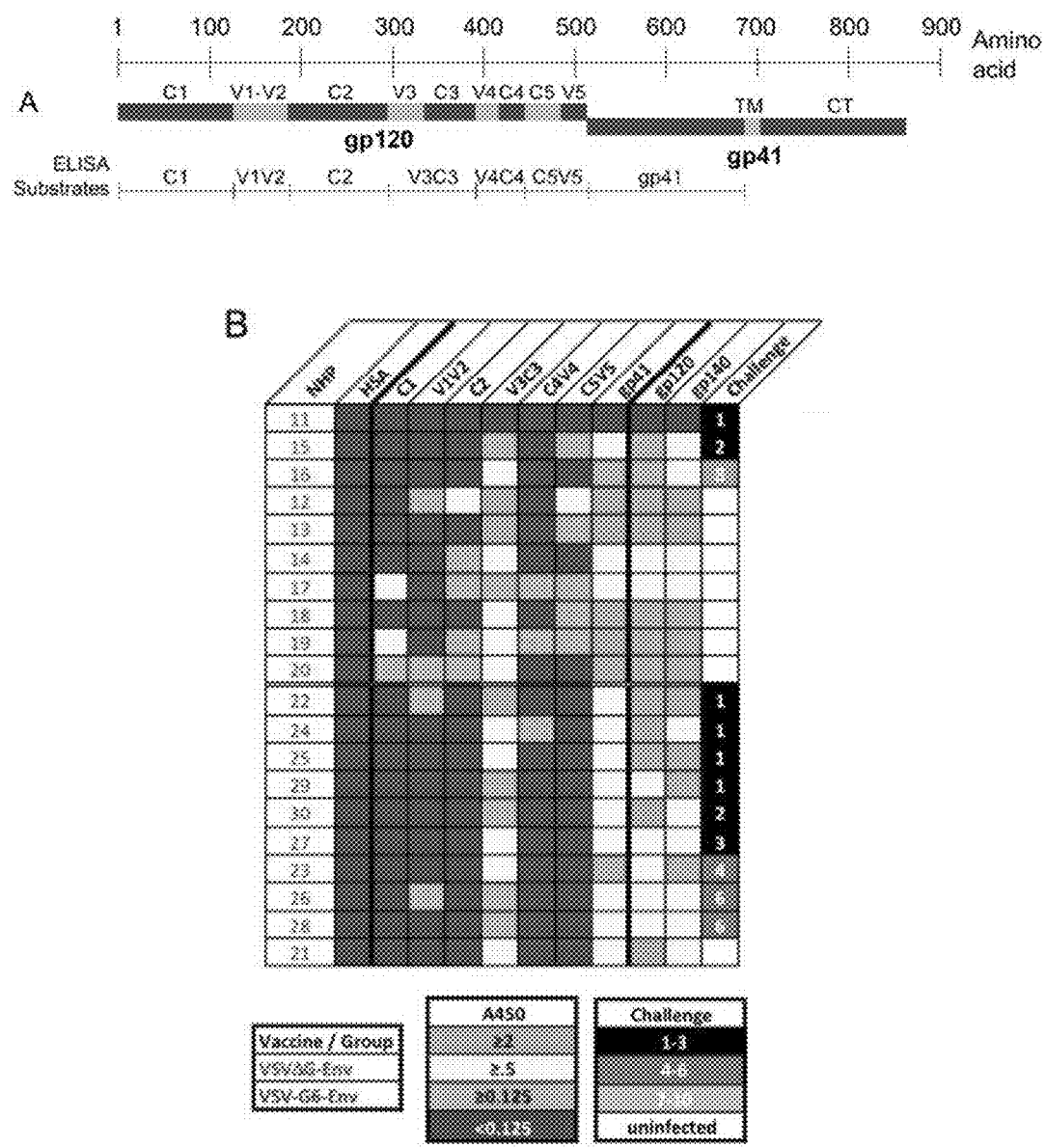

FIGS. 22A-22B. Mapping Env antibody binding regions. (A) Linear map of Env Constant (C1-C5) and Variable (V1-V5) domains. The map breaks at furin cleavage site between gp120 and gp41. The transmembrane (TM) region and cytoplasmic tail (CT) are labeled in gp41. Below the map, boundaries are shown for the Env fragments fused to human serum albumin (HSA) to generate ELISA substrates. (B) Analysis of sera using capture ELISA and the HSA fusion proteins shown in (A). HSA without a fused Env sequence was included as a negative control. Env gp120 and gp140 ELISA substrates were not fused to HSA. The data from an example experiment (absorbance at 450 nm; A450) is presented as a heat map with the scale shown at the bottom adjacent to a scale showing the SHIV challenge when infection occurred.

FIGS. 23A-23F. VSV-HIV vaccine design details. (A) Both vectors express HIV Env.BG505, which was modified to increase incorporation into the VSV particle by replacing the signal sequence, transmembrane region (TM) and cytoplasmic tail (CT) with sequence from G (serotype Indiana; IND). (B) VSVΔG-Env.BG505 particles used for vaccination were pseudotyped with G. Vaccinating with pseudotyped VSVΔG-Env.BG505 launches a more robust infection, because G binds ubiquitous cellular receptors allowing the initial round of infection to be independent of Env and the limited population of CD4+/CCR5+ cells. Pseudotyped virus was prepared by conducting the final amplification of vaccine material in VERO-CD4/CCR5 cells expressing G. (D-F) These schematics summarize how early stages of VSV vector infection progresses in macaques with pseudotyped VSVΔG-Env.BG505 (B) and VSV-G6-Env.BG505 (C). Both can use G to initiate primary infection (D), but subsequent cycles of VSVΔG-Env.BG505 infection and replication are Env-dependent while VSV-G6-Env.BG505 are G dependent. Additional information on the use of G in the vaccines is provided in FIG. 24.

Figures 24A, 24B, 24C:
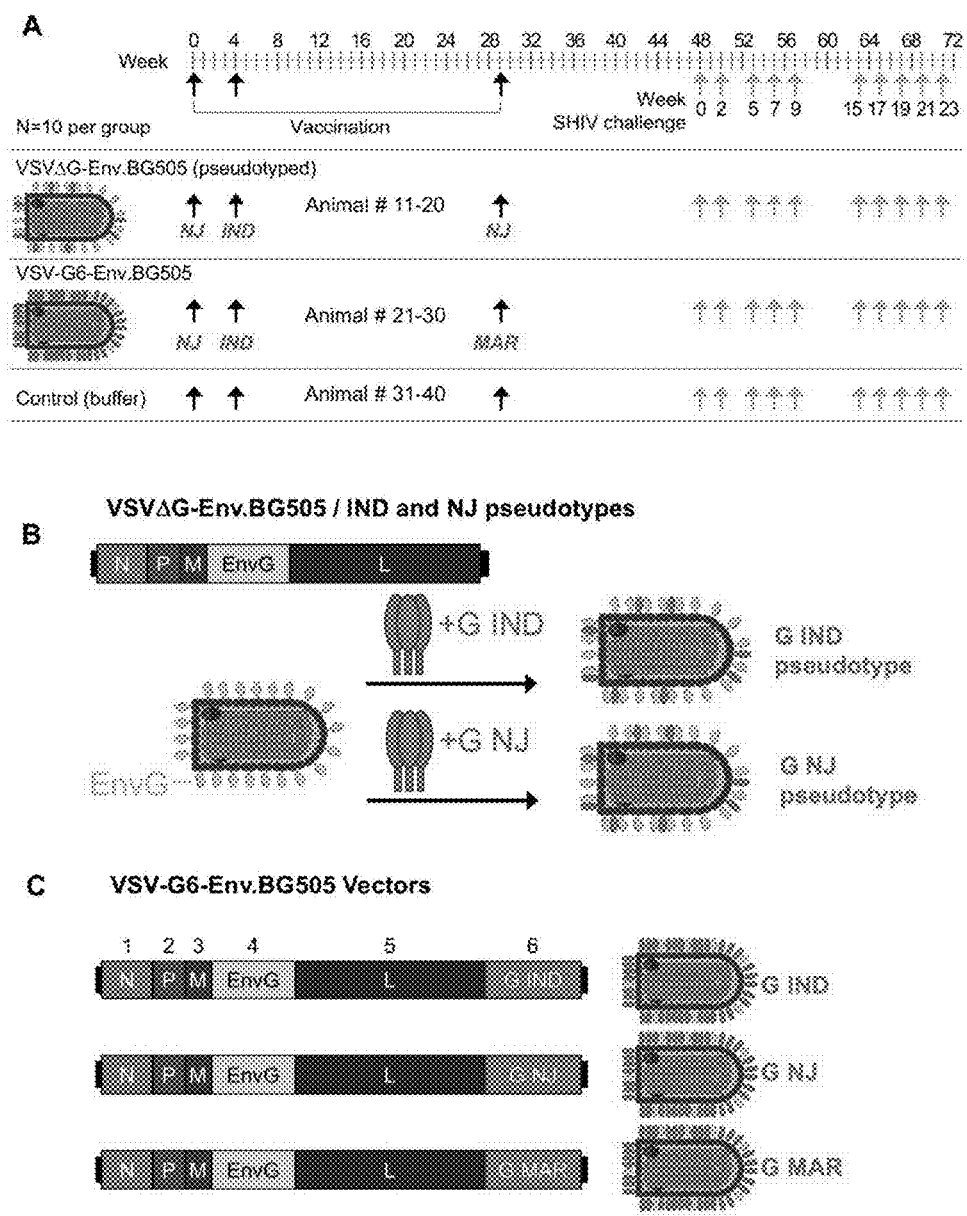

FIGS. 24A-24C. VSV G serotype exchange. Because 3 vaccinations were planned and anti-G antibodies were known to develop when using VSV vectors that express G like VSV-G6-Env (FIG. 19C), Applicants used a G serotype exchange strategy to minimize potential effects of anti-G immunity (A) Timeline of vaccination and SHIV challenge shows how the G composition in the vaccines was varied. (B) For VSVΔG-Env.BG505, G was exchanged simply by pseudotyping with G from serotype New Jersey (NJ) or G IND. Only two different G pseudotypes were used for the three sequential vaccinations (A), because interim ELISA data showed that transient mucosal exposure to G in the pseudotyped VSVΔG-Env.BG505 particle did not elicit substantial amounts of anti-G antibodies (data not shown). (C) For sequential vaccination with VSV-G6-Env.BG505 (B), three vectors were used that differed in their G genes. The G genes came from different vesiculoviruses including VSV serotypes NJ or IND, or Maraba virus.

Figure 25:
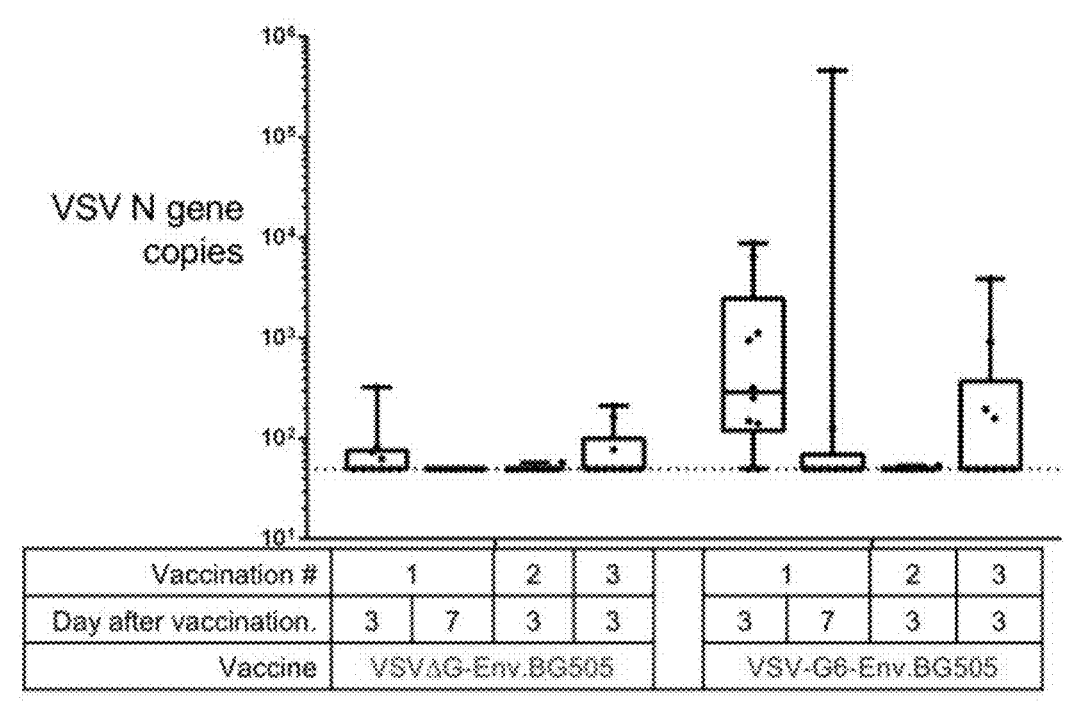

FIG. 25. VSV-HIV shedding in the oral cavity. Samples were collected at 3 days after each of the three vaccinations by swabbing the oral cavity. Samples also were collected 7 days after the first vaccination. Material collected on the swabs was purified using procedures described in the Methods for detecting SHIV genomes in plasma after which qPCR was performed with an amplicon specific for the N gene. The lower limit of measurement was 50 genome copies per reaction. Low quantities of VSVΔG-EnvG.BG505 genomes were detected at 3 days following the first vaccination in 4 animals and in 3 macaques after the third vaccination. VSV-G6-Env.BG505 genomes were detected in swabs from 8 animals in greater quantities after the first vaccination and in 4 macaques following the third vaccination. These results indicated that VSVΔG-Env.BG505 shedding into the oral cavity was minimal to undetectable, while the quantity of VSV-G6-Env.BG505 genomes indicated that some virus shedding occurred although it remains to be determined whether live virus was present.

Figure 26:
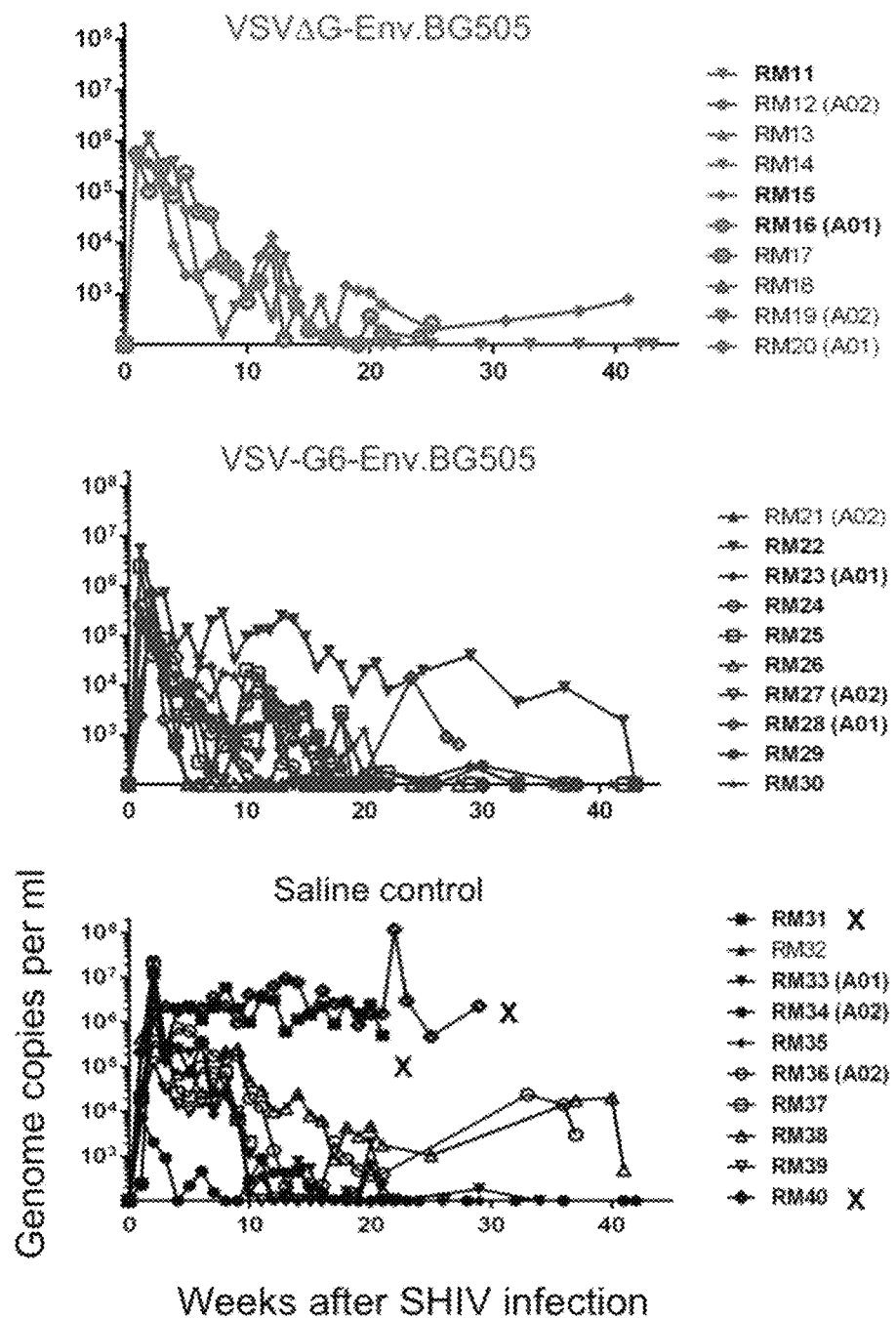

FIG. 26. SHIV infection and virus loads. Blood was collected at one and two weeks following each challenge to assess virus loads as described in the Methods. The plots show SHIV genome copies per ml of plasma as measured by RT-qPCR using a SIV Gag-specific amplicon. Animals with ≥200 copies on two successive blood draws were considered positive after which challenge was stopped. Animal numbers are shown to the right of the plots, and those positive for the Mamu-A*01 or Mamu-A*02 MHC alleles are indicated. Each group had two animals that were positive for Mamu-A*01 and two positive Mamu-A*02, which have been associated with control of disease progression. No macaques were included in the study with Mamu-B*17 or Mamu-B*08 alleles associated with strong replication control. Two animals in the Control group (indicated with X) experienced rapid disease progression and were euthanized before the end of the study.

Figures 27A, 27B, 27C:
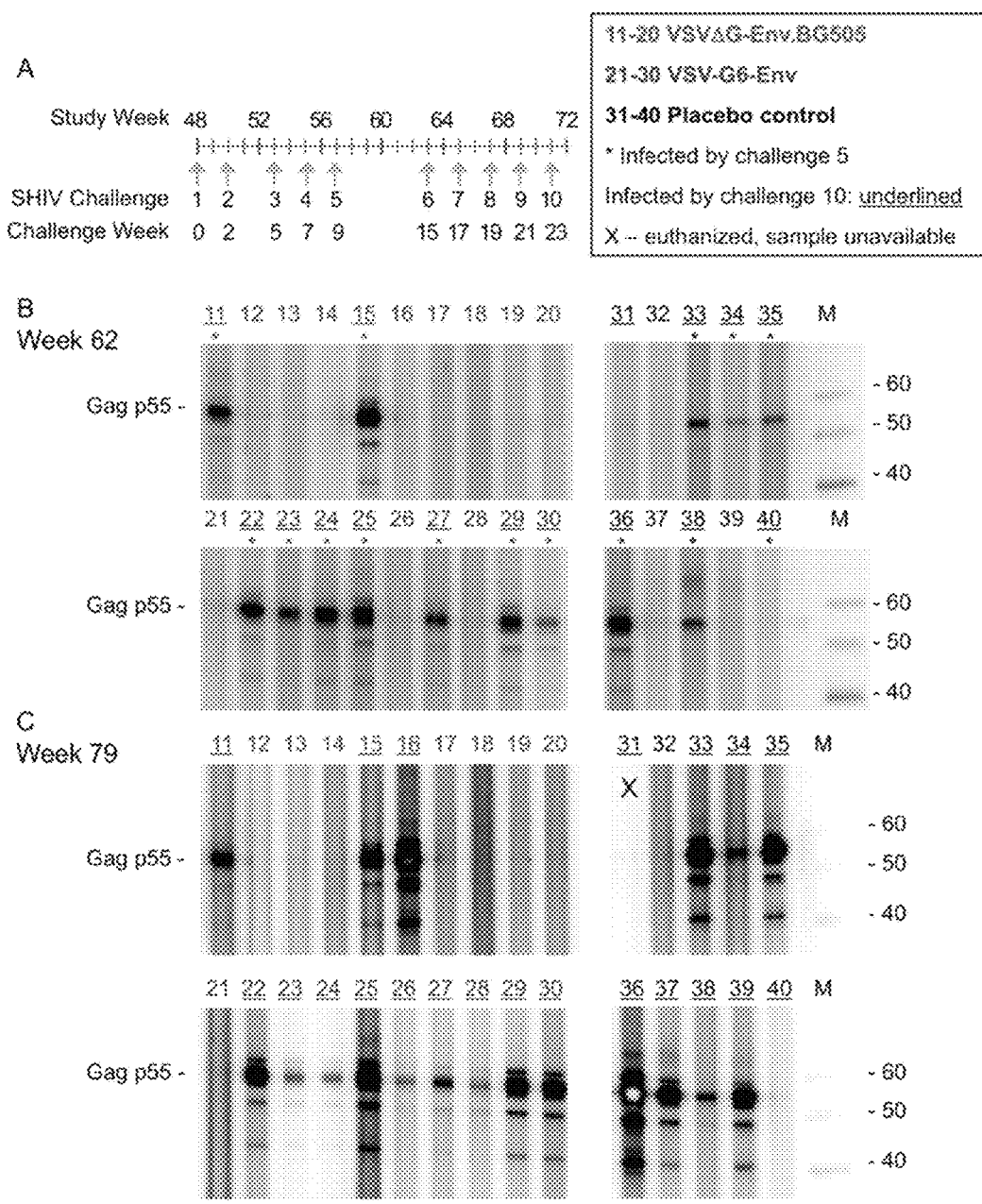

FIGS. 27A-27C. Analysis of anti-Gag response to SHIV infection by Western blotting. (A) SHIV challenge timeline and labeling key for the blots below. (B-C) Gag-specific serum antibodies were detected by reactivity with recombinant SIV Gag (SIVmac239, p55 Gag; Protein Sciences Corp.) on Western blot membranes. Week-62 serum (B) was collected after completing the first 5 challenges and week-79 serum (C) was collected two months after the 10th challenge. Animal numbers are indicated above each lane, and in (B), an asterisk indicates that macaques were infected by the fifth challenge. Two infected animals in the control group (31 and 40) did not have strong anti-Gag or anti-Env (FIG. 30C) antibody responses, which was due to rapid disease progression (FIG. 26) inhibiting development of antibodies.

Figures 28A, 28B:
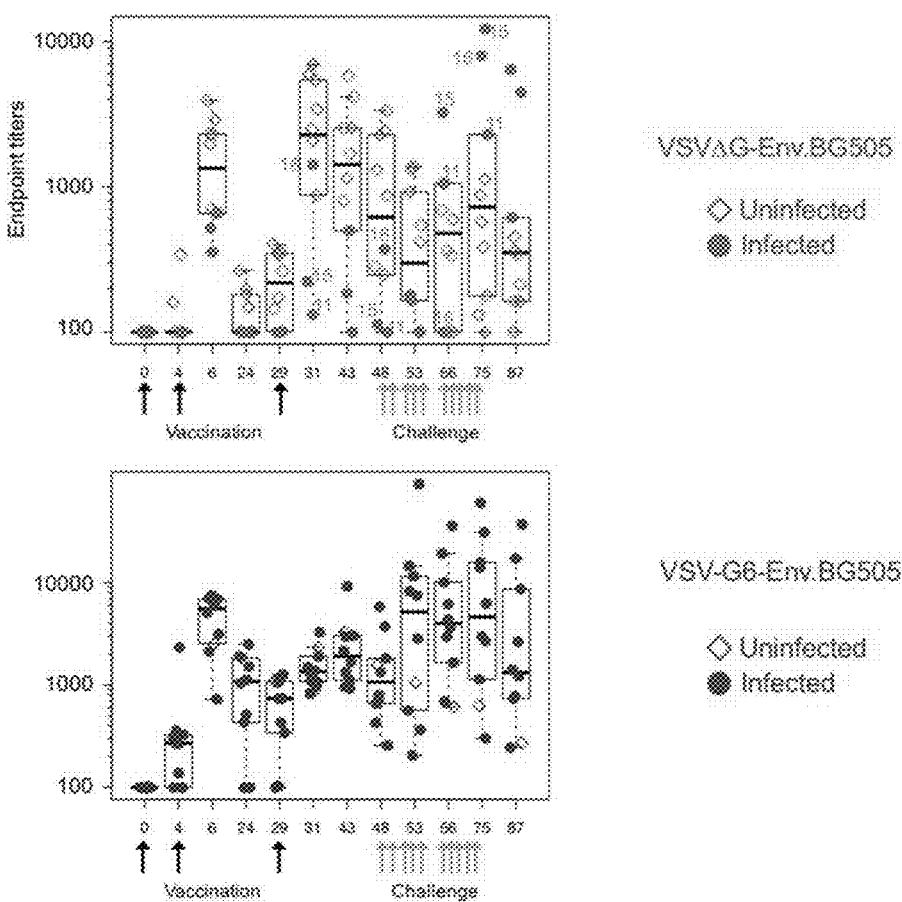

FIGS. 28A-28B. More detailed presentation of the SHIV infection timeline. (A) The Table supplements the survival curve shown in FIG. 20B and the antibody analysis in 3B by provides the timing of SHIV infection for each animal. (B) Boxplots showing ELISA titers during vaccination and challenge phases. The boxplots highlight the low titers in animals 11, 15, and 16 in the VSVΔG-Env.BG505 group prior to SHIV infection. Boxes show median and quartiles with whiskers extending at most 1.5 times the interquartile range.

Figure 29:
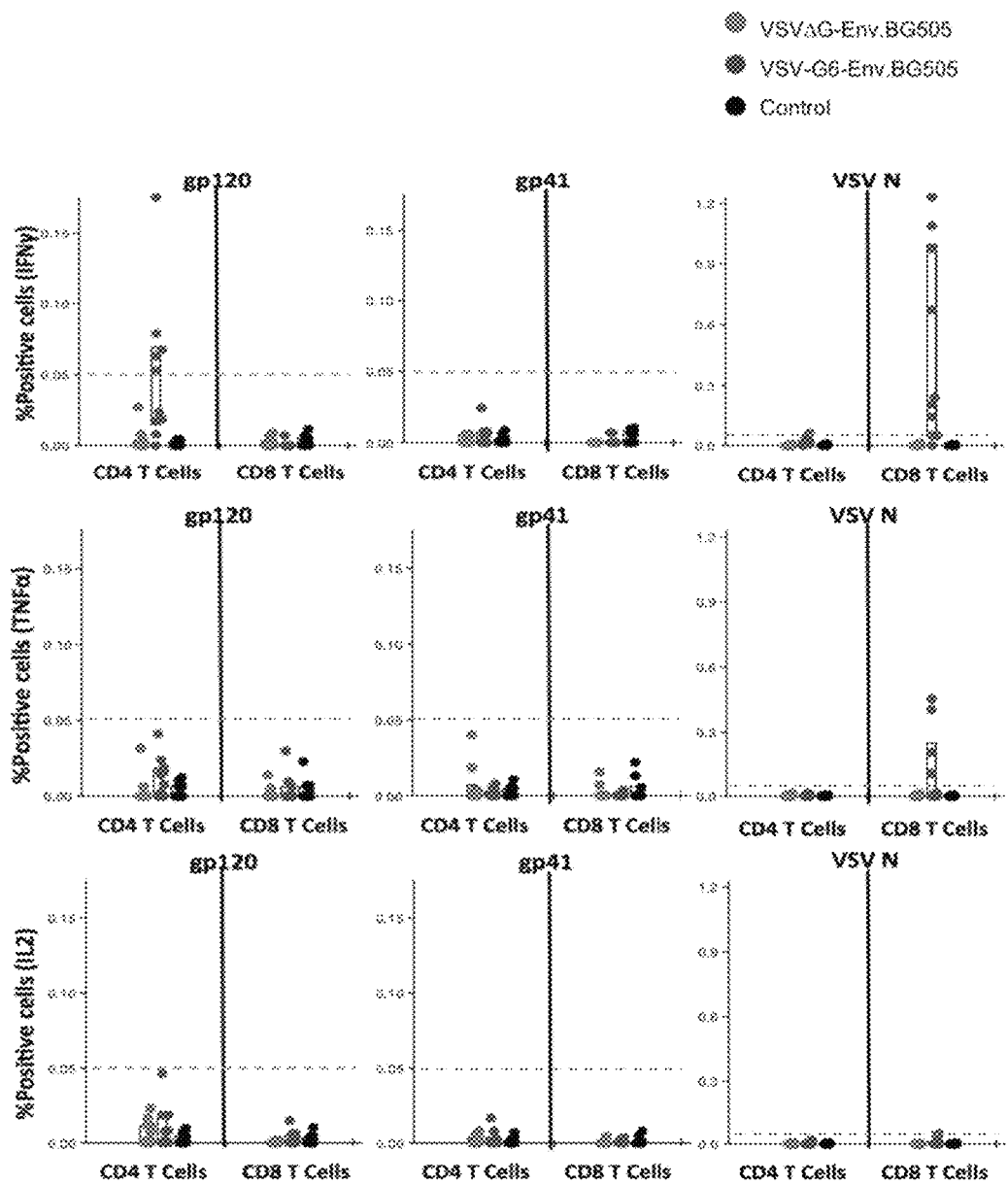

FIG. 29. CD4 and CD8 T cell frequencies in peripheral blood. PBMCs harvested two weeks after the third vaccination (week 31) were stimulated with peptides representing Env.BG505 gp120, gp41, or VSV N after which intracellular cytokine staining and flow cytometry was conducted to quantify CD4 and CD8 T cells. Overall, the Env-specific T cell frequencies in peripheral blood were low (measurable limit set at 0.05%). In the VSV-G6-Env.BG505 group 5 of 10 animals were positive for gp120-specific CD4 T cells secreting IFNγ. VSV N-specific CD8 T cells also were detected secreting IFNγ in 9 of 10 macaques and TNFα in 4 or 10 animals. Notably, the frequency of T cells in peripheral blood specific for Env or N were below measurable limits in the group vaccinated with VSVΔG-Env.BG505.

Figures 21A, 21B, 21C, 21D:
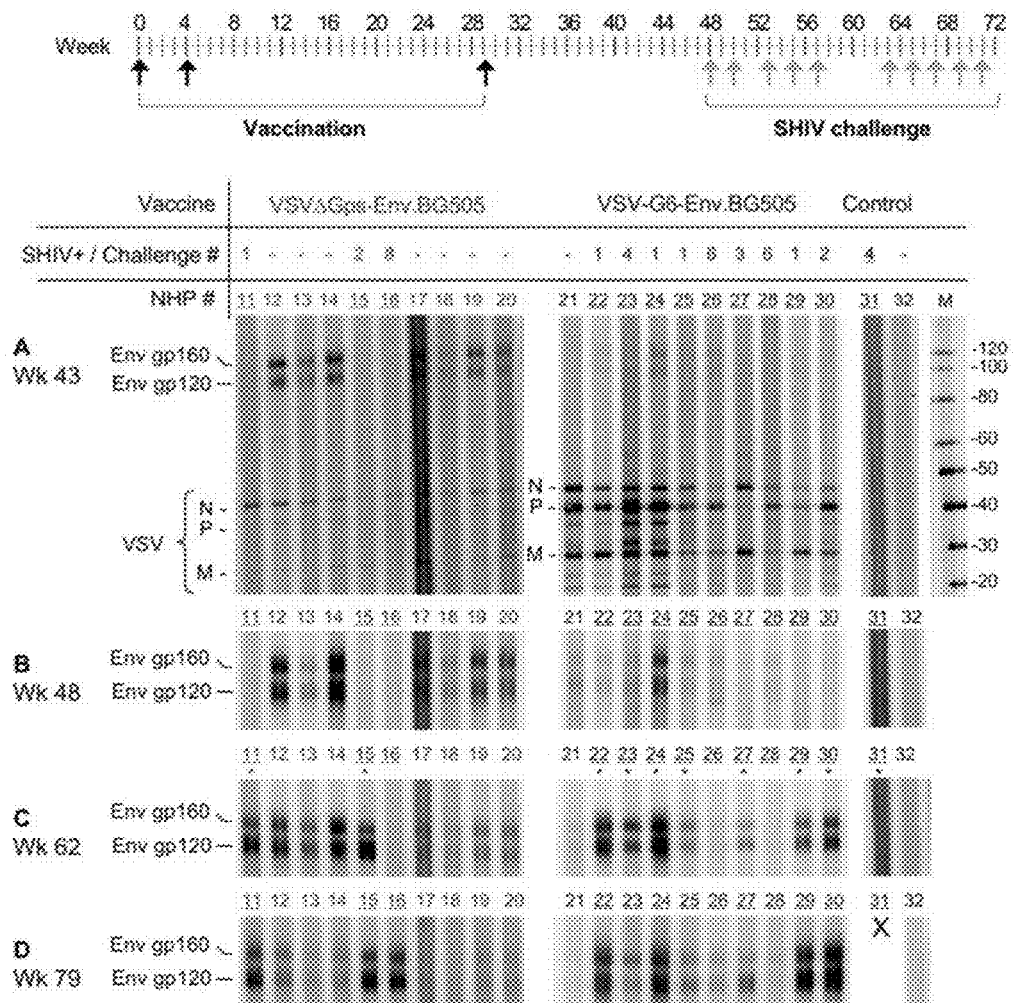

FIGS. 30A-30C. Additional characterization of serum antibodies by Western blot. Assays were performed as in FIG. 21. (A) An independent week-48 Western blot, like the one in FIG. 21B, is shown with all control animals included. The full-length blot also shows reactivity with VSV polypeptides as described in FIG. 21A. Sera from control animals lacked significant VSV and Env signals as expected, except for occasional detection of bands that migrated at positions consistent with VSV M and P. (B) A Western blot performed with sera collected at study week 16, which was 12 weeks after the second vaccination. The result showed that the Env signal was detectable at this earlier time even though the ELISA titers were considerably lower in the VSVΔG-Env.BG505 group after the second vaccination. (C) An independent week-79 Western blot similar to the one in FIG. 21D. The full length blot shows that serum from infected macaques was able to detect gp41. Most control macaques also developed antibodies that bound gp41 except for two animals that had had progressive infections (macaques 31 and 40; FIG. 26) and uninfected animal 32. Animal 31 was euthanized prior to this time point.

FIG. 31. Cross clade Env binding detected with Western blot. A Western blot assay was performed using three different VSVΔG-Env.BG505 chimeras as the source of proteins on the blot. These included clade A.BG505 (different blot than in FIG. 4B), B.SF162.p3, and C.CH505 (week 100). The assay was performed as described in FIG. 21 using sera from the VSVΔG-Env.BG505 group (week 48). Animal numbers are at the top of the blot. Underlined animals were not protected during SHIV challenge.

Figure 32:
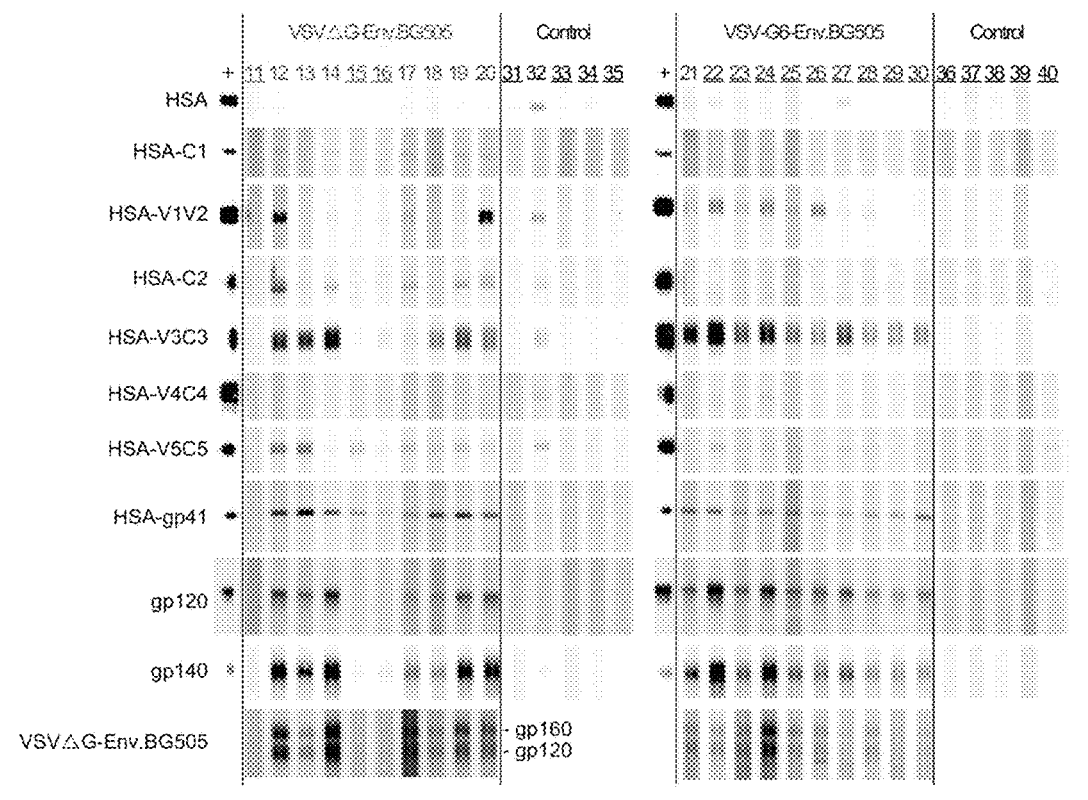

FIG. 32. Analysis of serum antibody binding to different Env regions by Western blotting. Sera from week 48 was analyzed as described in FIG. 21 except that recombinant gp120, gp140, and HSA fusion proteins (FIG. 22A) were used as substrates. The positive control lane (+) included anti-HIS antibody.

Figure 33A:
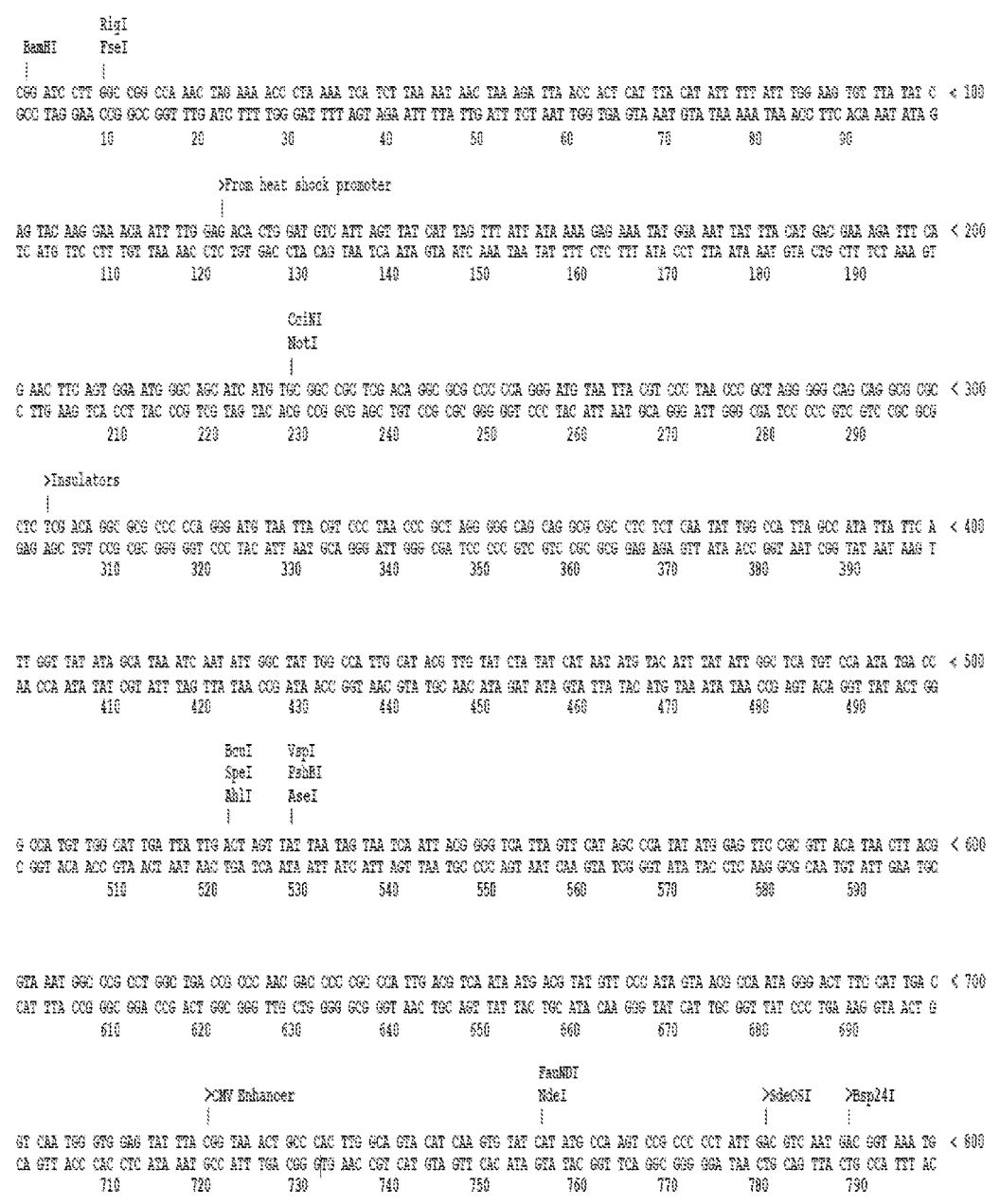
Figure 33B:
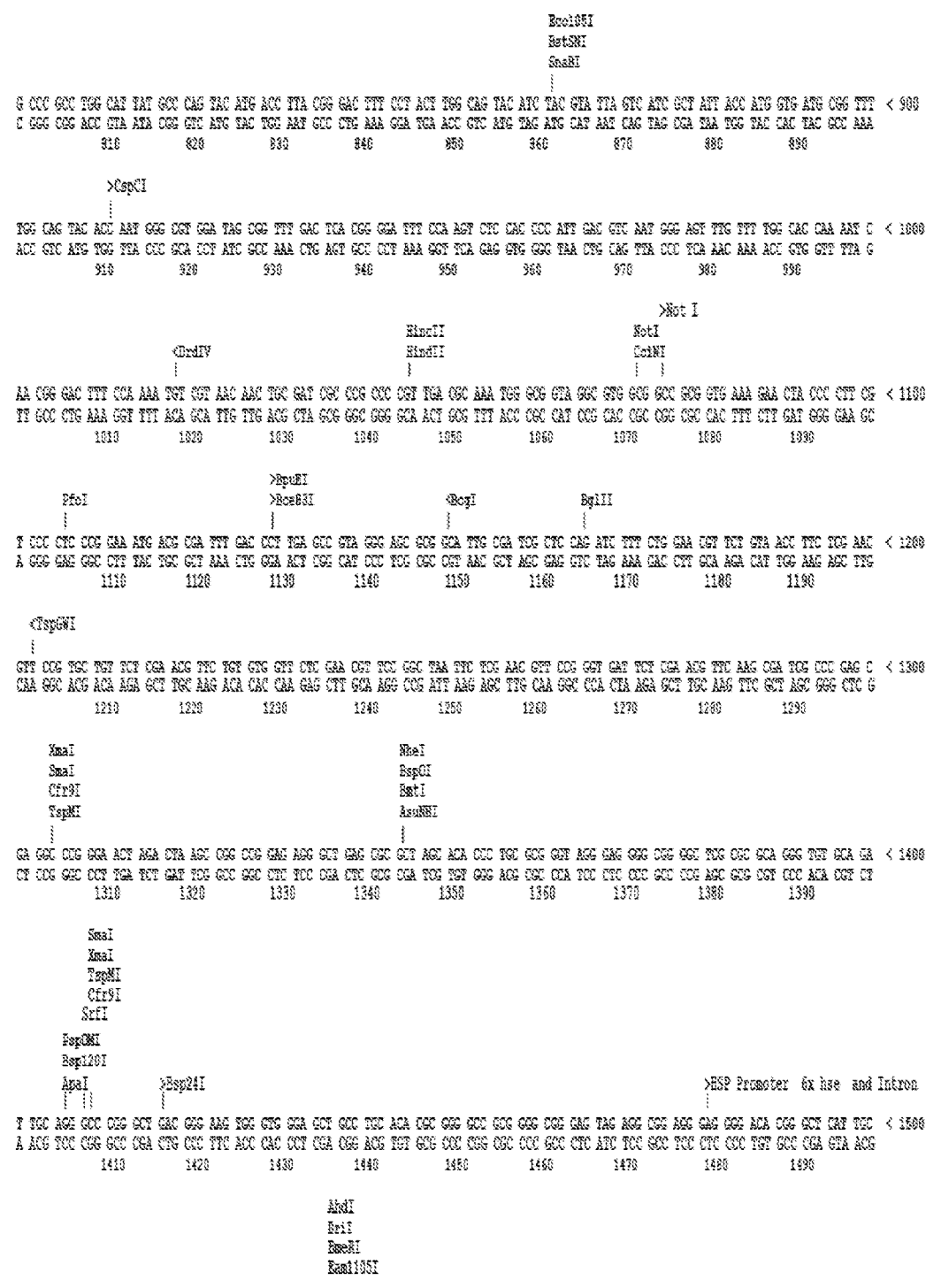
Figure 33C:
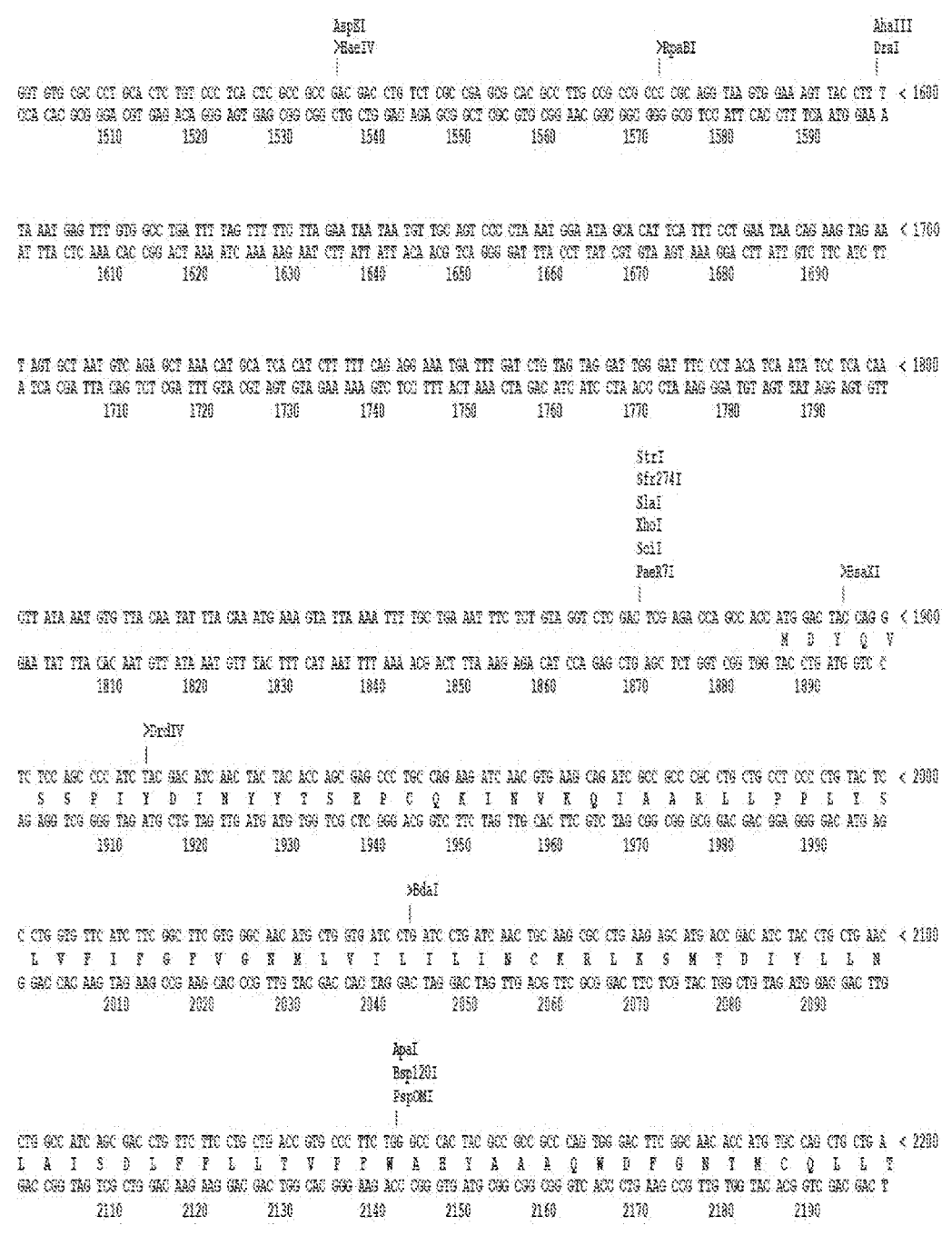
Figure 33D:
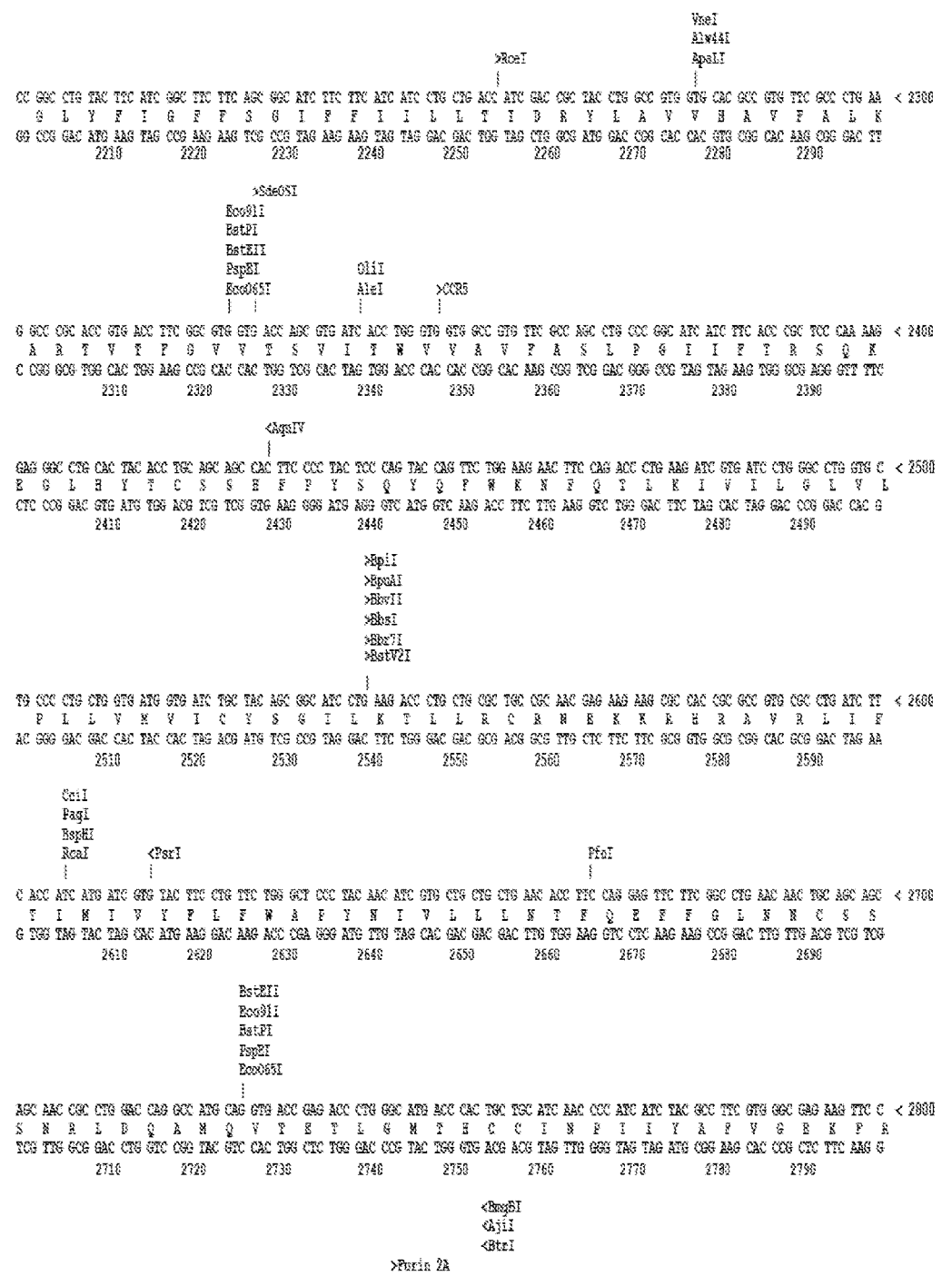
Figure 33E:
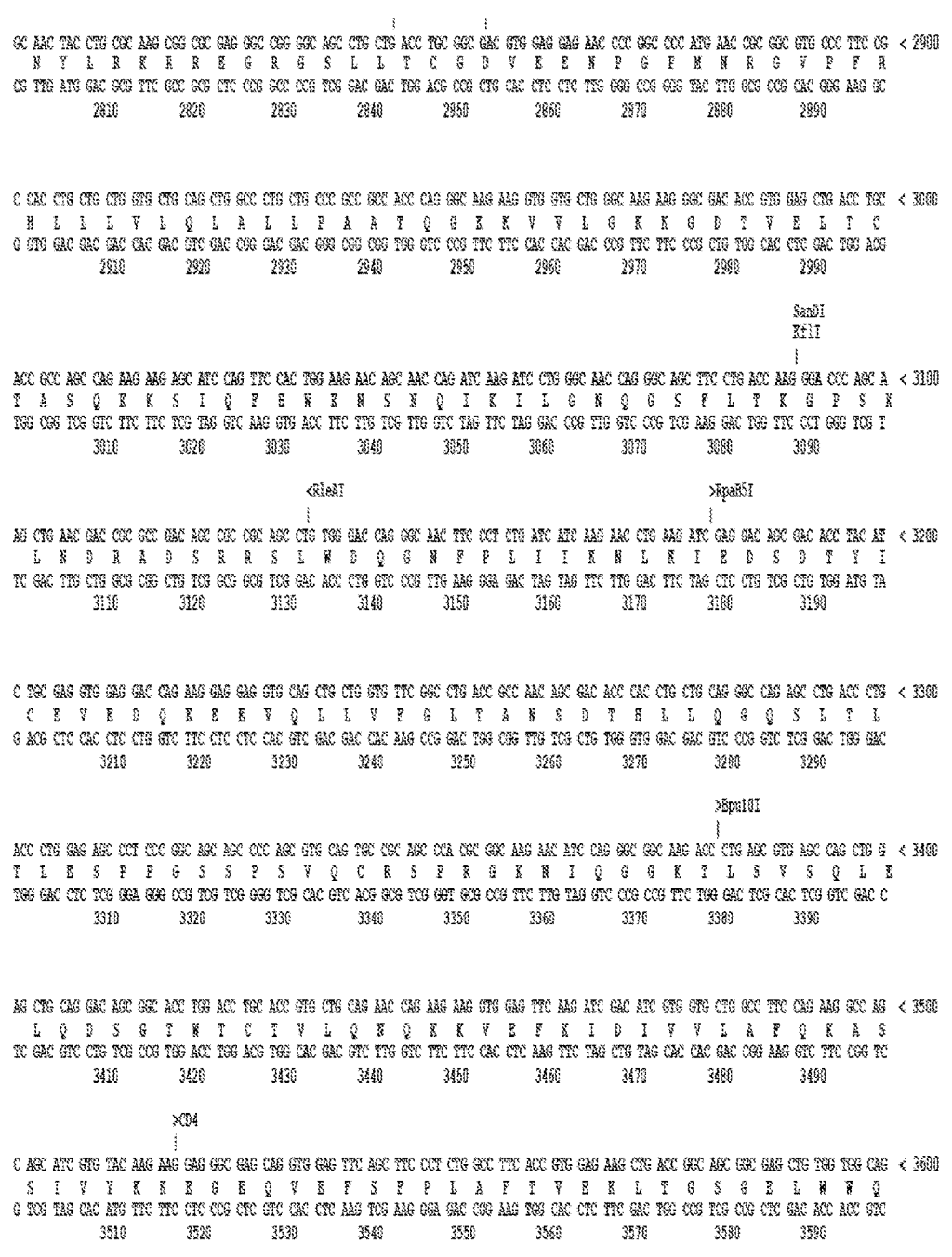
Figure 33F:
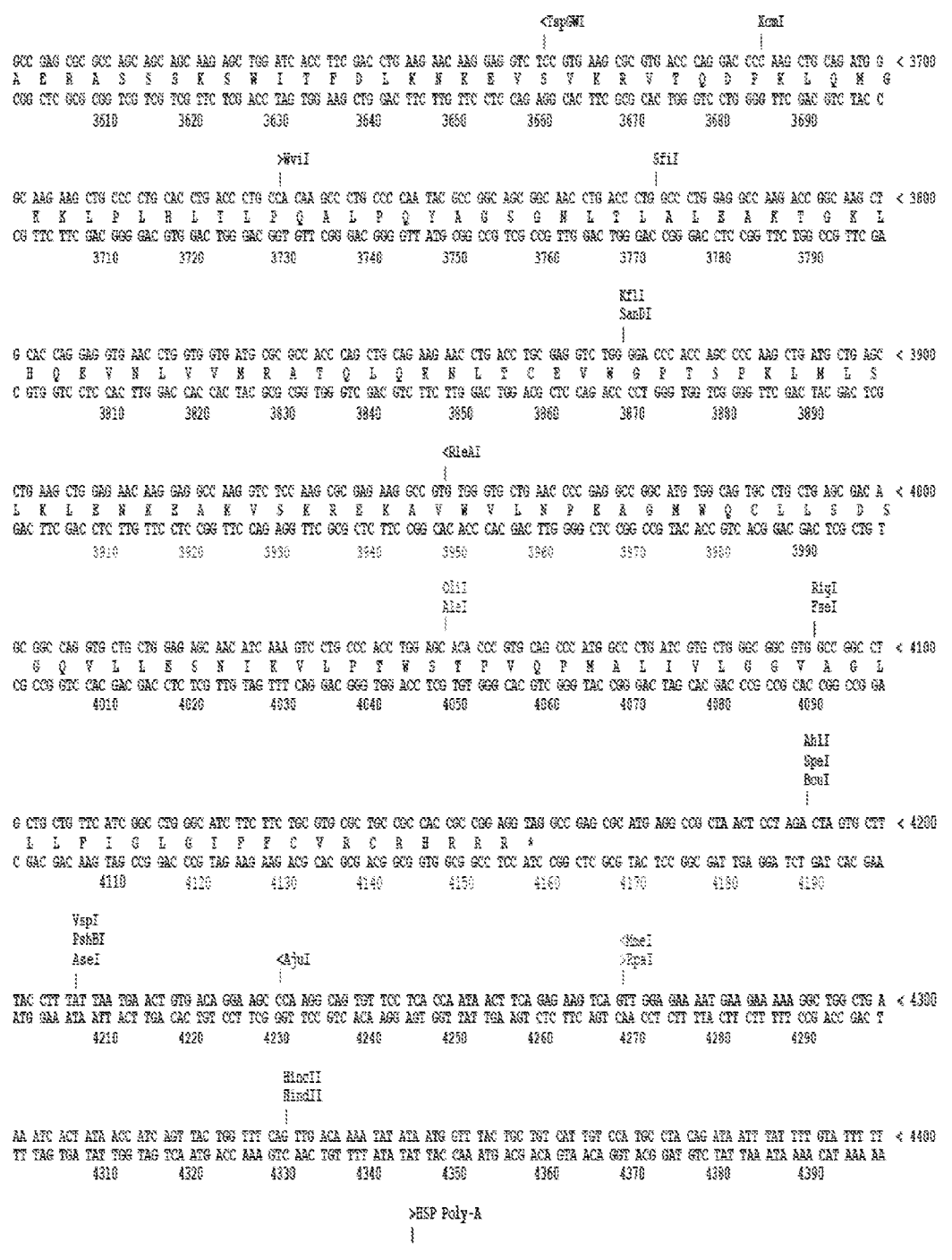
Figure 33G:
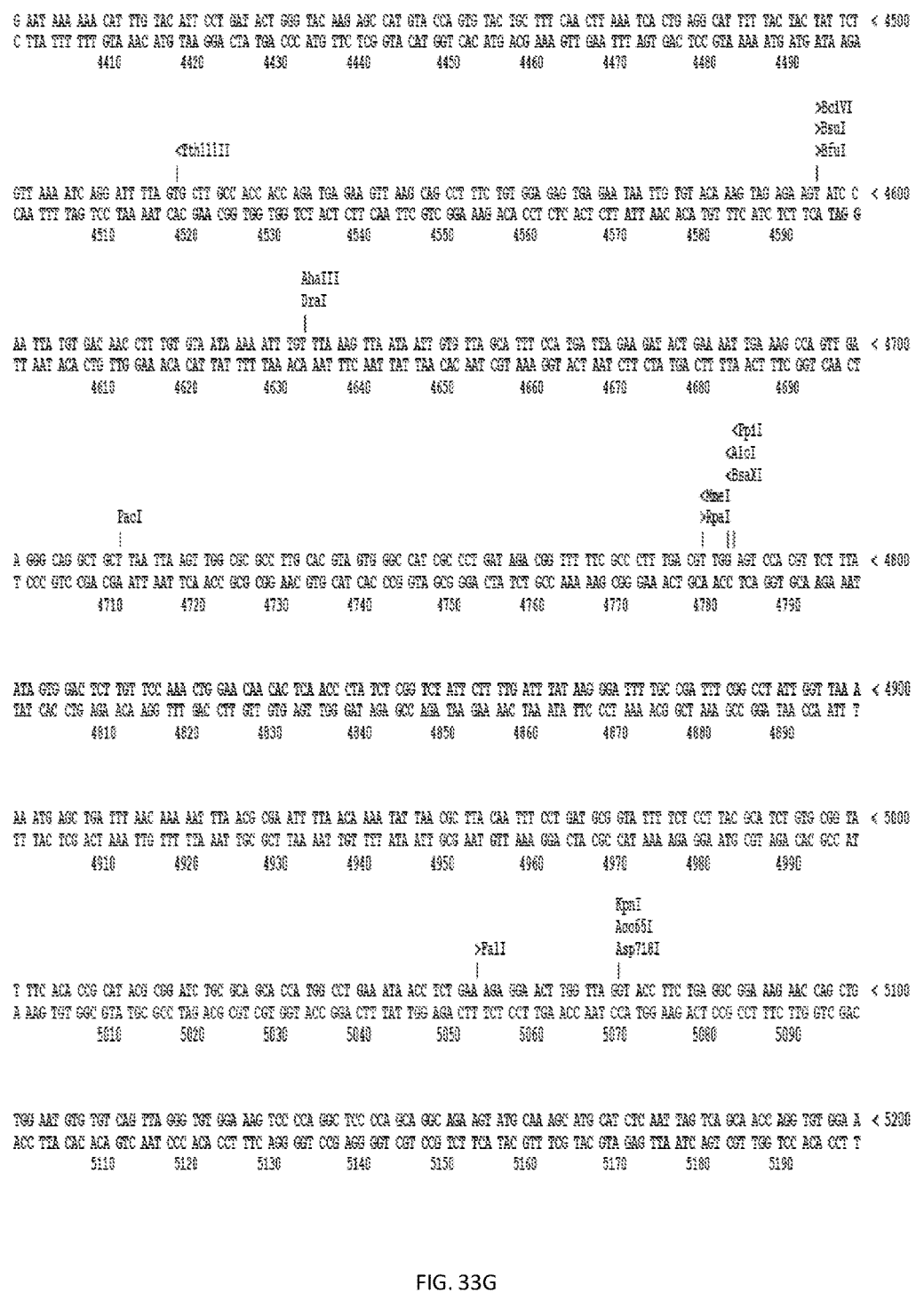
Figure 33H:
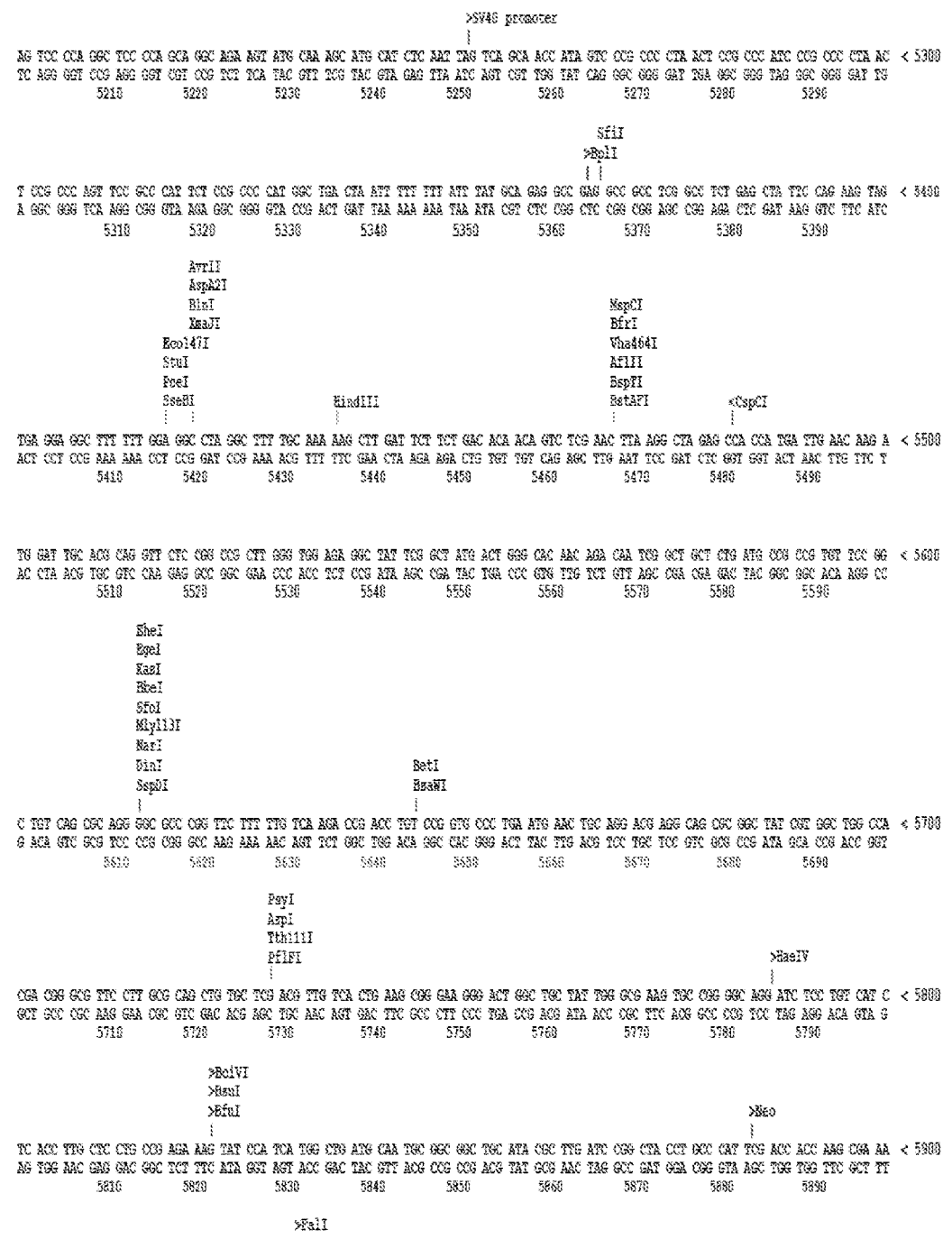
Figure 33I:
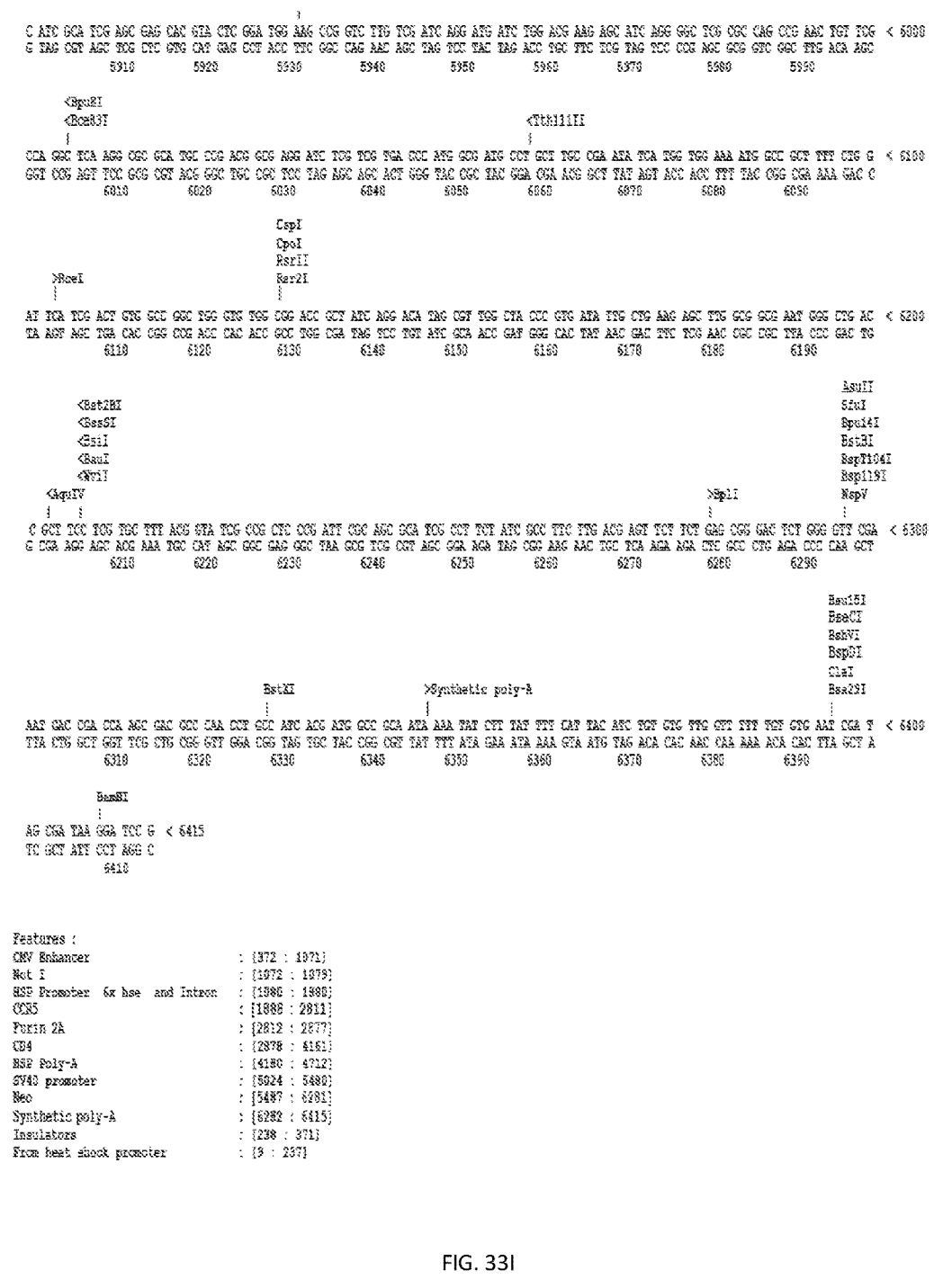

FIGS. 33A-33I. Sequence annotation of VERO-hCD4/CCR5 gene. A restriction map of the Vert construct shows restriction enzymes cutting a maximum of two times, using RELibrary as a restriction enzyme library. FIGS. 33A-33I disclose the top nucleic acid sequence as SEQ ID NO: 7 and the coded protein sequence as SEQ ID NO: 8.

Figure 34:

FIG. 34. Gene design: VERO-CD4/CCR5 Cell Line (VERT). VERO-hCD4/CCR5: Transgenic Vero cells expression human CD4 and CCR5 receptors. sVERT3: Transgenic Vero cells expression simian CD4 and CCR5 receptors.

Figure 35:
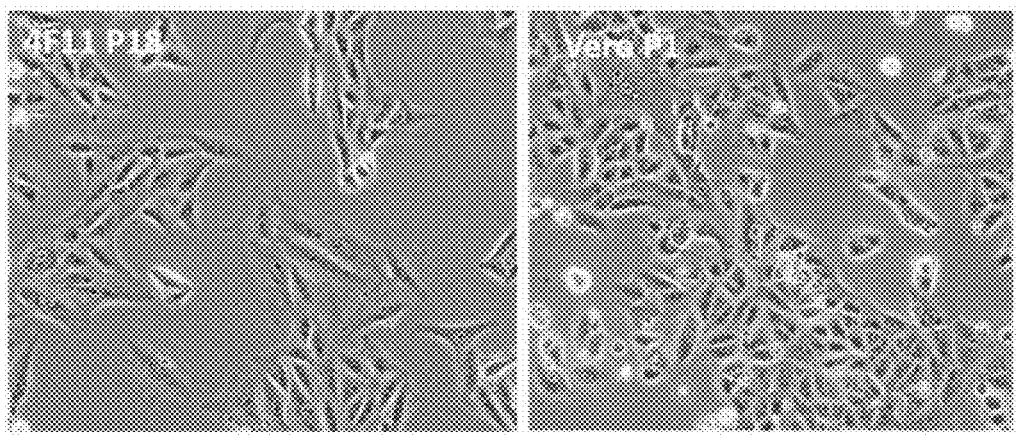

FIG. 35. VERO-hCD4/CCR5 clone 4F11 resembles the Vero cell.

Figure 36:
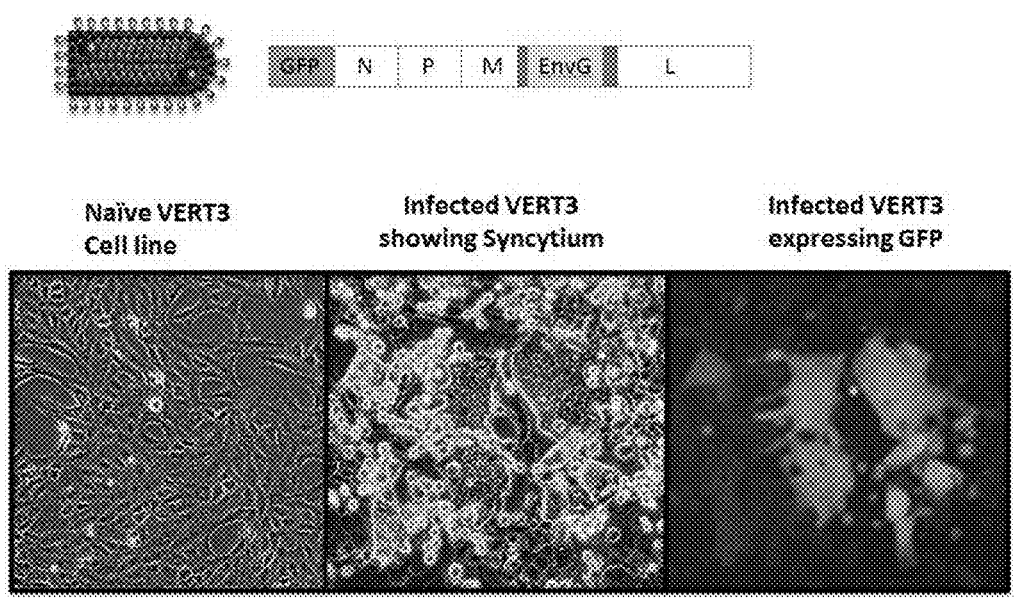

FIG. 36. VERO-hCD4/CCR5 cytopathic effect when infected by VSV chimera.

Figure 37:
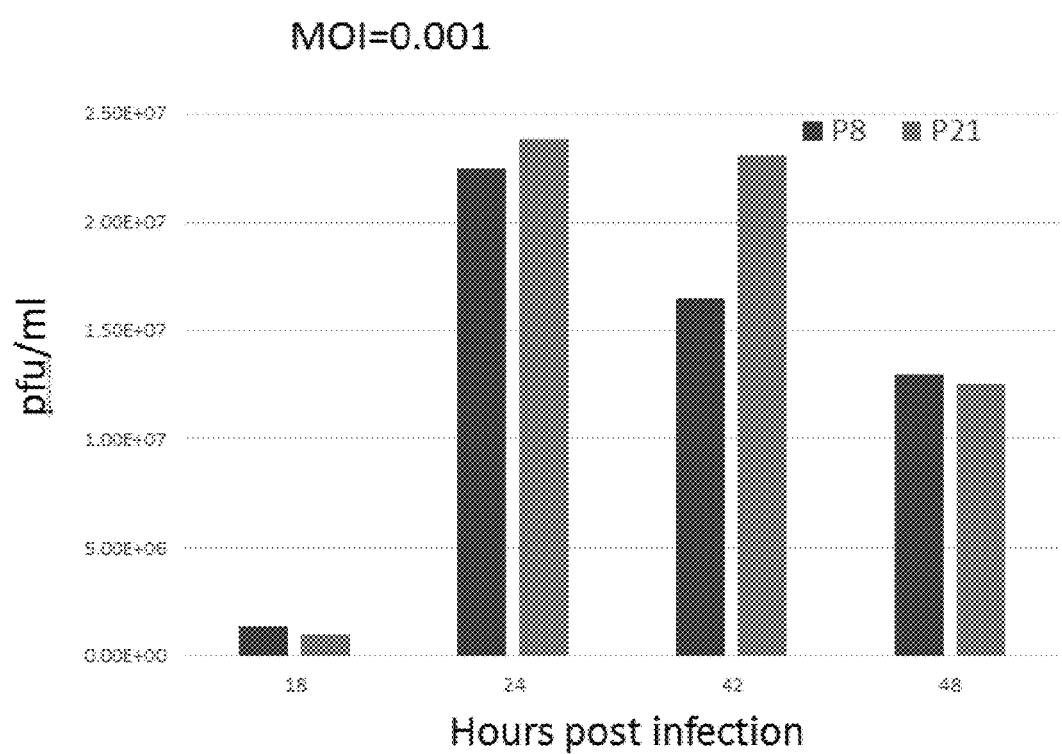

FIG. 37. VERO-hCD4/CCR5 maintains infectivity over 20 passages.

Figure 38:
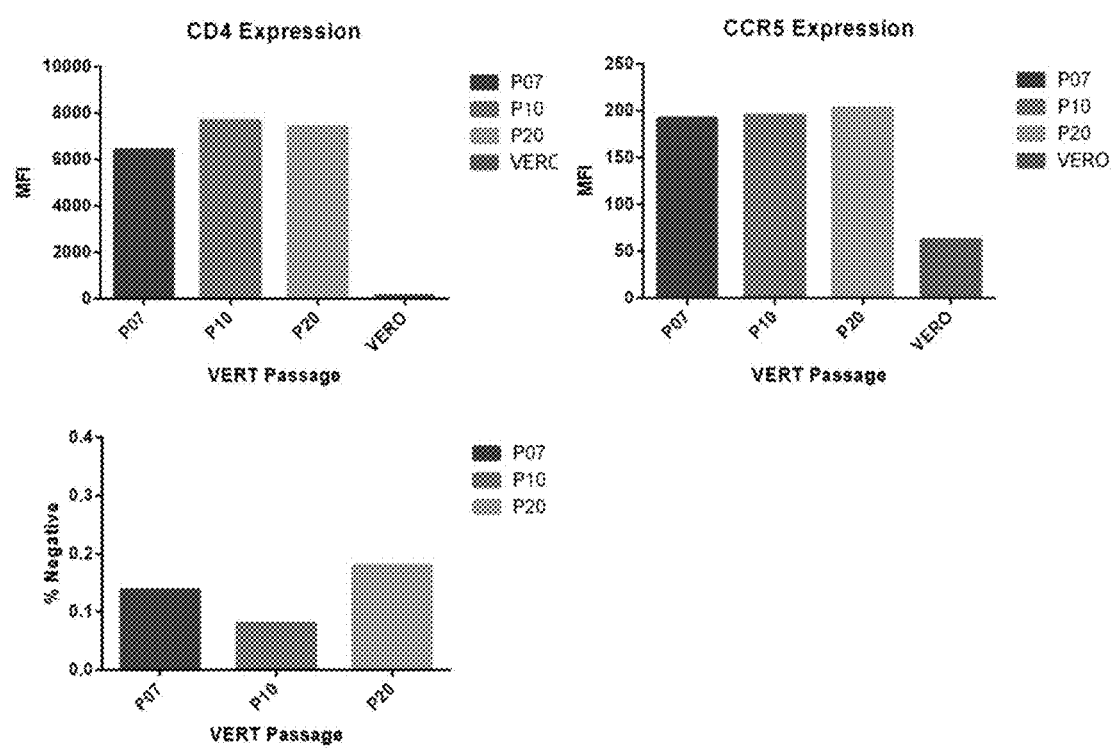

FIG. 38. VERO-hCD4/CCR5 maintains the receptor expression over 20 passages.

DETAILED DESCRIPTION

The terms "protein", "peptide", "polypeptide", and "amino acid sequence" are used interchangeably herein to refer to polymers of amino acid residues of any length. The polymer may be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

As used herein, the terms "antigen" or "immunogen" are used interchangeably to refer to a substance, typically a protein, which is capable of inducing an immune response in a subject. The term also refers to proteins that are immunologically active in the sense that once administered to a subject (either directly or by administering to the subject a nucleotide sequence or vector that encodes the protein) is able to evoke an immune response of the humoral and/or cellular type directed against that protein.

The term "antibody" includes intact molecules as well as fragments thereof, such as Fab, F(ab')$_2$, Fv and scFv which are capable of binding the epitope determinant. These antibody fragments retain some ability to selectively bind with its antigen or receptor and include, for example:

(i) Fab, the fragment which contains a monovalent antigen-binding fragment of an antibody molecule can be produced by digestion of whole antibody with the enzyme papain to yield an intact light chain and a portion of one heavy chain;

(ii) Fab', the fragment of an antibody molecule can be obtained by treating whole antibody with pepsin, followed by reduction, to yield an intact light chain and a portion of the 20 heavy chain; two Fab' fragments are obtained per antibody molecule;

(iii) F(ab')$_2$, the fragment of the antibody that can be obtained by treating whole antibody with the enzyme pepsin without subsequent reduction; F(ab')$_2$ is a dimer of two Fab' fragments held together by two disulfide bonds;

(iv) scFv, including a genetically engineered fragment containing the variable region of a heavy and a light chain as a fused single chain molecule.

General methods of making these fragments are known in the art. (See for example, Harlow and Lane, Antibodies: A Laboratory Manual, Cold Spring Harbor Laboratory, New York (1988), which is incorporated herein by reference).

It should be understood that the proteins, including the proteins of the invention may differ from the exact sequences illustrated and described herein. Thus, the invention contemplates deletions, additions and substitutions to the sequences shown, so long as the sequences function in accordance with the methods of the invention. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. It is reasonably predictable that an isolated replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the sequences illustrated and described but possessing minor amino acid substitutions that do not substantially affect the immunogenicity of the protein are, therefore, within the scope of the invention.

As used herein the terms "nucleotide sequences" and "nucleic acid sequences" refer to deoxyribonucleic acid (DNA) or ribonucleic acid (RNA) sequences, including, without limitation, messenger RNA (mRNA), DNA/RNA hybrids, or synthetic nucleic acids. The nucleic acid can be single-stranded, or partially or completely double-stranded (duplex). Duplex nucleic acids can be homoduplex or heteroduplex.

As used herein the term "transgene" may be used to refer to "recombinant" nucleotide sequences that may be derived from any of the nucleotide sequences encoding the proteins of the present invention. The term "recombinant" means a nucleotide sequence that has been manipulated "by man" and which does not occur in nature, or is linked to another nucleotide sequence or found in a different arrangement in nature. It is understood that manipulated "by man" means manipulated by some artificial means, including by use of machines, codon optimization, restriction enzymes, etc.

For example, in one embodiment the nucleotide sequences may be mutated such that the activity of the encoded proteins in vivo is abrogated. For example, each of the Gag, Pol, Env, Nef, RT, and Int sequences of the invention may be altered in these ways.

As regards codon optimization, the nucleic acid molecules of the invention have a nucleotide sequence that encodes the antigens of the invention and can be designed to employ codons that are used in the genes of the subject in which the antigen is to be produced. Many viruses, including HIV and other lentiviruses, use a large number of rare codons and, by altering these codons to correspond to codons commonly used in the desired subject, enhanced expression of the antigens can be achieved. In a preferred embodiment, the codons used are "humanized" codons, i.e., the codons are those that appear frequently in highly expressed human genes (Andre et al., J. Virol. 72:1497-1503, 1998) instead of those codons that are frequently used by HIV. Such codon usage provides for efficient expression of the transgenic HIV proteins in human cells. Any suitable method of codon optimization may be used. Such methods, and the selection of such methods, are well known to those of skill in the art. In addition, there are several companies that will optimize codons of sequences, such as Geneart (geneart.com). Thus, the nucleotide sequences of the invention can readily be codon optimized.

Advantageously, Applicants codon optimize the Env gene so it has the codon bias that is characteristic of VSV. This also results in a relatively low Guanine+ Cytosine content of about 40-45%. See, e.g., Rabinovich et al., PLoS One. 2014 Sep. 12; 9(9):e106597. doi: 10.1371/journal.pone.0106597. eCollection 2014.

The invention further encompasses nucleotide sequences encoding functionally and/or antigenically equivalent variants and derivatives of the antigens of the invention and functionally equivalent fragments thereof. These functionally equivalent variants, derivatives, and fragments display the ability to retain antigenic activity. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide.

Conservative amino acid substitutions are glycine/alanine; valine/isoleucine/leucine; asparagine/glutamine; aspartic acid/glutamic acid; serine/threonine/methionine; lysine/arginine; and phenylalanine/tyrosine/tryptophan. In one embodiment, the variants have at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% homology or identity to the antigen, epitope, immunogen, peptide or polypeptide of interest.

For the purposes of the present invention, sequence identity or homology is determined by comparing the sequences when aligned so as to maximize overlap and identity while minimizing sequence gaps. In particular, sequence identity may be determined using any of a number of mathematical algorithms. A nonlimiting example of a mathematical algorithm used for comparison of two sequences is the algorithm of Karlin & Altschul, Proc. Natl. Acad. Sci. USA 1990; 87: 2264-2268, modified as in Karlin & Altschul, Proc. Natl. Acad. Sci. USA 1993; 90: 5873-5877.

Another example of a mathematical algorithm used for comparison of sequences is the algorithm of Myers & Miller, CABIOS 1988; 4: 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman, Proc. Natl. Acad. Sci. USA 1988; 85: 2444-2448.

Advantageous for use according to the present invention is the WU-BLAST (Washington University BLAST) version 2.0 software. WU-BLAST version 2.0 executable programs for several UNIX platforms can be downloaded from ftp://blast.wustl.edu/blast/executables. This program is based on WU-BLAST version 1.4, which in turn is based on the public domain NCBI-BLAST version 1.4 (Altschul & Gish, 1996, Local alignment statistics, Doolittle ed., Methods in Enzymology 266: 460-480; Altschul et al., Journal of Molecular Biology 1990; 215: 403-410; Gish & States, 1993; Nature Genetics 3: 266-272; Karlin & Altschul, 1993; Proc. Natl. Acad. Sci. USA 90: 5873-5877; all of which are incorporated by reference herein).

The various recombinant nucleotide sequences and proteins of the invention are made using standard recombinant DNA and cloning techniques. Such techniques are well known to those of skill in the art. See for example, "Molecular Cloning: A Laboratory Manual", second edition (Sambrook et al. 1989).

The nucleotide sequences of the present invention may be inserted into "vectors." The term "vector" is widely used and understood by those of skill in the art, and as used herein the term "vector" is used consistent with its meaning to those of skill in the art. For example, the term "vector" is commonly used by those skilled in the art to refer to a vehicle that allows or facilitates the transfer of nucleic acid molecules from one environment to another or that allows or facilitates the manipulation of a nucleic acid molecule.

Any vector that allows expression of the proteins of the present invention may be used in accordance with the present invention. In certain embodiments, the antigens and/or antibodies of the present invention may be used in vitro (such as using cell-free expression systems) and/or in cultured cells grown in vitro in order to produce the encoded antigens, such as HIV-antigens, and/or antibodies which may then be used for various applications such as in the production of proteinaceous vaccines. For such applications, any vector that allows expression of the antigens and/or antibodies in vitro and/or in cultured cells may be used.

For applications where it is desired that the proteins be expressed in vivo, for example when the transgenes of the invention are used in DNA or DNA-containing vaccines, any vector that allows for the expression of the proteins of the present invention and is safe for use in vivo may be used. In preferred embodiments the vectors used are safe for use in humans, mammals and/or laboratory animals.

For the proteins of the present invention to be expressed, the protein coding sequence should be "operably linked" to regulatory or nucleic acid control sequences that direct transcription and translation of the protein. As used herein, a coding sequence and a nucleic acid control sequence or promoter are said to be "operably linked" when they are covalently linked in such a way as to place the expression or transcription and/or translation of the coding sequence under the influence or control of the nucleic acid control sequence. The "nucleic acid control sequence" can be any nucleic acid element, such as, but not limited to promoters, enhancers, IRES, introns, and other elements described herein that direct the expression of a nucleic acid sequence or coding sequence that is operably linked thereto. The term "promoter" will be used herein to refer to a group of transcriptional control modules that are clustered around the initiation site for RNA polymerase II and that when operationally linked to the protein coding sequences of the invention lead to the expression of the encoded protein. The expression of the transgenes of the present invention can be under the control of a constitutive promoter or of an inducible promoter, which initiates transcription only when exposed to some particular external stimulus, such as, without limitation, antibiotics such as tetracycline, hormones such as ecdysone, or heavy metals. The promoter can also be specific to a particular cell-type, tissue or organ. Many suitable promoters and enhancers are known in the art, and any such suitable promoter or enhancer may be used for expression of the transgenes of the invention. For example, suitable promoters and/or enhancers can be selected from the Eukaryotic Promoter Database (EPDB).

The present invention relates to a Vero cell line transformed with and expressing a cluster of differentiation 4 (CD4) receptor and a C-C chemokine receptor type 5 (CCR5 receptor).

The Vero cell lineage was isolated from kidney epithelial cells extracted from an African green monkey (*Chlorocebus* sp.; formerly called *Cercopithecus aethiops*, this group of monkeys has been split into several different species). The genome sequence was determined by Osada N, Kohara A, Yamaji T, Hirayama N, Kasai F, Sekizuka T, Kuroda M, Hanada K (2014). "The genome landscape of the African green monkey kidney-derived Vero cell line". DNA Research. 21: 673-83. doi:10.1093/dnares/dsu029. The ATCC supplies various different Vero cells under catalog numbers CCL-81, CCL-81.2, CRL-1586 and CRL-1587. Vero cells support the growth of pathogens such as: pneumoviruses, such as RSV-A and RSV-B; human metapneumoviruses (HMPV); morbilliviruses, such as measles virus; paramyxoviruses, such as mumps virus and parainfluenza virus; rubellavirus; human and avian coronaviruses; picornaviruses, such as entroviruses, echoviruses and coxsackie viruses, and porcine SVDV and Teschen-Talfan virus; mammalian and avian reoviruses; herpesviruses, such as HSV-1 and HSV-2; simian and human adenoviruses; varicella zoster virus (VZV); polyomaviruses, such as JC, BK and SV-40; bimaviruses, such as gumborovirus; porcine circoviruses; canine parvovirus; and *Chlamydia*.

CD4 is a co-receptor that assists the T cell receptor (TCR) in communicating with an antigen-presenting cell. Using its intracellular domain, CD4 amplifies the signal generated by the TCR by recruiting an enzyme, the tyrosine kinase Lck, which is essential for activating many molecular components of the signaling cascade of an activated T cell. Various types of T helper cells are thereby produced. CD4 also interacts directly with MHC class II molecules on the surface of the antigen-presenting cell using its extracellular domain. The extracellular domain adopts an immunoglobulin-like beta-sandwich with seven strands in 2 beta sheets, in a Greek key topology.

During antigen presentation, both the TCR complex and CD4 are recruited to bind to different regions of the MHCII molecule (α1/β1 and β2, respectively). Close proximity between the TCR complex and CD4 in this situation means the Lck kinase bound to the cytoplasmic tail of CD4 is able to tyrosine-phosphorylate the Immunoreceptor tyrosine activation motifs (ITAM) present on the cytoplasmic domains of CD3. Phosphorylated ITAM motifs on CD3 recruits and activates SH2 domain-containing protein tyrosine kinases (PTK) such as Zap70 to further mediate downstream signal transduction via tyrosine phosphorylation, leading to transcription factor activation including NF-κB and consequent T cell activation.

Human CD4 amino acid sequences may be found, for example, in Crise et al., J. Virol. 64:5585-5593(1990); Lusso et al., Proc. Natl. Acad. Sci. U.S.A. 91:3872-3876(1994); Sharma et al., Biochemistry 44:16192-16202(2005); Lindwasser et al., Curr. Mol. Med. 7:171-184(2007) and Kwong et al., Nature 393:648-659(1998).

Simian CD4 amino acid sequences may be found, for example, in Fomsgaard et al., Eur J Immunol. 1992 November; 22(11):2973-81.

C-C chemokine receptor type 5, also known as CCR5 or CD195, is a protein on the surface of white blood cells that is involved in the immune system as it acts as a receptor for chemokines. This is the process by which T cells are attracted to specific tissue and organ targets. Many forms of HIV, the virus that causes AIDS, initially use CCR5 to enter and infect host cells.

Human CD4 amino acid sequences may be found, for example, in Rizzuto et al., Science 280:1949-1953(1998) and Schnur et al., J. MOl. Biol. 410:778-797(2011).

Simian CD4 amino acid sequences may be found, for example, in Kunstman et al., J Virol. 2003 November; 77(22): 12310-12318.

In an advantageous embodiment, HIV-1 utilizes CD4 to gain entry into host T-cells and achieves this through viral envelope protein gp120. The binding to CD4 creates a shift in the conformation of gp120 allowing HIV-1 to bind to a CCR5 or CXCR4 co-receptor expressed on the host cell. Following a structural change in viral protein gp41, HIV inserts a fusion peptide into the host cell that allows the outer membrane of the virus to fuse with the cell membrane.

The present invention relates to a recombinant vesicular stomatitis virus (VSV) vector expressing a foreign epitope. Advantageously, the epitope is an HIV epitope. Any HIV epitope may be expressed in a VSV vector. Advantageously, the HIV epitope is an HIV antigen, HIV epitope or an HIV immunogen, such as, but not limited to, the HIV antigens, HIV epitopes or HIV immunogens of U.S. Pat. Nos. 7,341,731; 7,335,364; 7,329,807; 7,323,553; 7,320,859; 7,311,920; 7,306,798; 7,285,646; 7,285,289; 7,285,271; 7,282,364; 7,273,695; 7,270,997; 7,262,270; 7,244,819; 7,244,575; 7,232,567; 7,232,566; 7,223,844; 7,223,739; 7,223,534; 7,223,368; 7,220,554; 7,214,530; 7,211,659; 7,211,432; 7,205,159; 7,198,934; 7,195,768; 7,192,555; 7,189,826; 7,189,522; 7,186,507; 7,179,645; 7,175,843; 7,172,761; 7,169,550; 7,157,083; 7,153,509; 7,147,862; 7,141,550; 7,129,219; 7,122,188; 7,118,859; 7,118,855; 7,118,751; 7,118,742; 7,105,655; 7,101,552; 7,097,971 7,097,842; 7,094,405; 7,091,049; 7,090,648; 7,087,377; 7,083,787; 7,070,787; 7,070,781; 7,060,273; 7,056,521; 7,056,519; 7,049,136; 7,048,929; 7,033,593; 7,030,094; 7,022,326; 7,009,037; 7,008,622; 7,001,759; 6,997,863; 6,995,008; 6,979,535; 6,974,574; 6,972,126; 6,969,609; 6,964,769; 6,964,762; 6,958,158; 6,956,059; 6,953,689; 6,951,648; 6,946,075; 6,927,031; 6,919,319; 6,919,318; 6,919,077; 6,913,752; 6,911,315; 6,908,617; 6,908,612; 6,902,743; 6,900,010; 6,893,869; 6,884,785; 6,884,435; 6,875,435; 6,867,005; 6,861,234; 6,855,539; 6,841,381 6,841,345; 6,838,477; 6,821,955; 6,818,392; 6,818,222; 6,815,217; 6,815,201; 6,812,026; 6,812,025; 6,812,024; 6,808,923; 6,806,055; 6,803,231; 6,800,613; 6,800,288; 6,797,811; 6,780,967; 6,780,598; 6,773,920; 6,764,682; 6,761,893; 6,753,015; 6,750,005; 6,737,239; 6,737,067; 6,730,304; 6,720,310; 6,716,823; 6,713,301; 6,713,070; 6,706,859; 6,699,722; 6,699,656; 6,696,291; 6,692,745; 6,670,181; 6,670,115; 6,664,406; 6,657,055; 6,657,050; 6,656,471; 6,653,066; 6,649,409; 6,649,372; 6,645,732; 6,641,816; 6,635,469; 6,613,530; 6,605,427; 6,602,709 6,602,705; 6,600,023; 6,596,477; 6,596,172; 6,593,103; 6,593,079; 6,579,673; 6,576,758; 6,573,245; 6,573,040; 6,569,418; 6,569,340; 6,562,800; 6,558,961; 6,551,828; 6,551,824; 6,548,275; 6,544,780; 6,544,752; 6,544,728; 6,534,482; 6,534,312; 6,534,064; 6,531,572; 6,531,313; 6,525,179; 6,525,028; 6,524,582; 6,521,449; 6,518,030; 6,518,015; 6,514,691; 6,514,503; 6,511,845; 6,511,812; 6,511,801; 6,509,313; 6,506,384; 6,503,882; 6,495,676; 6,495,526; 6,495,347; 6,492,123; 6,489,131; 6,489,129; 6,482,614; 6,479,286; 6,479,284; 6,465,634; 6,461,615 6,458,560; 6,458,527; 6,458,370; 6,451,601; 6,451,592; 6,451,323; 6,436,407; 6,432,633; 6,428,970; 6,428,952; 6,428,790; 6,420,139; 6,416,997; 6,410,318; 6,410,028; 6,410,014; 6,407,221; 6,406,710; 6,403,092; 6,399,295; 6,392,013; 6,391,657; 6,384,198; 6,380,170; 6,376,170; 6,372,426; 6,365,187; 6,358,739; 6,355,248; 6,355,247; 6,348,450; 6,342,372; 6,342,228; 6,338,952; 6,337,179; 6,335,183; 6,335,017; 6,331,404; 6,329,202; 6,329,173; 6,328,976; 6,322,964; 6,319,666; 6,319,665; 6,319,500; 6,319,494; 6,316,205; 6,316,003; 6,309,633; 6,306,625 6,296,807; 6,294,322; 6,291,239; 6,291,157; 6,287,568; 6,284,456; 6,284,194; 6,274,337; 6,270,956; 6,270,769; 6,268,484; 6,265,562; 6,265,149; 6,262,029; 6,261,762; 6,261,571; 6,261,569; 6,258,599; 6,258,358; 6,248,332; 6,245,331; 6,242,461; 6,241,986; 6,235,526; 6,235,466; 6,232,120; 6,228,361; 6,221,579; 6,214,862; 6,214,804; 6,210,963; 6,210,873; 6,207,185; 6,203,974; 6,197,755; 6,197,531; 6,197,496; 6,194,142; 6,190,871; 6,190,666; 6,168,923; 6,156,302; 6,153,408; 6,153,393; 6,153,392; 6,153,378; 6,153,377; 6,146,635; 6,146,614; 6,143,876 6,140,059; 6,140,043; 6,139,746; 6,132,992; 6,124,306; 6,124,132; 6,121,006; 6,120,990; 6,114,507; 6,114,143; 6,110,466; 6,107,020; 6,103,521; 6,100,234; 6,099,848; 6,099,847; 6,096,291; 6,093,405; 6,090,392; 6,087,476; 6,083,903; 6,080,846; 6,080,725; 6,074,650; 6,074,646; 6,070,126; 6,063,905; 6,063,564; 6,060,256; 6,060,064; 6,048,530; 6,045,788; 6,043,347; 6,043,248; 6,042,831; 6,037,165; 6,033,672; 6,030,772; 6,030,770; 6,030,618; 6,025,141;

6,025,125; 6,020,468; 6,019,979; 6,017,543; 6,017,537; 6,015,694; 6,015,661; 6,013,484; 6,013,432 6,007,838; 6,004,811; 6,004,807; 6,004,763; 5,998,132; 5,993,819; 5,989,806; 5,985,926; 5,985,641; 5,985,545; 5,981,537; 5,981,505; 5,981,170; 5,976,551; 5,972,339; 5,965,371; 5,962,428; 5,962,318; 5,961,979; 5,961,970; 5,958,765; 5,958,422; 5,955,647; 5,955,342; 5,951,986; 5,951,975; 5,942,237; 5,939,277; 5,939,074; 5,935,580; 5,928,930; 5,928,913; 5,928,644; 5,928,642; 5,925,513; 5,922,550; 5,922,325; 5,919,458; 5,916,806; 5,916,563; 5,914,395; 5,914,109; 5,912,338; 5,912,176; 5,912,170; 5,906,936; 5,895,650; 5,891,623; 5,888,726; 5,885,580 5,885,578; 5,879,685; 5,876,731; 5,876,716; 5,874,226; 5,872,012; 5,871,747; 5,869,058; 5,866,694; 5,866,341; 5,866,320; 5,866,319; 5,866,137; 5,861,290; 5,858,740; 5,858,647; 5,858,646; 5,858,369; 5,858,368; 5,858,366; 5,856,185; 5,854,400; 5,853,736; 5,853,725; 5,853,724; 5,852,186; 5,851,829; 5,851,529; 5,849,475; 5,849,288; 5,843,728; 5,843,723; 5,843,640; 5,843,635; 5,840,480; 5,837,510; 5,837,250; 5,837,242; 5,834,599; 5,834,441; 5,834,429; 5,834,256; 5,830,876; 5,830,641; 5,830,475; 5,830,458; 5,830,457; 5,827,749; 5,827,723; 5,824,497 5,824,304; 5,821,047; 5,817,767; 5,817,754; 5,817,637; 5,817,470; 5,817,318; 5,814,482; 5,807,707; 5,804,604; 5,804,371; 5,800,822; 5,795,955; 5,795,743; 5,795,572; 5,789,388; 5,780,279; 5,780,038; 5,776,703; 5,773,260; 5,770,572; 5,766,844; 5,766,842; 5,766,625; 5,763,574; 5,763,190; 5,762,965; 5,759,769; 5,756,666; 5,753,258; 5,750,373; 5,747,641; 5,747,526; 5,747,028; 5,736,320; 5,736,146; 5,733,760; 5,731,189; 5,728,385; 5,721,095; 5,716,826; 5,716,637; 5,716,613; 5,714,374; 5,709,879; 5,709,860; 5,709,843; 5,705,331; 5,703,057; 5,702,707 5,698,178; 5,688,914; 5,686,078; 5,681,831; 5,679,784; 5,674,984; 5,672,472; 5,667,964; 5,667,783; 5,665,536; 5,665,355; 5,660,990; 5,658,745; 5,658,569; 5,643,756; 5,641,624; 5,639,854; 5,639,598; 5,637,677; 5,637,455; 5,633,234; 5,629,153; 5,627,025; 5,622,705; 5,614,413; 5,610,035; 5,607,831; 5,606,026; 5,601,819; 5,597,688; 5,593,972; 5,591,829; 5,591,823; 5,589,466; 5,587,285; 5,585,254; 5,585,250; 5,580,773; 5,580,739; 5,580,563; 5,573,916; 5,571,667; 5,569,468; 5,558,865; 5,556,745; 5,550,052; 5,543,328; 5,541,100; 5,541,057; 5,534,406 5,529,765; 5,523,232; 5,516,895; 5,514,541; 5,510,264; 5,500,161; 5,480,967; 5,480,966; 5,470,701; 5,468,606; 5,462,852; 5,459,127; 5,449,601; 5,447,838; 5,447,837; 5,439,809; 5,439,792; 5,418,136; 5,399,501; 5,397,695; 5,391,479; 5,384,240; 5,374,519; 5,374,518; 5,374,516; 5,364,933; 5,359,046; 5,356,772; 5,354,654; 5,344,755; 5,335,673; 5,332,567; 5,320,940; 5,317,009; 5,312,902; 5,304,466; 5,296,347; 5,286,852; 5,268,265; 5,264,356; 5,264,342; 5,260,308; 5,256,767; 5,256,561; 5,252,556; 5,230,998; 5,230,887; 5,227,159; 5,225,347; 5,221,610, 5,217,861; 5,208,321; 5,206,136; 5,198,346; 5,185,147; 5,178,865; 5,173,400; 5,173,399; 5,166,050; 5,156,951, 5,135,864; 5,122,446; 5,120,662; 5,103,836; 5,100,777; 5,100,662; 5,093,230; 5,077,284; 5,070,010; 5,068,174; 5,066,782; 5,055,391; 5,043,262; 5,039,604; 5,039,522; 5,030,718; 5,030,555; 5,030,449; 5,019,387; 5,013,556; 5,008,183; 5,004,697; 4,997,772; 4,983,529; 4,983,387; 4,965,069; 4,945,082; 4,921,787; 4,918,166; 4,900,548; 4,888,290; 4,886,742; 4,885,235; 4,870,003; 4,869,903; 4,861,707; 4,853,326; 4,839,288; 4,833,072 and 4,795,739.

The vector of the present invention advantageously encodes for an Env.BG505 immunogen which may be encoded by a VSVΔG-Env.BG505 vaccine. The immunogen advantageously has the sequence as provided in SEQ ID NO: 2.

In another embodiment, the vector of the present invention may comprise a sequence of a VSVΔG-Env.BG505 genomic clone. The genomic clone advantageously has the sequence as provided as SEQ ID NO: 1.

Advantageously, the HIV epitope may be an Env precursor or gp160 epitope or immunogen. The Env precursor or gp160 epitope may be recognized by antibodies PG9, PG16, 2G12, b12, 15 2F5, 4E10, Z13, or other broad potent neutralizing antibodies.

Adaptive mutations emerged in Env during vector rescue and propagation that increased Env-dependent replication in VeroCD4/CCR5 cells (human CD4/CCR5) (see, e.g., FIG. 15). The substitutions are stable and included in vaccine vector tested in macaques. The 'adapted virus' is advanced as a genomic DNA clone containing these coding changes and has been show to support rescue of recombinant virus. Therefore, the present invention also encompasses mutations of env that may increase Env-dependent replication and/or contribute to immunogenicity. The Env-VSV G hybrid (EnvG) mutations may include mutations of the lysine at AA position 169, the isoleucine at AA position 307 and/or the tryptophan at AA position 672. In an especially advantageous embodiment, the mutations are K169T, I307T and/or W672R. Other env mutations may be at P493, M343, K168, E168, Q440 and/or L494. In an advantageous embodiment, the mutations may be M343T, K168E, E168K, E164G, Q440R and/or L494F. see, e.g., Hoffenberg et al., J. Virol. May 2013 vol. 87 no. 10 5372-5383 for Env sequences and alignments.

In another embodiment, HIV, or immunogenic fragments thereof, may be utilized as the HIV epitope. For example, the HIV nucleotides of U.S. Pat. Nos. 7,393,949, 7,374,877 7,306,901, 7,303,754, 7,173,014, 7,122,180, 7,078,516, 7,022,814, 6,974,866, 6,958,211, 6,949,337, 6,946,254, 6,896,900, 6,887,977, 6,870,045, 6,803,187, 6,794,129, 6,773,915, 6,768,004, 6,706,268, 6,696,291, 6,692,955, 6,656,706, 6,649,409, 6,627,442, 6,610,476, 6,602,705, 6,582,920, 6,557,296, 6,531,587, 6,531,137, 6,500,623, 6,448,078, 6,429,306, 6,420,545, 6,410,013, 6,407,077, 6,395,891, 6,355,789, 6,335,158, 6,323,185, 6,316,183, 6,303,293, 6,300,056, 6,277,561, 6,270,975, 6,261,564, 6,225,045, 6,222,024, 6,194,391, 6,194,142, 6,162,631, 6,114,167, 6,114,109, 6,090,392, 6,060,587, 6,057,102, 6,054,565, 6,043,081, 6,037,165, 6,034,233, 6,033,902, 6,030,769, 6,020,123, 6,015,661, 6,010,895, 6,001,555, 5,985,661, 5,980,900, 5,972,596, 5,939,538, 5,912,338, 5,869,339, 5,866,701, 5,866,694, 5,866,320, 5,866,137, 5,864,027, 5,861,242, 5,858,785, 5,858,651, 5,849,475, 5,843,638, 5,840,480, 5,821,046, 5,801,056, 5,786,177, 5,786,145, 5,773,247, 5,770,703, 5,756,674, 5,741,706, 5,705,612, 5,693,752, 5,688,637, 5,688,511, 5,684,147, 5,665,577, 5,585,263, 5,578,715, 5,571,712, 5,567,603, 5,554,528, 5,545,726, 5,527,895, 5,527,894, 5,223,423, 5,204,259, 5,144,019, 5,051,496 and 4,942,122 are useful for the present invention.

Any epitope recognized by an anti-HIV antibody may be used in the present invention. For example, the anti-HIV antibodies of U.S. Pat. Nos. 6,949,337, 6,900,010, 6,821, 744, 6,768,004, 6,613,743, 6,534,312, 6,511,830, 6,489,131, 6,242,197, 6,114,143, 6,074,646, 6,063,564, 6,060,254, 5,919,457, 5,916,806, 5,871,732, 5,824,304, 5,773,247, 5,736,320, 5,637,455, 5,587,285, 5,514,541, 5,317,009, 4,983,529, 4,886,742, 4,870,003 and 4,795,739 are useful for the present invention. Furthermore, monoclonal anti-HIV antibodies of U.S. Pat. Nos. 7,074,556, 7,074,554, 7,070,787, 7,060,273, 7,045,130, 7,033,593, RE39,057, 7,008,622, 6,984,721, 6,972,126, 6,949,337, 6,946,465, 6,919,077, 6,916,475, 6,911,315, 6,905,680, 6,900,010, 6,825,217, 6,824,975, 6,818,392, 6,815,201, 6,812,026, 6,812,024, 6,797,811, 6,768,004, 6,703,019, 6,689,118, 6,657,050, 6,608,179, 6,600,023, 6,596,497, 6,589,748, 6,569,143, 6,548,275, 6,525,179, 6,524,582, 6,506,384, 6,498,006, 6,489,131, 6,465,173, 6,461,612, 6,458,933, 6,432,633, 6,410,318, 6,406,701, 6,395,275, 6,391,657, 6,391,635, 6,384,198, 6,376,170, 6,372,217, 6,344,545, 6,337,181, 6,329,202, 6,319,665, 6,319,500, 6,316,003, 6,312,931, 6,309,880, 6,296,807, 6,291,239, 6,261,558, 6,248,514, 6,245,331, 6,242,197, 6,241,986, 6,228,361, 6,221,580, 6,190,871, 6,177,253, 6,146,635, 6,146,627, 6,146,614, 6,143,876, 6,132,992, 6,124,132, RE36,866, 6,114,143, 6,103,238, 6,060,254, 6,039,684, 6,030,772, 6,020,468, 6,013,484, 6,008,044, 5,998,132, 5,994,515, 5,993,812, 5,985,545, 5,981,278, 5,958,765, 5,939,277, 5,928,930, 5,922,325, 5,919,457, 5,916,806, 5,914,109, 5,911,989, 5,906,936, 5,889,158, 5,876,716, 5,874,226, 5,872,012, 5,871,732, 5,866,694, 5,854,400, 5,849,583, 5,849,288, 5,840,480, 5,840,305, 5,834,599, 5,831,034, 5,827,723, 5,821,047, 5,817,767, 5,817,458, 5,804,440, 5,795,572, 5,783,670, 5,776,703, 5,773,225, 5,766,944, 5,753,503, 5,750,373, 5,747,641, 5,736,341, 5,731,189, 5,707,814, 5,702,707, 5,698,178, 5,695,927, 5,665,536, 5,658,745, 5,652,138, 5,645,836, 5,635,345, 5,618,922, 5,610,035, 5,607,847, 5,604,092, 5,601,819, 5,597,896, 5,597,688, 5,591,829, 5,558,865, 5,514,541, 5,510,264, 5,478,753, 5,374,518, 5,374,516, 5,344,755, 5,332,567, 5,300,433, 5,296,347, 5,286,852, 5,264,221, 5,260,308, 5,256,561, 5,254,457, 5,230,998, 5,227,159, 5,223,408, 5,217,895, 5,180,660, 5,173,399, 5,169,752, 5,166,050, 5,156,951, 5,140,105, 5,135,864, 5,120,640, 5,108,904, 5,104,790, 5,049,389, 5,030,718, 5,030,555, 5,004,697, 4,983,529, 4,888,290, 4,886,742 and 4,853,326, are also useful for the present invention.

The vectors used in accordance with the present invention should typically be chosen such that they contain a suitable gene regulatory region, such as a promoter or enhancer, such that the proteins of the invention can be expressed.

For example, when the aim is to express the proteins of the invention in vitro, or in cultured cells, or in any prokaryotic or eukaryotic system for the purpose of producing the protein(s), then any suitable vector can be used depending on the application. For example, plasmids, viral vectors, bacterial vectors, protozoal vectors, insect vectors, baculovirus expression vectors, yeast vectors, mammalian cell vectors, and the like, can be used. Suitable vectors can be selected by the skilled artisan taking into consideration the characteristics of the vector and the requirements for expressing the proteins under the identified circumstances.

When the aim is to express the proteins of the invention in vivo in a subject, for example in order to generate an immune response against an antigen and/or protective immunity, expression vectors that are suitable for expression on that subject, and that are safe for use in vivo, should be chosen. In an advantageous embodiment, the antigen is an HIV-antigen. For example, in some embodiments it may be desired to express the proteins of the invention in a laboratory animal, such as for pre-clinical testing of the immunogenic compositions and vaccines of the invention. In other embodiments, it will be desirable to express the proteins of the invention in human subjects, such as in clinical trials and for actual clinical use of the immunogenic compositions and vaccine of the invention. Any vectors that are suitable for such uses can be employed, and it is well within the capabilities of the skilled artisan to select a suitable vector. In some embodiments it may be preferred that the vectors used for these in vivo applications are attenuated to vector from amplifying in the subject. For example, if plasmid vectors are used, preferably they will lack an origin of replication that functions in the subject so as to enhance safety for in vivo use in the subject. If viral vectors are used, preferably they are attenuated or replication-defective in the subject, again, so as to enhance safety for in vivo use in the subject.

In preferred embodiments of the present invention viral vectors are used. Viral expression vectors are well known to those skilled in the art and include, for example, viruses such as adenoviruses, adeno-associated viruses (AAV), alphaviruses, herpesviruses, retroviruses and poxviruses, including avipox viruses, attenuated poxviruses, vaccinia viruses, and particularly, the modified vaccinia Ankara virus (MVA; ATCC Accession No. VR-1566). Such viruses, when used as expression vectors are innately non-pathogenic in the selected subjects such as humans or have been modified to render them non-pathogenic in the selected subjects. For example, replication-defective adenoviruses and alphaviruses are well known and can be used as gene delivery vectors.

The present invention relates to recombinant vesicular stomatitis (VSV) vectors, however, other vectors may be contemplated in other embodiments of the invention such as, but not limited to, prime boost administration which may comprise administration of a recombinant VSV vector in combination with another recombinant vector expressing one or more HIV epitopes.

VSV is a very practical, safe, and immunogenic vector for conducting animal studies, and an attractive candidate for developing vaccines for use in humans. VSV is a member of the Rhabdoviridae family of enveloped viruses containing a nonsegmented, negative-sense RNA genome. The genome is composed of 5 genes arranged sequentially 3'-N-P-M-G-L-5', each encoding a polypeptide found in mature virions. Notably, the surface glycoprotein G is a transmembrane polypeptide that is present in the viral envelope as a homotrimer, and like Env, it mediates cell attachment and infection.

General procedures for recovery of non-segmented negative-stranded RNA viruses according to the invention can be summarized as follows. A cloned DNA equivalent (which is positive-strand, message sense) of the desired viral genome is placed between a suitable DNA-dependent RNA polymerase promoter (e.g., a T7, T3 or SP6 RNA polymerase promoter) and a self-cleaving ribozyme sequence (e.g., the hepatitis delta ribozyme) which is inserted into a suitable transcription vector (e.g. a propagatable bacterial plasmid). This transcription vector provides the readily manipulable DNA template from which the RNA polymerase (e.g., T7 RNA polymerase) can faithfully transcribe a single-stranded RNA copy of the viral antigenome (or genome) with the precise, or nearly precise, 5' and 3' termini. The orientation of the viral DNA copy of the genome and the flanking promoter and ribozyme sequences determine whether antigenome or genome RNA equivalents are transcribed.

Also required for rescue of new virus progeny according to the invention are virus-specific trans-acting support proteins needed to encapsidate the naked, single-stranded viral antigenome or genome RNA transcripts into functional nucleocapsid templates. These generally include the viral nucleocapsid (N) protein, the polymerase-associated phosphoprotein (P) and the polymerase (L) protein.

Functional nucleocapsid serves as a template for genome replication, transcription of all viral mRNAs, and accumulation of viral proteins, triggering ensuing events in the viral replication cycle including virus assembly and budding. The mature virus particles contain the viral RNA polymerase necessary for further propagation in susceptible cells.

Certain attenuated viruses selected for rescue require the addition of support proteins, such as G and M for virus assembly and budding. For example, the attenuated VSV may be a propagation-defective VSV vector comprising a deletion of sequence encoding either all of the G protein ($\Delta$G) or most of the G protein ectodomain (Gstem). Both $\Delta$G and Gstem are unable to spread beyond primary infected cells in vivo. This results in a virus that can propagate only in the presence of transcomplementing G protein. Typically, although not necessarily exclusively, rescue of non-segmented negative-stranded RNA viruses also requires an RNA polymerase to be expressed in host cells carrying the viral cDNA, to drive transcription of the cDNA-containing transcription vector and of the vectors encoding the support proteins. Within the present invention, rescue of attenuated VSV typically involves transfecting host cells with: a viral cDNA expression vector containing a polynucleotide encoding a genome or antigenome of the attenuated VSV; one or more support plasmids encoding N, P, L and G proteins of VSV; and a plasmid encoding a DNA-dependent RNA polymerase, such as T7 RNA polymerase. The VSV G protein encoded by the support plasmid employed during viral rescue may be encoded by a native VSV G gene. However, the VSV G protein of a support plasmid used during viral rescue may be encoded by an optimized VSV G gene. In some embodiments, the cells are also transfected with a support plasmid encoding an M protein of VSV. The transfected cells are grown in culture, and attenuated VSV is rescued from the culture. The rescued material may then be co-cultured with plaque expansion cells for further viral expansion, as described in further detail below.

The host cells used for viral rescue are often impaired in their ability to support further viral expansion. Therefore, the method of producing attenuated VSV in a cell culture typically further includes infecting plaque expansion cells with the rescued, attenuated VSV. In some embodiments of the present invention, cells expressing VSV G protein encoded by an optimized VSV G gene are infected with the rescued attenuated VSV; the infected cells are grown; and the attenuated VSV is recovered from the culture of infected cells.

In some embodiments of viral rescue, the polynucleotide encoding the genome or antigenome of the attenuated VSV is introduced into the cell in the form of a viral cDNA expression vector that includes the polynucleotide operatively linked to an expression control sequence to direct synthesis of RNA transcripts from the cDNA expression vector. In some embodiments, the expression control sequence is a suitable DNA-dependent RNA polymerase promoter (e.g., a 17, T3 or SP6 RNA polymerase promoter). In some embodiments, the support plasmids, as well as the viral cDNA expression vector used during viral rescue are under the control of a promoter of the DNA-dependent RNA polymerase. For example, in embodiments where the RNA polymerase is T7 RNA polymerase, the support plasmids and the viral cDNA expression vector would preferably be under the control of a T7 promoter. In some other embodiments, the expression of the DNA-dependent RNA polymerase is under the control of a cytomegalovirus-derived RNA polymerase Il promoter. The immediate-early human cytomegalovirus [hCMV] promoter and enhancer is described, for e.g., in U.S. Pat. No. 5,168,062, incorporated herein by reference.

In some embodiments, the method for recovering attenuated VSV from cDNA involves introducing a viral cDNA expression vector encoding a genome or antigenome of the subject virus into a host cell, and coordinately introducing: a polymerase expression vector encoding and directing expression of an RNA polymerase. Useful RNA polymerases in this context include, but are not limited to, a T7, T3, or SP6 phage polymerase. The host cells also express, before, during, or after coordinate introduction of the viral cDNA expression vector, the polymerase expression vector and the N, P, L, M and G support proteins necessary for production of mature attenuated VSV particles in the host cell. Typically, the viral cDNA expression vector and polymerase expression vector will be coordinately transfected into the host cell with one or more additional expression vector(s) that encode(s) and direct(s) expression of the support proteins. The support proteins may be wild-type or mutant proteins of the virus being rescued, or may be selected from corresponding support protein(s) of a heterologous non-segmented negative-stranded RNA virus. In alternate embodiments, additional viral proteins may be co-expressed in the host cell, for example a polymerase elongation factor (such as M2-1 for RSV) or other viral proteins that may enable or enhance recovery or provide other desired results within the subject methods and compositions. In other embodiments, one or more of the support protein(s) may be expressed in the host cell by constitutively expressing the protein(s) in the host cell, or by co-infection of the host cell with a helper virus encoding the support protein(s).

The viral cDNA vector is introduced into a host cell transiently expressing an RNA polymerase and the following VSV support proteins: an N protein, a P protein, an L protein, an M protein and a G protein. Each of the RNA polymerase and the N, P, L, M and G proteins may be expressed from one or more transfected expression vector(s). Often, each of the RNA polymerase and the support proteins will be expressed from separate expression vectors, commonly from transient expression plasmids. Following a sufficient time and under suitable conditions, an assembled infectious, attenuated VSV is rescued from the host cells.

To produce infectious, attenuated VSV particles from a cDNA-expressed genome or antigenome, the genome or antigenome is coexpressed with those viral proteins necessary to produce a nucleocapsid capable of RNA replication, and render progeny nucleocapsids competent for both RNA replication and transcription. Such viral proteins include the N, P and L proteins. In the instant invention, attenuated VSV vectors with lost G function also require the addition of the G viral protein. Moreover, an M protein may also be added for a productive infection. The G and M viral proteins can be supplied by coexpression. In some embodiments, the VSV G support plasmid employed during viral rescue contains a non-optimized VSV G gene. However, in other embodiments, as described below, the VSV G support plasmid employed during viral rescue contains an optimized VSV G gene.

In certain embodiments of the invention, complementing sequences encoding proteins necessary to generate a transcribing, replicating viral nucleocapsid (i.e., L, P and N), as well as the M and G proteins are provided by expression plasmids. In other embodiments, such proteins are provided by one or more helper viruses. Such helper viruses can be wild type or mutant. In certain embodiments, the helper virus can be distinguished phenotypically from the virus encoded by the recombinant viral cDNA. For example, it may be desirable to provide monoclonal antibodies that react immunologically with the helper virus but not the virus encoded by the recombinant viral cDNA. Such antibodies can be neutralizing antibodies. In some embodiments, the antibodies can be used in affinity chromatography to separate the helper virus from the recombinant virus. To aid the procurement of such antibodies, mutations can be introduced into the viral cDNA to provide antigenic diversity from the helper virus, such as in a glycoprotein gene.

A recombinant viral genome or antigenome may be constructed for use in the present invention by, e.g., assembling cloned cDNA segments, representing in aggregate the complete genome or antigenome, by polymerase chain reaction or the like (PCR; described in, e.g., U.S. Pat. Nos. 4,683,195 and 4,683,202, and PCR Protocols: A Guide to Methods and Applications, Innis et al., eds., Academic Press, San Diego, 1990) of reverse-transcribed copies of viral mRNA or genome RNA. For example, a first construct may be generated which comprises cDNAs containing the left hand end of the antigenome, spanning from an appropriate promoter (e.g., T7, T3, or SP6 RNA polymerase promoter) and assembled in an appropriate expression vector (such as a plasmid, cosmid, phage, or DNA virus vector). The vector may be modified by mutagenesis and/or insertion of a synthetic polylinker containing unique restriction sites designed to facilitate assembly. The right hand end of the antigenome plasmid may contain additional sequences as desired, such as a flanking ribozyme and single or tandem T7 transcriptional terminators. The ribozyme can be hammerhead type, which would yield a 3' end containing a single nonviral nucleotide, or can be any of the other suitable ribozymes such as that of hepatitis delta virus (Perrotta et al., Nature 350:434-436, 1991) that would yield a 31 end free of non-viral nucleotides.

Alternative means to construct cDNA encoding the viral genome or antigenome include reverse transcription-PCR using improved PCR conditions (e.g., as described in Cheng et al., Proc. Natl. Acad. Sci. USA 91/5695-5699, 1994, incorporated herein by reference) to reduce the number of subunit cDNA components to as few as one or two pieces. In other embodiments different promoters can be used (e.g., T3 or SPQ). Different DNA vectors (e.g., cosmids) can be used for propagation to better accommodate the larger size genome or antigenome.

As noted above, defined mutations can be introduced into an infectious viral clone by a variety of conventional techniques (e.g., site-directed mutagenesis) into a cDNA copy of the genome or antigenome. The use of genomic or antigenomic cDNA subfragments to assemble a complete genome or antigenome cDNA as described herein has the advantage that each region can be manipulated separately, where small cDNA constructs provide for better ease of manipulation than large cDNA constructs, and then readily assembled into a complete cDNA.

Certain of the attenuated viruses of the invention will be constructed or modified to limit the growth potential, replication competence, or infectivity of the recombinant virus. Such attenuated viruses and subviral particles are useful as vectors and immunogens, but do not pose certain risks that would otherwise attend administration of a fully infectious (i.e., having approximately a wild-type level of growth and/or replication competence) virus to a host. By attenuated, it is meant a virus or subviral particle that is limited in its ability to grow or replicate in a host cell or a mammalian subject, or is otherwise defective in its ability to infect and/or propagate in or between cells. By way of example, ΔG and G stem are attenuated viruses that are propagation-defective, but replication competent. Often, attenuated viruses and subviral particles will be employed as "vectors", as described in detail herein below.

Thus, various methods and compositions are provided for producing attenuated VSV particles. In more detailed embodiments, the attenuated virus will exhibit growth, replication and/or infectivity characteristics that are substantially impaired in comparison to growth, replication and/or infectivity of a corresponding wild-type or parental virus. In this context, growth, replication, and/or infectivity may be impaired in vitro and/or in vivo by at least approximately 10-20%, 20-50%, 50-75% and up to 95% or greater compared to wild-type or parental growth, replication and/or infectivity levels. In some embodiments, viruses with varying degrees of growth or replication defects may be rescued using a combined heat shock/T7-plasmid rescue system described in detail below. Exemplary strains include highly attenuated strains of VSV that incorporate modifications as described below (e.g., a C-terminal G protein truncation, or translocated genes) (see, e.g., Johnson et al., J. Virol. 71:5060-5078, 1997, Schnell et al., Proc. Natl. Acad. Sci. USA 93:11359-11365, 1996; Schnell et al., Cell 90:849-857, 1997; Roberts et al., J. Virol. 72:4704-4711, 1998; and Rose et al., Cell 0.106:539-549, 2001, each incorporated herein by reference).

The VSVs of U.S. Pat. Nos. 7,468,274; 7,419,829; 7,419, 674; 7,344,838; 7,332,316; 7,329,807; 7,323,337; 7,259, 015; 7,244,818; 7,226,786; 7,211,247; 7,202,079; 7,198, 793; 7,198,784; 7,153,510; 7,070,994; 6,969,598; 6,958, 226; RE38,824; PP15,957; 6,890,735; 6,887,377; 6,867, 326; 6,867,036; 6,858,205; 6,835,568; 6,830,892; 6,818, 209; 6,790,641; 6,787,520; 6,743,620; 6,740,764; 6,740, 635; 6,740,320; 6,682,907; 6,673,784; 6,673,572; 6,669, 936; 6,653,103; 6,607,912; 6,558,923; 6,555,107; 6,533, 855; 6,531,123; 6,506,604; 6,500,623; 6,497,873; 6,489, 142; 6,410,316; 6,410,313; 6,365,713; 6,348,312; 6,326, 487; 6,312,682; 6,303,331; 6,277,633; 6,207,455; 6,200, 811; 6,190,650; 6,171,862; 6,143,290; 6,133,027; 6,121, 434; 6,103,462; 6,069,134; 6,054,127; 6,034,073; 5,969, 211; 5,935,822; 5,888,727; 5,883,081; 5,876,727; 5,858, 740; 5,843,723; 5,834,256; 5,817,491; 5,792,604; 5,789, 229; 5,773,003; 5,763,406; 5,760,184; 5,750,396; 5,739, 018; 5,698,446; 5,686,279; 5,670,354; 5,540,923; 5,512, 421; 5,090,194; 4,939,176; 4,738,846; 4,622,292; 4,556,556 and 4,396,628 may be contemplated by the present invention.

Canine distemper virus (CDV) is a member of the *Morbillivirus* genus, which also includes measles virus (MV), rinderpest virus (RPV), peste des petits ruminants virus and morbilliviruses that infect aquatic mammals. CDV infection has been observed in monkey colonies indicating that its host range can extend to, but so far, there is no conclusive evidence linking CDV to human disease in spite of its speculative association to illness of unknown etiology. Lab-adapted CDV has been injected into humans without causing symptoms of infection suggesting that humans are a non-permissive host for CDV, which is consistent with recent studies showing that mutations facilitating both entry and replication are needed for CDV to efficiently adapt to human cells.

CDV enters host cells through attachment of H to specific cell receptors and subsequent F-mediated fusion of viral envelope and cell membrane. Wild-type CDV isolates primarily target signaling lymphocyte activation molecule (SLAM) and nectin-4 positive cells while vaccine strains of CDV gain broader cell tropisms besides recognizing these two receptors (ref 1: The *morbillivirus* receptor SLAM (CD150). Tatsuo H, Yanagi Y. Microbiol Immunol. 2002; 46(3):135-42. Ref 2: Dog nectin-4 is an epithelial cell receptor for canine distemper virus that facilitates virus entry and syncytia formation. Noyce R S, Delpeut S, Richardson C D. Virology. 2013 Feb. 5; 436(1):210-20). Therefore, cell tropisms of CDV vectors differ depending on usage of wild-type or vaccine CDV H proteins. In addition, extra specificity determinants can be added to H protein ectodomain for specific cancer cell targeting and natural receptor interactions deactivated by H mutations, which has been developed in MV-based oncolytic vector research (ref: Paramyxovirus entry and targeted vectors for cancer therapy. Cattaneo R, PLoS Pathog. 2010 Jun. 24; 6(6)). Cell retargeting can also be achieved through F modifications. Because F function is activated after protease cleavage, paramyxovirus vectors including MV and Sendai virus can be modified to retarget cancer cells through cancer-specific cleavage of F (ref 1: Generation of a recombinant Sendai virus that is selectively activated and lyses human tumor cells expressing matrix metalloproteinases. Kinoh H, Inoue M, Washizawa K, Yamamoto T, Fujikawa S, et al. Gene Ther. 2004; 11:1137-1145. Ref 2: Oncolytic efficacy and enhanced safety of measles virus activated by tumor-secreted matrix metalloproteinases. Springfeld C, von Messling V, Frenzke M, Ungerechts G, Buchholz CJ, Cattaneo R. Cancer Res. 2006; 66:7694-7700). CDV polymerase protein L has genome transcription and replication functions. Modifications in L of vaccine or oncolytic CDV vectors can change viral replication ability, which can serve as a tool to modulate level of CDV attenuation (ref: Development of a challenge-protective vaccine concept by modification of the viral RNA-dependent RNA polymerase of canine distemper virus. Silin D, Lyubomska O, Ludlow M, Duprex W P, Rima BK. J Virol. 2007 December; 81(24): 13649-58).

Recombinant strains of CDV may be developed, for example, as described by, Miura R, Kooriyama T, Yoneda M, Takenaka A, Doki M, Goto Y, et al. (2015) Efficacy of Recombinant Canine Distemper Virus Expressing *Leishmania* Antigen against *Leishmania* Challenge in Dogs. PLoS Negl Trop Dis 9(7): e0003914. doi:10.1371/journal.pntd.0003914. Briefly, an antigen of interest may be introduced into a restriction site of a full-length cDNA of a CDV strain RNA genome. CDV rescue may be accomplished by transfecting HEK293 cells infected with MVA-TV with a full-genome plasmid, together with expression plasmids encoding viral nucleoprotein (N), phosphoprotein (P), and large protein (L) (pKS-N, pKS-P, and pGEM-L, respectively), using FuGENE6 Transfection Reagent (Invitrogen, Carlsbad, Calif., USA). Two days later, the transfected HEK293 cells were overlain with B95a cells. Syncytia formed by the rescued viruses were observed approximately 3 days later. The viruses were harvested, and their titers determined with the limiting dilution method and expressed as the 50% tissue culture infective dose ($TCID_{50}$).

The CDVs of U.S. Pat. Nos. 9,526,780; 9,505,812; 9,505,807; 9,327,137; 8,709,713; 8,309,531; 7,951,587; 6,664,066; 6,497,882; 6,368,603; 6,328,975; 6,309,647; 6,172,979; 5,843,456 and 5,756,102 may be contemplated by the present invention.

The nucleotide sequences and vectors of the invention can be delivered to cells, for example if aim is to express and the HIV-1 antigens in cells in order to produce and isolate the expressed proteins, such as from cells grown in culture. For expressing the proteins in cells any suitable transfection, transformation, or gene delivery methods can be used. Such methods are well known by those skilled in the art, and one of skill in the art would readily be able to select a suitable method depending on the nature of the nucleotide sequences, vectors, and cell types used. For example, transfection, transformation, microinjection, infection, electroporation, lipofection, or liposome-mediated delivery could be used. Expression of the proteins can be carried out in any suitable type of host cells, such as bacterial cells, yeast, insect cells, and mammalian cells. The proteins of the invention can also be expressed using including in vitro transcription/translation systems. All of such methods are well known by those skilled in the art, and one of skill in the art would readily be able to select a suitable method depending on the nature of the nucleotide sequences, vectors, and cell types used.

In preferred embodiments, the nucleotide sequences, proteins of the invention are administered in vivo, for example where the aim is to produce an immunogenic response in a subject. A "subject" in the context of the present invention may be any animal. For example, in some embodiments it may be desired to express the transgenes of the invention in a laboratory animal, such as for pre-clinical testing of the HIV-1 immunogenic compositions and vaccines of the invention. In other embodiments, it will be desirable to express the proteins of the invention in human subjects, such as in clinical trials and for actual clinical use of the immunogenic compositions and vaccine of the invention. In preferred embodiments the subject is a human, for example a human that is infected with, or is at risk of infection with, HIV-1.

For such in vivo applications the nucleotide sequences, proteins of the invention are preferably administered as a component of an immunogenic composition which may comprise the nucleotide sequences and/or antigens of the invention in admixture with a pharmaceutically acceptable carrier. The immunogenic compositions of the invention are useful to stimulate an immune response against HIV-1 and may be used as one or more components of a prophylactic or therapeutic vaccine against HIV-1 for the prevention, amelioration or treatment of AIDS. The nucleic acids and vectors of the invention are particularly useful for providing genetic vaccines, i.e. vaccines for delivering the nucleic acids encoding the proteins of the invention to a subject, such as a human, such that the proteins are then expressed in the subject to elicit an immune response.

The compositions of the invention may be injectable suspensions, solutions, sprays, lyophilized powders, syrups, elixirs and the like. Any suitable form of composition may be used. To prepare such a composition, a nucleic acid or vector of the invention, having the desired degree of purity, is mixed with one or more pharmaceutically acceptable carriers and/or excipients. The carriers and excipients must be "acceptable" in the sense of being compatible with the other ingredients of the composition. Acceptable carriers, excipients, or stabilizers are nontoxic to recipients at the dosages and concentrations employed, and include, but are not limited to, water, saline, phosphate buffered saline, dextrose, glycerol, ethanol, or combinations thereof, buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

An immunogenic or immunological composition can also be formulated in the form of an oil-in-water emulsion. The oil-in-water emulsion can be based, for example, on light liquid paraffin oil (European Pharmacopea type); isoprenoid oil such as squalane, squalene, EICOSANE™ or tetratetracontane; oil resulting from the oligomerization of alkene(s), e.g., isobutene or decene; esters of acids or of alcohols containing a linear alkyl group, such as plant oils, ethyl oleate, propylene glycol di(caprylate/caprate), glyceryl tri (caprylate/caprate) or propylene glycol dioleate; esters of branched fatty acids or alcohols, e.g., isostearic acid esters. The oil advantageously is used in combination with emulsifiers to form the emulsion. The emulsifiers can be nonionic surfactants, such as esters of sorbitan, mannide (e.g., anhydromannitol oleate), glycerol, polyglycerol, propylene glycol, and oleic, isostearic, ricinoleic, or hydroxystearic acid, which are optionally ethoxylated, and polyoxypropylene-polyoxyethylene copolymer blocks, such as the Pluronic® products, e.g., L121. The adjuvant can be a mixture of emulsifier(s), micelle-forming agent, and oil such as that which is commercially available under the name Provax® IDEC Pharmaceuticals, San Diego, Calif.).

The immunogenic compositions of the invention can contain additional substances, such as wetting or emulsifying agents, buffering agents, or adjuvants to enhance the effectiveness of the vaccines (Remington's Pharmaceutical Sciences, 18th edition, Mack Publishing Company, (ed.) 1980).

Adjuvants may also be included. Adjuvants include, but are not limited to, mineral salts (e.g., $AlK(SO_4)_2$, $AlNa(SO_4)_2$, $AlNH(SO_4)_2$, silica, alum, $Al(OH)_3$, $Ca_3(PO_4)_2$, kaolin, or carbon), polynucleotides with or without immune stimulating complexes (ISCOMs) (e.g., CpG oligonucleotides, such as those described in Chuang, T. H. et al, (2002) J. Leuk. Biol. 71(3): 538-44; Ahmad-Nejad, P. et al (2002) Eur. J. Immunol. 32(7): 1958-68; poly IC or poly AU acids, polyarginine with or without CpG (also known in the art as IC31; see Schellack, C. et al (2003) Proceedings of the 34th Annual Meeting of the German Society of Immunology; Lingnau, K. et al (2002) Vaccine 20(29-30): 3498-508), JuvaVax™ (U.S. Pat. No. 6,693,086), certain natural substances (e.g., wax D from *Mycobacterium tuberculosis*, substances found in *Cornyebacterium parvum, Bordetella pertussis*, or members of the genus *Brucella*), flagellin (Toll-like receptor 5 ligand; see McSorley, S. J. et al (2002) J. Immunol. 169(7): 3914-9), saponins such as QS21, QS17, and QS7 (U.S. Pat. Nos. 5,057,540; 5,650,398; 6,524,584; 6,645,495), monophosphoryl lipid A, in particular, 3-de-O-acylated monophosphoryl lipid A (3D-MPL), imiquimod (also known in the art as IQM and commercially available as Aldara®; U.S. Pat. Nos. 4,689,338; 5,238,944; Zuber, A. K. et al (2004) 22(13-14): 1791-8), and the CCR5 inhibitor CMPD167 (see Veazey, R. S. et al (2003) J. Exp. Med. 198: 1551-1562).

Aluminum hydroxide or phosphate (alum) are commonly used at 0.05 to 0.1% solution in phosphate buffered saline. Other adjuvants that can be used, especially with DNA vaccines, are cholera toxin, especially CTA1-DD/ISCOMs (see Mowat, A. M. et al (2001) J. Immunol. 167(6): 3398-405), polyphosphazenes (Allcock, H.R. (1998) App. Organometallic Chem. 12(10-11): 659-666; Payne, L. G. et al (1995) Pharm. Biotechnol. 6: 473-93), cytokines such as, but not limited to, IL-2, IL-4, GM-CSF, IL-12, IL-15 IGF-1, IFN-α, IFN-β, and IFN-γ (Boyer et al., (2002) J. Liposome Res. 121:137-142; WO01/095919), immunoregulatory proteins such as CD4OL (ADX40; see, for example, WO03/063899), and the CD1a ligand of natural killer cells (also known as CRONY or α-galactosyl ceramide; see Green, T. D. et al, (2003) J. Virol. 77(3): 2046-2055), immunostimulatory fusion proteins such as IL-2 fused to the Fc fragment of immunoglobulins (Barouch et al., Science 290:486-492, 2000) and co-stimulatory molecules B7.1 and B7.2 (Boyer), all of which can be administered either as proteins or in the form of DNA, on the same expression vectors as those encoding the antigens of the invention or on separate expression vectors.

In an advantageous embodiment, the adjuvants may be lecithin is combined with an acrylic polymer (Adjuplex-LAP), lecithin coated oil droplets in an oil-in-water emulsion (Adjuplex-LE) or lecithin and acrylic polymer in an oil-in-water emulsion (Adjuplex-LAO) (Advanced BioAdjuvants (ABA)).

The immunogenic compositions can be designed to introduce the nucleic acids or expression vectors to a desired site of action and release it at an appropriate and controllable rate. Methods of preparing controlled-release formulations are known in the art. For example, controlled release preparations can be produced by the use of polymers to complex or absorb the immunogen and/or immunogenic composition. A controlled-release formulation can be prepared using appropriate macromolecules (for example, polyesters, polyamino acids, polyvinyl, pyrrolidone, ethylenevinylacetate, methylcellulose, carboxymethylcellulose, or protamine sulfate) known to provide the desired controlled release characteristics or release profile. Another possible method to control the duration of action by a controlled-release preparation is to incorporate the active ingredients into particles of a polymeric material such as, for example, polyesters, polyamino acids, hydrogels, polylactic acid, polyglycolic acid, copolymers of these acids, or ethylene vinylacetate copolymers. Alternatively, instead of incorporating these active ingredients into polymeric particles, it is possible to entrap these materials into microcapsules prepared, for example, by coacervation techniques or by interfacial polymerization, for example, hydroxymethylcellulose or gelatin-microcapsule and poly-(methylmethacrylate) microcapsule, respectively, in colloidal drug delivery systems (for example, liposomes, albumin microspheres, microemulsions, nano-particles and nanocapsules) or in macroemulsions. Such techniques are disclosed in New Trends and Developments in Vaccines, Voller et al. (eds.), University Park Press, Baltimore, Md., 1978 and Remington's Pharmaceutical Sciences, 16th edition.

Suitable dosages of the nucleic acids and expression vectors of the invention (collectively, the immunogens) in the immunogenic composition of the invention can be readily determined by those of skill in the art. For example, the dosage of the immunogens can vary depending on the route of administration and the size of the subject. Suitable doses can be determined by those of skill in the art, for example by measuring the immune response of a subject, such as a labratry animal, using conventional immunological techniques, and adjusting the dosages as appropriate. Such techniques for measuring the immune response of the subject include but are not limited to, chromium release assays, tetramer binding assays, IFN-γ ELISPOT assays, IL-2 ELISPOT assays, intracellular cytokine assays, and other immunological detection assays, e.g., as detailed in the text "Antibodies: A Laboratory Manual" by Ed Harlow and David Lane.

When provided prophylactically, the immunogenic compositions of the invention are ideally administered to a subject in advance of HIV infection, or evidence of HIV infection, or in advance of any symptom due to AIDS, especially in high-risk subjects. The prophylactic administration of the immunogenic compositions can serve to provide protective immunity of a subject against HIV-1 infection or to prevent or attenuate the progression of AIDS in a subject already infected with HIV-1. When provided therapeutically, the immunogenic compositions can serve to ameliorate and treat AIDS symptoms and are advantageously used as soon after infection as possible, preferably before appearance of any symptoms of AIDS but may also be used at (or after) the onset of the disease symptoms.

The immunogenic compositions can be administered using any suitable delivery method including, but not limited to, intramuscular, intravenous, intradermal, mucosal, and topical delivery. Such techniques are well known to those of skill in the art. More specific examples of delivery methods are intramuscular injection, intradermal injection, and subcutaneous injection. However, delivery need not be limited to injection methods. Further, delivery of DNA to animal tissue has been achieved by cationic liposomes (Watanabe et al., (1994) Mol. Reprod. Dev. 38:268-274; and WO 96/20013), direct injection of naked DNA into animal muscle tissue (Robinson et al., (1993) Vaccine 11:957-960; Hoffman et al., (1994) Vaccine 12: 1529-1533; Xiang et al., (1994) Virology 199: 132-140; Webster et al., (1994) Vaccine 12: 1495-1498; Davis et al., (1994) Vaccine 12: 1503-1509; and Davis et al., (1993) Hum. Mol. Gen. 2: 1847-1851), or intradermal injection of DNA using "gene gun" technology (Johnston et al., (1994) Meth. Cell Biol. 43:353-365). Alternatively, delivery routes can be oral, intranasal or by any other suitable route. Delivery also be accomplished via a mucosal surface such as the anal, vaginal or oral mucosa.

Immunization schedules (or regimens) are well known for animals (including humans) and can be readily determined for the particular subject and immunogenic composition. Hence, the immunogens can be administered one or more times to the subject. Preferably, there is a set time interval between separate administrations of the immunogenic composition. While this interval varies for every subject, typically it ranges from 10 days to several weeks, and is often 2, 4, 6 or 8 weeks. For humans, the interval is typically from 2 to 6 weeks. The immunization regimes typically have from 1 to 6 administrations of the immunogenic composition, but may have as few as one or two or four. The methods of inducing an immune response can also include administration of an adjuvant with the immunogens. In some instances, annual, biannual or other long interval (5-10 years) booster immunization can supplement the initial immunization protocol.

The present methods also include a variety of prime-boost regimens, for example DNA prime-Adenovirus boost regimens. In these methods, one or more priming immunizations are followed by one or more boosting immunizations. The actual immunogenic composition can be the same or different for each immunization and the type of immunogenic composition (e.g., containing protein or expression vector), the route, and formulation of the immunogens can also be varied. For example, if an expression vector is used for the priming and boosting steps, it can either be of the same or different type (e.g., DNA or bacterial or viral expression vector). One useful prime-boost regimen provides for two priming immunizations, four weeks apart, followed by two boosting immunizations at 4 and 8 weeks after the last priming immunization. It should also be readily apparent to one of skill in the art that there are several permutations and combinations that are encompassed using the DNA, bacterial and viral expression vectors of the invention to provide priming and boosting regimens.

The prime-boost regimen can also include VSV vectors that derive their G protein protein from different serotype vesicular stomatitis viruses (Rose N F, Roberts A, Buonocore L, Rose J K. Glycoprotein exchange vectors based on vesicular stomatitis virus allow effective boosting and generation of neutralizing antibodies to a primary isolate of human immunodeficiency virus type 1. J Virol. 2000 December; 74(23):10903-10). The VSV vectors used in these examples contain a G protein derived from the Indiana serotype of VSV. Vectors can also be constructed to express epitopes in the context of G molecules derived from other VSV serotypes (i.e. vesicular stomatitis New Jersey virus or vesicular stomatitis Alagoas virus) or other vesiculoviruses (i.e. Chandipura virus, Cocal virus, Isfahan virus). Thus an epitope like the HIV MPER can be delivered in a prime in the context of a G molecule that is from the Indiana serotype and the immune system can be boosted with a vector that expresses epitopes in the context of second serotype like New Jersey. This circumvents anti-G immunity elicited by the prime, and helps focus the boost response against the foreign epitope.

A specific embodiment of the invention provides methods of inducing an immune response against HIV in a subject by administering an immunogenic composition of the invention, preferably which may comprise an adenovirus vector containing DNA encoding one or more of the epitopes of the invention, one or more times to a subject wherein the epitopes are expressed at a level sufficient to induce a specific immune response in the subject. Such immunizations can be repeated multiple times at time intervals of at least 2, 4 or 6 weeks (or more) in accordance with a desired immunization regime.

The immunogenic compositions of the invention can be administered alone, or can be co-administered, or sequentially administered, with other HIV immunogens and/or HIV immunogenic compositions, e.g., with "other" immunological, antigenic or vaccine or therapeutic compositions thereby providing multivalent or "cocktail" or combination compositions of the invention and methods of employing them. Again, the ingredients and manner (sequential or co-administration) of administration, as well as dosages can be determined taking into consideration such factors as the age, sex, weight, species and condition of the particular subject, and the route of administration.

When used in combination, the other HIV immunogens can be administered at the same time or at different times as part of an overall immunization regime, e.g., as part of a prime-boost regimen or other immunization protocol. In an advantageous embodiment, the other HIV immunogen is env, preferably the HIV env trimer.

Many other HIV immunogens are known in the art, one such preferred immunogen is HIVA (described in WO 01/47955), which can be administered as a protein, on a plasmid (e.g., pTHr.HIVA) or in a viral vector (e.g., MVA-.HIVA). Another such HIV immunogen is RENTA (described in PCT/US2004/037699), which can also be administered as a protein, on a plasmid (e.g., pTHr.RENTA) or in a viral vector (e.g., MVA.RENTA).

For example, one method of inducing an immune response against HIV in a human subject may comprise administering at least one priming dose of an HIV immunogen and at least one boosting dose of an HIV immunogen, wherein the immunogen in each dose can be the same or different, provided that at least one of the immunogens is an epitope of the present invention, a nucleic acid encoding an epitope of the invention or an expression vector, preferably a VSV vector, encoding an epitope of the invention, and wherein the immunogens are administered in an amount or expressed at a level sufficient to induce an HIV-specific immune response in the subject. The HIV-specific immune response can include an HIV-specific T-cell immune response or an HIV-specific B-cell immune response. Such immunizations can be done at intervals, preferably of at least 0-29 or more weeks.

Preclinical efficacy in the SHIV challenge model was observed following mucosal vaccination with a total dose of $2\times10^8$ pfu per ml. The vaccine dose may be split between two sites, such as mucosal surfaces in the nasal and oral cavities, where each received $1\times10^8$ pfu applied in a buffered solution. Dosages ranging from about $1\times10^4$ to $1\times10^9$ pfu per ml are also contemplated. Single doses are also contemplated. Alternatively, a vaccination schedule from about 0 to 40 weeks is contemplated. A vaccination schedule may be at 0, 4 and 29 weeks.

Preclinical efficacy in the SHIV challenge model was observed with a vaccination schedule of 0, 4, and 29 weeks. Other vaccination schedules are also contemplated.

```
SEQ ID NO: 1:
   1 aaattaatac gactcactat agggagacca caacggtttc cctctagcgt tgtcttcgtc 61 tgatgagtcc gtgaggacga aactatagga aaggaattcc tatagtcACG AAGACAAACA

121 AACCATTATT ATCATTAAAA GGCTCAGGAG AAACTTTAAC AGTAATCAAA ATGTCTGTTA

181 CAGTCAAGAG AATCATTGAC AACACAGTCA TAGTTCCAAA ACTTCCTGCA AATGAGGATC

241 CAGTGGAATA CCCGGCAGAT TACTTCAGAA AATCAAAGGA GATTCCTCTT TACATCAATA

301 CTACAAAAAG TTTGTCAGAT CTAAGAGGAT ATGTCTACCA AGGCCTCAAA TCCGGAAATG

361 TATCAATCAT ACATGTCAAC AGCTACTTGT ATGGAGCATT GAAGGACATC CGGGGTAAGT

421 TGGATAAAGA TTGGTCAAGT TTCGGAATAA ACATCGGGAA GGCAGGGGAT ACAATCGGAA

481 TATTTGACCT TGTATCCTTG AAAGCCCTGG ACGGTGTACT TCCAGATGGA GTATCGGATG

541 CTTCCAGAAC CAGCGCAGAT GACAAATGGT TGCCTTTGTA TCTACTTGGC TTATACAGAG

601 TGGGCAGAAC ACAAATGCCT GAATACAGAA AAAGGCTCAT GGATGGGCTG ACAAATCAAT

661 GCAAAATGAT CAATGAACAG TTTGAACCTC TTGTGCCAGA AGGTCGTGAC ATTTTTGATG

721 TGTGGGGAAA TGACAGTAAT TACACAAAAA TTGTCGCTGC AGTGGACATG TTCTTCCACA

781 TGTTCAAAAA ACATGAATGT GCCTCGTTCA GATACGGAAC TATTGTTTCC AGATTCAAAG

841 ATTGTGCTGC ATTGGCAACA TTTGGACACC TCTGCAAAAT AACCGGAATG TCTACAGAAG

901 ATGTGACGAC CTGGATCTTG AACCGAGAAG TTGCAGATGA GATGGTCCAA ATGATGCTTC

961 CAGGCCAAGA AATTGACAAG GCTGATTCAT ACATGCCTTA TTTGATCGAC TTTGGATTGT

1021 CTTCTAAGTC TCCATATTCT TCCGTCAAAA ACCCTGCCTT CCACTTCTGG GGGCAATTGA

1081 CAGCTCTTCT GCTCAGATCC ACCAGAGCAA GGAATGCCCG ACAGCCTGAT GACATTGAGT

1141 ATACATCTCT TACTACAGCA GGTTTGTTGT ACGCTTATGC AGTAGGATCC TCTGCTGACT

1201 TGGCACAACA GTTTTGTGTT GGAGATAGCA AATACACTCC AGATGATAGT ACCGGAGGAT

1261 TGACGACTAA TGCACCGCCA CAAGGCAGAG ATGTGGTCGA ATGGCTCGGA TGGTTTGAAG

1321 ATCAAAACAG AAAACCGACT CCTGATATGA TGCAGTATGC GAAACGAGCA GTCATGTCAC

1381 TGCAAGGCCT AAGAGAGAAG ACAATTGGCA AGTATGCTAA GTCAGAGTTT GACAAATGAC

1441 CCTATAATTC TCAGATCACC TATTATATAT TATGCTAGCT ATGAAAAAAA CTAACAGATA

1501 TCATGGATAA TCTCACAAAA GTTCGTGAGT ATCTCAAGTC CTATTCTCGT CTAGATCAGG

1561 CGGTAGGAGA GATAGATGAG ATCGAAGCAC AACGAGCTGA AAAGTCCAAT TATGAGTTGT

1621 TCCAAGAGGA CGGAGTGGAA GAGCATACTA GGCCCTCTTA TTTTCAGGCA GCAGATGATT

1681 CTGACACAGA ATCTGAACCA GAAATTGAAG ACAATCAAGG CTTGTATGTA CCAGATCCGG

1741 AAGCTGAGCA AGTTGAAGGC TTTATACAGG GGCCTTTAGA TGACTATGCA GATGAGGACG
```

-continued

```
1801 TGGATGTTGT ATTCACTTCG GACTGGAAAC AGCCTGAGCT TGAATCCGAC GAGCATGGAA

1861 AGACCTTACG GTTGACATTG CCAGAGGGTT AAGTGGAGA GCAGAAATCC CAGTGGCTTT

1921 TGACGATTAA AGCAGTCGTT CAAAGTGCCA AACACTGGAA TCTGGCAGAG TGCACATTTG

1981 AAGCATCGGG AGAAGGGGTC ATCATAAAAA AGCGCCAGAT AACTCCGGAT GTATATAAGG

2041 TCACTCCAGT GATGAACACA CATCCGTCCC AATCAGAAGC CGTATCAGAT GTTTGGTCTC

2101 TCTCAAAGAC ATCCATGACT TTCCAACCCA AGAAAGCAAG TCTTCAGCCT CTCACCATAT

2161 CCTTGGATGA ATTGTTCTCA TCTAGAGGAG AATTCATCTC TGTCGGAGGT AACGGACGAA

2221 TGTCTCATAA AGAGGCCATC CTGCTCGGTC TGAGGTACAA AAAGTTGTAC AATCAGGCGA

2281 GAGTCAAATA TTCTCTGTAG ACTAGTATGA AAAAAGTAA CAGATATCAC AATCTAAGTG

2341 TTATCCCAAT CCATTCATCA TGAGTTCCTT AAAGAAGATT CTCGGTCTGA AGGGGAAAGG

2401 TAAGAAATCT AAGAAATTAG GGATCGCACC ACCCCCTTAT GAAGAGGACA CTAACATGGA

2461 GTATGCTCCG AGCGCTCCAA TTGACAAATC CTATTTTGGA GTTGACGAGA TGGACACTCA

2521 TGATCCGAAT CAATTAAGAT ATGAGAAATT CTTCTTTACA GTGAAAATGA CGGTTAGATC

2581 TAATCGTCCG TTCAGAACAT ACTCAGATGT GGCAGCCGCT GTATCCCATT GGGATCACAT

2641 GTACATCGGA ATGGCAGGGA AACGTCCCTT CTACAAGATC TTGGCTTTTT TGGGTTCTTC

2701 TAATCTAAAG GCCACTCCAG CGGTATTGGC AGATCAAGGT CAACCAGAGT ATCATGCTCA

2761 CTGTGAAGGC AGGGCTTATT TGCCACACAG AATGGGGAAG ACCCCTCCCA TGCTCAATGT

2821 ACCAGAGCAC TTCAGAAGAC CATTCAATAT AGGTCTTTAC AAGGGAACGA TTGAGCTCAC

2881 AATGACCATC TACGATGATG AGTCACTGGA AGCAGCTCCT ATGATCTGGG ATCATTTCAA

2941 TTCTTCCAAA TTTTCTGATT TCAGAGAGAA GGCCTTAATG TTTGGCCTGA TTGTCGAGAA

3001 AAAGGCATCT GGAGCTTGGG TCCTGGATTC TGTCAGCCAC TTCAAATGAG CTAGTCTAGC

3061 TTCCAGCTTC TGAACAATCC CCGGTTTACT CAGTCTCTCC TAATTCCAGC CTTTCGAACA

3121 ACTAATATCC TGTCTTCTCT ATCCCTATGA AAAAACTAA CAGAGATCGA TCTGTTTCCT

3181 TGACACCAGG AGCCACCATG AAGTGCCTTT TGTACTTAGC TTTTTTATTC ATCGGGGTGA

3241 ATTGCAAGGC TAGCGCAGAG AATTTGTGGG TAACAGTCTA CTATGGAGTC CCTGTATGGA

3301 AGGATGCAGA GACAACATTG TTCTGTGCTA GTGACGCAAA GGCTTACGAG ACGGAGAAGC

3361 ACAATGTGTG GGCAACTCAC GCATGTGTCC CAACCGATCC AAATCCTCAA GAGATTCATC

3421 TAGAGAATGT GACTGAAGAA TTCAATATGT GGAAGAATAA TATGGTAGAG CAAATGCATA

3481 CAGATATCAT TAGTTTATGG GACCAGTCAC TTAAACCCTG CGTTAAATTG ACGCCTCTAT

3541 GTGTGACACT TCAATGTACT AATGTTACAA ACAACATAAC AGATGATATG AGAGGAGAAC

3601 TGAAGAACTG TAGTTTCAAC ATGACGACAG AGTTGCGTGA CAAGAAACAG AAAGTGTATT

3661 CACTATTCTA TCGGTTGGAT GTAGTACAGA TAAATGAGAA TCAAGGAAAC AGGTCCAACA

3721 ACTCTAACAA AGAGTACAGA CTTATTAATT GCAATACCAG TGCTATCACG CAAGCCTGCC

3781 CAAAGGTTTC ATTTGAACCA ATACCTATTC ATTATTGTGC ACCTGCTGGA TTCGCCATCC

3841 TCAAATGTAA AGACAAGAAG TTCAATGGAA CAGGACCCTG CCCATCAGTT TCAACCGTTC

3901 AGTGCACCCA CGGAATCAAG CCTGTAGTTA GTACTCAATT ATTGTTAAAT GGGAGCTTAG

3961 CTGAAGAAGA AGTTATGATT AGATCAGAGA ATATTACCAA TAATGCGAAG AACATCTTGG

4021 TTCAATTCAA TACTCCAGTC CAGATCAATT GCACAAGGCC TAATAATAAT ACCAGAAAGA

4081 GTATAAGAAT TGGGCCAGGA CAGGCATTCT ATGCAACAGG AGATATAATC GGAGACATTC

4141 GACAAGCGCA CTGCACTGTT TCTAAGGCCA CTTGGAATGA ACATTGGGT AAAGTTGTAA

4201 AGCAACTTCG GAAGCATTTC GGAAATAACA CAATTATTAG ATTTGCGAAC TCATCTGGAG
```

```
4261 GGGATCTGGA AGTGACAACA CACTCTTTCA ATTGCGGTGG CGAGTTCTTC TATTGTAATA

4321 CAAGTGGATT ATTTAACTCT ACTTGGATTT CAAATACCTC AGTCCAAGGA TCTAATTCAA

4381 CAGGGTCTAA CGATTCTATA ACATTACCTT GCCGTATAAA GCAAATTATT AATATGTGGC

4441 AAAGAATCGG GCAAGCGATG TATGCTCCAC CTATTCAAGG CGTGATTCGT TGCGTTTCAA

4501 ACATAACAGG GTTGATCCTG ACCAGGGATG GAGGCTCTAC CAATTCCACC ACCGAGACCT

4561 TCCGTCCCGG TGGCGGAGAT ATGCGGGATA ACTGGAGATC AGAGCTCTAT AAGTATAAGG

4621 TTGTGAAGAT TGAACCTCTT GGAGTTGCCC CTACAAGAGC AAAGAGAAGG GTGGTTGGCC

4681 GAGAGAAGAG AGCAGTTGGC ATCGGTGCTG TCTTTCTCGG ATTTCTTGGA GCAGCTGGAT

4741 CCACTATGGG AGCAGCATCA ATGACACTAA CAGTGCAGGC TAGAAATTTG CTTAGCGGAA

4801 TCGTTCAGCA GCAGAGCAAT TTACTAAGAG CAATTGAAGC ACAGCAACAT CTCTTAAAGT

4861 TGACGGTGTG GGGCATTAAA CAACTACAAG CGAGAGTGCT TGCCGTCGAA AGATATTTGC

4921 GAGACCAACA GCTATTGGGT ATTTGGGGTT GTTCTGGGAA ATTAATTTGC ACAACAAATG

4981 TTCCATGGAA CTCCTCCTGG AGTAATAGGA ATTTAAGTGA GATATGGGAC AACATGACAT

5041 GGTTGCAGTG GGACAAGGAA ATCTCAAATT ATACACAGAT AATCTATGGA TTATTAGAAG

5101 AGTCTCAGAA TCAGCAAGAG AAGAATGAAC AGGATTTGCT TGCATTGGAT AAGTGGGCTT

5161 CTCTATGGAA CTGGTTCGAT ATTAGTAATT GGCTCTGGTA TATTAAGAGC TCTATTGCCT

5221 CTTTTTTCTT TATCATAGGG TTAATCATTG ACTATTCTT GGTTCTCCGA GTTGGTATTT

5281 ATCTTTGCAT TAAATTAAAG CACACCAAGA AAAGACAGAT TTATACAGAC ATAGAGATGA

5341 ACCGACTTGG AAAGTAAAGC TCAAATCCTG CACAACAGAT TCTTCATGTT TGAACCAAAT

5401 CAACTTGTGA TATCATGCTC AAAGAGGCCT TAATTAAATT TTAATTTTTA ATTTTTATGA

5461 AAAAAACTAA CAGCAATCAT GGAAGTCCAC GATTTTGAGA CCGACGAGTT CAATGATTTC

5521 AATGAAGATG ACTATGCCAC AAGAGAATTC CTGAATCCCG ATGAGCGCAT GACGTACTTG

5581 AATCATGCTG ATTACAATTT GAATTCTCCT CTAATTAGTG ATGATATTGA CAATTTGATC

5641 AGGAAATTCA ATTCTCTTCC GATTCCCTCG ATGTGGGATA GTAAGAACTG GGATGGAGTT

5701 CTTGAGATGT TAACATCATG TCAAGCCAAT CCCATCTCAA CATCTCAGAT GCATAAATGG

5761 ATGGGAAGTT GGTTAATGTC TGATAATCAT GATGCCAGTC AAGGGTATAG TTTTTTACAT

5821 GAAGTGGACA AAGAGGCAGA ATAACATTT GACGTGGTGG AGACCTTCAT CCGCGGCTGG

5881 GGCAACAAAC CAATTGAATA CATCAAAAAG GAAAGATGGA CTGACTCATT CAAAATTCTC

5941 GCTTATTTGT GTCAAAAGTT TTTGGACTTA CACAAGTTGA CATTAATCTT AAATGCTGTC

6001 TCTGAGGTGG AATTGCTCAA CTTGGCGAGG ACTTTCAAAG GCAAAGTCAG AAGAAGTTCT

6061 CATGGAACGA ACATATGCAG GCTTAGGGTT CCCAGCTTGG GTCCTACTTT TATTTCAGAA

6121 GGATGGGCTT ACTTCAAGAA ACTTGATATT CTAATGGACC GAAACTTTCT GTTAATGGTC

6181 AAAGATGTGA TTATAGGGAG GATGCAAACG GTGCTATCCA TGGTATGTAG AATAGACAAC

6241 CTGTTCTCAG AGCAAGACAT CTTCTCCCTT CTAAATATCT ACAGAATTGG AGATAAAATT

6301 GTGGAGAGGC AGGGAAATTT TTCTTATGAC TTGATTAAAA TGGTGGAACC GATATGCAAC

6361 TTGAAGCTGA TGAAATTAGC AAGAGAATCA AGGCCTTTAG TCCCACAATT CCCTCATTTT

6421 GAAAATCATA TCAAGACTTC TGTTGATGAA GGGGCAAAAA TTGACCGAGG TATAAGATTC

6481 CTCCATGATC AGATAATGAG TGTGAAAACA GTGGATCTCA CACTGGTGAT TTATGGATCG

6541 TTCAGACATT GGGGTCATCC TTTTATAGAT TATTACGCTG GACTAGAAAA ATTACATTCC

6601 CAAGTAACCA TGAAGAAAGA TATTGATGTG TCATATGCAA AAGCACTTGC AAGTGATTTA
```

-continued

```
6661 GCTCGGATTG TTCTATTTCA ACAGTTCAAT GATCATAAAA AGTGGTTCGT GAATGGAGAC

6721 TTGCTCCCTC ATGATCATCC CTTTAAAAGT CATGTTAAAG AAAATACATG GCCTACAGCT

6781 GCTCAAGTTC AAGATTTTGG AGATAAATGG CATGAACTTC CGCTGATTAA ATGTTTTGAA

6841 ATACCCGACT TACTAGACCC ATCGATAATA TACTCTGACA AAAGTCATTC AATGAATAGG

6901 TCAGAGGTGT TGAAACATGT CCGAATGAAT CCGAACACTC CTATCCCTAG TAAAAGGTG

6961 TTGCAGACTA TGTTGGACAC AAAGGCTACC AATTGGAAAG AATTTCTTAA AGAGATTGAT

7021 GAGAAGGGCT TAGATGATGA TGATCTAATT ATTGGTCTTA AAGGAAAGGA GAGGGAACTG

7081 AAGTTGGCAG GTAGATTTTT CTCCCTAATG TCTTGGAAAT TGCGAGAATA CTTTGTAATT

7141 ACCGAATATT TGATAAAGAC TCATTTCGTC CCTATGTTTA AAGGCCTGAC AATGGCGGAC

7201 GATCTAACTG CAGTCATTAA AAAGATGTTA GATTCCTCAT CCGGCCAAGG ATTGAAGTCA

7261 TATGAGGCAA TTTGCATAGC CAATCACATT GATTACGAAA AATGGAATAA CCACCAAAGG

7321 AAGTTATCAA ACGGCCCAGT GTTCCGAGTT ATGGGCCAGT TCTTAGGTTA TCCATCCTTA

7381 ATCGAGAGAA CTCATGAATT TTTTGAGAAA AGTCTTATAT ACTACAATGG AAGACCAGAC

7441 TTGATGCGTG TTCACAACAA CACACTGATC AATTCAACCT CCCAACGAGT TTGTTGGCAA

7501 GGACAAGAGG GTGGACTGGA AGGTCTACGG CAAAAAGGAT GGAGTATCCT CAATCTACTG

7561 GTTATTCAAA GAGAGGCTAA AATCAGAAAC ACTGCTGTCA AAGTCTTGGC ACAAGGTGAT

7621 AATCAAGTTA TTTGCACACA GTATAAAACG AAGAAATCGA GAAACGTTGT AGAATTACAG

7681 GGTGCTCTCA ATCAAATGGT TTCTAATAAT GAGAAAATTA TGACTGCAAT CAAAATAGGG

7741 ACAGGGAAGT TAGGACTTTT GATAAATGAC GATGAGACTA TGCAATCTGC AGATTACTTG

7801 AATTATGGAA AAATACCGAT TTTCCGTGGA GTGATTAGAG GGTTAGAGAC CAAGAGATGG

7861 TCACGAGTGA CTTGTGTCAC CAATGACCAA ATACCCACTT GTGCTAATAT AATGAGCTCA

7921 GTTTCCACAA ATGCTCTCAC CGTAGCTCAT TTTGCTGAGA ACCCAATCAA TGCCATGATA

7981 CAGTACAATT ATTTTGGGAC ATTTGCTAGA CTCTTGTTGA TGATGCATGA TCCTGCTCTT

8041 CGTCAATCAT TGTATGAAGT TCAAGATAAG ATACCGGGCT TGCACAGTTC TACTTTCAAA

8101 TACGCCATGT TGTATTTGGA CCCCTTCCATT GGAGGAGTGT CGGGCATGTC TTTGTCCAGG

8161 TTTTTGATTA GAGCCTTCCC AGATCCCGTA ACAGAAAGTC TCTCATTCTG GAGATTCATC

8221 CATGTACATG CTCGAAGTGA GCATCTGAAG GAGATGAGTG CAGTATTTGG AAACCCCGAG

8281 ATAGCCAAGT TCCGAATAAC TCACATAGAC AAGCTAGTAG AAGATCCAAC CTCTCTGAAC

8341 ATCGCTATGG GAATGAGTCC AGCGAACTTG TTAAAGACTG AGGTTAAAAA ATGCTTAATC

8401 GAATCAAGAC AAACCATCAG GAACCAGGTG ATTAAGGATG CAACCATATA TTTGTATCAT

8461 GAAGAGGATC GGCTCAGAAG TTTCTTATGG TCAATAAATC CTCTGTTCCC TAGATTTTTA

8521 AGTGAATTCA AATCAGGCAC TTTTTTGGGA GTCGCAGACG GGCTCATCAG TCTATTTCAA

8581 AATTCTCGTA CTATTCGGAA CTCCTTTAAG AAAAAGTATC ATAGGGAATT GGATGATTTG

8641 ATTGTGAGGA GTGAGGTATC CTCTTTGACA CATTTAGGGA AACTTCATTT GAGAAGGGGA

8701 TCATGTAAAA TGTGGACATG TTCAGCTACT CATGCTGACA CATTAAGATA CAAATCCTGG

8761 GGCCGTACAG TTATTGGGAC AACTGTACCC CATCCATTAG AAATGTTGGG TCCACAACAT

8821 CGAAAAGAGA CTCCTTGTGC ACCATGTAAC ACATCAGGGT TCAATTATGT TTCTGTGCAT

8881 TGTCCAGACG GGATCCATGA CGTCTTTAGT TCACGGGGAC CATTGCCTGC TTATCTAGGG

8941 TCTAAAACAT CTGAATCTAC ATCTATTTTG CAGCCTTGGG AAAGGGAAAG CAAAGTCCCA

9001 CTGATTAAAA GAGCTACACG TCTTAGAGAT GCTATCTCTT GGTTTGTTGA ACCCGACTCT

9061 AAACTAGCAA TGACTATACT TTCTAACATC CACTCTTTAA CAGGCGAAGA ATGGACCAAA
```

-continued

```
9121  AGGCAGCATG GGTTCAAAAG AACAGGGTCT GCCCTTCATA GGTTTTCGAC ATCTCGGATG
9181  AGCCATGGTG GGTTCGCATC TCAGAGCACT GCAGCATTGA CCAGGTTGAT GGCAACTACA
9241  GACACCATGA GGGATCTGGG AGATCAGAAT TTCGACTTTT TATTCCAAGC AACGTTGCTC
9301  TATGCTCAAA TTACCACCAC TGTTGCAAGA GACGGATGGA TCACCAGTTG TACAGATCAT
9361  TATCATATTG CCTGTAAGTC CTGTTTGAGA CCCATAGAAG AGATCACCCT GGACTCAAGT
9421  ATGGACTACA CGCCCCCAGA TGTATCCCAT GTGCTGAAGA CATGGAGGAA TGGGGAAGGT
9481  TCGTGGGGAC AAGAGATAAA ACAGATCTAT CCTTTAGAAG GGAATTGGAA GAATTTAGCA
9541  CCTGCTGAGC AATCCTATCA AGTCGGCAGA TGTATAGGTT TTCTATATGG AGACTTGGCG
9601  TATAGAAAAT CTACTCATGC CGAGGACAGT TCTCTATTTC CTCTATCTAT ACAAGGTCGT
9661  ATTAGAGGTC GAGGTTTCTT AAAAGGGTTG CTAGACGGAT TAATGAGAGC AAGTTGCTGC
9721  CAAGTAATAC ACCGGAGAAG TCTGGCTCAT TTGAAGAGGC CGGCCAACGC AGTGTACGGA
9781  GGTTTGATTT ACTTGATTGA TAAATTGAGT GTATCACCTC CATTCCTTTC TCTTACTAGA
9841  TCAGGACCTA TTAGAGACGA ATTAGAAACG ATTCCCCACA AGATCCCAAC CTCCTATCCG
9901  ACAAGCAACC GTGATATGGG GGTGATTGTC AGAAATTACT TCAAATACCA ATGCCGTCTA
9961  ATTGAAAAGG GAAAATACAG ATCACATTAT TCACAATTAT GGTTATTCTC AGATGTCTTA
10021 TCCATAGACT TCATTGGACC ATTCTCTATT TCCACCACCC TCTTGCAAAT CCTATACAAG
10081 CCATTTTTAT CTGGGAAAGA TAAGAATGAG TTGAGAGAGC TGGCAAATCT TTCTTCATTG
10141 CTAAGATCAG GAGAGGGGTG GGAAGACATA CATGTGAAAT TCTTCACCAA GGACATATTA
10201 TTGTGTCCAG AGGAAATCAG ACATGCTTGC AAGTTCGGGA TTGCTAAGGA TAATAATAAA
10261 GACATGAGCT ATCCCCCTTG GGGAAGGGAA TCCAGAGGGA CAATTACAAC AATCCCTGTT
10321 TATTATACGA CCACCCCTTA CCCAAAGATG CTAGAGATGC CTCCAAGAAT CCAAAATCCC
10381 CTGCTGTCCG GAATCAGGTT GGGCCAATTA CCAACTGGCC CTCATTATAA AATTCGGAGT
10441 ATATTACATG GAATGGGAAT CCATTACAGG GACTTCTTGA GTTGTGGAGA CGGCTCCGGA
10501 GGGATGACTG CTGCATTACT ACGAGAAAAT GTGCATAGCA GAGGAATATT CAATAGTCTG
10561 TTAGAATTAT CAGGGTCAGT CATGCGAGGC GCCTCTCCTG AGCCCCCCAG TGCCCTAGAA
10621 ACTTTAGGAG GAGATAAATC GAGATGTGTA AATGGTGAAA CATGTTGGGA ATATCCATCT
10681 GACTTATGTG ACCCAAGGAC TTGGGACTAT TTCCTCCGAC TCAAAGCAGG CTTGGGGCTT
10741 CAAATTGATT TAATTGTAAT GGATATGGAA GTTCGGGATT CTTCTACTAG CCTGAAAATT
10801 GAGACGAATG TTAGAAATTA TGTGCACCGG ATTTTGGATG AGCAAGGAGT TTTAATCTAC
10861 AAGACTTATG AACATATAT TTGTGAGAGC GAAAAGAATG CAGTAACAAT CCTTGGTCCC
10921 ATGTTCAAGA CGGTCGACTT AGTTCAAACA GAATTTAGTA GTTCTCAAAC GTCTGAAGTA
10981 TATATGGTAT GTAAAGGTTT GAAGAAATTA ATCGATGAAC CCAATCCCGA TTGGTCTTCC
11041 ATCAATGAAT CCTGGAAAAA CCTGTACGCA TTCCAGTCAT CAGAACAGGA ATTTGCCAGA
11101 GCAAAGAAGG TTAGTACATA CTTTACCTTG ACAGGTATTC CCTCCCAATT CATTCCTGAT
11161 CCTTTTGTAA ACATTGAGAC TATGCTACAA ATATTCGGAG TACCCACGGG TGTGTCTCAT
11221 GCGGCTGCCT TAAAATCATC TGATAGACCT GCAGATTTAT TGACCATTAG CCTTTTTTAT
11281 ATGGCGATTA TATCGTATTA TAACATCAAT CATATCAGAG TAGGACCGAT ACCTCCGAAC
11341 CCCCCATCAG ATGGAATTGC ACAAAATGTG GGGATCGCTA TAACTGGTAT AAGCTTTTGG
11401 CTGAGTTTGA TGGAGAAAGA CATTCCACTA TATCAACAGT GTTTAGCAGT TATCCAGCAA
11461 TCATTCCCGA TTAGGTGGGA GGCTGTTTCA GTAAAAGGAG GATACAAGCA GAAGTGGAGT
```

-continued

```
11521 ACTAGAGGTG ATGGGCTCCC AAAAGATACC CGAATTTCAG ACTCCTTGGC CCCAATCGGG

11581 AACTGGATCA GATCTCTGGA ATTGGTCCGA AACCAAGTTC GTCTAAATCC ATTCAATGAG

11641 ATCTTGTTCA ATCAGCTATG TCGTACAGTG GATAATCATT TGAAATGGTC AAATTTGCGA

11701 AAAAACACAG GAATGATTGA ATGGATCAAT AGACGAATTT CAAAGAAGA CCGGTCTATA

11761 CTGATGTTGA AGAGTGACCT ACACGAGGAA AACTCTTGGA GAGATTAAAA AATCATGAGG

11821 AGACTCCAAA CTTTAAGTAT GAAAAAAACT TTGATCCTTA AGACCCTCTT GTGGTTTTTA

11881 TTTTTTATCT GGTTTTGTGG TCTTCGTggc cggcatggtc ccagcctcct cgctggcgcc 11941 ggctgggcaa cattccgagg ggaccgtccc ctcggtaatg gcgaatggga cctgctaaca 12001 aagcccgaaa ggaagctgag ttggctgctg ccaccgctga gcaataacta gcataacccc 12061 ttggggcctc taaacgggtc ttgaggggtt ttttgctgaa aggaggaact atatccggat 12121 gcggccgatc cggctgctaa caaagcccga aaggaagctg agttggctgc tgccaccgct 12181 gagcaataac tagcataacc ccttggggcc tctaaacggg tcttgagggg ttttttgctg 12241 aaaggaggaa ctatatccgg gttaacctgc attaatgaat cggccaacgc gcgggagag 12301 gcggtttgcg tattgggcgc tcttccgctt cctcgctcac tgactcgctg cgctcggtcg 12361 ttcggctgcg gcgagcggta tcagctcact caaaggcggt aatacggtta ccacagaat 12421 caggggataa cgcaggaaag aacatgtgag caaaaggcca gcaaaaggcc aggaaccgta 12481 aaaaggccgc gttgctggcg ttttccata ggctccgccc cctgacgag catcacaaaa 12541 atcgacgctc aagtcagagg tggcgaaacc cgacaggact ataaagatac caggcgtttc 12601 ccctggaag ctccctcgtg cgctctcctg ttccgaccct gccgcttacc ggatacctgt 12661 ccgcctttct cccttcggga agcgtggcgc tttctcaatg ctcacgctgt aggtatctca 12721 gttcggtgta ggtcgttcgc tccaagctgg gctgtgtgca cgaaccccc gttcagcccg 12781 accgctgcgc cttatccggt aactatcgtc ttgagtccaa cccggtaaga cacgacttat 12841 cgccactggc agcagccact ggtaacagga ttagcagagc gaggtatgta ggcggtgcta 12901 cagagttctt gaagtggtgg cctaactacg gctacactag aaggacagta tttggtatct 12961 gcgctctgct gaagccagtt accttcggaa aaagagttgg tagctcttga tccggcaaac 13021 aaaccaccgc tggtagcggt ggttttttg tttgcaagca gcagattacg cgcagaaaaa 13081 aaggatctca agaagatcct ttgatctttt ctacggggtc tgacgctcag tggaacgaaa 13141 actcacgtta agggattttg gtcatgagat tatcaaaaag gatcttcacc tagatccttt 13201 taaattaaaa atgaagtttt aaatcaatct aaagtatata tgagtaaact tggtctgaca 13261 gttaccaatg cttaatcagt gaggcaccta tctcagcgat ctgtctattt cgttcatcca 13321 tagttgcctg actccccgtc gtgtagataa ctacgatacg ggagggctta ccatctggcc 13381 ccagtgctgc aatgataccg cgagacccac gctcaccggc tccagattta tcagcaataa 13441 accagccagc cggaagggcc gagcgcagaa gtggtcctgc aactttatcc gcctccatcc 13501 agtctattaa ttgttgccgg gaagctagag taagtagttc gccagttaat agtttgcgca 13561 acgttgttgc cattgctaca ggcatcgtgg tgtcacgctc gtcgtttggt atggcttcat 13621 tcagctccgg ttcccaacga tcaaggcgag ttacatgatc ccccatgttg tgcaaaaag 13681 cggttagctc cttcggtcct ccgatcgttg tcagaagtaa gttggccgca gtgttatcac 13741 tcatggttat ggcagcactg cataattctc ttactgtcat gccatccgta agatgctttt 13801 ctgtgactgg tgagtactca accaagtcat tctgagaata gtgtatgcgg cgaccgagtt 13861 gctcttgccc ggcgtcaata cgggataata ccgcgccaca tagcagaact ttaaaagtgc 13921 tcatcattgg aaaacgttct cggggcgaaa actctcaag gatcttaccg ctgttgagat
```

-continued

```
13981 ccagttcgat gtaacccact cgtgcaccca actgatcttc agcatctttt actttcacca 14041 gcgtttctgg gtgagcaaaa acaggaaggc aaaatgccgc aaaaaaggga ataagggcga 14101 cacggaaatg ttgaatactc atactcttcc tttttcaata ttattgaagc atttatcagg 14161 gttattgtct catgagcgga tacatatttg aatgtattta gaaaaataaa caaatagggg 14221 ttccgcgcac atttccccga aaagtgccac ctgacgtc
```

An annotated sequence of SEQ ID NO 1 is provided below. The coded protein is disclosed as SEQ ID NO: 2.

```
                              >T7-g10 Promoter
                                   |
aa att aat acg act cac tat agg gag acc aca acg gtt tcc ctc tag cgt tgt ctt cgt c      < 60
           10          20          30          40          50

>Hammerhead Ribozyme
                         |
tg atg agt ccg tga gga cga aac tat agg aaa gga att cct ata gtc ACG AAG ACA AAC A      < 120
        70          80          90         100         110

>VSV Leader
                          |
AA CCA TTA TTA TCA TTA AAA GGC TCA GGA GAA ACT TTA ACA GTA ATC AAA ATG TCT GTT A      < 180
       130         140         150         160         170

CA GTC AAG AGA ATC ATT GAC AAC ACA GTC ATA GTT CCA AAA CTT CCT GCA AAT GAG GAT C      < 240
       190         200         210         220         230

CA GTG GAA TAC CCG GCA GAT TAC TTC AGA AAA TCA AAG GAG ATT CCT CTT TAC ATC AAT A      < 300
       250         260         270         280         290

CT ACA AAA AGT TTG TCA GAT CTA AGA GGA TAT GTC TAC CAA GGC CTC AAA TCC GGA AAT G      < 360
       310         320         330         340         350

TA TCA ATC ATA CAT GTC AAC AGC TAC TTG TAT GGA GCA TTG AAG GAC ATC CGG GGT AAG T      < 420
       370         380         390         400         410

TG GAT AAA GAT TGG TCA AGT TTC GGA ATA AAC ATC GGG AAG GCA GGG GAT ACA ATC GGA A      < 480
       430         440         450         460         470

TA TTT GAC CTT GTA TCC TTG AAA GCC CTG GAC GGT GTA CTT CCA GAT GGA GTA TCG GAT G      < 540
       490         500         510         520         530

CT TCC AGA ACC AGC GCA GAT GAC AAA TGG TTG CCT TTG TAT CTA CTT GGC TTA TAC AGA G      < 600
       550         560         570         580         590

TG GGC AGA ACA CAA ATG CCT GAA TAC AGA AAA AGG CTC ATG GAT GGG CTG ACA AAT CAA T      < 660
       610         620         630         640         650

GC AAA ATG ATC AAT GAA CAG TTT GAA CCT CTT GTG CCA GAA GGT CGT GAC ATT TTT GAT G      < 720
       670         680         690         700         710

TG TGG GGA AAT GAC AGT AAT TAC ACA AAA ATT GTC GCT GCA GTG GAC ATG TTC TTC CAC A      < 780
       730         740         750         760         770

>N
                                      |
TG TTC AAA AAA CAT GAA TGT GCC TCG TTC AGA TAC GGA ACT ATT GTT CCA AGA TTC AAA G      < 840
       790         800         810         820         830

AT TGT GCT GCA TTG GCA ACA TTT GGA CAC CTC TGC AAA ATA ACC GGA ATG TCT ACA GAA G      < 900
       850         860         870         880         890

AT GTG ACG ACC TGG ATC TTG AAC CGA GAA GTT GCA GAT GAG ATG GTC CAA ATG ATG CTT C      < 960
       910         920         930         940         950

CA GGC CAA GAA ATT GAC AAG GCT GAT TCA TAC ATG CCT TAT TTG ATC GAC TTT GGA TTG T      < 1020
       970         980         990        1000        1010

CT TCT AAG TCT CCA TAT TCT TCC GTC AAA AAC CCT GCC TTC CAC TTC TGG GGG CAA TTG A      < 1080
      1030        1040        1050        1060        1070

CA GCT CTT CTG CTC AGA TCC ACC AGA GCA AGG AAT GCC CGA CAG CCT SAT GAC ATT GAG T      < 1140
      1090        1100        1110        1120        1130
```

```
AT ACA TCT CTT ACT ACA GCA GGT TTG TTG TAC GCT TAT GCA GTA GGA TCC TCT GCT GAC T        < 1200
      1150          1160          1170          1180          1190

TG GCA CAA CAG TTT TGT GTT GGA GAT AGC AAA TAC ACT CCA GAT GAT AGT ACC GGA GGA T        < 1260
      1210          1220          1230          1240          1250

TG ACG ACT AAT GCA CCG CCA CAA GGC AGA GAT GTG GTC GAA TGG CTC GGA TGG TTT GAA G        < 1320
      1270          1280          1290          1300          1310

AT CAA AAC AGA AAA CCG ACT CCT GAT ATG ATG CAG TAT GCG AAA CGA GCA GTC ATG TCA C        < 1380
      1330          1340          1350          1360          1370

TG CAA GGC CTA AGA GAG AAG ACA ATT GGC AAG TAT GCT AAG TCA GAG TTT GAC AAA TGA C        < 1440
      1390          1400          1410          1420          1430

CC TAT AAT TCT CAG ATC ACC TAT TAT ATA TTA TGC TAG CTA TGA AAA AAA CTA ACA GAT A       < 1500
      1450          1460          1470          1480          1490

TC ATG GAT AAT CTC ACA AAA GTT CGT GAG TAT CTC AAG TCC TAT TCT CGT CTA GAT CAG G       < 1560
      1510          1520          1530          1540          1550

CG GTA GGA GAG ATA GAT GAG ATC GAA GCA CAA CGA GCT GAA AAG TCC AAT TAT GAG TTG T       < 1620
      1570          1580          1590          1600          1610

TC CAA GAG GAC GGA GTG GAA GAG CAT ACT AGG CCC TCT TAT TTT CAG GCA GCA GAT GAT T       < 1680
      1630          1640          1650          1660          1670

CT GAC ACA GAA TCT GAA CCA GAA ATT GAA GAC AAT CAA GGC TTG TAT GTA CCA GAT CCG G       < 1740
      1690          1700          1710          1720          1730

AA GCT GAG CAA GTT GAA GGC TTT ATA CAG GGG CCT TTA GAT GAC TAT GCA GAT GAG GAC G       < 1800
      1750          1760          1770          1780          1790

TG GAT GTT GTA TTC ACT TCG GAC TGG AAA CAG CCT GAG CTT GAA TCC GAC GAG CAT GGA A       < 1860
      1810          1820          1830          1840          1850

>P
                                                         |
AG ACC TTA CGG TTG ACA TTG CCA GAG GGT TTA AGT GGA GAG CAG AAA TCC CAG TGG CTT T       < 1920
      1870          1880          1890          1900          1910

TG ACG ATT AAA GCA GTC GTT CAA AGT GCC AAA CAC TGG AAT CTG GCA GAG TGC ACA TTT G       < 1980
      1930          1940          1950          1960          1970

AA GCA TCG GGA GAA GGG GTC ATC ATA AAA AAG CGC CAG ATA ACT CCG GAT GTA TAT AAG G       < 2040
      1990          2000          2010          2020          2030

TC ACT CCA GTG ATG AAC ACA CAT CCG TCC AAT CAA GAA GCC GTA TCA GAT GTT TGG TCT C       < 2100
      2050          2060          2070          2080          2090

TC TCA AAG ACA TCC ATG ACT TTC CAA CCC AAG AAA GCA AGT CTT CAG CCT CTC ACC ATA T      < 2160
      2110          2120          2130          2140          2150

CC TTG GAT GAA TTG TTC TCA TCT AGA GGA GAA TTC ATC TCT GTC GGA GGT AAC GGA CGA A      < 2220
      2170          2180          2190          2200          2210

TG TCT CAT AAA GAG GCC ATC CTG CTC GGT CTG AGG TAC AAA AAG TTG TAC AAT CAG GCG A      < 2280
      2230          2240          2250          2260          2270

GA GTC AAA TAT TCT CTG TAG ACT AGT ATG AAA AAA AGT AAC AGA TAT CAC AAT CTA AGT G      < 2340
      2290          2300          2310          2320          2330

TT ATC CCA ATC CAT TCA TCA TGA GTT CCT TAA AGA AGA TTC TCG GTC TGA AGG GGA AAG G      < 2400
      2350          2360          2370          2380          2390

TA AGA AAT CTA AGA AAT TAG GGA TCG CAC CAC CCC CTX ATG AAG AGG ACA CTA ACA TGG A      < 2460
      2410          2420          2430          2440          2450

GT ATG CTC CGA GCG CTC CAA TTG ACA AAT CCT ATT TTG GAG TTG ACQ AGA TGG ACA CTC A      < 2520
      2470          2480          2490          2500          2510

TG ATC CGA ATC AAT TAA GAT ATG AGA AAT TCT TCT TTA CAG TGA AAA TGA CGG TTA GAT C      < 2580
      2530          2540          2550          2560          2570

TA ATC GTC CGT TCA GAA CAT ACT CAG ATG TGG CAG CCG CTG TAT CCC ATT GGG ATC ACA T      < 2640
      2590          2600          2610          2620          2630

GT ACA TCG GAA TGG CAG GGA AAC GTC CCT TCT ACA AGA TCT TGG CTT TTT GGG TT CTT C       < 2700
      2650          2660          2670          2680          2690
```

```
    >M
     |
TA ATC TAA AGG CCA CTC CAG CGG TAT TGG CAG ATC AAG GTC AAC CAG AGT ATC ATG CTC A   < 2760
       2710         2720         2730         2740         2750

CT GTG AAG GCA GGG CTT ATT TGC CAC ACA GAA TGG GGA AGA CCC CTC CCA TGC TCA ATG T   < 2820
       2770         2780         2790         2800         2810

AC CAG AGC ACT TCA GAA GAC CAT TCA ATA TAG GTC TTT ACA AGG GAA CGA TTG AGC TCA C   < 2880
       2830         2840         2850         2860         2870

AA TGA CCA TCT ACG ATG ATG AGT CAC TGG AAG CAG CTC CTA TGA TCT GGG ATC ATT TCA A   < 2940
       2890         2900         2910         2920         2930

TT CTT CCA AAT TTT CTG ATT TCA GAG AGA AGG CCT AAA TGT TTG GCC TGA TTG TCG AGA A   < 3000
       2950         2960         2970         2980         2990

AA AGG CAT CTG GAG CTT GGG TCC TGG ATT CTG TCA GCC ACT TCA AAT GAG CTA GTC TAG C   < 3060
       3010         3020         3030         3040         3050

TT CCA GCT TCT GAA CAA TCC CCG GTT TAC TCA GTC TCT CCT AAT TCC AGC CTT TCG AAC A   < 3120
       3070         3080         3090         3100         3110

AC TAA TAT CCT GTC TTC TCT ATC CCT ATG AAA AAA ACT AAC AGA GAT CGA TCT GTT TCC T   < 3180
       3130         3140         3150         3160         3170

TG ACA CCA GGA GCC ACC ATG AAG TGC CTT TTG TAC TTA GCT TTT TTA TTC ATC GGG GTG A   < 3240
                           M   K   C   L   L   Y   L   A   F   L   F   I   G   V   N
       3190         3200         3210         3220         3230

AT TGC AAG GCT AGC GCA GAG AAT TTG TGG GTA ACA GTC TAC TAT GGA GTC CCT GTA TGG A   < 3300
    C   K   A   S   A   E   N   L   W   V   T   V   Y   Y   G   V   P   V   W   K
       3250         3260         3270         3280         3290

AG GAT GCA GAG ACA ACA TTG TTC TGT GCT AGT GAC GCA AAG GCT TAG GAG ACG GAG AAG C   < 3360
    D   A   E   T   T   L   F   C   A   S   D   A   K   A   Y   E   T   E   K   H
       3310         3320         3330         3340         3350

AC AAT GTG TGG GCA ACT CAC GCA TGT GTC CCA ACC GAT CCA AAT CCT CAA GAG ATT CAT C   < 3420
    N   V   W   A   T   H   A   C   V   P   T   D   P   N   P   Q   E   I   H   L
       3370         3380         3390         3400         3410

TA GAG AAT GTG ACT GAA GAA TTC AAT ATG TGG AAG AAT AAT ATG GTA GAG CAA ATG CAT A   < 3480
    E   N   V   T   E   E   F   N   M   W   K   N   N   M   V   E   Q   M   H   T
       3430         3440         3450         3460         3470

CA GAT ATC ATT AGT TTA TGG GAC CAG TCA CTT AAA CCC TGC GTT AAA TTG ACG CCT CTA T   < 3540
    D   I   I   S   L   W   D   Q   S   L   K   P   C   V   K   L   T   P   L   C
       3490         3500         3510         3520         3530

GT GTG ACA CTT CAA TGT ACT AAT GTT ACA AAC AAC ATA ACA GAT GAT ATG AGA GGA GAA C   < 3600
    V   T   L   Q   C   T   N   V   T   N   N   I   T   D   D   M   R   G   E   L
       3550         3560         3570         3580         3590

TG AAG AAC TGT AGT TTC AAC ATG ACG ACA GAG TTG CGT GAC AAG AAA CAG AAA GTG TAT T   < 3660
    K   N   C   S   F   N   K   T   T   E   L   R   D   K   K   Q   K   V   Y   S
       3610         3620         3630         3640         3650

CA CTA TTC TAT CGG TTG GAT GTA GTA CAG ATA AAT GAG AAT CAA GGA AAC AGG TCC AAC A   < 3720
    L   F   Y   R   L   D   V   V   Q   I   N   E   N   Q   G   N   R   S   N   N
       3670         3680         3690         3700         3710

AC TCT AAC AAA GAG TAC AGA CTT ATT AAT TGC AAT ACC AGT GCT ATC ACG CAA GCC TGC C   < 3780
    S   N   K   E   Y   R   L   I   N   C   N   T   S   A   I   T   Q   A   C   P
       3730         3740         3750         3760         3770

CA AAG GTT TCA TTT GAA CCA ATA CCT ATT CAT TAT TGT GCA CCT GCT GGA TTC GCC ATC C   < 3840
    K   V   S   F   E   P   I   P   I   H   Y   C   A   P   A   G   F   A   I   L
       3790         3800         3810         3820         3830

TC AAA TGT AAA GAC AAG AAG TTC AAT GGA ACA GGA CCC TGC CCA TCA GTT TCA ACC GTT C   < 3900
    K   C   K   D   K   K   F   N   G   T   G   P   C   P   S   V   S   T   V   Q
       3850         3860         3870         3880         3890

AG TGC ACC CAC GGA ATC AAG CCT GTA GTT AGT ACT CAA TTA TTG TTA AAT GGG AGC TTA G   < 3960
    C   T   H   G   I   K   P   V   V   S   T   Q   L   L   L   N   G   S   L   A
       3910         3920         3930         3940         3950

CT GAA GAA GAA GTT ATG ATT AGA TCA GAG AAT ATT ACC AAT AAT GCG AAG AAC ATC TTG G   < 4020
    E   E   E   V   M   I   R   S   E   N   I   T   N   N   A   K   N   I   L   V
       3970         3980         3990         4000         4010
```

```
TT CAA TTC AAT ACT CCA GTC CAG ATC AAT TGC ACA AGG CCT AAT AAT AAT ACC AGA AAG A    < 4080
   Q   F   N   T   P   V   Q   I   N   C   T   R   P   N   N   N   T   R   K   S
             4030        4040        4050        4060        4070

GT ATA AGA ATT GGG CCA GGA CAG GCA TTC TAT GCA ACA GGA GAT ATA ATC GGA GAC ATT C    < 4140
   I   R   I   G   P   G   Q   A   F   Y   A   T   G   D   I   I   G   D   I   R
             4090        4100        4110        4120        4130

GA CAA GCG CAC TGC ACT GTT TCT AAG GCC ACT TGG AAT GAA ACA TTG GGT AAA GTT GTA A    < 4200
   Q   A   H   C   T   V   S   K   A   T   W   N   E   T   L   G   K   V   V   K
             4150        4160        4170        4180        4190

AG CAA CTT CGG AAG CAT TTC GGA AAT AAC ACA ATT ATT AGA TTT GCG AAC TCA TCT GGA G    < 4260
   Q   L   R   K   H   F   G   N   N   T   I   I   R   F   A   S   S   S   G   G
             4210        4220        4230        4240        4250

>Env.BG505 immunogen
                  |
GG GAT CTG GAA GTG ACA ACA CAC TCT TTC AAT TGC GGT GGC GAG TTC TTC TAT TGT AAT A    < 4320
   D   L   E   V   T   T   H   S   F   N   C   G   G   E   F   F   Y   C   N   T
             4270        4280        4290        4300        4310

CA AGT GGA TTA TTT AAC TCT ACT TGG ATT TCA AAT ACC TCA GTC CAA GGA TCT AAT TCA A    < 4380
   S   G   L   F   N   S   T   W   I   S   N   T   S   V   Q   G   S   N   S   T
             4330        4340        4350        4360        4370

CA GGG TCT AAC GAT TCT ATA ACA TTA CCT TGC CGT ATA AAG CAA ATT ATT AAT ATG TGG C    < 4440
   G   S   N   D   S   I   T   L   P   C   R   I   K   Q   I   I   N   M   W   Q
             4390        4400        4410        4420        4430

AA AGA ATC GGG CAA GCG ATG TAT GCT CCA CCT ATT CAA GGC GTG ATT CGT TGC GTT TCA A    < 4500
   R   I   G   Q   A   M   Y   A   P   P   I   Q   G   V   I   R   C   V   S   N
             4450        4460        4470        4480        4490

AC ATA ACA GGG TTG ATC CTG ACC AGG GAT GGA GGC TCT ACC AAT TCC ACC ACC GAG ACC T    < 4560
   I   T   G   L   I   L   T   R   D   G   G   S   T   N   S   T   T   E   T   F
             4510        4520        4530        4540        4550

TC CGT CCC GGT GGC GGA GAT ATG CGG GAT AAC TGG AGA TCA GAG CTC TAT AAG TAT AAG G    < 4620
   R   P   G   G   G   D   M   R   D   N   W   R   S   E   L   Y   K   Y   K   V
             4570        4580        4590        4600        4610

TT GTG AAG ATT GAA CCT CTT GGA GTT GCC CCT ACA AGA GCA AAG AGA AGG GTG GTT GGC C    < 4680
   V   K   I   E   P   L   G   V   A   P   T   R   A   K   R   R   V   V   G   R
             4630        4640        4650        4660        4670

GA GAG AAG AGA GCA GTT GGC ATC GGT GCT GTC TTT CTC GGA TTT CTT GGA GCA GCT GGA T    < 4740
   E   K   R   A   V   G   I   G   A   V   F   L   G   F   L   G   A   A   G   S
             4690        4700        4710        4720        4730

CC ACT ATG GGA GCA GCA TCA ATG ACA CTA ACA GTG CAG GCT AGA AAT TTG CTT AGC GGA A    < 4800
   T   M   G   A   A   S   M   T   L   T   V   Q   A   R   N   L   L   S   G   I
             4750        4760        4770        4780        4790

TC GTT CAG CAG CAG AGC AAT TTA CTA AGA GCA ATT GAA GCA CAG CAA CAT CTC TTA AAG T    < 4860
   V   Q   Q   Q   S   N   L   L   R   A   I   E   A   Q   Q   H   L   L   K   L
             4810        4820        4830        4840        4850

TC ACG GTG TGG GGC ATT AAA CAA CTA CAA GCG AGA GTG CTT GCC GTC GAA AGA TAT TTG C    < 4920
   T   V   W   G   I   K   Q   L   Q   A   R   V   L   A   V   E   R   Y   L   R
             4870        4880        4890        4900        4910

GA GAC CAA CAG CTA TTG GGT ATT TGG GGT TGT TCT GGG AAA TTA ATT TGC ACA ACA AAT G    < 4980
   D   Q   Q   L   L   G   I   W   G   C   S   G   K   L   I   C   T   T   N   V
             4930        4940        4950        4960        4970

TT CCA TGG AAC TCC TCC TGG AGT AAT AGG AAT TTA AGT GAG ATA TGG GAC AAC ATG ACA T    < 5040
   P   W   N   S   S   W   S   N   R   N   L   S   E   I   W   D   N   M   T   W
             4990        5000        5010        5020        5030

GG TTG CAG TGG GAC AAG GAA ATC TCA AAT TAT ACA CAG ATA ATC TAT GGA TTA TTA GAA G    < 5100
   L   Q   W   D   K   E   I   S   N   Y   T   Q   I   I   Y   G   L   L   E   E
             5050        5060        5070        5080        5090

AG TCT CAG AAT CAG CAA GAG AAG AAT GAA CAG GAT TTG CTT GCA TTG GAT AAG TGG GCT T    < 5160
   S   Q   N   Q   Q   E   K   N   E   Q   D   L   L   A   L   D   K   W   A   S
             5110        5120        5130        5140        5150

CT CTA TGG AAC TGG TTC GAT ATT AGT AAT TGG CTC TGG TAT ATT AAG AGC TCT ATT GCC T    < 5220
   L   W   N   W   F   D   I   S   N   W   L   W   Y   I   K   S   S   I   A   S
```

```
                                                     -continued
      5170          5180          5190          5200          5210
CT TTT TTC TTT ATC ATA GGG TTA ATC ATT GGA CTA TTC TTG GTT CTC CGA GTT GGT ATT T    < 5280
   F   F   F   I   I   G   L   I   I   G   L   F   L   V   L   R   V   G   I   Y
      5230          5240          5250          5260          5270

AT CTT TGC ATT AAA TTA AAG CAC ACC AAG AAA AGA CAG ATT TAT ACA GAC ATA GAG ATG A    < 5340
   L   C   I   K   L   K   H   T   K   K   R   Q   I   Y   T   D   I   E   M   N
      5290          5300          5310          5320          5330

AC CGA CTT GGA AAG TAA AGC TCA AAT CCT GCA CAA CAG ATT CTT CAT GTT TGA ACC AAA T    < 5400
   R   L   G   K   *
      5350          5360          5370          5380          5390

CA ACT TGT GAT ATC ATG CTC AAA GAG GCC TTA ATT AAA TTT TAA TTT TTA ATT TTT ATG A    < 5460
      5410          5420          5430          5440          5450

AA AAA ACT AAC AGC AAT CAT GGA AGT CCA CGA TTT TGA GAC CGA CGA GTT CAA TGA TTT C    < 5520
      5470          5480          5490          5500          5510

AA TGA AGA TGA CTA TGC CAC AAG AGA ATT CCT GAA TCC GAT GAG CGC ATG ACG TAC TTG    < 5580
      5530          5540          5550          5560          5570

AA TCA TGC TGA TTA CAA TTT GAA TTC TCC TCT AAT TAG TGA TGA TAT TGA CAA TTT GAT C    < 5640
      5590          5600          5610          5620          5630

AG GAA ATT CAA TTC TCT TCC GAT TCC CTC GAT GTG GGA TAG TAA GAA CTG GGA TGG AGT T    < 5700
      5650          5660          5670          5680          5690

CT TGA GAT GTT AAC ATC ATG TCA AGC CAA TCC CAT CTC AAC ATC TCA GAT GCA TAA ATG G    < 5760
      5710          5720          5730          5740          5750

AT GGG AAG TTG GTT AAT GTC TGA TAA TCA TGA TGC CAG TCA AGG GTA TAG TTT TTT ACA T    < 5820
      5770          5780          5790          5800          5810

GA AGT GGA CAA AGA GGC AGA AAT AAC ATT TGA CGT GGT GGA GAC CTT CAT CCG CGG CTG G    < 5880
      5830          5840          5850          5860          5870

GG CAA CAA ACC AAT TGA ATA CAT CAA AAA GGA AAG ATG GAC TGA CTC ATT CAA AAT TCT C    < 5940
      5890          5900          5910          5920          5930

GC TTA TTT GTG TCA AAA GTT TTT GGA CTT ACA CAA GTT GAC ATT AAT CTT AAA TGC TGT C    < 6000
      5950          5960          5970          5980          5990

TC TGA GGT GGA ATT GCT CAA CTT GGC GAG GAC TTT CAA AGG CAA AGT CAG AAG AAG TTC T    < 6060
      6010          6020          6030          6040          6050

CA TGG AAC GAA CAT ATG CAG GCT TAG GGT TCC CAG CTT GGG TCC TAC TTT TAT TTC AGA A    < 6120
      6070          6080          6090          6100          6110

GG ATG GGC TTA CTT CAA GAA ACT TGA TAT TCT AAT GGA CCG AAA CTT TCT GTT AAT GGT C    < 6180
      6130          6140          6150          6160          6170

AA AGA TGT GAT TAT AGG GAG GAT GCA AAC GGT GCT ATC CAT GGT ATG TAG AAT AGA CAA C    < 6240
      6190          6200          6210          6220          6230

CT GTT CTC AGA GCA AGA CAT CTT CTC CCT TCT AAA TAT CTA CAG AAT TGG AGA TAA AAT T    < 6300
      6250          6260          6270          6280          6290

GT GGA GAG GCA GGG AAA TTT TTC TTA TGA CTT GAT TAA AAT GGT GGA ACC GAT ATG CAA C    < 6360
      6310          6320          6330          6340          6350

TT GAA GCT GAT GAA ATT AGC AAG AGA ATC AAG GCC TTT AGT CCC ACA ATT CCC TCA TTT T    < 6420
      6370          6380          6390          6400          6410

GA AAA TCA TAT CAA GAC TTC TGT TGA TGA AGG GGC AAA AAT TGA CCG AGG TAT AAG ATT C    < 6480
      6430          6440          6450          6460          6470

CT CCA TGA TCA GAT AAT GAG TGT GAA AAC AGT GGA TCT CAC ACT GGT GAT TTA TGG ATC G    < 6540
      6490          6500          6510          6520          6530

TT CAG ACA TTG GGG TCA TCC TTT TAT AGA TTA TTA CGC TGG ACT AGA AAA ATT ACA TTC C    < 6600
      6550          6560          6570          6580          6590

CA AGT AAC CAT GAA GAA AGA TAT TGA TGT GTC ATA TGC AAA AGC ACT TGC AAG TGA TTT A    < 6660
      6610          6620          6630          6640          6650

GC TCG GAT TGT TCT ATT TCA ACA GTT CAA TGA TCA TAA AAA GTG GTT CGT GAA TGG AGA C    < 6720
      6670          6680          6690          6700          6710

TT GCT CCC TCA TGA TCA TCC CTT TAA AAG TCA TGT TAA AGA AAA TAC ATG GCC TAC AQC T    < 6780
```

```
                6730        6740        6750        6760        6770
GC TCA AGT TCA AGA TTT TGG AGA TAA ATG GCA TGA ACT TCC GCT GAT TAA ATG TTT TGA A    < 6840
          6790        6800        6810        6820        6830
AT ACC CGA CTT ACT AGA CCC ATC GAT AAT ATA CTC TGA CAA AAG TCA TTC AAT GAA TAG G    < 6900
          6850        6860        6870        6880        6890
TC AGA GGT GTT GAA ACA TGT CCG AAT GAA TCC GAA CAC TCC TAT CCC TAG TAA AAA GGT G    < 6960
          6910        6920        6930        6940        6950
TT GCA GAC TAT GTT GGA CAC AAA GGC TAC CAA TTG GAA AGA ATT TCT AAA GA GAT TGA T    < 7020
          6970        6980        6990        7000        7010
GA GAA GGG CTT AGA TGA TGA TGA TCT AAT TAT TGG TCT AAA GG AAA GGA GAG GGA ACT G    < 7080
          7030        7040        7050        7060        7070
AA GTT GGC AGG TAG ATT TTT CTC CCT AAT GTC TTG GAA ATT GCG AGA ATA CTT TGT AAT T    < 7140
          7090        7100        7110        7120        7130
AC CGA ATA TTT GAT AAA GAC TCA TTT CGT CCC TAT GTT TAA AGG CCT GAC AAT GGC GGA C    < 7200
          7150        7160        7170        7180        7190
GA TCT AAC TGC AGT CAT TAA AAA GAT GTT AGA TTC CTC ATC CGG CCA AGG ATT GAA GTC A    < 7260
          7210        7220        7230        7240        7250
TA TGA GGC AAT TTG CAT AGC CAA TCA CAT TGA TTA CGA AAA ATG GAA TAA CCA CCA AAG G    < 7320
          7270        7280        7290        7300        7310
AA GTT ATC AAA CGG CCC AQT GTT CCG AGT TAT GGG CCA GTT CTT AGG TTA TCC ATC CTT A    < 7380
          7330        7340        7350        7360        7370
AT CGA GAG AAC TCA TGA ATT TTT TGA GAA AAG TCT TAT ATA CTA CAA TGG AAG ACC AGA C    < 7440
          7390        7400        7410        7420        7430
TT GAT GCG TGT TCA CAA CAA CAC ACT GAT CAA TTC AAC CTC CCA ACQ AGT TTG TTG GCA A    < 7500
          7450        7460        7470        7480        7490
GG ACA AGA GGG TGG ACT GGA AGG TCT ACG GCA AAA AGG ATG GAG TAT CCT CAA TCT ACT G    < 7560
          7510        7520        7530        7540        7550
GT TAT TCA AAG AGA GGC TAA AAT CAG AAA CAC TGC TGT CAA AGT CTT GGC ACA AGG TGA T    < 7620
          7570        7580        7590        7600        7610
AA TCA AGT TAT TTG CAC ACA GTA TAA AAC GAA GAA ATC GAG AAA CGT TGT AGA ATT ACA G    < 7680
          7630        7640        7650        7660        7670
GG TGC TCT CAA TCA AAT GGT TTC TAA TAA TGA GAA AAT TAT GAC TGC AAT CAA AAT AGG G    < 7740
          7690        7700        7710        7720        7730
AC AGG GAA GTT AGG ACT TTT GAT AAA TGA CGA TGA GAC TAT GCA ATC TGC AGA TTA CTT G    < 7800
          7750        7760        7770        7780        7790
AA TTA TGG AAA AAT ACC GAT TTT CCG TGG AGT GAT TAG AGG GTT AGA GAC CAA GAG ATG G    < 7860
          7810        7820        7830        7840        7850
TC ACG AGT GAC TTG TGT CAC CAA TGA CCA AAT ACC CAC TTG TGC TAA TAT AAT GAG CTC A    < 7920
          7870        7880        7890        7900        7910
GT TTC CAC AAA TGC TCT CAC CGT AGC TCA TTT TGC TGA GAA CCC AAT CAA TGC CAT GAT A    < 7980
          7930        7940        7950        7960        7970
CA GTA CAA TTA TTT TGG GAC ATT TGC TAG ACT CTT GTT GAT GAT GCA TGA TCC TGC TCT T    < 8040
          7990        8000        8010        8020        8030
CG TCA ATC ATT GTA TGA AGT TCA AGA TAA GAT ACC GGG CTT GCA CAG TTC TAC TTT CAA A    < 8100
          8050        8060        8070        8080        8090
TA CGC CAT GTT GTA TTT GGA CCC TTC ATT GGG AGT GTC GGG CAT GTC TTT GTC CAG G    < 8160
          8110        8120        8130        8140        8150
TT TTT GAT TAG AGC CTT CCC AGA TCC CGT AAC AGA AAG TCT CTC ATT CTG GAG ATT CAT C    < 8220
          8170        8180        8190        8200        8210
CA TGT ACA TGC TCG AAG TGA GCA TCT GAA GGA GAT GAG TGC AGT ATT TGG AAA CCC CGA G    < 8280
          8230        8240        8250        8260        8270
AT AGC CAA GTT CCG AAT AAC TCA CAT AGA CAA GCT AGT AGA AGA TCC AAC CTC TCT GAA C    < 8340
          8290        8300        8310        8320        8330
AT CGC TAT GGG AAT GAG TCC AGC GAA CTT GTT AAA GAC TGA GGT TAA AAA ATG CTT AAT C    < 8400
```

-continued

```
                  8350        8360        8370        8380        8390
GA ATC AAG ACA AAC CAT CAG GAA CCA GGT GAT TAA GGA TGC AAC CAT ATA TTT GTA TCA T    < 8460
              8410        8420        8430        8440        8450

GA AGA GGA TCG GCT CAG AAG TTT CTT ATG GTC AAT AAA TCC TCT GTT CCC TAG ATT TTT A    < 8520
              8470        8480        8490        8500        8510

AG TGA ATT CAA ATC AGG CAC TTT TTT GGG AGT CGC AGA CGG GCT CAT CAG TCT ATT TCA A    < 8580
              8530        8540        8550        8560        8570

AA TTC TCG TAC TAT TCG AAA CTC CTT TAA GAA AAA GTA TCA TAG GGA ATT GGA TGA TTT G    < 8640
              8590        8600        8610        8620        8630

>L
    |
AT TGT GAG GAG TGA GGT ATC CTC TTT GAC ACA TTT AGG GAA ACT TCA TTT GAG AAG GGG A    < 8700
              8650        8660        8670        8680        8690

TC ATG TAA AAT GTG GAC ATG TTC AGC TAG TCA TGC TGA CAC ATT AAG ATA CAA ATC CTG G    < 8760
              8710        8720        8730        8740        8750

GG CCG TAC AGT TAT TGG GAC AAC TGT ACC CCA TCC ATT AGA AAT GTT GGG TCC ACA ACA T    < 8820
              8770        8780        8790        8800        8810

CG AAA AGA GAC TCC TTG TGC ACC ATG TAA CAC ATC AGG GTT CAA TTA TGT TTC TGT GCA T    < 8880
              8830        8840        8850        8860        8870

TG TCC AGA CGG GAT CCA TGA CGT CTT TAG TTC ACG GGA CCA TTG CCT GCT TAT CT AGG G    < 8940
              8890        8900        8910        8920        8930

TC TAA AAC ATC TGA ATC TAC ATC TAT TTT GCA GCC TTG GGA AAG GGA AAG CAA AGT CCC A    < 9000
              8950        8960        8970        8980        8990

CT GAT TAA AAG AGC TAC ACG TCT TAG AGA TGC TAT CTC TTG GTT TGT TGA ACC CGA CTC T    < 9060
              9010        9020        9030        9040        9050

AA ACT AGC AAT GAC TAT ACT TTC TAA CAT CCA CTC TTT AAC AGG CGA AGA ATG GAC CAA A    < 9120
              9070        9080        9090        9100        9110

AG GCA GCA TGG GTT CAA AAG AAC AGG GTC TGC CCT TCA TAG GTT TTC GAC ATC TCG GAT G    < 9180
              9130        9140        9150        9160        9170

AG CCA TGG TGG GTT CGC ATC TCA GAG CAC TGC AGC ATT GAC CAG GTT GAT GGC AAC TAC A    < 9240
              9190        9200        9210        9220        9230

GA CAC CAT GAG GGA TCT GGG AGA TCA GAA TTT CGA CTT TTT ATT CCA AGC AAC GTT GCT C    < 9300
              9250        9260        9270        9280        9290

TA TQC TCA AAT TAC CAC CAC TGT TGC AAG AGA CGG ATG GAT CAC CAG TTG TAC AGA TCA T    < 9360
              9310        9320        9330        9340        9350

TA TCA TAT TGC CTG TAA GTC CTG TTT GAG ACC CAT AGA AGA GAT CAC CCT GGA CTC AAG T    < 9420
              9370        9380        9390        9400        9410

AT GGA CTA CAC GCC CCC AGA TGT ATC CCA TGT GCT GAA GAC ATG GAG GAA TGG GGA AGG T    < 9480
              9430        9440        9450        9460        9470

TC GTG GGG ACA AGA GAT AAA ACA GAT CTA TCC TTT AGA AGG GAA TTG GAA GAA TTT AGC A    < 9540
              9490        9500        9510        9520        9530

CC TGC TGA GCA ATC CTA TCA AGT CGG CAG ATG TAT AGG TTT TCT ATA TGG AGA CTT GGC G    < 9600
              9550        9560        9570        9580        9590

TA TAG AAA ATC TAC TCA TGC CGA GGA CAG TTC TCT ATT TCC TCT ATC TAT ACA AGG TCG T    < 9660
              9610        9620        9630        9640        9650

AT TAG AGG TCG AGG TTT CTT AAA AGG GTT GCT AGA CGG ATT AAT GAG AGC AAG TTG CTG C    < 9720
              9670        9680        9690        9700        9710

CA AGT AAT ACA CCG GAG AAG TCT GGC TCA TTT GAA GAG GCC GGC CAA CGC AGT GTA CGG A    < 9780
              9730        9740        9750        9760        9770

GG TTT GAT TTA CTT GAT TGA TAA ATT GAG TGT ATC ACC TCC ATT CCT TTC TCT TAC TAG A    < 9840
              9790        9800        9810        9820        9830

TC AGG ACC TAT TAG AGA CGA ATT AGA AAC GAT TCC CCA CAA GAT CCC AAC CTC CTA TCC G    < 9900
              9850        9860        9870        9880        9890

AC AAG CAA CCG TGA TAT GGG GGT GAT TGT CAG AAA TTA CTT CAA ATA CCA ATG CCG TCT A    < 9960
              9910        9920        9930        9940        9950
```

```
AT TGA AAA GGG AAA ATA CAG ATC ACA TTA TTC ACA ATT ATG GTT ATT CTC AGA TGT CTT A    < 10020
       9970         9980         9990        10000        10010

TC CAT AGA CTT CAT TGG ACC ATT CTC TAT TTC CAC CAC CCT CTT GCA AAT CCT ATA CAA G    < 10080
      10030        10040        10050        10060        10070

CC ATT TTT ATC TGG GAA AGA TAA GAA TGA GTT GAG AGA GCT GGC AAA TCT TTC TTC ATT G    < 10140
      10090        10100        10110        10120        10130

CT AAG ATC AGG AGA GGG GTG GGA AGA CAT ACA TGT GAA ATT CTT CAC CAA GGA CAT ATT A    < 10200
      10150        10160        10170        10180        10190

TT GTG TCC AGA GGA AAT CAG ACA TGC TTG CAA GTT CGG GAT TGC TAA GGA TAA TAA TAA A    < 10260
      10210        10220        10230        10240        10250

GA CAT GAG CTA TCC CCC TTG GGG AAG GGA ATC CAG AGG GAC AAT TAC AAC AAT CCC TGT T    < 10320
      10270        10280        10290        10300        10310

TA TTA TAC GAC CAC CCC TTA CCC AAA GAT GCT AGA GAT GCC TCC AAG AAT CCA AAA TCC C    < 10380
      10330        10340        10350        10360        10370

CT GCT GTC CGG AAT CAG GTT GGG CCA ATT ACC AAC TGG CGC TCA TTA TAA AAT TCG AGT     < 10440
      10390        10400        10410        10420        10430

AT ATT ACA TGG AAT GGG AAT CCA TTA CAG GGA CTT CTT GAG TTG TGG AGA CGG CTC CGG A    < 10500
      10450        10460        10470        10480        10490

GG GAT GAC TGC TGC ATT ACT ACG AGA AAA TGT GCA TAG CAG AGG AAT ATT CAA TAG TCT G    < 10560
      10510        10520        10530        10540        10550

TT AGA ATT ATC AGG GTC AGT CAT GCG AGG CGC CTC TCC TGA GCC CCG CAG TGC CCT AGA A    < 10620
      10570        10580        10590        10600        10610

AC TTT AGG AGG AGA TAA ATC GAG ATG TGT AAA TGG TGA AAC ATG TTG GAA ATA TCC ATC T    < 10680
      10630        10640        10650        10660        10670

GA CTT ATG TGA CCC AAG GAG TTG GGA CTA TTT CCT CCG ACT CAA AGC AGG CTT GGG GCT T    < 10740
      10690        10700        10710        10720        10730

CA AAT TGA TTT AAT TGT AAT GGA TAT GGA AGT TCG GGA TTC TTC TAG TAG CCT GAA AAT T    < 10800
      10750        10760        10770        10780        10790

GA GAC GAA TGT TAG AAA TTA TGT GCA CCG GAT TTT GGA TGA GCA AGG AGT TTT AAT CTA C    < 10860
      10810        10820        10830        10840        10850

AA GAC TTA TGG AAC ATA TAT TTG TGA GAG CGA AAA GAA TGC AGT AAC AAT CCT TGG TCC C    < 10920
      10870        10880        10890        10900        10910

AT GTT CAA GAC GGT CGA CTT AGT TCA AAC AGA ATT TAG TAG TTC TCA AAC GTC TGA AGT A    < 10980
      10930        10940        10950        10960        10970

TA TAT GGT ATG TAA AGG TTT GAA GAA ATT AAT CGA TGA ACC CAA TCC CGA TTG GTC TTC C    < 11040
      10990        11000        11010        11020        11030

AT CAA TGA ATC CTG GAA AAA CCT GTA CGC ATT CCA GTC ATC AGA ACA GGA ATT TGC CAG A    < 11100
      11050        11060        11070        11080        11090

GC AAA GAA GGT TAG TAC ATA CTT TAG CTT GAC AGG TAT TCC CTC CCA ATT CAT TCC TGA T    < 11160
      11110        11120        11130        11140        11150

CC TTT TGT AAA CAT TGA GAC TAT GCT ACA AAT ATT CGG AGT ACC CAC GGG TGT GTC TCA T    < 11220
      11170        11180        11190        11200        11210

GC GGC TGC CTT AAA ATC ATC TGA TAG ACC TGC AGA TTT ATT GAC CAT TAG CCT TTT TTA T    < 11280
      11230        11240        11250        11260        11270

AT GGC GAT TAT ATC GTA TTA TAA CAT CAA TCA TAT CAG AGT AGG ACC GAT ACC TCC GAA C    < 11340
      11290        11300        11310        11320        11330

CC CCC ATC AGA TGG AAT TGC ACA AAA TGT GGG GAT CGC TAT AAC TGG TAT AAG CTT TTG G    < 11400
      11350        11360        11370        11380        11390

CT GAG TTT GAT GGA GAA AGA CAT TCC ACT ATA TCA ACA GTG TTT AGC AGT TAT CCA GCA A    < 11460
      11410        11420        11430        11440        11450

TC ATT CCC GAT TAG GTG GGA GGC TGT TTC AGT AAA AGG AGG ATA CAA GCA GAA GTG GAG T    < 11520
      11470        11480        11490        11500        11510

AC TAG AGG TGA TGG GCT CCC AAA AGA TAG CCG AAT TTC AGA CTC CTT GGC CCC AAT CGG G    < 11580
      11530        11540        11550        11560        11570
```

-continued

```
AA CTG GAT CAG ATC TCT GGA ATT GGT CCG AAA CCA AGT TCG TCT AAA TCC ATT CAA TGA G      < 11640
       11590          11600          11610          11620          11630

AT CTT GTT CAA TCA GCT ATG TCG TAC AGT GGA TAA TCA TTT GAA ATG GTC AAA TTT GCG A       < 11700
       11650          11660          11670          11680          11690

AA AAA CAC AGG AAT GAT TGA ATG GAT CAA TAG ACG AAT TTC AAA AGA AGA CCG TCT ATA         < 11760
       11710          11720          11730          11740          11750

CT GAT GTT GAA GAG TGA CCT AGA CGA GGA AAA CTC TTG GAG AGA TTA AAA AAT CAT GAG G       < 11820
       11770          11780          11790          11800          11810
```

>VSV Trailer

```
AG ACT CCA AAC TTT AAG TAT GAA AAA AAC TTT GAT CCT AAA GAC CCT CTT GTG GTT TTT A      < 11880
       11830          11840          11850          11860          11870

TT TTT TAT CTG GTT TTG TGG TCT TCG Tgg ccg cca tgg tcc cag cct cct cgc tgg cgc c      < 11940
       11890          11900          11910          11920          11930
```

>Hepatitis Delta Virus Ribozyme

```
gg ctg ggc aac att ccg agg gga ccg tcc cct cgg taa tgg cga atg gaa cct gct aac a      < 12000
       11950          11960          11970          11980          11990 aa gcc cga aag gaa gct gag ttg gct gct gcc acc gct gag caa taa cta gca taa ccc c      < 12060
       12010          12020          12030          12040          12050 tt ggg gcc tct aaa cgg gtc ttg agg ggt ttt ttg ctg aaa gga gga act ata tcc gga t      < 12120
       12070          12080          12090          12100          12110
```

>T7 Terminators

```
gc ggc cga tcc ggc tgc taa caa agc ccg aaa gga agc tga gtt ggc tgc tgc cac cgc t      < 12180
       12130          12140          12150          12160          12170 ga gca ata act agc ata acc cct tgg ggc ctc taa acg ggt ctt gag ggg ttt ttt gct g      < 12240
       12190          12200          12210          12220          12230 aa agg agg aac tat atc cgg gtt aac ctg cat aa tga atc ggc caa cgc gcg ggg aga g       < 12300
       12250          12260          12270          12280          12290 gc ggt ttg cgt att ggg cgc tct tcc gct tcc tcg ctc act gac tcg ctg cgc tcg gtc g      < 12360
       12310          12320          12330          12340          12350 tt cgg ctg cgg cga gcg gta tca gct cac tca aag gcg gta ata cgg tta tcc aca gaa t      < 12420
       12370          12380          12390          12400          12410 ca ggg gat aac gca gga aag aac atg tga gca aaa ggc cag caa aag gcc agg aac cgt a      < 12480
       12430          12440          12450          12460          12470 aa aag gcc gcg ttg ctg gcg ttt ttc cat agg ctc cgc ccc cct gac gag cat cac aaa a      < 12540
       12490          12500          12510          12520          12530 at cga cgc tca agt cag agg tgg cga aac ccg aca gga cta taa aga tac cag gcg ttt c      < 12600
       12550          12560          12570          12580          12590 cc cct gga agc tcc ctc gtg cgc tct cct gtt ccg acc ctg ccg ctt acc gga tac ctg t      < 12660
       12610          12620          12630          12640          12650 cc gcc ttt ctc cct tcg gga agc gtg gcg ctt tct caa tgc tca cgc tgt agg tat ctc a      < 12720
       12670          12680          12690          12700          12710 gt tcg gtg tag gtc gtt cgc tcc aag ctg ggc tgt gtg cac gaa ccc ccc gtt cag ccc g      < 12780
       12730          12740          12750          12760          12770 ac cgc tgc gcc tta tcc ggt aac tat cgt ctt gag tcc aac ccg gta aga cac gac tta t      < 12840
       12790          12800          12810          12820          12830 cg cca ctg gca gca gcc act ggt aac agg att agc aga gcg agg tat gta ggc ggt gct a      < 12900
       12850          12860          12870          12880          12890 ca gag ttc ttg aag tgg tgg cct aac tac ggc tac act aga agg aca gta ttt ggt atc t      < 12960
       12910          12920          12930          12940          12950 gc gct ctg ctg aag cca gtt acc ttc gga aaa aga gtt ggt agc tct tga tcc ggc aaa c      < 13020
       12970          12980          12990          13000          13010 aa acc acc gct ggt agc ggt ggt ttt ttt gtt tgc aag cag cag att acg cgc aga aaa a      < 13080
       13030          13040          13050          13060          13070
```

```
aa gga tct caa gaa gat cct ttg atc ttt tct acg ggg tct gac gct cag tgg aac gaa a      < 13140
        13090         13100         13110         13120         13130 ac tca cgt taa ggg att ttg gtc atg aga tta tca aaa agg atc ttc acc tag atc ctt t      < 13200
        13150         13160         13170         13180         13190

>pSP72
                                                                            |
ta aat taa aaa tga agt ttt aaa tca atc taa agt ata tat gag taa act tgg tct gac a       < 13260
        13210         13220         13230         13240         13250 gt tac caa tgc tta atc agt gag gca cct atc tca gcg atc tgt cta ttt cgt tca tcc a       < 13320
        13270         13280         13290         13300         13310 ta gtt gcc tga ctc ccc gtc gtg tag ata act acg ata cgg gag ggc tta cca tct ggc c       < 13380
        13330         13340         13350         13360         13370 cc agt gct gca atg ata ccg cga gac cca cgc tca ccg gct cca gat tta tca gca ata a       < 13440
        13390         13400         13410         13420         13430 ac cag cca gcc gga agg gcc gag cgc aga agt ggt cct gca act tta tcc gcc tcc atc c       < 13500
        13450         13460         13470         13480         13490 ag tct att aat tgt tgc cgg gaa gct aga gta agt agt tcg cca gtt aat agt ttg cgc a       < 13560
        13510         13520         13530         13540         13550 ac gtt gtt gcc att gct aca ggc atc gtg gtg tca cgc tcg tcg ttt ggt atg gct tca t       < 13620
        13570         13580         13590         13600         13610 tc agc tcc ggt tcc caa cga tca agg cga gtt aca tga tcc ccc atg ttg tgc aaa aaa g       < 13680
        13630         13640         13650         13660         13670 cg gtt agc tcc ttc ggt cct ccg atc gtt gtc aga agt aag ttg gcc gca gtg tta tca c       < 13740
        13690         13700         13710         13720         13730 tc atg gtt atg gca gca ctg cat aat tct ctt act gtc atg cca tcc gta aga tgc ttt t      < 13800
        13750         13760         13770         13780         13790 ct gtg act ggt gag tac tca acc aag tca ttc tga gaa tag tgt atg cgg cga ccg agt t      < 13860
        13810         13820         13830         13840         13850 gc tct tgc ccg gcg tca ata cgg gat aat acc gcg cca cat agc aga act tta aaa gtg c      < 13920
        13870         13880         13890         13900         13910 tc atc att gga aaa cgt tct tcg ggg cga aaa ctc tca agg atc tta ccg ctg ttg aga t      < 13980
        13930         13940         13950         13960         13970 cc agt tcg atg taa ccc act cgt gca ccc aac tga tct tca gca tct ttt act ttc acc a      < 14040
        13990         14000         14010         14020         14030 gc gtt tct ggg tga gca aaa aca gga agg caa aat gcc gca aaa aag gga ata agg gcg a      < 14100
        14050         14060         14070         14080         14090 ca cgg aaa tgt tga ata ctc ata ctc ttc ctt ttt caa tat tat tga agc att tat cag g      < 14160
        14110         14120         14130         14140         14150 gt tat tgt ctc atg agc gga tac ata ttt gaa tgt att tag aaa aat aaa caa ata ggg g      < 14220
        14170         14180         14190         14200         14210 tt ccg cgc aca ttt ccc cga aaa gtg cca cct gac gtc                                     < 14258
        14230         14240         14250
```

Features:
T7-g10 Promoter: [1:49]
Hammerhead Ribozyme: [50:107]
VSV Leader: [108:170]
N: [171:1439]
P: [1503:2300]
M: [2360:3049]
Env.EG505 immunogen: [3198:5357]
L: [5479:11808]
VSV Trailer: [11809:11907]
Hepatitis Delta Virus Ribozyme: [11913:11991]
T7 Terminators: [11992:12260]
pSP72: [12261:14258]

```
                                                                SEQ ID NO: 2
  1  mkcllylafl  figvnckasa  enlwvtvyyg  vpvwkdaett  lfcasdakay  etekhnvwat
 61  hacvptdpnp  qeihlenvte  efnmwknnmv  eqmhtdiisl  wdqslkpcvk  ltplcvtlqc
121  tnvtnnitdd  mrgelkncsf  nmttelrdkk  qkvyslfyrl  dvvqinengg  nrsnnsnkey
181  rlincntsai  tqacpkvsfe  pipihycapa  gfailkckdk  kfngtgpcps  vstvqcthgi
241  kpvvstqlll  ngslaeeevm  irsenitnna  knilvqfntp  vqinctrpnn  ntrksirigp
301  gqafyatgdi  igdirqahct  vskatwnetl  gkvvkqlrkh  fgnntiirfa  nssggdlevt
361  thsfncggef  fycntsglfn  stwisntsvq  gsnstgsnds  itlpcrikqi  inmwqrigqa
421  myappiqgvi  rcvsnitgli  ltrdggstns  ttetfrpggg  dmrdnwrsel  ykykvvkiep
481  lgvaptrakr  rvvgrekrav  gigavflgfl  gaagstmgaa  smtltvqarn  llsgivqqqs
541  nllraieaqq  hllkltvwgi  kqlqarvlav  erylrdqqll  giwgcsgkli  cttnvpwnss
601  wsnrnlseiw  dnmtwlqwdk  eisnytqiiy  glleesqnqq  ekneqdllal  dkwaslwnwf
661  disnwlwyik  sstasffiii  gliiglglyi  rwgiyleiki  khtkkrglyt  dtemnrlgk
VSV G signal peptide
Ala-Ser amino acid linker
Env. BG505 ectodomain
VSV G transmembrane region
VSV G cytoplasmic tail
```

It is to be understood and expected that variations in the principles of invention as described above may be made by one skilled in the art and it is intended that such modifications, changes, and substitutions are to be included within the scope of the present invention.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

Example 1: VSVΔG-Env.BG505 Vaccine—Live Attenuated VSV-HIV Chimera Delivering Env Trimers Vesicular stomatitis virus (VSV) has been modified to generate a live chimeric virus vaccine (VSVΔG-Env.BG505) for active immunization against HIV. The replication-competent recombinant chimera delivers a functional HIV Env glycoprotein trimer (clade A.BG505) in the context of viral replication mimicking native HIV spike presentation during an HIV infection.

The VSVΔG-Env.BG505 chimera was constructed by replacing the natural VSV glycoprotein (G) gene with coding sequence for Env.BG505 (FIG. 1). As a result, Env is the only transmembrane glycoprotein encoded by the chimera, and virus propagation and spread is dependent on expression of functional Env trimers and infection of CD4+/CCR5+ cells.

VSVΔG-Env.BG505 is generated from a VSV genomic DNA clone that was developed from a lab-adapted strain of VSV (Indiana serotype). The genomic sequence is similar, but not identical, to the VSV genomic clone developed at Yale University (1), which is used for other VSV-based vaccine candidates including the attenuated VSV-N4CT1 vector developed by Profectus and NIAID (2), and the VSVΔG-Ebola virus chimera developed by the National Microbiology Laboratory in Canada (3), NewLink Genetics, and Merck Vaccines (4-6). About 100 nucleotides out 11 kb differ between the Yale and IAVI genomic clones.

Live VSVΔG-Env.BG505 is recovered from plasmid DNA by electroporating cells with the modified VSV genomic clone (FIG. 1C), a plasmid encoding T7 RNA polymerase to synthesize genomic RNA copies, and five plasmids that provide VSV polypeptides (N, P, M, G, L) in trans to initiate virus replication (9). The virus rescue protocol does not require proprietary transfection reagents or helper virus, and it has been optimized for use with Vero cell substrates (protocol adapted from (10, 11)). Recovery of infectious VSVΔG-Env.BG505 can be initiated by electroporating plasmids into Vero cells derived from a qualified cell bank (cells from Meridian Life Science, Inc. are used at IAVI), after which the virus must be propagated in cells that express CD4 and CCR5 to support Env-dependent replication. Thus, recombinant virus amplification, clonal isolation, virus seed preparation, and vaccine production is performed with a modified Vero cell line that contains the genes for human CD4 and CCR5 (VeroCD4/CCR5).

Applicants developed a stable VeroCD4/CCR5 cell line for propagation of the VSVΔG-Env.BG505 chimera. The cell line used in the lab currently encodes human CD4 and CCR5 and was developed under research conditions starting with cells obtained from the Meridian Life Science qualified Vero cell bank. The research VeroCD4/CCR5 cell line is stable and has been used for several years to support work on VSVΔG-Env.BG505 and a number of similar chimeric viruses. Yields of VSVΔG-Env.BG505 produced in VeroCD4/CCR5 monolayers typically are >1×10$^7$ pfus per ml of harvested culture medium. Work on deriving a new cell line has been initiated for the purpose of generating VeroCD4/CCR5 cells that will meet requirements associated with future VSVΔG-Env.BG505 cGMP manufacturing. As used herein, VERO-CD4/CCR5, VeroCD4/CCR5 and VERT or VERT3 are used interchangeably.

The VSVΔG-Env.BG505 vaccine tested in rhesus macaques contained 'pseudotyped' (12) virus particles to enhance vaccine uptake and promote a vigorous initial round of infection and replication. When virus was grown to produce a batch of vaccine, infection was conducted under conditions in which the VSV G glycoprotein was transiently expressed in VeroCD4/CCR5 cells allowing production of particles containing G. An efficient laboratory method was developed to simplify addition of the G pseudotype. A suspension of VeroCD4/CCR5 cells is mixed with plasmid DNA encoding G and VSVΔG-Env.BG505 particles after which the mixture is subjected to electroporation. The electroporated cells are then distributed into cell factories containing culture medium. Virus is harvested and purified 48 hours post-electroporation.

Figures 2A, 2B, 2C, 2D:
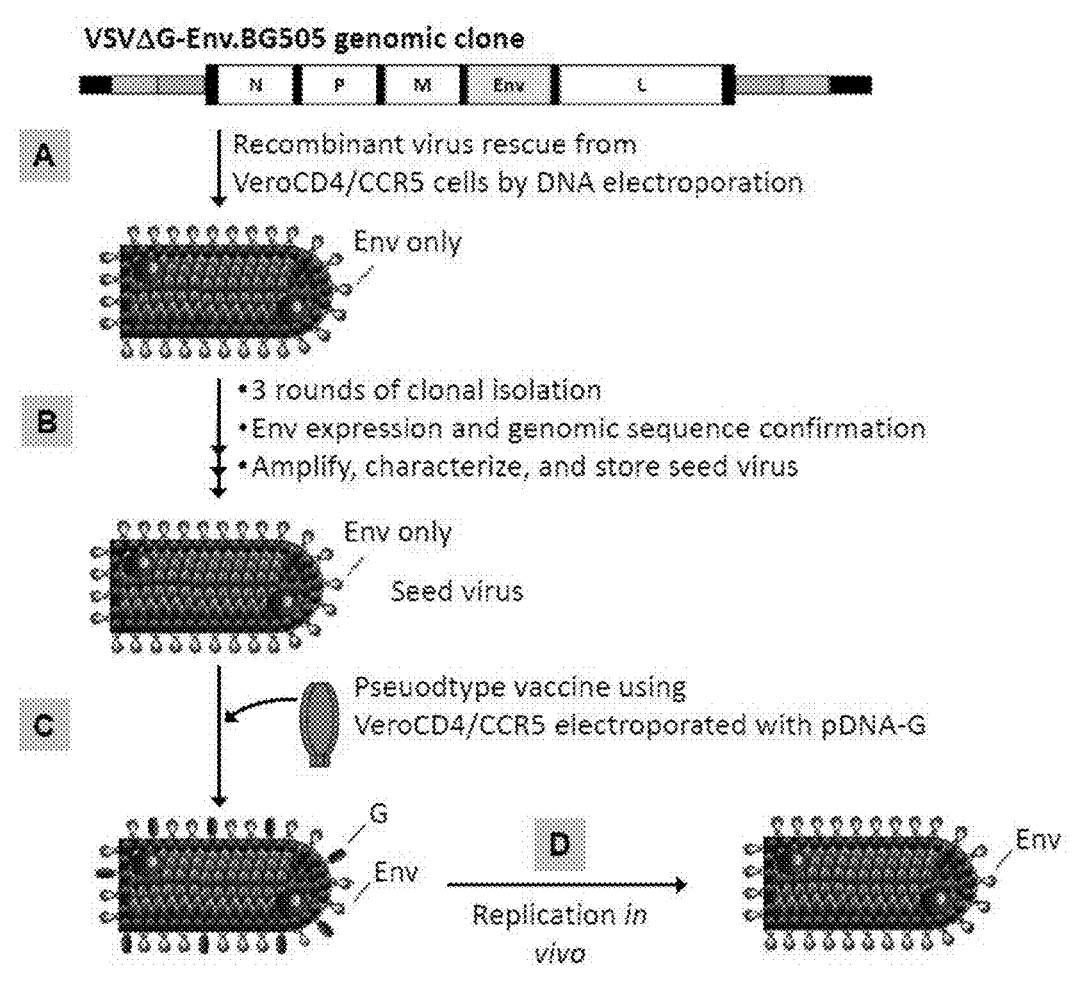

Two points about G pseudotyping and the VSVΔG-Env.BG505 vaccine are worth emphasizing. First, VSVΔG-Env.BG505 does not contain the G gene; thus, infected cells do not express G and the VSV glycoprotein is present only in pseudotyped virus particles used for vaccination. Following vaccination, progeny VSVΔG-Env.BG505 particles produced by the first round of replication will lack the G glycoprotein making all subsequent rounds of infection dependent on HIV Env and infection of CD4+/CCR5+ cells of lymphoid origin. Because G is present only transiently (FIG. 2), it cannot promote spread of infection to other types of cells and tissues (i.e. neurons in the central nervous system).

The second point is related to the benefit of the pseudotyping. It is well established that G is a very effective virus attachment protein, which has been used to pseudotype a variety of different candidate viral vaccines, gene therapy vectors, and oncolytic agents (12-15). A positive effect of pseudotyping on immunogenicity of a prototype VSVΔG-SIV Env chimera was demonstrated experimentally in a small pilot macaque study in which animals were vaccinated mucosally (combination of oral and nasal cavity) with a vaccine prepared with and without a G pseudotype. In animals vaccinated with pseudotyped virus particles, anti-SIV Env antibody titers were greater than 100-fold higher (FIG. 5). Moreover, the transient exposure to G in the virus inoculum did not elicit significant titers of anti-G antibodies (data not shown).

Many different glycoproteins may be used to pseudotype VSV particles besides G. Alternative pseudotypes may be useful for targeting vaccine delivery to different areas. Examples include F plus H from morbilliviruses, the F and HN from various parainfluenza viruses, the F and G from various pneumoviruses, the F plus HN from various rubulla viruses. Also, the glycorpteins from filoviruses or arena viruses, among others.

Although the efficacious VSVΔG-Env.BG505 vaccine was a pseudotyped particle, it is important to note that studies have not yet been done in macaques to assess whether pseudotyping contributes to vaccine efficacy. Furthermore, G was selected for pseudotyping because it was known to be highly effective, but other alternative viral glycoproteins can be used if it becomes necessary to develop a pseudotyped vaccine that targets a more limited cell population.

The VSVΔG-Env.BG505 vaccine was designed to deliver authentic HIV envelope (Env) trimers mimicking the presentation of Env spikes by HIV infection or a live attenuated HIV vaccine. As designed, the replication competent chimeric virus provides several important immunostimulants once administered, including: 1) innate signaling initiated by infection and replication of an RNA virus; 2) infected cells containing Env incorporated in the cell surface membrane; and 3) progeny virus particles containing Env spikes arrayed on their surface. Moreover, like HIV or SIV, Env-dependent VSVΔG-Env.BG505 propagation in vivo might contribute to vaccine efficacy by providing more persistent antigen exposure and immune stimulation that is associated with infection occurring in lymphoid tissues (16, 17).

VSVΔG-Env.BG505 is designed to propagate using Env as its attachment and entry protein. This has several important consequences during chimeric virus replication in the vaccinee, including: 1) there is strong selective pressure to maintain the gene encoding functional Env; 2) it ensures that the replicating chimeric virus will present the immune system with authentic Env spike targets; and 3) because Env is functional and incorporated in the membrane, it has the conformational flexibility of a native spike and will expose the immune system with a full range of authentic antigenic determinants. Related to the last point, it also is important to emphasize that the functional Env.BG505 trimer expressed by VSVΔG-Env.BG505 is not a conformationally constrained trimer like some other experimental vaccines that have been develop recently like Env.BG505 SOSIP or Env.BG505 NFL described by others (18, 19).

Rose and colleagues first demonstrated that it was feasible to generate an infectious VSVΔG-Env chimera using a clade B Env (23), but additional development was necessary to advance an effective vaccine candidate. First, the Env.BG505 immunogen was selected specifically because it was known to have a broad antigenicity profile (24) and it was isolated from an infected infant that produced bnAbs (25, 26). Second, it was necessary to investigate Env modifications for a number of reasons, including 1) to ensure Env gene genetic stability; 2) to enable vigorous replication in cell culture that would support vaccine production; and 3) to substantially increase Env incorporation into to the infected cell membrane and virus particle to provide improved display of Env spike immunogens. Following an approached suggested by earlier data showing that the Env cytoplasmic tail caused vector genetic instability (unpublished and (27)) and suppressed incorporation into VSV particles (28), a number of hybrid Envs were designed and evaluated (FIG. 3) in which various combinations of the Env signal peptide (SP), transmembrane (TM) region, and cytoplasmic tail (CT) were replaced with sequence from VSV G (Indiana serotype). A hybrid Env containing the VSV G SP, TM and CT was found to be expressed abundantly on the cell surface of transfected cells and also was found to support efficient Env-dependent replication of the VSVΔG-Env.BG505 chimera in CD4+/CCR5+ cells. A hybrid in which the Env membrane-proximal external region (MPER) also was replaced with the analogous 'Stem' domain of G was expressed in modestly greater quantities on the surface of transfected cells, but since it lacked the important Env MPER epitope, all subsequent vector design has focused on the Env hybrids where the SP, TM, and CT are substituted with VSV G sequences. Therefore, the VSVΔG-Env.BG505 vaccine encodes a highly expressed Env-G hybrid, which is designed so that all sequence displayed on the membrane surface is Env ectodomain while intracellular and membrane-spanning sequences are derived from G.

The Env-G hybrid immunogen incorporated on the surface of infected cells and VSVΔG-Env.BG505 particles is broadly antigenic. An example of infected cells analyzed by flow cytometry (FIG. 4B) shows that multiple mAbs bind the cell surface including PGT145, PGT151 and VRC06, which bind preferentially to determinants formed by well-ordered trimers (19, 21, 22). Similarly, bnAbs recognize purified virions when they are adsorbed to alum and the alum-virus complexes are analyzed by flow cytometry (FIG. 4D), which agrees with electron microscope images (FIG. 4C) showing surface density consistent with the present of glycoprotein complexes on the surface of VSVΔG-Env.BG505 particles.

Part of the vaccine design objective was to develop a chimeric virus that could be administered effectively by a mucosal route to stimulate immune protection at the mucosal barrier. Even though a mucosal application of the live vaccine may be advantageous, Applicants do not envision the vaccine to be limited to this route of administration. Because research and development on lentivirus virus vectors has shown that Env is not an effective attachment protein for virus particle delivery, VSVΔG-Env.BG505 modifications were considered that might significantly improve virus uptake without changing the key feature of the chimeric virus, which is its unique design in which Env is the sole glycoprotein expressed following infection. Thus, rather than genetically modifying the VSVΔG-Env.BG505 vector further, a decision was made to test vaccines in which the virus particles were prepared with a G pseudotype, as a considerable body of work on lentiviruses (12) as well as a variety of chimeric VSV vectors (29) showed that pseudotyping with G was effective.

To support testing of a pseudotyped VSVΔG-Env vaccine, a simple system was developed to add G to virus particles. Briefly, a suspension of VeroCD4/CCR5 cells is mixed with plasmid DNA encoding G and VSVΔG-Env.BG505 particles and then mixture is subjected to electroporation. The electroporated cell suspension is then distributed into cell stacks and cultured for ~48 hours after which pseudotyped virus particles are harvested and purified. The efficiency of pseudotyping can then be quantified by evaluating plaque formation on CD4+/CCR5+ cell monolayers in which Env or G can direct infection, and comparing this to G-mediated infection of standard Vero monolayers, which support a single-cycle of infection that can be quantified by immunostaining to detect individual cells expressing viral proteins.

A pilot study was conducted in Indian rhesus macaques with a prototype VSVΔG-SIV chimera (FIG. 5A, VSVΔG-SIV-GagEnv). Macaques were used for this early study because transgenic or 'humanized' small animal models that can support replication of a CD4/CCR5-tropic virus have limitations. The macaque study was conducted for three primary reasons: 1) assess the ability to safely vaccinate mucosally in the nasal and oral cavity with a chimeric virus; 2) detect and quantify serum anti-Env antibodies elicited by mucosal vaccination; and 3) compare vaccines prepared with and without a G pseudotype.

Macaques were vaccinated (FIG. 5B) at weeks 0 and 6 by applying virus solution to the nasal and oral cavities ($1 \times 10^8$ pfus per site). Importantly, animal behavior was normal following vaccination and no lesions were observed in or around the nose or mouth. Quantification of antibody titers by bioplex assay (30) showed that the chimeric virus vaccines were immunogenic and that the pseudotyped vaccine was significantly more potent. Following the first vaccination, samples analyzed at week 6 showed that the pseudotyped VSVΔG-SIV-GagEnv vaccine elicited low but detectable antibody titers, while animals vaccinated with an 'empty' VSV vector or the chimeric virus lacking the G pseudotype had values near baseline. Env antibody titers increased after homologous boost at week 6, and it was clear that the peak titer elicited by the pseudotyped chimera was considerably stronger ($\geq 1,000 \times$) compared to the magnitude of the response generated by the vaccine lacking the G pseudotype, and the titers also remained substantial $\geq 2.5$ months after the week-6 boost. It also is worth highlighting that two mucosal vaccinations with the pseudotyped VSVΔG-SIV-GagEnv vaccine generated antibody titers that were in the same range as peak responses seen with a relatively potent vaccination regimen based on 3×DNA-SIV-Env prime (intramuscular electroporation) and Ad5-SIV Env (intramuscular) boost (31).

Several conclusions were drawn from this pilot study. First, the chimeric virus vaccine was able to safely elicit anti-Env antibodies against a membrane anchored Env spike. Second, antibody titers of this magnitude elicited by mucosal vaccination indicated that the VSVΔG-SIV chimera replicated following vaccination and that the antibody response was not elicited simply by exposure to the virus particles delivered in a buffered solution. This assumption also is consistent with the fact that G in the pseudotyped particles did not elicit an anti-G response significantly above background in an ELISA (data not shown). Finally, it was evident that the chimeric virus vaccine prepared with the G pseudotype was more immunogenic, thus the HIV vaccine based on VSVΔG-Env.BG505 was advanced for testing in macaques as a pseudotyped vaccine.

The preclinical efficacy of the VSVΔG-Env.BG505 vaccine prepared with a G pseudotype is being evaluated in Indian rhesus macaques using the rectal SHIV challenge model. The study was designed with the three main objectives: 1) show that the VSVΔG-Env.BG505 chimera could be administered safely to the nasal and oral cavities; 2) demonstrate that vaccination elicits anti-Env antibodies; and 3) establish that vaccination provides measurable protection from rectal exposure with a heterologous clade B SHIV (SHIV SF162p3).

The study also included a head-to-head comparison with a second VSV vector encoding the same Env.BG505 trimer immunogen. The main purpose of this comparison was to evaluate an alternative Env.BG505 delivery vector (VSV-G6-Env.BG505, FIG. 6) that would have increased replicative capacity in vivo. To achieve greater replicative capacity, the VSV-G6-Env.BG505 vector was designed to contain genes encoding Env.BG505 and G; therefore, the vector coexpresses the glycoproteins in infected cells, and incorporate both trimeric complexes in virus particles. As designed, the VSV-G6-Env.BG505 vector can propagate and spread in a wider range of cells in vivo because the continuous expression of G allows infection and spread into a much broader range of cell types. Thus, both the pseudotyped VSVΔG-Env.BG505 chimera and VSV-G6-Env.BG505 can infect most cell types at the site of vaccine administration using G, but after the initial round of replication, secondary infection initiated by progeny virus particles will be significantly different, with the VSVΔG-Env.BG505 targeted specifically to CD4+/CCR5+ cells and VSV-G6-Env.BG505 being able to spread into multiple cell types.

The preclinical efficacy study was designed with three groups of 10 macaques (negative for Mamu-B*08 and -B*17 MHC alleles associated with immune control) that were vaccinated at weeks 0, 4, and 29 with pseudotyped VSVΔG-Env.BG505, VSV-G6-Env.BG505 or a saline control. It is important to highlight that vaccination was conducted only with the live VSV vectors, and no boost was performed with a heterologous vaccine. Vaccines were administered by application to mucosal surfaces in the nasal and oral cavity of sedated animals ($1 \times 10^8$ pfus per site). No local lesions were observed and all macaques behaved normally after vaccination.

All macaques immunized with a VSV-based Env.BG505 vaccine developed detectable anti-Env serum antibodies after the second vaccination. The third vaccination at week 29 provided a boost, and perhaps more importantly, increased the durability of the antibody titers, which persisted during the 5-month rest period before challenge in 8 out of 10 macaques vaccinated with VSVΔG-Env.BG505 and all animals vaccinated with VSV-G6-Env.BG505. The TZM-bl assay (33) also was used to analyse serum for virus-neutralizing antibodies (nAbs). The resulted showed that nAb titers were low (titers ≤100) and were detectable in only some vaccinated animals (summarized on the ELISA chart in FIG. 8). In macaques vaccinated with the VSVΔG-Env.BG505 chimera, 4 animals were positive for nAbs active against HIV SF162p3 pseudovirus at week 31, but the titers waned to undetectable by the day of SHIV challenge. Vaccination with VSV-G6-Env.BG505 elicited nAbs against SF162p3 and homologous BG505 pseudovirus that were detectable at week 31 and 48, but not in all animals.

Clade B SHIV SF162p3 challenge commenced at week 48, which was about 5 months after the final vaccination (FIG. 7). The challenge protocol was composed of 3 stages: the first 5 rectal exposures conducted approximately every two weeks, a 6-week rest period, and the final 5 biweekly exposures. Macaques with ≥200 genome SHIV copies per ml of plasma were considered infected after which challenge was stopped. All infected macaques were viremic for weeks following the initial infection (FIG. 9) as determined by detection of SHIV genomes in the blood, and accordingly, the infected animals developed antibodies against Gag expressed by the SHIV (data not shown).

The SHIV infection rate was significantly reduced in macaques vaccinated with the VSVΔG-Env.BG505 chimera compared to animals vaccinated with VSV-G6-Env.BG505 or saline control (FIG. 10). Over the course of 9 challenges, 9 out of 10 macaques in the Control and VSV-G6-Env.BG505 groups became chronically infected with SHIV at a similar frequency. In contrast, in macaques vaccinated with VSVΔG-Env.BG505, just 3 were infected with challenge virus indicating that VSΔG-Env.BG505 immunization significantly increased resistance to mucosal SHIV infection. Thus, vaccine efficacy as measured by prevention of rectal infection with a heterologous clade B SHIV was 67%.

Immunologic assessment continues, but current results point to a potential relationship between the reduced frequency of infection seen in the animals vaccinated with the VSVΔG-Env.BG505 vaccine (FIG. 10) and Env-specific serum antibodies. First, both replication-competent VSV vectors elicited serum antibodies that persisted for the 5-month period between the final vaccination and the beginning of the repetitive SHIV challenge protocol (FIG. 8). In the animals vaccinated with VSVΔG-Env.BG505, there were 2 animals in which the antibody titers waned to baseline levels by week 48 when challenge commenced (FIG. 8), and interestingly, these were the same two animals that appeared least resistant in this group and became infected by challenge 2 (FIG. 10). The third animal that became infected in this group resisted 7 challenges conducted over a period of about 4.5 months, but became infected at exposure 8 by which time the serum antibody titers had waned. These results imply that there is a relationship between Env.BG505 gp120 binding antibody titers and SHIV infection resistance. This trend is summarized graphically in FIG. 11.

In contrast to the results seen in animals vaccinated with the VSVΔG-Env.BG505 chimera, that rate of infection in macaques vaccinated with VSV-G6-Env.BG505 was very similar to the control group indicating that vaccination did not have measurable effect on SHIV infection frequency (FIG. 10). This was observed even though all animals had developed Env antibodies in response to vaccination, including some macaques that had nAbs (FIG. 8).

Taken together, the results of vaccination with the different live VSV-based vectors show that both types of vaccine elicit Env antibodies, but that the quality of the antiviral immunity is very different. What is responsible for this difference in protection is not understood at this time, but perhaps it is related to antibody binding site specificity, the diversity of Env epitopes recognized, or IgG effector functions. Alternatively, the two live vectors might elicit different profiles of Env-specific T cells with antiviral activity that is affecting infection resistance. Ongoing and future immunologic assessment will help identify differences in the immune responses elicited by the two vaccines, which will provide guidance for vector and immunogen improvements.

The results produced with two different replicating VSV-based vaccines also illustrates clearly that specific vaccine design details can have a pronounced effect on efficacy. Some of the unique features of the VSVΔG-Env.BG505 vaccine that might contribute to efficacy, include; 1) CD4+/CCR5+ tropism that targets replication to lymphoid cells and tissues; 2) chimeric virus propagation in vivo that is dependent on expression of functional Env and will provide immune system exposure to authentic Env spikes; 3) the only glycoprotein expressed is Env, thus there is no other competing glycoprotein immunogen that might dominate immune responses; and 4) the lack of other vector-encoded glycoproteins eliminates development of potent anti-vector antibodies that might interfere with multiple immunizations.

Preclinical efficacy in the SHIV challenge model was observed following mucosal vaccination with a total dose of $2 \times 10^8$ pfu per ml. The vaccine dose was split between two sites. Mucosal surfaces in the nasal and oral cavities each received $1 \times 10^8$ pfu applied in a buffered solution.

Preclinical efficacy in the SHIV challenge model was observed with a vaccination schedule of 0, 4, and 29 weeks. Other vaccination schedules are also contemplated.

Mucosal vaccination in the nasal and oral cavity was tested primarily because the goal was to stimulate enhanced mucosal immunity. Other considerations supporting this vaccination route included: 1) providing access to submucosal CD4+/CCR5+ lymphocytes that would be targets for VSVΔG-Env.BG505 replication, and 2) VSV naturally infects these mucosal sites.

VSVΔG-Env.BG505 is a recombinant chimeric virus based on the VSV Indiana serotype. The VSV G gene deleted and replaced with sequence encoding functional HIV Env.BG505. The live vaccine is replication competent and propagates specifically in cells that contain the CD4/CCR5 receptors.

The efficacious preclinical vaccine is a G-pseudotyped VSVΔG-Env.BG505 that is applied to nasal and oral cavity mucosal surfaces at 0, 4, and 29 weeks.

The VSVΔG-Env.BG505 vaccine is expected to be safe for use in humans, because 1) no observable adverse reactions occurred in vaccinated macaques, and 2) the chimeric virus design makes propagation dependent on Env, thus virus spread in vivo is restricted to lymphoid cell and tissues that express CD4 and CCR5 and will prevent virus replication in other sites like the central nervous system.

The preferred cell line for vaccine production is VeroCD4/CCR5, which has been used to support preclinical development of the VSVΔG-Env.BG505 chimeric virus vaccine. A similar cell line must be 'rederived' using conditions and materials that are consistent with using the cells for vaccine manufacturing. Manufacturing processes and steps are set forth in FIG. 12. Preparation of VSVΔG-Env.BG505 with G pseudotype is set forth in FIG. 13.

Preclinical material tested in macaques may be purified by 2 round of centrifugation through sucrose cushion and the method is based on tangential flow filtration.

Preclinical vaccine material is stored frozen (−80) in Hank's Balanced Salt Solution (HBSS) supplemented with 15% trehalose.

Raw material and biological starting material suitability, quality, and characterization (e.g., passage history of cell substrate and viral seed material) may include:

Recombinant VSVΔG-Env.BG505 is generated from a plasmid DNA containing a modified VSV genomic clone in which the G gene is replaced with sequence encoding HIV Env.BG505. Rescue of recombinant virus is initiated by electroporating the genomic clone with supporting plasmids that direct expression of VSV N, P, M, G, and L proteins and T7 phage RNA polymerase.

The VSV genomic clone is based on the VSV Indiana serotype.

The VeroCD4/CCR5 cell line used for preclinical development was generated starting with Vero cells from a cell bank qualified cell bank (obtained from Meridian Life Science, Inc). The VeroCD4/CCR5 cell line was generated by microporating cells with a plasmid that contains genes for expression of human CD4 and CCR5 and the Neo resistance marker.

VeroCD4/CCR5 is typically propagated in monolayer cultures. Cell factories are used for virus production. The cells are grown in DMEM supplemented with 10% fetal bovine serum from certified suppliers. Virus amplification can be conducted in monolayers in which the medium is exchanged with serum-free growth medium such as VPSFM.

Preclinical Vaccine Characterization May Include:

Potency: Virus is quantified by plaque assay on VeroCD4/CCR5 cells. To confirm virus particles are pseudotyped with G, standard Vero monolayers are infected and the single-cycle infection in incubated overnight. Monolayers are subsequently immunostained to quantify infected cells.

Additional Vaccine Virus Characterization:
Genome copies (qPCR) per infectious unit
Genomic nucleotide sequence
Env insert integrity by PCR
Env expression by Western blot
Env expression detected on infected cells by flow cytometry and bnAbs
Virus purity by denaturing gel electrophoresis and silver stain
*Mycoplasma* testing by PCR
Endotoxin testing
Assay Development Required to Support Lot Release or Product Characterization May Include:
Potency—see above, plaque assay and genome-to-pfu ratio
Safety:
  Env insert integrity by PCR
  Lack of VSV G gene by PCR
  Genomic sequence
  Infection of Vero cells with pseudotyped virus and subsequent blind passage to confirm lack of CPE indicating that virus is CD4/CCR5-dependent as expected
Preparation of Reagents to Develop Assays May Include:
Primers and probes are available to assess genomic sequences, quantify genome copies, and specifically detect the Env gene insert.
Antibodies that can neutralize the pseudotyped VSVΔG-Env.BG505 chimera are required for adventitious agent testing. Antibodies recognizing the G pseudotype block infection in eggs, mice, and most cell lines provided they do not express primate CD4/CCR5.

Reference Citations

1. Lawson N D, Stillman E A, Whitt M A, Rose J K. Recombinant vesicular stomatitis viruses from DNA. Proceedings of the National Academy of Sciences of the United States of America. 1995; 92(10):4477-81. PubMed PMID: 7753828.
2. Clarke D K, Nasar F, Chong S, Johnson J E, Coleman J W, Lee M, Witko S E, Kotash C S, Abdullah R, Megati S, Luckay A, Nowak B, Lackner A, Price R E, Little P, Kalyan N, Randolf V, Javadian A, Zamb T J, Parks C L, Egan M A, Eldridge J, Hendry M, Udem S A. Neurovirulence and immunogenicity of attenuated recombinant vesicular stomatitis viruses in nonhuman primates. J Virol. 2014; 88(12):6690-701. doi: 10.1128/JVI.03441-13. PubMed PMID: 24696472; PubMed Central PMCID: PMC4054374.
3. Jones S M, Feldmann H, Stroher U, Geisbert J B, Fernando L, Grolla A, Klenk H D, Sullivan N J, Volchkov V E, Fritz E A, Daddario K M, Hensley L E, Jahrling P B, Geisbert T W. Live attenuated recombinant vaccine protects nonhuman primates against Ebola and Marburg viruses. Nature medicine. 2005; 11(7):786-90. PubMed PMID: 15937495.
4. Regules J A, Beigel J H, Paolino K M, Voell J, Castellano A R, Munoz P, Moon J E, Ruck R C, Bennett J W, Twomey P S, Gutierrez R L, Remich S A, Hack H R, Wisniewski M L, Josleyn M D, Kwilas S A, Van Deusen N, Mbaya O T, Zhou Y, Stanley D A, Bliss R L, Cebrik D, Smith K S, Shi M, Ledgerwood J E, Graham B S, Sullivan N J, Jagodzinski L L, Peel S A, Alimonti J B, Hooper J W, Silvera P M, Martin B K, Monath T P, Ramsey W J, Link C J, Lane H C, Michael N L, Davey R T, Jr., Thomas S J, r V-Z-GPSG. A Recombinant Vesicular Stomatitis Virus Ebola Vaccine—Preliminary Report. The New England journal of medicine. 2015. doi: 10.1056/NEJMoa1414216. PubMed PMID: 25830322.
5. Henao-Restrepo A M, Longini I M, Egger M, Dean N E, Edmunds W J, Camacho A, Carroll M W, Doumbia M, Draguez B, Duraffour S, Enwere G, Grais R, Gunther S, Hossmann S, Konde M K, Kone S, Kuisma E, Levine M M, Mandal S, Norheim G, Riveros X, Soumah A, Trelle S, Vicari A S, Watson C H, Keita S, Kieny M P, Rottingen J A. Efficacy and effectiveness of an rVSV-vectored vaccine expressing Ebola surface glycoprotein: interim results from the Guinea ring vaccination cluster-randomised trial. Lancet. 2015; 386(9996):857-66. doi: 10.1016/S0140-6736(15)61117-5. PubMed PMID: 26248676.
6. Agnandji S T, Huttner A, Zinser M E, Njuguna P, Dahlke C, Fernandes J F, Yerly S, Dayer J A, Kraehling V, Kasonta R, Adegnika A A, Altfeld M, Auderset F, Bache E B, Biedenkopf N, Borregaard S, Brosnahan J S, Burrow R, Combescure C, Desmeules J, Eickmann M, Fehling S K, Finckh A, Goncalves A R, Grobusch M P, Hooper J, Jambrecina A, Kabwende A L, Kaya G, Kimani D, Lell B, Lemaitre B, Lohse A W, Massinga-Loembe M, Matthey A, Mordmuller B, Nolting A, Ogwang C, Ramharter M, Schmidt-Chanasit J, Schmiedel S, Silvera P, Stahl F R, Staines H M, Strecker T, Stubbe H C, Tsofa B, Zaki S, Fast P, Moorthy V, Kaiser L, Krishna S, Becker S, Kieny M P, Bejon P, Kremsner P G, Addo M M, Siegrist C A. Phase 1 Trials of rVSV Ebola Vaccine in Africa and Europe—Preliminary Report. The New England journal of medicine. 2015. doi: 10.1056/NEJMoa1502924. PubMed PMID: 25830326.
7. Barr J N, Whelan S P, Wertz G W. Transcriptional control of the RNA-dependent RNA polymerase of vesicular stomatitis virus. Biochim Biophys Acta. 2002; 1577(2): 337-53. PubMed PMID: 12213662.
8. Wertz G W, Perepelitsa V P, Ball L A. Gene rearrangement attenuates expression and lethality of a nonsegmented negative strand RNA virus. Proceedings of the National Academy of Sciences of the United States of America. 1998; 95(7):3501-6. PubMed PMID: 9520395.
9. Rabinovich S, Powell R L, Lindsay R W, Yuan M, Carpov A, Wilson A, Lopez M, Coleman J W, Wagner D, Sharma P, Kemelman M, Wright K J, Seabrook J P, Arendt H, Martinez J, DeStefano J, Chiuchiolo M J, Parks C L. A novel, live-attenuated vesicular stomatitis virus vector displaying conformationally intact, functional HIV-1 envelope trimers that elicits potent cellular and humoral responses in mice. PLoS ONE. 2014; 9(9):e106597. doi: 10.1371/journal.pone.0106597. PubMed PMID: 25215861; PubMed Central PMCID: PMC4162551.
10. Witko S E, Johnson J E, Kalyan N K, Felber B K, Pavlakis G N, Sidhu M K, Hendry R M, Udem S A, Parks C L. Refined methods for propagating vesicular stomatitis virus vectors that are defective for G protein expression. J Virol Methods. 2010; 164(1-2):43-50. Epub 2009/11/28. doi: 10.1016/j.jviromet.2009.11.023. PubMed PMID: 19941901; PubMed Central PMCID: PMC2837098.
11. Witko S E, Kotash C S, Nowak R M, Johnson J E, Boutilier L A, Melville K J, Heron S G, Clarke D K, Abramovitz A S, Hendry R M, Sidhu M S, Udem S A, Parks C L. An efficient helper-virus-free method for rescue of recombinant paramyxoviruses and rhadoviruses from a cell line suitable for vaccine development. J Virol Methods. 2006; 135(1):91-101. PubMed PMID: 16569439.
12. Cronin J, Zhang X Y, Reiser J. Altering the tropism of lentiviral vectors through pseudotyping. Current gene therapy. 2005; 5(4):387-98. PubMed PMID: 16101513.
13. Levy C, Verhoeyen E, Cosset F L. Surface engineering of lentiviral vectors for gene transfer into gene therapy target cells. Curr Opin Pharmacol. 2015; 24:79-85. doi: 10.1016/j.coph.2015.08.003. PubMed PMID: 26298515.
14. Kahn J S, Roberts A, Weibel C, Buonocore L, Rose J K. Replication-competent or attenuated, nonpropagating vesicular stomatitis viruses expressing respiratory syncytial virus (RSV) antigens protect mice against RSV challenge. J Virol. 2001; 75(22):11079-87. PubMed PMID: 11602747.
15. Kapadia S U, Simon I D, Rose J K. SARS vaccine based on a replication-defective recombinant vesicular stomatitis virus is more potent than one based on a replication-competent vector. Virology. 2008; 376(1):165-72. PubMed PMID: 18396306.
16. Fukazawa Y, Lum R, Okoye A A, Park H, Matsuda K, Bae J Y, Hagen S I, Shoemaker R, Deleage C, Lucero C, Morcock D, Swanson T, Legasse A W, Axthelm M K, Hesselgesser J, Geleziunas R, Hirsch V M, Edlefsen P T, Piatak M, Jr., Estes J D, Lifson J D, Picker L J. B cell follicle sanctuary permits persistent productive simian immunodeficiency virus infection in elite controllers. Nature medicine. 2015; 21(2):132-9. doi: 10.1038/nm.3781. PubMed PMID: 25599132; PubMed Central PMCID: PMC4320022.
17. Fukazawa Y, Park H, Cameron M J, Lefebvre F, Lum R, Coombes N, Mahyari E, Hagen S I, Bae J Y, Reyes M D, 3rd, Swanson T, Legasse A W, Sylwester A, Hansen S G, Smith A T, Stafova P, Shoemaker R, Li Y, Oswald K, Axthelm M K, McDermott A, Ferrari G, Montefiori D C, Edlefsen P T, Piatak M, Jr., Lifson J D, Sekaly R P, Picker L J. Lymph node T cell responses predict the efficacy of live attenuated SIV vaccines. Nature medicine. 2012; 18(11):1673-81. doi: 10.1038/nm.2934. PubMed PMID: 22961108; PubMed Central PMCID: PMC3493820.
18. Sanders R W, van Gils M J, Derking R, Sok D, Ketas T J, Burger J A, Ozorowski G, Cupo A, Simonich C, Goo L, Arendt H, Kim H J, Lee J H, Pugach P, Williams M, Debnath G, Moldt B, van Breemen M J, Isik G, Medina-Ramirez M, Back J W, Koff W C, Julien J P, Rakasz E G, Seaman M S, Guttman M, Lee K K, Klasse P J, LaBranche C, Schief W R, Wilson I A, Overbaugh J, Burton D R, Ward A B, Montefiori D C, Dean H, Moore J P. HIV-1 neutralizing antibodies induced by native-like envelope trimers. Science. 2015. doi: 10.1126/science.aac4223. PubMed PMID: 26089353.
19. Sharma S K, de Val N, Bale S, Guenaga J, Tran K, Feng Y, Dubrovskaya V, Ward A B, Wyatt R T. Cleavage-Independent HIV-1 Env Trimers Engineered as Soluble Native Spike Mimetics for Vaccine Design. Cell Rep. 2015; 11(4):539-50. doi: 10.1016/j.celrep.2015.03.047. PubMed PMID: 25892233.
20. Burton D R, Mascola J R. Antibody responses to envelope glycoproteins in HIV-1 infection. Nature immunology. 2015; 16(6):571-6. doi: 10.1038/ni.3158. PubMed PMID: 25988889.
21. Blattner C, Lee J H, Sliepen K, Derking R, Falkowska E, de la Pena A T, Cupo A, Julien J P, van Gils M, Lee P S, Peng W, Paulson J C, Poignard P, Burton D R, Moore J P, Sanders R W, Wilson I A, Ward A B. Structural Delineation of a Quaternary, Cleavage-Dependent Epitope at the gp41-gp120 Interface on Intact HIV-1 Env Trimers. Immunity. 2014. doi: 10.1016/j.immuni.2014.04.008. PubMed PMID: 24768348.
22. Falkowska E, Le K M, Ramos A, Doores K J, Lee J H, Blattner C, Ramirez A, Derking R, van Gils M J, Liang C H, McBride R, von Bredow B, Shivatare S S, Wu C Y, Chan-Hui P Y, Liu Y, Feizi T, Zwick M B, Koff W C, Seaman M S, Swiderek K, Moore J P, Evans D, Paulson J C, Wong C H, Ward A B, Wilson I A, Sanders R W, Poignard P, Burton D R. Broadly Neutralizing HIV Antibodies Define a Glycan-Dependent Epitope on the Prefusion Conformation of gp41 on Cleaved Envelope Trimers. Immunity. 2014. doi: 10.1016/j.immuni.2014.04.009. PubMed PMID: 24768347.
23. Boritz E, Gerlach J, Johnson J E, Rose J K. Replication-competent rhabdoviruses with human immunodeficiency virus type 1 coats and green fluorescent protein: entry by a pH-independent pathway. J Virol. 1999; 73(8):6937-45. Epub 1999/07/10. PubMed PMID: 10400792; PubMed Central PMCID: PMC112779.
24. Hoffenberg S, Powell R, Carpov A, Wagner D, Wilson A, Kosakovsky Pond S, Lindsay R, Arendt H, Destefano J, Phogat S, Poignard P, Fling S P, Simek M, Labranche C, Montefiori D, Wrin T, Phung P, Burton D, Koff W, King C R, Parks C L, Caulfield M J. Identification of an HIV-1 clade A envelope that exhibits broad antigenicity and neutralization sensitivity and elicits antibodies targeting three distinct epitopes. J Virol. 2013; 87(10):5372-83. doi: 10.1128/JVI.02827-12. PubMed PMID: 23468492; PubMed Central PMCID: PMC3648150.
25. Goo L, Chohan V, Nduati R, Overbaugh J. Early development of broadly neutralizing antibodies in HIV-1-infected infants. Nature medicine. 2014; 20(6):655-8.

26. Wu X, Parast A B, Richardson B A, Nduati R, John-Stewart G, Mbori-Ngacha D, Rainwater S M, Overbaugh J. Neutralization escape variants of human immunodeficiency virus type 1 are transmitted from mother to infant. J Virol. 2006; 80(2):835-44. doi: 10.1128/JVI.80.2.835-844.2006. PubMed PMID: 16378985; PubMed Central PMCID: PMC1346878.

27. Wyatt L S, Belyakov I M, Earl P L, Berzofsky J A, Moss B. Enhanced cell surface expression, immunogenicity and genetic stability resulting from a spontaneous truncation of HIV Env expressed by a recombinant MVA. Virology. 2008; 372(2):260-72. Epub 2007/12/01. doi: 10.1016/j.virol.2007.10.033. PubMed PMID: 18048074; PubMed Central PMCID: PMC2289778.

28. Johnson J E, Rodgers W, Rose J K. A plasma membrane localization signal in the HIV-1 envelope cytoplasmic domain prevents localization at sites of vesicular stomatitis virus budding and incorporation into VSV virions. Virology. 1998; 251(2):244-52. Epub 1998/12/05. doi: 10.1006/viro.1998.9429. PubMed PMID: 9837788.

29. Tani H, Morikawa S, Matsuura Y. Development and Applications of VSV Vectors Based on Cell Tropism. Front Microbiol. 2011; 2:272. doi: 10.3389/fmicb.2011.00272. PubMed PMID: 22279443; PubMed Central PMCID: PMCPMC3260743.

30. Powell R L, Ouellette I, Lindsay R W, Parks C L, King C R, McDermott A B, Morrow G. A Multiplex Microsphere-Based Immunoassay Increases the Sensitivity of SIV-Specific Antibody Detection in Serum Samples and Mucosal Specimens Collected from Rhesus Macaques Infected with SIVmac239. BioResearch open access. 2013; 2(3):171-8. doi: 10.1089/biores.2013.0009. PubMed PMID: 23741627; PubMed Central PMCID: PMC3666263.

31. Winstone N, Wilson A J, Morrow G, Boggiano C, Chiuchiolo M J, Lopez M, Kemelman M, Ginsberg A A, Mullen K, Coleman J W, Wu C D, Narpala S, Ouellette I, Dean H J, Lin F, Sardesai N Y, Cassamasa H, McBride D, Felber B K, Pavlakis G N, Schultz A, Hudgens M G, King C R, Zamb T J, Parks C L, McDermott A B. Enhanced control of pathogenic Simian immunodeficiency virus SIVmac239 replication in macaques immunized with an interleukin-12 plasmid and a DNA prime-viral vector boost vaccine regimen. J Virol. 2011; 85(18):9578-87. Epub 2011/07/08. doi: 10.1128/JVI.05060-11. PubMed PMID: 21734035; PubMed Central PMCID: PMC3165762.

32. Barouch D H, Alter G, Broge T, Linde C, Ackerman M E, Brown E P, Borducchi E N, Smith K M, Nkolola J P, Liu J, Shields J, Parenteau L, Whitney J B, Abbink P, Ng'ang'a D M, Seaman M S, Lavine C L, Perry J R, Li W, Colantonio A D, Lewis M G, Chen B, Wenschuh H, Reimer U, Piatak M, Lifson J D, Handley S A, Virgin H W, Koutsoukos M, Lorin C, Voss G, Weijtens M, Pau M G, Schuitemaker H. HIV-1 vaccines. Protective efficacy of adenovirus/protein vaccines against SIV challenges in rhesus monkeys. Science. 2015; 349(6245):320-4. doi: 10.1126/science.aab3886. PubMed PMID: 26138104.

33. Sarzotti-Kelsoe M, Bailer R T, Turk E, Lin C L, Bilska M, Greene K M, Gao H, Todd C A, Ozaki D A, Seaman M S, Mascola J R, Montefiori D C. Optimization and validation of the TZM-bl assay for standardized assessments of neutralizing antibodies against HIV-1. J Immunol Methods. 2014; 409:131-46. doi: 10.1016/j.jim.2013.11.022. PubMed PMID: 24291345; PubMed Central PMCID: PMCPMC4040342.

Example 2: Vaccination with a Live Vesicular Stomatitis Virus-HIV Env Chimera Prevents SHIV Infection Seven of 10 Indian rhesus macaques vaccinated with a novel replication-competent vesicular stomatitis virus vector designed with functional HIV Env substituting for the native VSV glycoprotein remained uninfected after repeated rectal challenge with a heterologous clade B SHIV.

HIV is a challenging vaccine target because its functional envelope glycoproteins (Envs) are highly glycosylated, sequence diverse, and assembled into a compact trimeric complex (the Env spike) that restricts epitope access. Moreover, vaccines based on non-native forms of Env are either ineffective or provide limited protection. Therefore, Applicants developed a novel spike delivery vaccine (VSVΔG-Env.BG505) from vesicular stomatitis virus (VSV) by replacing the VSV glycoprotein (G) with functional clade A HIV Env. Rhesus macaques vaccinated with live VSVΔG-Env.BG505 developed Env antibodies, and importantly, 7 of 10 remained uninfected after repeated rectal challenge with heterologous clade B SHIV SF162p3. In contrast, a second more typical VSV vector expressing both Env and G induced Env antibodies but failed to protect, showing that the VSVΔG-Env.BG505 vector design was associated with preclinical efficacy. Applicants' results indicate that the VSVΔG chimeric virus platform is an important developing vaccine technology for HIV Env glycoprotein delivery.

HIV is a challenging vaccine target because its functional envelope glycoproteins (Envs) are highly glycosylated, sequence diverse, and assembled into a compact trimeric complex (the Env spike) that restricts epitope access. Moreover, vaccines based on non-native forms of Env are either ineffective or provide limited protection. Therefore, Applicants developed a novel spike delivery vaccine (VSVΔG-Env.BG505) from vesicular stomatitis virus (VSV) by replacing the VSV glycoprotein (G) with functional clade A HIV Env. Rhesus macaques vaccinated with live VSVΔG-Env.BG505 developed Env antibodies, and importantly, 7 of 10 remained uninfected after repeated rectal challenge with heterologous clade B SHIV SF162p3. In contrast, a second more typical VSV vector expressing both Env and G induced Env antibodies but failed to protect, showing that the VSVΔG-Env.BG505 vector design was associated with preclinical efficacy. Applicants' results indicate that the VSVΔG chimeric virus platform is an important developing vaccine technology for HIV Env glycoprotein delivery.

Replication-Competent VSV-HIV Env Vaccine Vectors.

Figures 19A, 19B, 19C, 19D, 19E:
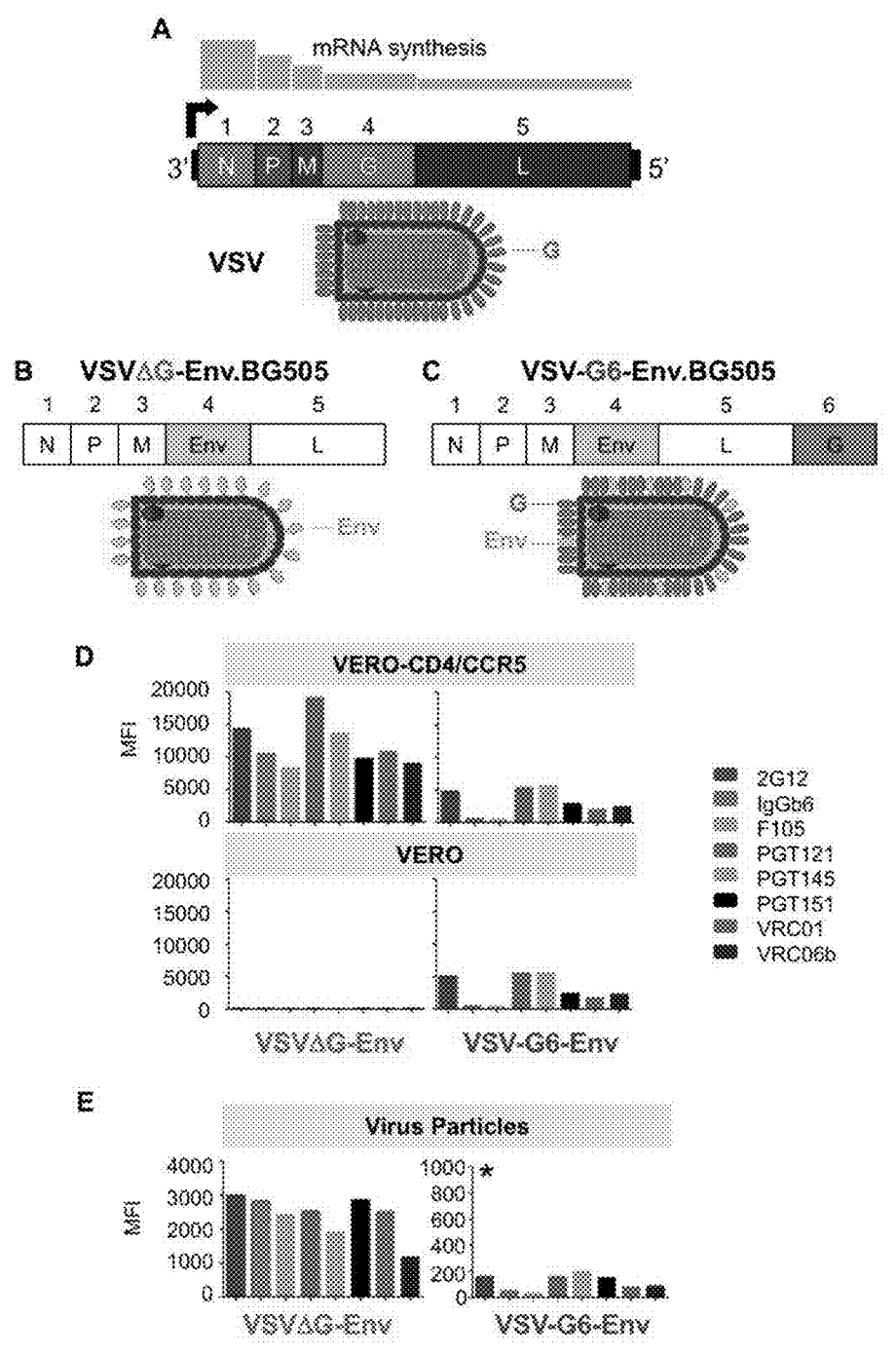

The VSVΔG-Env.BG505 chimera was developed by replacing the VSV G gene with sequence encoding functional Env.BG505 (FIGS. 19A-B with more detail in the Materials and Methods). In addition to expressing Env and replicating with the cell tropism of HIV, the VSVΔG-Env.BG505 chimera has several other features to highlight. First, its dependence on Env.BG505 for propagation ensures that some functionally-configured Env is expressed during viral replication that will expose the immune system to authentic Env spikes. Second, because the vector lacks the G gene, negative effects caused by G expression are avoided, such as the VSV glycoprotein dominating B cell responses or inducing potent anti-vector immunity. Finally, cells infected with VSVΔG-Env.BG505 produce progeny virus particles containing Env arrayed on their surface, which is expected to substantially enhance immunogen presentation to B lymphocytes (11).

To directly investigate whether the live VSVΔG-Env.BG505 chimera was advantageous for the reasons mentioned above, VSV-G6-Env.BG505 (FIG. 19C) was developed as a comparator for use in the macaque study described below. VSV-G6-Env.BG505 is a more typical VSV vector in which the Env.BG505 gene was added as an extra transcription while retaining G. The vector was generated by reintroducing the G gene at the terminus of the negative-sense RNA genome (FIGS. 19A and C; G in genome position 6), which maintained Env in the same genomic position relative to the promoter (FIG. 19A) as in VSVΔG-Env.BG505 and modestly downregulated G expression (16). VSV-G6-Env.BG505 propagates efficiently using G, which recognizes a ubiquitous cellular receptor that enables infection of a broad range of cell types (17); thus, including VSV-G6-Env.BG505 in the vaccine study allowed us to ask whether this G-dependent vector might deliver the Env spike more effectively, perhaps because constitutive G expression confers increased replicative capacity in vivo, a different cell and tissue tropism, or both.

Env.BG505 expression by the two different VSV vectors was compared by infecting cultured cells and conducting flow cytometry using monoclonal antibodies that bind a variety of Env epitopes (4-6). When VERO cells or a stable VERO derivative (VERO-CD4/CCR5) expressing human CD4 and CCR5 were exposed to VSVΔG-Env.BG505, only the CD4+/CCR5+ cells were infected as shown by Env detected on the cell surface (FIG. 19D). The expanded tropism conferred by G allowed VSV-G6-Env.BG505 to infect both cell types although the intensity of Env surface staining was reduced compared to VERO-CD4/CCR5 cells infected with VSVΔG-Env.BG505. The more intense cell surface staining produced by VSVΔG-Env.BG505 infection was due at least in part to increased Env expression, which was detectable by Western blot analysis (data not shown), but it also was possible that G co-expression by cells infected with VSV-G6-Env.BG505 had a negative effect on Env incorporation into the cell plasma membrane. It also is important to note that the panel of monoclonal antibodies used for flow cytometry included some that recognize native Env spikes structures (PGT145, PGT151, and VRC06b) as well as others (IgGb6 and F105) that bind epitopes that are exposed when the Env subunits are not assembled into a compact spike (18-20). Infected cells were bound by all antibodies included in the panel demonstrating that multiple forms of Env were expressed on the cell surface including well-ordered Env spikes, as is typical for an HIV infection (21).

Because Env spikes arrayed on progeny virions produced during replication in vivo were expected to be important immunogens (11), the antigenicity of purified virus particles was analyzed with a modified flow cytometry assay. In this assay, virus particles are adsorbed to aluminum phosphate (alum) to generate alum-virus complexes that can be incubated with monoclonal antibodies and are large enough to be analyzed with a flow cytometer (16). Subsequent analysis with the same monoclonal antibody panel showed that substantially more Env was incorporated in the VSVΔG-Env.BG505 chimera compared to VSV-G6-Env.BG505 (FIG. 19E and note different Y axes), which also was confirmed by Western blotting (data not shown). The flow cytometry data also showed that the antigenicity of VSVΔG-Env.BG505 virions was similar to the infected cell surface (FIG. 19D), including binding by VRC06b, PGT145 and PGT151. In summary, analysis of purified virions showed that both VSVΔG-Env.BG505 and VSV-G6-Env.BG505 contained Env, but the immunogen was considerably more abundant in the VSVΔG chimeric virus particle.

Vaccination and Preclinical Efficacy.

Three groups of 10 male Indian rhesus macaques were vaccinated by administering live vector or saline control to both intranasal and intraoral surfaces at 0, 4 and 29 weeks (FIG. 20A). The five-month break between the second and third vaccination was included to provide time for germinal center reactions and B cell differentiation (22). All immunizations were conducted with a VSV vector, and no booster vaccinations were administered with a heterologous vector or subunit vaccine.

No adverse reactions were observed after vaccination. Virus shedding into the oral cavity was analyzed using qRT-PCR, which showed that viral genomes were low to undetectable for VSVΔG-Env.BG505 but increased for VSV-G6-Env.BG505 particularly following the first vaccination (FIG. 25). This result implied that the replicative capacity of VSV-G6-Env.BG505 was greater, but it might also be due to differences in cell and tissue tropism affecting shedding into the oral cavity. VSV genomes were not detected in the blood (data not shown) in either group, which was consistent with lack of viremia detected in earlier studies (23). Interestingly, VSVΔG-ZEBOV did cause transient viremia in macaques (13) and clinical trial participants (14, 15), which might reflect an effect of cell tropism conferred by the Ebola virus glycoprotein.

Intrarectal SHIV SF162p3 challenge commenced at week 48, about 4.5 months after the third vaccination (FIG. 20A). This rest period prior to SHIV challenge allowed waning of peak adaptive immune responses as well as decay of innate immunity that might have been triggered by VSV. A maximum of 10 sequential challenges were planned (FIG. 20A), with the first five being conducted approximately every 2 weeks after which a brief rest period was included to allow innate immune responses to decline if any were induced by repeated SHIV exposure (24, 25). Challenged animals that had 200 SHIV genome copies or more on two successive blood draws were considered positive (FIG. 26), at which time challenge was stopped. All vaccinated animals that tested positive for SHIV genomes also developed antibodies against Gag expressed by the SHIV (FIG. 27).

After completing repetitive SHIV challenge, 9 of 10 placebo control animals were infected but just 3 of 10 in the VSVΔG-Env.BG505 group (FIG. 20B). This indicated that the VSVΔG-Env.BG505 group was significantly protected with an overall efficacy of 67% (P=0.014). The per-challenge vaccine efficacy for VSVΔG-Env.BG505 was estimated to be 79.8% based on a Leaky vaccine model (26). In contrast, vaccination with VSV-G6-Env.BG505 had no protective effect (FIG. 20B, and Table 1).

Antibody titers in animals 11 and 15 were at the lower measurable limit when SHIV challenge was initiated at week 48 (FIGS. 20A and B), and both macaques were infected right away at challenge 1 and 2, respectively (FIG. 20B with more detail in FIG. 29). Animal 16 resisted 7 challenges conducted over a period of ~5 months (FIGS. 20B and 29). By challenge 8 (week 67) when infection occurred in animal 16, titers had declined to near baseline (FIG. 29B). Thus, in the three unprotected macaques in the VSVΔG-Env.BG505 group, low binding antibody titers were associated with the timing of SHIV infection.

To determine what regions of Env might be targeted in response to VSVΔG-Env.BG505 vaccination, additional mapping of serum antibody binding specificity was performed with several assays. For conducting ELISAs and Western blots, seven different regions of Env.BG505 (FIG. 22A) were expressed as fusion proteins using human serum albumin (HSA) as the N-terminal fusion partner. Fusion to HSA enabled expression of the Env.BG505 fragments as secreted glycoproteins (31). For the ELISA results shown in FIG. 22B, the purified recombinant proteins were captured on microtiter plates (capture ELISA) using their C-terminal His tag after which they were reacted with sera from week 48. Four conclusions can be drawn from the capture ELISA data. First, the predominant positive signal in both vaccine groups was against the HSA-V3C3 and HSA-gp41 (gp41 ectodomain only). These fusion proteins also generated the most frequent and intense signals when used in a Western blot assay (FIG. 32). Second, sera from the three unprotected macaques in the VSVΔG-Env.BG505 group (11, 15, and 16) had lower HSA-V3C3 and HSA-gp41 values consistent with these animals being low responders, as observed earlier with Western blots (FIGS. 21A-B). Finally, the HSA-gp41 substrate allowed unambiguous detection of antibodies specific for gp41 in vaccinated animals (FIGS. 22B and 32), which were not observed in the earlier Western blot assays (FIGS. 21A and 30). Lack of gp41 signals in the prior Western blots likely was due to lower gp41 quantities being present on the blot membrane, but perhaps conformation assumed by the different gp41 substrates played some role.

Seven of 10 macaques vaccinated with the live Env-dependent VSVΔG-Env.BG505 chimera remained uninfected after repeated rectal challenge with heterologous clade B SHIV SF162p3 (FIG. 20). Notably, this level of efficacy was produced with a three-dose regimen of VSVΔG-Env.BG505, which differentiates this vaccine from some others evaluated before where protection was observed after immunization with multiple types of vaccine used either in combination or in a heterologous prime-boost regimen (8, 33, 34).

In the 7 protected macaques vaccinated with VSVΔG-Env.BG505, resistance to SHIV infection was associated with persistent Env-specific serum antibodies, while in the three animals that became infected, poor vaccine take or waning antibody titers were a marker of susceptibility (FIGS. 21, 22 and 29). Perhaps the most visual evidence for this was the gp120 ELISA data (FIG. 29) and Western blot results (FIG. 21), which clearly showed that the unprotected animals had reduced quantities of Env-specific serum antibodies. Further analysis of the sera from this group identified statistically significant correlations between the magnitude of antibody binding activity and SHIV infection resistance (6D), but it remains to be determined if the more abundant Env antibodies are directly involved in the protective mechanism or whether they primarily are indicators of VSVΔG-Env.BG505 vaccine take. The suggestion that they contribute to the mechanism of protection might gain support from the data showing that gp120 V3 and gp41 (FIG. 22) were prominent targets of the antibody response induced by VSVΔG-Env.BG505. Antibody binding to V3 and gp41 has been linked to protection before, for example, reduced infection risk was correlated with anti-V3 antibodies in the RV144 clinical trial (32) and anti-gp41 antibodies have been associated with protection from progressive SIV infection in the macaque model (35).

Functional activities associated with the protective antibodies remain to be identified. Even if undetectable quantities of neutralizing serum antibodies were present, their activity likely would not be adequate to mediate protection (36). Maybe mucosal vaccination with VSVΔG-Env.BG505 resulted in neutralizing antibody being tissue associated or in mucosal secretions rather than in circulation, although anti-gp120 antibodies were not detected in oral or rectal swab samples (data not shown). It seems more likely that protection was due to Env-specific immunoglobulins that direct antibody-mediated effector functions, like those induced by other Env vaccine candidates evaluated in recent preclinical studies (33, 34) or the RV144 clinical trial (8). There is growing recognition that antibodies lacking classic in vitro virus neutralizing activity contribute substantially to protection from viral infections, as illustrated by some recent studies on influenza virus (37, 38); thus, further investigation and comparison of effector functions associated with IgG induced by protective VSVΔG-Env.BG505 or nonprotective VSV-G6-Env.BG505 will be informative.

The Western blot results indicated that binding activity persisted for at least a year in protected animals (FIG. 21D). This might resemble what is observed during vaccination with live attenuated viruses like in the measles vaccine. Antibody titers established by measles vaccination are considerably lower than those reached during natural infection, but the attenuated virus replicates sufficiently to establish durable protective antibodies (39). There likely is a similar requirement for VSVΔG-Env.BG505 to achieve replication threshold that provides an adequate quantity and duration of Env expression, results in release of immunogenic virus particles containing Env arrayed on their surface (11), and distributes immunogen to lymphoid tissues (40). Possibly, vaccine failure in the three unprotected macaques in the VSVΔG-Env.BG505 group was caused by inadequate replication, thus future studies that investigate VSVΔG-Env.BG505 propagation in vivo will be important.

Replicative capacity might also contribute to a notable difference between the VSVΔG-ZEBOV and VSVΔG-Env.BG505 chimeric virus vaccines. In preclinical and clinical studies (13-15), a single vaccination with VSVΔG-ZEBOV was sufficient for efficacy. A single vaccination with VSVΔG-ZEBOV may be sufficient because the virus apparently replicates and disseminates more extensively based on finding virus in the blood of macaques and clinical trial volunteers (13-15).This suggests that further development of the VSVΔG-Env.BG505 vaccine may benefit from investigating how to safely increase virus replication. This might be achieved by launching a more robust initial infection using a different vaccination route or higher dose, or alternatively, maybe a VSVΔG-Env.BG505 vector can be developed that has increased replicative capacity. A follow up study in macaques is being initiated to investigate some of these variables.

The VSVΔG chimeric virus design appears to be emerging as an important vaccine technology for delivery of viral glycoprotein immunogens. The VSVΔG-ZEBOV clinical trials showed that the Ebola virus vaccine was safe and efficacious (13-15). Promising preclinical results also have been produced with other hemorrhagic fever virus glycoproteins (41), and now Applicants' data shows that this strategy can be adapted for use with an HIV Env trimer immunogen, which is well known to be a very difficult vaccine target (5). The effectiveness of the VSVΔG chimera design probably is due to its ability to reproduce features of a natural pathogen infection without pathology that inhibits development of protective adaptive immunity. Vaccine features such as expression of the native transmembrane glycoprotein on the surface of infected cells, infection directed to cells and tissues specified by the tropism of the foreign glycoprotein, and the presentation of immunogen arrayed on virus particles all likely play important roles in shaping the immune response. Moreover, the lack of a G gene in the vector is very important, because it eliminates expression of a dominant off-target B cell immunogen, prevents development of potent anti-G antibodies, and allows the foreign glycoprotein to be repetitively arrayed on the virus particle without interference from G.

To evaluate whether the promising preclinical performance of VSVΔG-Env.BG505 can be extended to humans, as it was for the VSVΔG-ZEBOV vaccine, Applicants are developing a clinical trial candidate. It is relevant to clinical development to mention that the G gene deletion in VSVΔG-ZEBOV resulted in loss of the VSV neurovirulence phenotype that is observed in some preclinical models (42). Advancing VSVΔG-Env.BG505 to clinical trial will be valuable, as it will answer whether the live chimeric virus platform can be used to safely induce Env binding antibodies with properties like those described above in healthy clinical trial volunteers.

Molecular Cloning, Recombinant Proteins, and Cell Line Development.

The VSV genomic clone is based on the VSV Indiana (IND) serotype (16). The plasmid vector containing the VSV genomic clone was similar to one used before (46) except that the T7 RNA polymerase promoter was replaced with a longer version that improves T7 RNA polymerase processivity (T7-g10 (47) and a hammerhead ribozyme sequence was positioned between the T7-g10 promoter and the beginning of the VSV nucleotide sequence (48). The hepatitis delta virus ribozyme and T7 terminator sequences downstream of the 3' end of the VSV antigenome were the same as used before (46). Modified genomic clones with the G IND or G New Jersey (NJ) gene moved to genomic position 6 (VSV-G6, FIG. 19C) were described earlier (16) and a third clone was developed for this study using Maraba (MAR) virus G (Genbank HQ660076.1). Plasmids that express the VSV structural proteins (N, P, M, G, and L) under control of the CMV promoter were used to support VSV rescue (16) instead of those controlled by the T7 promoter used in the earlier procedure (46). A plasmid designed to express T7 RNA polymerase from the CMV promoter was designed similarly to the one described previously (46).

Figures 23A, 23B, 23C, 23D, 23E, 23F:
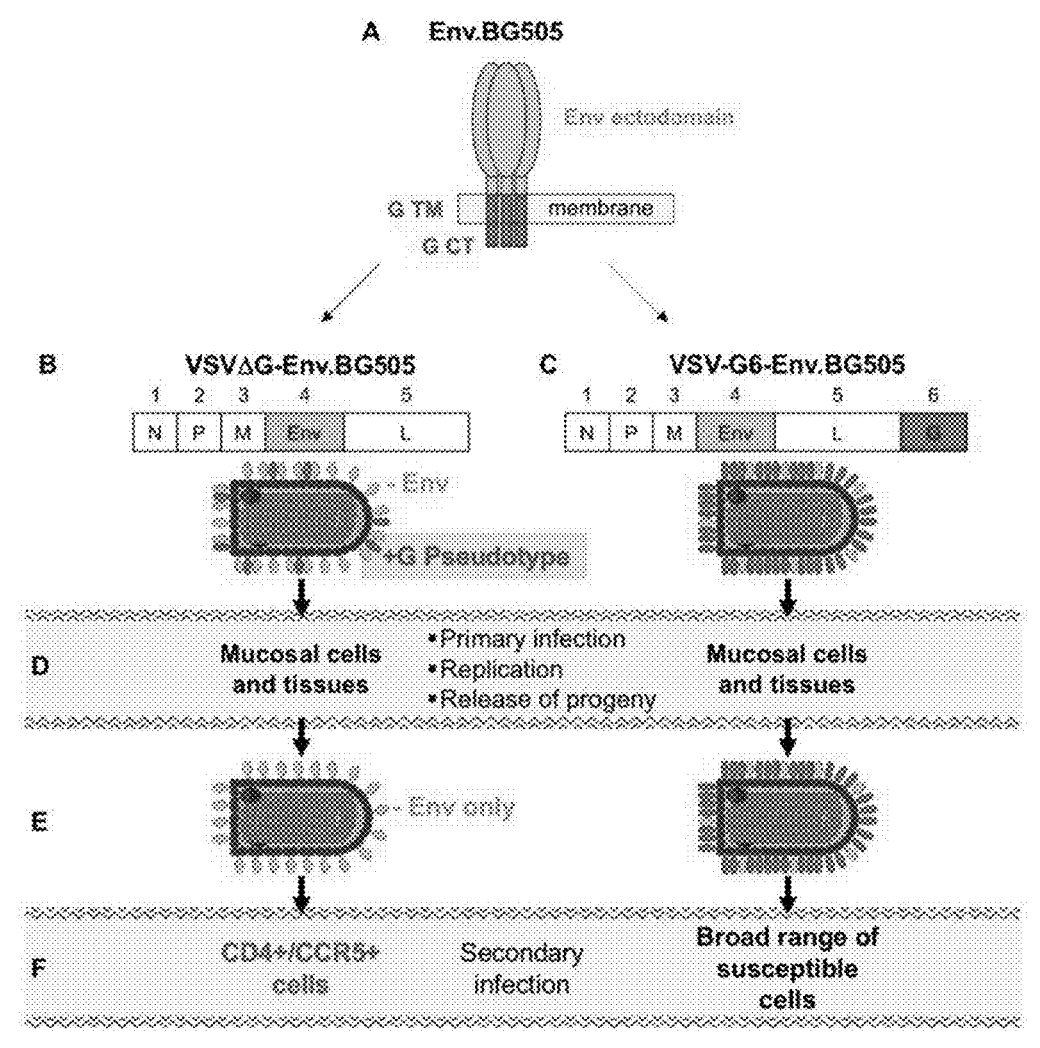

The Env immunogen expressed by VSVΔG-Env.BG505 and VSV-G6-Env.BG505 was based on the wild-type clade A Env.BG505 amino acid sequence (Genbank ABA61516, 49, 50). Env.BG505 was modified by replacing the signal sequence, transmembrane region and cytoplasmic tail with corresponding regions of G from VSV IND (FIG. 23A). The nucleotide sequence encoding the modified Env.BG505 was optimized with a VSV codon bias as described previously (16) after which the gene was inserted in the VSV genomic clone in place of G. Additional VSVΔG-Env chimeras were developed similarly based on Env C.CH505 (week 100; Genbank KC247391.1) and Env B. SF162p3 (Genbank KF042063).

A series of plasmids also were constructed to allow expression of several different domains of Env.BG505 fused to the C-terminus of human serum (HSA, 31). A glycine-serine linker (GGGGS(SEQ ID NO: 3)) was inserted between the C-terminus of HSA and the Env sequence, and a C-terminal histidine tag was added to enable chromatographic purification of HSA-fusion proteins secreted from transfected cells. The HSA fusion proteins were expressed by transfecting 293T cells and purified as described previously (49). His-tagged Env.BG505 gp120 (49) and gp140 containing a flexible linker in place of the furin cleavage site (51) were expressed and purified similarly.

A stable VERO cell line expressing human CD4 and CCR5 (VERO-CD4/CCR5) was developed for propagating the VSVΔG-Env.BG505 vector. The human CD4 and CCR5 coding sequences were joined by a 2A-like element (52) to form a single cistron (CCR5-2A-CD4), which was inserted into a plasmid under the control of a transcription unit developed from the human heat shock protein 60 gene (53). A stable cell line was generated by introducing DNA into cells by microporation (Neon Transfection System, Invitrogen) and selecting clonal isolates resistant to G418.

Cell Culture and Virus.

Recombinant virus recovery from DNA and virus propagation was performed using VERO or VERO-CD4/CCR5 cells. Three media were used for VERO cell propagation and electroporation procedures that were similar to those described before (46). VERO cell medium 1 (VCM1) is Dulbecco's modified Eagle's medium (DMEM) supplemented with 10% heat-inactivated fetal bovine serum, 220 µM 2-mercaptoethanol, 2 mM L-glutamine, 1 mM sodium pyruvate, and 0.1 mM MEM nonessential amino acids. VCM2 is Iscove's modified Dulbecco's medium (IMDM) supplemented with 220 µM 2-mercaptoethanol, 1% DMSO, 2 mM L-glutamine, 1 mM sodium pyruvate, and 0.1 mM MEM nonessential amino acids. VCM3 is the same as VCM1 with addition of 50 µg/mL Gentamicin. The VERO-CD4/CCR5 cell line was propagated in VCM3 containing 1 mg per mL G418. All medium and supplements were obtained from ThermoFisher.

Recombinant VSV was rescued from DNA using a helper-virus-free method adapted from Witko et al. (46) using the modified plasmids described above. Virus rescue was initiated by electroporation of plasmids encoding T7 RNA polymerase, VSV N, P, M, G, and L, and the appropriate VSV genomic clone into VERO (for VSV-G6) or VERO-CD4-CCR5 (for VSVΔG) cells. Conditions for electroporation with a BTX ECM 830 instrument (Harvard Apparatus) and subsequent virus recovery were similar to those used in the earlier method (46).

To ensure efficient vaccination with either vaccine, two vector-specific modifications were applied, but the fundamental vaccine designs shown in FIGS. 19A-C were not changed. These modifications enhanced vaccine delivery without altering the Env-dependent propagation of VSVΔG-Env.BG505 or the G-dependent propagation of VSV-G6-Env.BG505. The modifications are illustrated in FIGS. 23 and 24). To enhance mucosal VSVΔG-Env.BG505 uptake, vaccine material was prepared as a pseudotyped virus particle bearing G (G pseudotype; FIGS. 23B and 24A-B). This was done simply by amplifying vaccine material in VERO-CD4/CCR5 cells that transiently expressed VSV G. Pseudotyped VSVΔG-Env.BG505 launches a more robust initial infection, because G recognizes a ubiquitous receptor found on a wide range of cells (17). Importantly, G is not expressed by cells infected with pseudotyped VSVΔG-Env.BG505 and all subsequent rounds of infection in vivo are Env dependent (FIG. 23). For VSV-G6-Env.BG505, it was modified to reduce the negative effects of anti-G antibodies that develop during repeated vaccination with vectors expressing G. Three versions of VSV-G6-Env.BG505 (FIGS. 24A and C) were used in sequence during the three-dose regimen (FIG. 24A). Each version of VSV-G6-Env.BG505 differed only in the G gene (FIG. 24C), which was exchanged with sequences from three different vesiculoviruses including VSV IND, VSV NJ, and Maraba virus (16, 54).

Large batches of VSVΔG-Env.BG505 or VSV-G6-Env.BG505 were amplified using VERO-CD4/CCR5 or VERO cells, respectively. Cell monolayers were grown in Cell Factories (Corning) using VCM3, but once infection was initiated, the medium was changed to Virus Production Serum-Free Medium (VPSFM, supplemented with 4 mM L-Glutamine, 50 U/mL Penicillin and 50 µg/mL Streptomycin; ThermoFisher). Cells were infected with ~0.1 plaque-forming units per cell and then incubated for about 24h before the medium supernatant was harvested and clarified by centrifugation at 900×g for 30 m at room temperature. Clarified supernatants were overlaid on 20% sucrose cushions prepared in phosphate-buffered saline (PBS), then centrifuged for 2 hrs (18,000 rpm, 42,900 g, 4° C.) using a SW28 rotor (Beckman Coulter). The sucrose solution was aspirated completely from the virus pellet after which virus was suspended in Hank's Balanced Salt Solution (HBSS, ThermoFisher) containing 15% Trehalose (Life Sciences Advanced Technologies) that was adjusted to pH 7.2. Virus suspensions were stored at −80° C. in aliquots.

Pseudotyped VSVΔG-Env.BG505 was produced in VERO-CD4/CCR5 cells that were electroporated with plasmid expressing VSV G IND or NJ. In preparation for electroporation, cells were harvested and treated as described before (46) and were suspended in 0.7 ml of VCM2 (~2×10$^7$ cells). Purified VSVΔG-Env.BG505 (0.1 pfu per cell) and 50 ug of pCMV-G expression plasmid was added to the cell suspension before performing electroporation with the BTX ECM830 instrument. After electroporation, the cells were processed and transferred to one T175 flask per electroporation cuvette, after which they were cultured in VCM1 for 3-4 hours at 37° C. before performing heat shock (43° C.) for 3 hours (46). After heat shock, the cells were returned to 37° C. and allowed to recover for 2 h before the medium was removed and replaced VPSFM supplemented with 4 mM L-Glutamine. Incubation was continued 24-48 hours at 37° C. until cytopathic effect was evident throughout the culture after which virus was harvested and purified as described above.

VSV vector infectious units were quantified by plaque assay (16). For VSVΔG-Env.BG505, GHOST-CD4-CCR5 cell monolayers were used (NIH AIDS Reagent Program, Division of AIDS, NIAID, NIH, catalog number 3944, 55) while VERO cells were used for VSV-G6-Env.BG505. Near-confluent cell monolayers were infected with serially diluted virus before being overlaid with VCM3 containing 0.8% agarose. When plaques were visible, cells were fixed with 7% formaldehyde and stained with a solution of 7% crystal violet in water. Plaques were counted from duplicate wells and infectious titers were expressed as plaque-forming units (pfus) per ml.

Western blotting was used to confirm Env expression by infected cells and also to characterize purified VSV vector particles. For analysis of Env expression, cytoplasmic lysates were prepared from infected monolayers using Cell-Lytic M reagent (Sigma). Lysate proteins were then subjected to denaturing SDS polyacrylamide gel electrophoresis (SDS PAGE) and transferred to nitrocellulose membranes. Proteins were detected with monoclonal antibodies or polyclonal serum specific for Env gp120.BG505 or VSV structural proteins. Secondary antibodies conjugated to horseradish peroxidase and chemiluminescence detection was used to visualize specific bands. Protein composition of VSV vector particles was analyzed by Western blot using similar methods applied to virus purified by centrifugation through sucrose cushions.

VSV vector vaccine material was subjected to several tests to ensure the quality. Endotoxin levels were tested using the Endosafe Portable Test System (Charles River Laboratories, Boston). All vaccine lots had endotoxin levels less than 10 EU/ml. The absence of *Mycoplasma* was confirmed by PCR using the MycoSEQ® *Mycoplasma* Detection System (Life Technologies). Residual VERO cell DNA was less than 10 ng per dose as determined with the resDNASEQ® Vero Residual DNA Quantitation System (Life Technologies). Gene sequences were confirmed by nucleic acid sequencing as described before (16).

Vaccinations, SHIV Challenge, and Animal Care and Use.

Purpose-bred male Indian rhesus macaques were 4-7 years of age when they arrived at The State University of New York (SUNY) Downstate Medical Center, Division of Comparative Medicine. Animal care and use complied with The United States Department of Agriculture and The New York State Department of Health regulations. The SUNY Downstate Medical Center Institutional Animal Care and Use Committee reviewed all experimental procedures. Prior to receipt, all macaques were confirmed to be negative for Herpes B virus (BV), tuberculosis (TB), simian immunodeficiency virus (SIV), simian retrovirus (SRV), and simian T lymphotropic virus (STLV), as well as *Shigella* and *Campylobacter jejuni*.

No Macaques were included in the study if they were positive for MHC alleles Mamu-B*08 and B*17 associated with strong SIV replication control (56). Both groups vaccinated with VSV vectors each had 2 animals that were positive for Mamu-A*01 and two positive A*02, which have been associated with control of disease progression (56). The placebo control group also contained two animals that were positive for A*02 and one for A*01. For vaccination, macaques were sedated and positioned in dorsal recumbency after which vaccine was administered by the intraoral and intranasal routes. Vaccine or buffer control was administered by drops using a 1000 µl micropipette. 500 µl was delivered intranasally by alternating drops between the left and right nares, with time between drops allowed for the droplet to be inhaled. For intraoral, a total of 500 µl was administered by drops applied sublingually on the frenulum (250 µl) and to the anterior buccal surface of the inferior lip (250 µl) followed by 30-60 seconds of gentle massage to help distribute the inoculum. Animals were kept in dorsal recumbency throughout the procedure and were left in this position for an additional 5 minutes before being returned to their cages. Animals were singly housed for 48 h following all vaccinations, after which they were housed together (2-3 animals per cage) within the same vaccination group. Bedding material was analyzed for VSV genomes by qPCR and none was detected (data not shown).

Rectal challenge was performed using SHIV SF162p3 that was prepared in primary cultures of macaque PBMCs (34). The inoculum (total of 2.2×10$^4$ TCID50) consisted of virus in 1 ml of saline or RPMI medium. Sedated animals were positioned in sternal recumbency with the posterior elevated by placing an empty plastic container between the lower abdomen and the procedure table. Inoculation was performed by atraumatic insertion of a lightly lubricated 3 mL syringe approximately 5 cm into the rectum. The inoculum was slowly instilled over a one-minute period with the syringe left in place for and additional 4 minutes. After removing the syringe, macaques remained in sternal recumbency for 10 minutes. Challenged animals were caged separately for 48 h before being housed in groups of 2-3 within the same vaccination group.

SHIV infection was monitored by reverse transcription and quantitative PCR (RT-qPCR) using methods similar to those described earlier (57). Briefly, virus from 1.0 ml of plasma was collected by centrifugation at 25,000×g for 90 min (5° C.). The virus pellet was processed using the RNeasy Micro kit (Qiagen) by suspending virus in solution containing 300 µl of lysis buffer, 3 µl of 14.2 M 2-mercaptoethanol (Bio-Rad), and 16 µl of 20 mg/ml proteinase K (Qiagen). Samples were digested at 56° C. for 1 h, then RNA was purified using spin columns following the RNeasy Micro kit protocol. RNA was eluted in 50 µl of RNase-free water supplemented with 1 mM dithiothreitol (Sigma) and 1 U/µl RNAseOUT (Thermo Fisher Scientific) after which duplicate RT reactions were performed using 15 µl of purified RNA per reaction and 10 µl of a cocktail composed of reagents from the Sensiscript Reverse Transcriptase kit (Qiagen, Valencia, Calif., USA) including 1x reverse transcription buffer, 0.5 mM of each dNTP, 10 U/reaction RNase Inhibitor (Invitrogen, Carlsbad, Calif., USA), 10 Units Sensiscript Reverse transcriptase, and Gag-specific reverse primer (400 nM, 5'-CACTAGKTGTCTCTGCACTATPT-GTTT-3'(SEQ ID NO: 4)) that annealed to the positive-sense genomic RNA. Reverse transcription was performed at 50° C. for 45 min and terminated by heat inactivation (95° C. for 2 min). The heat-inactivated 25-µl reaction was adjusted for qPCR by adding 30 µl of a reagent mix composed of 1× QuantiTect Multiplex PCR Master Mix (Qiagen), 400 nM of Gag-specific forward primer (5'-GTCTGCGTCATPTGGT-GCAT-3' (SEQ ID NO: 5)) and Gag-specific reverse primer, and 200 nM 6-carboxyfluorescein (FAM)-labeled minor groove binder (MGB) probe (5'-6FAM-CTTCPTCAGTKT-GTTTCA-MGB-3' (SEQ ID NO: 6)). A Stratagene Mx3005P Sequence Detection System was used for amplification and detection with the following conditions: 15 min at 95° C. followed by 45 cycles of 60 secs at 94° C. and 90 secs at 60° C. Results from duplicate test samples were averaged and genome copy numbers were interpolated from a curve generated with known RNA standards. Positive samples were defined as 200 genome copies per ml of plasma.

Analysis of Immune Responses.

To prepare plasma and peripheral blood mononuclear cells (PBMCs), blood was collected in tubes coated with sodium heparin. Plasma was prepared by removing cells by centrifugation and storage at −20° C. PBMCs were isolated by density gradient centrifugation on Ficoll Hypaque (GE Healthcare) in Accuspin tubes (Sigma-Aldrich) as described previously (57). Harvested PBMCs were suspended in Recovery Cell Culture Freezing Medium (Thermo Fisher Scientific) and stored in liquid nitrogen. Serum used for ELISA, Western blot procedures, binding antibody multiplex assays, or HIV pseudovirus neutralization assays was prepared from whole blood collected and processed in serum separator tubes (SST). Aliquots were stored at −20° C.

Intracellular cytokine staining was performed as described before (57). T cells were stimulated with Env.BG505 peptide (Genscript) 15-mers overlapping by 11 amino acids. Two different Env.BG505 peptide pools, spanning gp120 or gp41, were used at 4 µg per ml. All flow cytometry data had mock background responses subtracted.

Infected VERO and VERO-CD4/CCR5 cells and VSV vector particles also were analyzed by flow cytometry. For infected cells, VERO or VERO-CD4/CCR5 monolayers were infected with 0.1 to 1.0 pfu per cell and incubated overnight at 37°. The following day, cells were washed with PBS and then treated with Enzyme-free Cell Dissociation Buffer (Life Sciences) to produce a cell suspension. The cells were collected by centrifugation and then suspended in PBS before being incubated with Env-specific monoclonal antibodies. Flow cytometry was performed as described earlier (16).

Env incorporated in VSV particles also was analyzed by flow cytometry (16). Typically, purified virus ($10^8$ pfus) was bound to 100 ug Alum (Adju-Phos, Brenntag, Denmark) and the alum/virus complexes were blocked with PBS containing 3% BSA before being incubated with primary antibodies. After primary antibody incubation, the complexes were collected by centrifugation, washed using PBS containing 3% BSA, and then incubated with labeled secondary antibody. Centrifugation and washing was repeated before analysis with a LSRII flow cytometer (Becton Dickinson). The flow cytometer was set to analyze 30,000 particles with forward scatter (FSC) and side scatter (SSC) set to log 10 scale and threshold set to 4000. Data was analyzed using FlowJo software version 9.4 (Tree Star), where complexes were gated according to positivity compared to an alum only control.

Western blotting also was used for analysis of serum antibodies. Polypeptide substrates used for the analysis were either purified VSVΔG-EnvG.BG505 particles (no G pseudotype, $5×10^8$ pfus) or purified Env proteins. Purified virus or protein was diluted to 162.5 µL in HBSS containing 15% Trehalose before being mixed with 62.5 µl LDS NuPAGE sample buffer (Novex) and 25 µL of NuPAGE Sample Reducing Agent (Novex). Samples were heat denatured before being electrophoresed in a denaturing preparative gel (NuPAGE 4-12% Bis-Tris 2D, ThermoFisher), and afterwards proteins were transferred to a nitrocellulose membrane. The membrane was rinsed with PBS and then incubated at room temperature for 1 h in blocking buffer composed of StartingBlock T20 buffer (ThermoFisher) supplemented with Clear Milk (Pierce/ThermoFisher) and 1% goat serum (Sigma). The blocked membrane was transferred to a multichannel Mini Protein II MultiScreen (Bio-Rad) device that created multiple channels for analysis of sera from individual macaques. Individual lanes were incubated for 1 h at room temperature with heat-inactivated macaque serum (diluted 1:300 in blocking buffer for a total volume of 550 µL) before the solution was aspirated completely from each lane. The membrane was then removed from the multiscreen device and rinsed 5 times with miliQ water (59) and then washed 3 times for 5 minutes each with PBS containing 0.1% Tween-20. The membrane was incubated with secondary antibody (mouse anti-monkey IgG, SouthernBiotech; diluted 1:10,000 in blocking buffer) for 45 mins at room temperature after which it was washed as described above. The blot was developed with chemiluminescence reagent (SuperSignal West Femto Maximum Sensitivity Substrate, ThermoFisher) and imaged with a Biorad ChemiDoc Touch Imaging System.

References and Notes

1. UNAIDS, Fact Sheet 2016 UNAIDS.
2. T. M. Harmon et al., Exploring the Potential Health Impact and Cost-Effectiveness of AIDS Vaccine within a Comprehensive HIV/AIDS Response in Low- and Middle-Income Countries. *PLoS ONE* 11, e0146387 (2016).
3. M. A. Checkley, B. G. Luttge, E. O. Freed, HIV-1 envelope glycoprotein biosynthesis, trafficking, and incorporation. *Journal of Molecular Biology* 410, 582-608 (2011).
4. D. R. Burton, J. R. Mascola, Antibody responses to envelope glycoproteins in HIV-1 infection. *Nature immunology* 16, 571-576 (2015).

5. P. D. Kwong, J. R. Mascola, G. J. Nabel, Broadly neutralizing antibodies and the search for an HIV-1 vaccine: the end of the beginning. *Nat Rev Immunol* 13, 693-701 (2013).
6. A. B. Ward, I. A. Wilson, Insights into the trimeric HIV-1 envelope glycoprotein structure. *Trends Biochem Sci* 40, 101-107 (2015).
7. R. J. O'Connell, J. H. Kim, L. Corey, N. L. Michael, Human immunodeficiency virus vaccine trials. *Cold Spring Harb Perspect Med* 2, a007351 (2012).
8. J. H. Kim, J. L. Excler, N. L. Michael, Lessons from the RV144 Thai phase III HIV-1 vaccine trial and the search for correlates of protection. *Annual review of medicine* 66, 423-437 (2015).
9. S. A. Plotkin, Correlates of protection induced by vaccination. *Clin Vaccine Immunol* 17, 1055-1065 (2010).
10. C. L. Parks, L. J. Picker, C. R. King, Development of replication-competent viral vectors for HIV vaccine delivery. *Curr Opin HIV AIDS* 8, 402-411 (2013).
11. M. F. Bachmann, G. T. Jennings, Vaccine delivery: a matter of size, geometry, kinetics and molecular patterns. *Nat Rev Immunol* 10, 787-796 (2010).
12. E. Boritz, J. Gerlach, J. E. Johnson, J. K. Rose, Replication-competent rhabdoviruses with human immunodeficiency virus type 1 coats and green fluorescent protein: entry by a pH-independent pathway. *J Virol* 73, 6937-6945 (1999).
13. S. M. Jones et al., Live attenuated recombinant vaccine protects nonhuman primates against Ebola and Marburg viruses. *Nature medicine* 11, 786-790 (2005).
14. A. M. Henao-Restrepo et al., Efficacy and effectiveness of an rVSV-vectored vaccine expressing Ebola surface glycoprotein: interim results from the Guinea ring vaccination cluster-randomised trial. *Lancet* 386, 857-866 (2015).
15. S. T. Agnandji et al., Phase 1 Trials of rVSV Ebola Vaccine in Africa and Europe. *The New England journal of medicine* 374, 1647-1660 (2016).
16. S. Rabinovich et al., A novel, live-attenuated vesicular stomatitis virus vector displaying conformationally intact, functional HIV-1 envelope trimers that elicits potent cellular and humoral responses in mice. *PLoS ONE* 9, e106597 (2014).
17. E. Hastie, M. Cataldi, I. Marriott, V. Z. Grdzelishvili, Understanding and altering cell tropism of vesicular stomatitis virus. *Virus Res* 176, 16-32 (2013).
18. R. W. Sanders et al., A next-generation cleaved, soluble HIV-1 Env trimer, BG505 SOSIP.664 gp140, expresses multiple epitopes for broadly neutralizing but not non-neutralizing antibodies. *PLoS Pathog* 9, e1003618 (2013).
19. E. Falkowska et al., Broadly Neutralizing HIV Antibodies Define a Glycan-Dependent Epitope on the Prefusion Conformation of gp41 on Cleaved Envelope Trimers. *Immunity*, (2014).
20. Y. Li et al., HIV-1 neutralizing antibodies display dual recognition of the primary and coreceptor binding sites and preferential binding to fully cleaved envelope glycoproteins. *J Virol* 86, 11231-11241 (2012).
21. P. L. Moore et al., Nature of nonfunctional envelope proteins on the surface of human immunodeficiency virus type 1. *J Virol* 80, 2515-2528 (2006).
22. F. Sallusto, A. Lanzavecchia, K. Araki, R. Ahmed, From vaccines to memory and back. *Immunity* 33, 451-463 (2010).
23. J. E. Johnson et al., Neurovirulence properties of recombinant vesicular stomatitis virus vectors in non-human primates. *Virology* 360, 36-49 (2007).
24. C. Selinger et al., Multiple low-dose challenges in a rhesus macaque AIDS vaccine trial result in an evolving host response that affects protective outcome. *Clin Vaccine Immunol* 21, 1650-1660 (2014).
25. R. R. Regoes, The role of exposure history on HIV acquisition: insights from repeated low-dose challenge studies. *PLoS Comput Biol* 8, e1002767 (2012).
26. M. G. Hudgens, P. B. Gilbert, Assessing vaccine effects in repeated low-dose challenge experiments. *Biometrics* 65, 1223-1232 (2009).
27. D. C. Montefiori, in *HIV Protocols: Second Edition*, vol. 485, V. R. Prasad, G. V. Kalpana, Eds. (Humana Press, New York, 2009), chap. 26, pp. 395-405.
28. Y. Fukazawa et al., Lymph node T cell responses predict the efficacy of live attenuated SIV vaccines. *Nature medicine* 18, 1673-1681 (2012).
29. B. F. Haynes et al., Immune-correlates analysis of an HIV-1 vaccine efficacy trial. *The New England journal of medicine* 366, 1275-1286 (2012).
30. G. D. Tomaras et al., Initial B-cell responses to transmitted human immunodeficiency virus type 1: virion-binding immunoglobulin M (IgM) and IgG antibodies followed by plasma anti-gp41 antibodies with ineffective control of initial viremia. *J Virol* 82, 12449-12463 (2008).
31. J. Carter et al., Fusion partners can increase the expression of recombinant interleukins via transient transfection in 2936E cells. *Protein Sci* 19, 357-362 (2010).
32. R. Gottardo et al., Plasma IgG to linear epitopes in the V2 and V3 regions of HIV-1 gp120 correlate with a reduced risk of infection in the RV144 vaccine efficacy trial. *PLoS ONE* 8, e75665 (2013).
33. D. H. Barouch et al., Protective efficacy of adenovirus/protein vaccines against SIV challenges in rhesus monkeys. *Science* 349, 320-324 (2015).
34. D. H. Barouch et al., Protective efficacy of a global HIV-1 mosaic vaccine against heterologous SHIV challenges in rhesus monkeys. *Cell* 155, 531-539 (2013).
35. Q. Li et al., Live simian immunodeficiency virus vaccine correlate of protection: local antibody production and concentration on the path of virus entry. *J Immunol* 193, 3113-3125 (2014).
36. M. Shingai et al., Passive transfer of modest titers of potent and broadly neutralizing anti-HIV monoclonal antibodies block SHIV infection in macaques. *J Exp Med* 211, 2061-2074 (2014).
37. C. J. Henry Dunand et al., Both Neutralizing and Non-Neutralizing Human H7N9 Influenza Vaccine-Induced Monoclonal Antibodies Confer Protection. *Cell host & microbe* 19, 800-813 (2016).
38. H. M. Yassine et al., Hemagglutinin-stem nanoparticles generate heterosubtypic influenza protection. *Nature medicine* 21, 1065-1070 (2015).
39. M. K. Slifka, I. Amanna, How advances in immunology provide insight into improving vaccine efficacy. *Vaccine* 32, 2948-2957 (2014).
40. N. Honke et al., Enforced viral replication activates adaptive immunity and is essential for the control of a cytopathic virus. *Nature immunology* 13, 51-57 (2012).
41. C. E. Mire et al., A Single-Vector, Single-Injection Trivalent Filovirus Vaccine: Proof of Concept Study in Outbred Guinea Pigs. *J Infect Dis* 212 Suppl 2, S384-388 (2015).
42. C. E. Mire et al., Recombinant vesicular stomatitis virus vaccine vectors expressing filovirus glycoproteins lack neurovirulence in nonhuman primates. *PLoS Negl Trop Dis* 6, e1567 (2012).

43. D. S. Lyles, I. Kuzmin, C. E. Rupprecht, in *Fields Virology*, D. M. Knipe, P. M. Howley, Eds. (Lippincott Williams and Wilkins, Philadelphia, 2013), vol. 1, chap. 31, pp. 885-922.
44. J. E. Johnson, M. J. Schnell, L. Buonocore, J. K. Rose, Specific targeting to CD4+ cells of recombinant vesicular stomatitis viruses encoding human immunodeficiency virus envelope proteins. *J Virol* 71, 5060-5068 (1997).
45. A. De Milito, B lymphocyte dysfunctions in HIV infection. *Curr HIV Res* 2, 11-21 (2004).
46. S. E. Witko et al., An efficient helper-virus-free method for rescue of recombinant paramyxoviruses and rhadoviruses from a cell line suitable for vaccine development. *J Virol Methods* 135, 91-101 (2006).
47. P. J. Lopez, J. Guillerez, R. Sousa, M. Dreyfus, The low processivity of T7 RNA polymerase over the initially transcribed sequence can limit productive initiation in vivo. *Journal of molecular biology* 269, 41-51 (1997).
48. K. Inoue et al., An improved method for recovering rabies virus from cloned cDNA. *J Virol Methods* 107, 229-236 (2003).
49. S. Hoffenberg et al., Identification of an HIV-1 clade A envelope that exhibits broad antigenicity and neutralization sensitivity and elicits antibodies targeting three distinct epitopes. *J Virol* 87, 5372-5383 (2013).
50. X. Wu et al., Neutralization escape variants of human immunodeficiency virus type 1 are transmitted from mother to infant. *J Virol* 80, 835-844 (2006).
51. S. K. Sharma et al., Cleavage-Independent HIV-1 Env Trimers Engineered as Soluble Native Spike Mimetics for Vaccine Design. *Cell Rep* 11, 539-550 (2015).
52. P. de Felipe et al., E unum pluribus: multiple proteins from a self-processing polyprotein. *Trends Biotechnol* 24, 68-75 (2006).
53. J. J. Hansen et al., Genomic structure of the human mitochondrial chaperonin genes: HSP60 and HSP10 are localised head to head on chromosome 2 separated by a bidirectional promoter. *Hum Genet* 112, 71-77 (2003).
54. N. F. Rose et al., An effective AIDS vaccine based on live attenuated vesicular stomatitis virus recombinants. *Cell* 106, 539-549 (2001).
55. A. Morner et al., Primary human immunodeficiency virus type 2 (HIV-2) isolates, like HIV-1 isolates, frequently use CCR5 but show promiscuity in coreceptor usage. *J Virol* 73, 2343-2349 (1999).
56. P. J. Goulder, D. I. Watkins, Impact of MHC class I diversity on immune control of immunodeficiency virus replication. *Nat Rev Immunol* 8, 619-630 (2008).
57. N. Winstone et al., Enhanced control of pathogenic Simian immunodeficiency virus SIVmac239 replication in macaques immunized with an interleukin-12 plasmid and a DNA prime-viral vector boost vaccine regimen. *J Virol* 85, 9578-9587 (2011).
58. N. L. Yates et al., Vaccine-induced Env V1-V2 IgG3 correlates with lower HIV-1 infection risk and declines soon after vaccination. *Sci Transl Med* 6, 228ra239 (2014).
59. M. Wu, P. G. Stockley, W. J. Martin, 2nd, An improved western blotting technique effectively reduces background. *Electrophoresis* 23, 2373-2376 (2002).
60. T. L. Nolen, M. G. Hudgens, P. K. Senb, G. G. Koch, Analysis of repeated low-dose challenge studies. *Stat Med* 34, 1981-1992 (2015).
61. J. E. Johnson et al., In vivo biodistribution of a highly attenuated recombinant vesicular stomatitis virus expressing HIV-1 Gag following intramuscular, intranasal, or intravenous inoculation. *Vaccine* 27, 2930-2939 (2009).
62. Y. Huang, P. B. Gilbert, D. C. Montefiori, S. G. Self, Simultaneous Evaluation of the Magnitude and Breadth of a Left and Right Censored Multivariate Response, with Application to HIV Vaccine Development. *Statistics in biopharmaceutical research* 1, 81-91 (2009).
63. H. X. Liao et al., Co-evolution of a broadly neutralizing HIV-1 antibody and founder virus. *Nature* 496, 469-476 (2013).

Example 3: Using VSV Evolution to Fine Tune the Env Immunogen

The EnvG hybrid was developed with the goal of producing an immunogen that was optimal for delivery with a live VSV vector. The Env-G design objectives were to generate a modified immunogen that enabled more abundant expression on the infected cell surface and increased incorporation in VSV particles while maintaining native Env antigenic properties and the ability to direct infection and replication in cells bearing the HIV coreceptors CD4 and CCR5 (CD4+/CCR5+ cells). Systematic evaluation of several Env domain substitutions demonstrated that replacement of the Env signal peptide (SP), transmembrane region (TM), and cytoplasmic tail (CT) with analogous domains from VSV G substantially improved expression of Env on the cell surface (FIG. 1). Moreover, the surface of cells expressing the Env-G hybrid was bound by a panel of anti-Env monoclonal antibodies demonstrating that the antigenic profile was very similar to Env expressed by cells infected with HIV. Importantly, when a chimeric VSVΔG-Env vector was developed in which the G gene was replaced with Env-G, replication-competent recombinant virus was isolated that replicated specifically in CD4+/CCR5+ cells demonstrating that the EnvG retained functions that are essential for cell attachment and virus replication.

The domain swap approach enabled development of a live VSVΔG-Env chimera that readily propagated in CD4+/CCR5+ cells. After conducting multiple rounds of amplification in CD4+/CCR5+ cells, virus emerged that grew to higher titers suggesting that one or more mutations occurred resulting in a virus with increased replicative fitness. Genomic sequence analysis conducted on this virus strain identified three amino acid substitutions in Env, which were (amino acid numbering according to reference strain HXB2): K169T in the second variable domain of Env (V2 domain), I307T in the V3 domain, and W672R in the membrane-proximal external region (MPER). Consistent with these substitutions being the adaptive mutations that improve replicative fitness of the virus, the three amino acid changes have been stable during numerous subsequent rounds of virus propagation. Moreover, there was a substantial difference in virus quantities produced from infected cultures; VSVΔG-Env.BG505 with the three substitutions routinely exceeds 1×10e7 PFU per ml of medium while VSVΔG-Env.BG505 amplified prior to adaptation produced titers closer to 1×10e6.

To provide additional evidence that the three substitutions were the result of adaptive mutations that improved replicative fitness, the mutations were incorporated into the VSVΔG-Env.BG505 genomic DNA clone and a new recombinant virus was recovered containing the Env substitutions. This new recombinant strain grew efficiently, maintained the three amino acid substitutions during many rounds of propagation, and accrued no additional EnvG mutations. These results indicated that the three amino acid substitutions provided a replicative fitness advantage for the VSVΔG-Env.BG505 chimera.

The accrual of the three amino acid substitutions that enhanced replicate fitness indicated that EnvG structure likely required some additional 'fine tuning' to support optimal VSVΔG-Env.BG505 growth. The substitutions probably compensated for some structural changes in the Env complex that resulted from replacement of TM and CT with VSV G sequence. Structural changes in the Env complex are known to occur when mutations are introduced into the Env TM (1) and CT (2); thus, it is reasonable to expect that replacement of the Env TM and CT with VSV G sequence will cause some structural alteration that requires compensatory second-site mutations to achieve optimal EnvG function and virus replicative fitness.

It was noticeable that the three Env substitutions occurred in the Env ectodomain rather than in the G TM or CT. This probably reflects strong selective pressure to maintain the wild-type G TM and CT sequence, as they are optimal for VSV particle structure, and in fact, the G CT makes contact with the underlying VSV matrix protein (3). Thus, selective pressure favored accrual of compensatory amino acid changes in the Env ectodomain rather than in the G TM or CT.

It was also notable that the adaptive mutations occurred in three separate regions of the Env ectodomain including the gp120 (V2 K169T and V3 I307T) and gp41 (MPER W672R) subunits. The mechanism by which this combination of amino acid substitutions improves replicative fitness is unknown. Furthermore, this makes it difficult to predict what substitutions might be useful for optimizing propagation of a chimeric virus like VSVΔG-EnvG.BG505; thus, VSV's ability to rapidly evolve when faced with selective pressure (4) is an important tool in the overall VSVΔG-Env vaccine design process.

TABLE

EnvG amino acid substitutions in VSVΔG-EnvG.BG505. Amino acid substitutions that accrued after multiple rounds of amplification in two independent VSVΔG-EnvG.BG505 recombinants are shown.

| | Env amino acids | | | |
|---|---|---|---|---|
| VSVΔG-Env.BG-505 vaccine | 169 | 307 | 672 | |
| DNA clone | K | I | W | |
| Adapted virus | T | T | R | |
| Repeat virus rescue and adaption | 164 | 440 | 434 | 494 |
| DNA clone | E | Q | M | L |
| Adapted virus | G | R | T | F |

To demonstrate the importance of VSV evolution in design of an optimal immunogen and chimeric virus vector, an independent VSVΔG-Env.BG505 recombinant was isolated that lacked adaptive mutations and it was allowed to evolved during serial rounds of propagation. The results showed that the virus did in fact accrue multiple amino acid substitutions as before, but the constellation of adaptive mutations was different. After multiple rounds of amplification, this new strain had 4 substitutions (Table). Interestingly, as before, one of the substitutions was in V2 (E164G). The other three were in constant (C) domains of Env (C4 M434T, C4 Q440R, and C5 L494F).

The VSVΔG-Env.BG505 vaccine containing the K169T, I307T and W672R was found to be efficacious in the Indian Rhesus macaque SHIV challenge model.

Citations

1. Lovelace E, Xu H, Blish C A, Strong R, Overbaugh J. The role of amino acid changes in the human immunodeficiency virus type 1 transmembrane domain in antibody binding and neutralization. Virology. 2011; 421(2): 235-44.
2. Chen J, Kovacs J M, Peng H, Rits-Volloch S, Lu J, Park D, et al. HIV-1 ENVELOPE. Effect of the cytoplasmic domain on antigenic characteristics of HIV-1 envelope glycoprotein. Science. 2015; 349(6244):191-5.
3. Ge P, Tsao J, Schein S, Green T J, Luo M, Zhou Z H. Cryo-EM model of the bullet-shaped vesicular stomatitis virus. Science. 2010; 327(5966):689-93.
4. Novella I S. Contributions of vesicular stomatitis virus to the understanding of RNA virus evolution. Curr Opin Microbiol. 2003; 6(4):399-405.

Example 4: Transgenic Vero-CD4/CCR5 Cell Line

Human immunodeficiency virus (HIV) or its simian equivalent simian immunodeficiency virus (SIV) initiates infection through the viral envelope (Env) membrane glycoprotein binding to cellular CD4 and a coreceptor such as CCR5. Similarly, Env pseudotyped viral vectors can also infect cells by recognizing the coreceptors. In vitro, HIV, SIV, and Env pseudotyped replicating viral vectors can be propagated on primate peripheral blood mononuclear cells (PBMCs) or transgenic cell lines that are engineered to constitutively express CD4/CCR5. To support propagation and production of chimeric vesicular stomatitis virus (VSV) and canine distemper virus (CDV) vectors that have Env in place of native vector membrane glycoproteins, Applicants generated a transgenic Vero cell lines that express either human or rhesus macaque CD4/CCR5. Optimized transgene design and transfection procedures make transgenic Vero-CD4/CCR5 derivation process efficient and reliable. Stable clones were selected through rigorous multiple rounds of limiting dilutions. The VSV- and CDV-Env chimeras grow efficiently on the transgenic Vero-CD4/CCR5 cell lines and express Env of native conformation and antigenicity. Because Vero is a FDA-approved cell substrate for human vaccine production, the transgenic Vero-CD4/CCR5 cells have substantial potential to be used for manufacturing of replicating viral vectored HIV vaccines that express functional Env immunogens.

Most CD4/CCR5 expressing transgenic cell lines (e.g. GHOST, HOS, A3R5, and TZM-bl) were for use in analytical assays, but are not suitable for HIV vaccine manufacturing. The Vero cell line is approved for producing human vaccines (e.g. inactivated polio vaccine), therefore transgenic Vero-CD4/CCR5 cells are useful for HIV vaccine production since many safety risks associated with cell substrates have been addressed for the Vero cell background. In addition, the unique CD4/CCR5 transgene design directs strong expression of a CCR5 and CD4 polyprotein linked by a 2A sequence that is subsequently self-cleaved resulting in 1 to 1 ratio of CD4 and CCR5 molecules.

The transgenic Vero-CD4/CCR5 cell lines can be used for producing replicating viral vectors expressing HIV or SIV Env. Their use can also be expanded for use in assays requiring cells expressing CD4 and CCR5.

As the expression cassette proved effective with CD4 and CCR5, it is useful for making cell lines expressing other polypeptides.

FIGS. 33A-33E. Sequence annotation of VERO-hCD4/CCR5 gene. A restriction map of the Vert construct shows restriction enzymes cutting a maximum of two times, using RELibrary as a restriction enzyme library.

FIG. 34. Gene design: VERO-CD4/CCR5 Cell Line (VERT). VERO-hCD4/CCR5: Transgenic Vero cells expression human CD4 and CCR5 receptors. sVERT3: Transgenic Vero cells expression simian CD4 and CCR5 receptors.

FIG. 35. VERO-hCD4/CCR5 clone 4F11 resembles the Vero cell.

FIG. 36. VERO-hCD4/CCR5 cytopathic effect when infected by VSV chimera.

FIG. 37. VERO-hCD4/CCR5 maintains infectivity over 20 passages.

FIG. 38. VERO-hCD4/CCR5 maintains the receptor expression over 20 passages.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A transgenic Vero cell line transformed with and directing expression of a differentiation 4 (CD4) receptor and a C-C chemokine receptor type 5 (CCR5 receptor) linked by a subsequently self-cleaved 2A sequence resulting in 1 to 1 ratio of CD4 and CCR5 molecules,
wherein the transgenic Vero cell line transformed with and directing expression of a CD4 receptor and a CCR5 receptor maintains infectivity and receptor expression over 20 passages.

2. The transgenic cell line of claim 1, wherein the CD4 receptor and CCR5 receptor is a human CD4 receptor and a human CCR5 receptor.

3. The transgenic cell line of claim 1, wherein the CD4 receptor and CCR5 receptor is a simian CD4 receptor and a simian CCR5 receptor.

4. A nucleic acid comprising the sequence of SEQ ID NO: 7.

5. The transgenic cell line of claim 1, wherein the transgenic cell line is transformed with the nucleic acid of claim 4.

6. The transgenic cell line of claim 1 transfected with a recombinant vesicular stomatitis virus (VSV) vector wherein a gene encoding the VSV surface glycoprotein G (VSV G) is functionally replaced by functional clade A HIV Env BG505.

7. The transgenic cell line of claim 1 transfected with a vector containing and expressing a nucleic acid sequence encoding an amino acid sequence of an Env.BG505 immunogen encoded by the VSVΔG-Env.BG505.

8. The transgenic cell line of claim 7, wherein the amino acid sequence of an Env.BG505 immunogen encoded by the VSVΔG-Env.BG505 is SEQ ID NO: 2.

9. The transgenic cell line of claim 7 wherein the vector comprises the sequence of a VSVΔG-Env.BG505 genomic clone.

10. The transgenic cell line of claim 9, wherein the sequence of a VSVΔG-Env.BG505 genomic clone is SEQ ID NO: 1.

11. A method for propagating a VSV vaccine vector wherein a VSV envelope is replaced with a HIV envelope protein comprising transfecting the transgenic cell line of any one of claims 1 to 3 with the VSV vaccine vector.

* * * * *